US012275682B2

(12) United States Patent
Montenegro et al.

(10) Patent No.: US 12,275,682 B2
(45) Date of Patent: Apr. 15, 2025

(54) MATERIALS FOR ELECTRONIC DEVICES

(71) Applicant: Merck Patent GmbH, Darmstadt (DE)

(72) Inventors: Elvira Montenegro, Weinheim (DE); Teresa Mujica-Fernaud, Darmstadt (DE); Florian Maier-Flaig, Weinheim (DE); Frank Voges, Bad Duerkheim (DE)

(73) Assignee: MERCK PATENT GMBH (DE)

( * ) Notice: Subject to any disclaimer, the term of this patent is extended or adjusted under 35 U.S.C. 154(b) by 969 days.

(21) Appl. No.: 17/415,972

(22) PCT Filed: Dec. 17, 2019

(86) PCT No.: PCT/EP2019/085484
§ 371 (c)(1),
(2) Date: Jun. 18, 2021

(87) PCT Pub. No.: WO2020/127145
PCT Pub. Date: Jun. 25, 2020

(65) Prior Publication Data
US 2022/0073447 A1    Mar. 10, 2022

(30) Foreign Application Priority Data
Dec. 20, 2018  (EP) .................................... 18214570

(51) Int. Cl.
| *H01L 51/54* | (2006.01) |
| *C07C 211/42* | (2006.01) |
| *C07D 493/00* | (2006.01) |
| *C07D 495/00* | (2006.01) |
| *C07F 7/02* | (2006.01) |
| *H10K 85/40* | (2023.01) |
| *H10K 85/60* | (2023.01) |
| *H10K 50/11* | (2023.01) |
| *H10K 101/10* | (2023.01) |
| *H10K 101/30* | (2023.01) |
| *H10K 101/40* | (2023.01) |

(52) U.S. Cl.
CPC .......... *C07C 211/42* (2013.01); *C07D 493/00* (2013.01); *C07D 495/00* (2013.01); *C07F 7/02* (2013.01); *H10K 85/40* (2023.02); *H10K 85/626* (2023.02); *H10K 85/633* (2023.02); *H10K 85/636* (2023.02); *H10K 85/6574* (2023.02); *H10K 85/6576* (2023.02); *H10K 50/11* (2023.02); *H10K 2101/10* (2023.02); *H10K 2101/30* (2023.02); *H10K 2101/40* (2023.02)

(58) Field of Classification Search
None
See application file for complete search history.

(56) References Cited

U.S. PATENT DOCUMENTS

| 10,014,477 | B2 | 7/2018 | Kato et al. |
| 10,516,112 | B2 | 12/2019 | Kato et al. |
| 10,840,455 | B1 | 11/2020 | Mun et al. |
| 2011/0092701 | A1 | 4/2011 | Pflumm et al. |
| 2014/0054559 | A1 | 2/2014 | Kim et al. |
| 2014/0175395 | A1 | 6/2014 | Kim et al. |
| 2015/0179953 | A1 | 6/2015 | Mujica-Fernaud et al. |
| 2015/0340613 | A1 | 11/2015 | Parham et al. |
| 2016/0043317 | A1 | 2/2016 | Takada et al. |
| 2016/0293843 | A1 | 10/2016 | Itoi |
| 2016/0351817 | A1 | 12/2016 | Kim et al. |
| 2017/0237268 | A1 | 8/2017 | Brannick et al. |
| 2020/0152874 | A1 | 5/2020 | Park et al. |
| 2020/0308129 | A1 | 10/2020 | Montenegro et al. |
| 2022/0158101 | A1 | 5/2022 | Montenegro et al. |

FOREIGN PATENT DOCUMENTS

| CN | 1774491 A | 5/2006 |
| CN | 102725268 A | 10/2012 |
| CN | 104037339 A | 9/2014 |
| CN | 104037361 A | 9/2014 |
| CN | 104073248 A | 10/2014 |
| CN | 104086447 A | 10/2014 |
| CN | 104487541 A | 4/2015 |
| CN | 107924999 A | 4/2018 |
| CN | 108203417 A | 6/2018 |
| CN | 108218664 A | 6/2018 |
| CN | 110835318 A | 2/2020 |
| CN | 111253264 A | 6/2020 |
| CN | 111465599 A | 7/2020 |
| CN | 113166089 A | 7/2021 |
| CN | 114423732 A | 4/2022 |
| JP | 2016-039187 A | 3/2016 |
| JP | 2019-198119 A | 11/2019 |
| JP | 2020-094033 A | 6/2020 |
| KR | 10-2018-0104579 A | 9/2018 |
| KR | 10-2018-0133097 A | 12/2018 |
| WO | 2014/015935 A2 | 1/2014 |

(Continued)

OTHER PUBLICATIONS

International Preliminary Report on Patentability received for PCT Patent Application No. PCT/EP2019/085484, mailed on Jul. 1, 2021, 20 pages (11 pages of English Translation and 9 pages of Original Document).

(Continued)

*Primary Examiner* — Andrew K Bohaty

(74) *Attorney, Agent, or Firm* — Faegre Drinker Biddle & Reath LLP

(57) ABSTRACT

The present application relates to materials for use in electronic devices, to processes for preparing the materials, and to electronic devices containing the materials.

21 Claims, No Drawings

(56) References Cited

FOREIGN PATENT DOCUMENTS

| WO | 2014/015937 A1 | 1/2014 |
| WO | 2014/034795 A1 | 3/2014 |
| WO | 2015/082056 A1 | 6/2015 |
| WO | 2015/099485 A1 | 7/2015 |
| WO | 2016/006709 A1 | 1/2016 |
| WO | 2016/006710 A1 | 1/2016 |
| WO | 2016/006711 A1 | 1/2016 |
| WO | 2018/225991 A1 | 12/2018 |
| WO | 2019/115577 A1 | 6/2019 |

OTHER PUBLICATIONS

International Search Report and Written Opinion received for PCT Patent Application No. PCT/EP2019/085484, mailed on Jun. 23, 2020, 26 pages (11 pages of English Translation and 15 pages of Original Document).

MATERIALS FOR ELECTRONIC DEVICES

CROSS-REFERENCE TO RELATED APPLICATIONS

This application is a national stage application (under 35 U.S.C. § 371) of PCT/EP2019/085484, filed Dec. 17, 2019, which claims benefit of European Application No. 18214570.6, filed Dec. 20, 2018, both of which are incorporated herein by reference in their entirety.

The present application relates to fluorenylamine compounds of a particular formula that each have different substitution in the 9 position and in the 9' position. The compounds are suitable for use in electronic devices.

Electronic devices in the context of this application are understood to mean what are called organic electronic devices, which contain organic semiconductor materials as functional materials. More particularly, these are understood to mean OLEDs (organic electroluminescent devices). The term OLEDs is understood to mean electronic devices which have one or more layers comprising organic compounds and emit light on application of electrical voltage. The construction and general principle of function of OLEDs are known to those skilled in the art.

In electronic devices, especially OLEDs, there is great interest in an improvement in the performance data. In these aspects, it has not yet been possible to find any entirely satisfactory solution.

A great influence on the performance data of electronic devices is possessed by emission layers and layers having a hole-transporting function. Novel compounds are also being sought for use in these layers, especially hole-transporting compounds and compounds that can serve as hole-transporting matrix material, especially for phosphorescent emitters, in an emitting layer. For this purpose, there is a search especially for compounds that have a high glass transition temperature, high stability, and high conductivity for holes. A high stability of the compound is a prerequisite for achieving a long lifetime of the electronic device.

In the prior art, triarylamine compounds in particular are known as hole transport materials and hole-transporting matrix materials for electronic devices. The triarylamine compounds known for use in electronic devices also include fluorenylamine compounds, i.e. triarylamine compounds in which at least one aryl group is a fluorenyl group.

However, there is still a need for alternative compounds suitable for use in electronic devices, especially for compounds having one or more of the abovementioned advantageous properties. There is still a need for improvement in the performance data achieved when the compounds are used in electronic devices, especially in respect of lifetime, operating voltage and efficiency of the devices.

It has been found that particular fluorenylamine compounds are of excellent suitability for use in electronic devices, especially for use in OLEDs, even more especially for use therein as hole transport materials and for use as hole-transporting matrix materials, especially for phosphorescent emitters. The compounds lead to high lifetime, high efficiency and low operating voltage of the devices. Further preferably, the compounds have a high glass transition temperature, high stability and high conductivity for holes.

The compounds found conform to a formula (I)

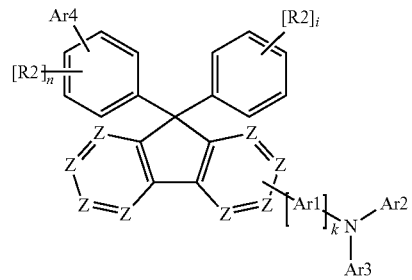

Formula (I)

where the variables that occur are as follows:

Z, when the -[Ar1]$_k$-N(Ar2)(Ar3) group is bonded thereto, is C, and Z, when the -[Ar1]$_k$-N(Ar2)(Ar3) group is not bonded thereto, is the same or different at each instance and is CR1 or N;

Ar1 is the same or different at each instance and is an aromatic ring system which has 6 to 40 aromatic ring atoms and is substituted by R3 radicals, or a heteroaromatic ring system which has 5 to 40 aromatic ring atoms and is substituted by R3 radicals;

Ar2 is an aromatic ring system which has 6 to 40 aromatic ring atoms and is substituted by R4 radicals, or a heteroaromatic ring system which has 5 to 40 aromatic ring atoms and is substituted by R4 radicals;

Ar3 is an aromatic ring system which has 6 to 40 aromatic ring atoms and is substituted by R4 radicals, or a heteroaromatic ring system which has 5 to 40 aromatic ring atoms and is substituted by R4 radicals;

Ar4 is phenyl which may be substituted by R2 radicals or naphthyl which may be substituted by R2 radicals;

R1 is the same or different at each instance and is selected from H, D, F, Cl, Br, I, C(=O)R5, CN, Si(R5)$_3$, N(R5)$_2$, P(=O)(R5)$_2$, OR5, S(=O)R5, S(=O)$_2$R5, straight-chain alkyl or alkoxy groups having 1 to 20 carbon atoms, branched or cyclic alkyl or alkoxy groups having 3 to 20 carbon atoms, alkenyl or alkynyl groups having 2 to 20 carbon atoms, aromatic ring systems having 6 to 40 aromatic ring atoms, and heteroaromatic ring systems having 5 to 40 aromatic ring atoms; where two or more R1 radicals may be joined to one another and may form a ring; where the alkyl, alkoxy, alkenyl and alkynyl groups mentioned and the aromatic ring systems and heteroaromatic ring systems mentioned are each substituted by R5 radicals; and where one or more CH$_2$ groups in the alkyl, alkoxy, alkenyl and alkynyl groups mentioned may be replaced by —R5C=CR5—, —C≡C—, Si(R5)$_2$, C=O, C=NR5, —C(=O)O—, —C(=O)NR5-, NR5, P(=O)(R5), —O—, —S—, SO or SO$_2$;

R2 is the same or different at each instance and is selected from D, F, CN, Si(R5)$_3$, N(R5)$_2$, aromatic ring systems which have 6 to 40 aromatic ring atoms and are substituted by R5 radicals, and heteroaromatic ring systems which have 5 to 40 aromatic ring atoms and are substituted by R5 radicals;

R3 is the same or different at each instance and is selected from H, D, F, Cl, Br, I, C(=O)R5, CN, Si(R5)$_3$, N(R5)$_2$, P(=O)(R5)$_2$, OR5, S(=O)R5, S(=O)$_2$R5, straight-chain alkyl or alkoxy groups having 1 to 20 carbon atoms, branched or cyclic alkyl or alkoxy groups having 3 to 20 carbon atoms, alkenyl or alkynyl groups having 2 to 20 carbon atoms, aromatic ring systems having 6 to 40 aromatic ring atoms, and heteroaromatic ring systems having 5 to 40 aromatic ring atoms; where two or more R3 radicals may be joined to one another and may form a ring; where the alkyl, alkoxy, alkenyl and alkynyl groups mentioned and the aromatic ring systems and heteroaromatic ring systems mentioned are each substituted by R5 radicals; and where one or more CH$_2$ groups in the alkyl, alkoxy, alkenyl and alkynyl groups mentioned may be replaced by —R5C=CR5-, —C≡C—, Si(R5)$_2$, C=O, C=NR5, —C(=O)O—, —C(=O)NR5-, NR5, P(=O)(R5), —O—, —S—, SO or SO$_2$;

R4 is the same or different at each instance and is selected from H, D, F, Cl, Br, I, C(=O)R5, CN, Si(R5)$_3$, N(R5)$_2$, P(=O)(R5)$_2$, OR5, S(=O)R5, S(=O)$_2$R5, straight-chain alkyl or alkoxy groups having 1 to 20 carbon atoms, branched or cyclic alkyl or alkoxy groups having 3 to 20 carbon atoms, alkenyl or alkynyl groups having 2 to 20 carbon atoms, aromatic ring systems having 6 to 40 aromatic ring atoms, and heteroaromatic ring systems having 5 to 40 aromatic ring atoms; where two or more R4 radicals may be joined to one another and may form a ring; where the alkyl, alkoxy, alkenyl and alkynyl groups mentioned and the aromatic ring systems and heteroaromatic ring systems mentioned are each substituted by R5 radicals; and where one or more CH$_2$ groups in the alkyl, alkoxy, alkenyl and alkynyl groups mentioned may be replaced by —R5C=CR5-, —C≡C—, Si(R5)$_2$, C=O, C=NR5, —C(=O)O—, —C(=O)NR5-, NR5, P(=O)(R5), —O—, —S—, SO or SO$_2$;

R5 is the same or different at each instance and is selected from H, D, F, Cl, Br, I, C(=O)R6, CN, Si(R6)$_3$, N(R6)$_2$, P(=O)(R6)$_2$, OR6, S(=O)R6, S(=O)$_2$R6, straight-chain alkyl or alkoxy groups having 1 to 20 carbon atoms, branched or cyclic alkyl or alkoxy groups having 3 to 20 carbon atoms, alkenyl or alkynyl groups having 2 to 20 carbon atoms, aromatic ring systems having 6 to 40 aromatic ring atoms, and heteroaromatic ring systems having 5 to 40 aromatic ring atoms; where two or more R5 radicals may be joined to one another and may form a ring; where the alkyl, alkoxy, alkenyl and alkynyl groups mentioned and the aromatic ring systems and heteroaromatic ring systems mentioned are each substituted by R6 radicals; and where one or more CH$_2$ groups in the alkyl, alkoxy, alkenyl and alkynyl groups mentioned may be replaced by —R6C=CR6-, —C≡C—, Si(R6)$_2$, C=O, C=NR6, —C(=O)O—, —C(=O)NR6-, NR6, P(=O)(R6), —O—, —S—, SO or SO$_2$;

R6 is the same or different at each instance and is selected from H, D, F, Cl, Br, I, CN, alkyl or alkoxy groups having 1 to 20 carbon atoms, alkenyl or alkynyl groups having 2 to 20 carbon atoms, aromatic ring systems having 6 to 40 aromatic ring atoms and heteroaromatic ring systems having 5 to 40 aromatic ring atoms; where the alkyl, alkoxy, alkenyl and alkynyl groups, aromatic ring systems and heteroaromatic ring systems mentioned may be substituted by one or more radicals selected from F and ON;

k is 0, 1, 2, 3 or 4, where, in the case that k=0, the Ar1 group is absent and the groups that bind to Ar1 in formula (I) are bonded directly to one another;

i is 0, 1, 2, 3, 4 or 5;

n is 0, 1, 2, 3 or 4;

where the two groups

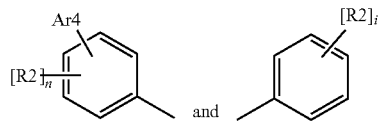

and in formula (I), each as a whole including their substituents, are not the same.

The case that i=1 means that an R2 group is bonded to exactly one position in the benzene ring in question. The case that n=1 means that an R2 group is bonded to exactly one position in the benzene ring in question.

The case that i=2, 3, 4 or 5 means that one R2 group is bonded to each of 2, 3, 4 or 5 different positions in the benzene ring in question. The case that n=2, 3 or 4 means that one R2 group is bonded to each of 2, 3 or 4 different positions in the benzene ring in question.

The case that i=0 or n=0 means that there are no R2 radicals but only hydrogen atoms bonded to the benzene ring in question.

The definitions which follow are applicable to the chemical groups that are used in the present applications. They are applicable unless any more specific definitions are given.

An aryl group in the context of this invention is understood to mean either a single aromatic cycle, i.e. benzene, or a fused aromatic polycycle, for example naphthalene, phenanthrene or anthracene. A fused aromatic polycycle in the context of the present application consists of two or more single aromatic cycles fused to one another. Fusion between cycles is understood here to mean that the cycles share at least one edge with one another. An aryl group in the context of this invention contains 6 to 40 aromatic ring atoms of which none is a heteroatom.

A heteroaryl group in the context of this invention is understood to mean either a single heteroaromatic cycle, for example pyridine, pyrimidine or thiophene, or a fused heteroaromatic polycycle, for example quinoline or carbazole. A fused heteroaromatic polycycle in the context of the present application consists of two or more single aromatic or heteroaromatic cycles that are fused to one another, where at least one of the aromatic and heteroaromatic cycles is a heteroaromatic cycle. Fusion between cycles is understood here to mean that the cycles share at least one edge with one another. A heteroaryl group in the context of this invention contains 5 to 40 aromatic ring atoms of which at least one is a heteroatom. The heteroatoms of the heteroaryl group are preferably selected from N, O and S.

An aryl or heteroaryl group, each of which may be substituted by the abovementioned radicals, is especially understood to mean groups derived from benzene, naphthalene, anthracene, phenanthrene, pyrene, dihydropyrene, chrysene, perylene, triphenylene, fluoranthene, benzanthracene, benzophenanthrene, tetracene, pentacene, benzopyrene, furan, benzofuran, isobenzofuran, dibenzofuran, thiophene, benzothiophene, isobenzothiophene, dibenzothiophene, pyrrole, indole, isoindole, carbazole, pyridine, quinoline, isoquinoline, acridine, phenanthridine, benzo-5,6-quinoline, benzo-6,7-quinoline, benzo-7,8-quinoline, phenothiazine, phenoxazine, pyrazole, indazole, imidazole, benzimidazole, benzimidazolo[1,2-a]benzimidazole, naphthimidazole, phenanthrimidazole, pyridimidazole, pyrazinimidazole, quinoxalinimidazole, oxazole, benzoxazole, naphthoxazole, anthroxazole, phenanthroxazole, isoxazole, 1,2-thiazole, 1,3-thiazole, benzothiazole, pyridazine, benzopyridazine, pyrimidine, benzopyrimidine, quinoxaline, pyrazine, phenazine, naphthyridine, azacarbazole, benzocarboline, phenanthroline, 1,2,3-triazole, 1,2,4-triazole, benzotriazole, 1,2,3-oxadiazole, 1,2,4-oxadiazole, 1,2,5-oxadiazole, 1,3,4-oxadiazole, 1,2,3-thiadiazole, 1,2,4-thiadiazole, 1,2,5-thiadiazole, 1,3,4-thiadiazole, 1,3,5-triazine, 1,2,4-triazine, 1,2,3-triazine, tetrazole, 1,2,4,5-tetrazine, 1,2,3,4-tetrazine, 1,2,3,5-tetrazine, purine, pteridine, indolizine and benzothiadiazole.

An aromatic ring system in the context of this invention is a system which does not necessarily contain solely aryl groups, but which may additionally contain one or more non-aromatic rings fused to at least one aryl group. These non-aromatic rings contain exclusively carbon atoms as ring atoms. Examples of groups covered by this definition are tetrahydronaphthalene, fluorene and spirobifluorene. In addition, the term "aromatic ring system" includes systems that consist of two or more aromatic ring systems joined to one another via single bonds, for example biphenyl, terphenyl, 7-phenyl-2-fluorenyl, quaterphenyl and 3,5-diphenyl-1-phenyl. An aromatic ring system in the context of this invention contains 6 to 40 carbon atoms and no heteroatoms in the ring system. The definition of "aromatic ring system" does not include heteroaryl groups.

A heteroaromatic ring system conforms to the abovementioned definition of an aromatic ring system, except that it must contain at least one heteroatom as ring atom. As is the case for the aromatic ring system, the heteroaromatic ring system need not contain exclusively aryl groups and heteroaryl groups, but may additionally contain one or more non-aromatic rings fused to at least one aryl or heteroaryl group. The nonaromatic rings may contain exclusively carbon atoms as ring atoms, or they may additionally contain one or more heteroatoms, where the heteroatoms are preferably selected from N, O and S. One example of such a heteroaromatic ring system is benzopyranyl. In addition, the term "heteroaromatic ring system" is understood to mean systems that consist of two or more aromatic or heteroaromatic ring systems that are bonded to one another via single bonds, for example 4,6-diphenyl-2-triazinyl. A heteroaromatic ring system in the context of this invention contains 5 to 40 ring atoms selected from carbon and heteroatoms, where at least one of the ring atoms is a heteroatom. The heteroatoms of the heteroaromatic ring system are preferably selected from N, O and S.

The terms "heteroaromatic ring system" and "aromatic ring system" as defined in the present application thus differ from one another in that an aromatic ring system cannot have a heteroatom as ring atom, whereas a heteroaromatic ring system must have at least one heteroatom as ring atom. This heteroatom may be present as a ring atom of a non-aromatic heterocyclic ring or as a ring atom of an aromatic heterocyclic ring.

In accordance with the above definitions, any aryl group is covered by the term "aromatic ring system", and any heteroaryl group is covered by the term "heteroaromatic ring system".

An aromatic ring system having 6 to 40 aromatic ring atoms or a heteroaromatic ring system having 5 to 40 aromatic ring atoms is especially understood to mean groups derived from the groups mentioned above under aryl groups and heteroaryl groups, and from biphenyl, terphenyl, quaterphenyl, fluorene, spirobifluorene, dihydrophenanthrene, dihydropyrene, tetrahydropyrene, indenofluorene, truxene, isotruxene, spirotruxene, spiroisotruxene, indenocarbazole, or from combinations of these groups.

In the context of the present invention, a straight-chain alkyl group having 1 to 20 carbon atoms and a branched or cyclic alkyl group having 3 to 20 carbon atoms and an alkenyl or alkynyl group having 2 to 40 carbon atoms in which individual hydrogen atoms or $CH_2$ groups may also be substituted by the groups mentioned above in the definition of the radicals are preferably understood to mean the methyl, ethyl, n-propyl, i-propyl, n-butyl, i-butyl, s-butyl, t-butyl, 2-methylbutyl, n-pentyl, s-pentyl, cyclopentyl, neopentyl, n-hexyl, cyclohexyl, neohexyl, n-heptyl, cycloheptyl, n-octyl, cyclooctyl, 2-ethylhexyl, trifluoromethyl, pentafluoroethyl, 2,2,2-trifluoroethyl, ethenyl, propenyl, butenyl, pentenyl, cyclopentenyl, hexenyl, cyclohexenyl, heptenyl, cycloheptenyl, octenyl, cyclooctenyl, ethynyl, propynyl, butynyl, pentynyl, hexynyl or octynyl radicals.

An alkoxy or thioalkyl group having 1 to 20 carbon atoms in which individual hydrogen atoms or $CH_2$ groups may also be replaced by the groups mentioned above in the definition of the radicals is preferably understood to mean methoxy, trifluoromethoxy, ethoxy, n-propoxy, i-propoxy, n-butoxy, i-butoxy, s-butoxy, t-butoxy, n-pentoxy, s-pentoxy, 2-methylbutoxy, n-hexoxy, cyclohexyloxy, n-heptoxy, cycloheptyloxy, n-octyloxy, cyclooctyloxy, 2-ethylhexyloxy, pentafluoroethoxy, 2,2,2-trifluoroethoxy, methylthio, ethylthio, n-propylthio, i-propylthio, n-butylthio, i-butylthio, s-butylthio, t-butylthio, n-pentylthio, s-pentylthio, n-hexylthio, cyclohexylthio, n-heptylthio, cycloheptylthio, n-octylthio, cyclooctylthio, 2-ethylhexylthio, trifluoromethylthio, pentafluoroethylthio, 2,2,2-trifluoroethylthio, ethenylthio, propenylthio, butenylthio, pentenylthio, cyclopentenylthio, hexenylthio, cyclohexenylthio, heptenylthio, cycloheptenylthio, octenylthio, cyclooctenylthio, ethynylthio, propynylthio, butynylthio, pentynylthio, hexynylthio, heptynylthio or octynylthio.

The wording that two or more radicals together may form a ring, in the context of the present application, shall be understood to mean, inter alia, that the two radicals are joined to one another by a chemical bond. In addition, however, the abovementioned wording should also be understood to mean that, if one of the two radicals is hydrogen, the second radical binds to the position to which the hydrogen atom was bonded, forming a ring.

The compound of the formula (I) is preferably a monoamine. A monoamine is understood to mean a compound containing a single triarylamino group and no further triarylamino groups, more preferably a compound containing a single amino group and no further amino groups.

Z, when the -[Ar1]$_k$-N(Ar2)(Ar3) group is not bonded thereto, is preferably CR1.

Ar1 is preferably selected from aromatic ring systems which have 6 to 20 aromatic ring atoms and may be substituted by one or more R3 radicals, and heteroaromatic ring systems which have 5 to 20 aromatic ring atoms and may be substituted by one or more R3 radicals. Particularly preferred Ar1 groups are selected from divalent groups derived from benzene, biphenyl, terphenyl, naphthalene, fluorene, indenofluorene, indenocarbazole, spirobifluorene, dibenzofuran, dibenzothiophene, and carbazole, each of which may be substituted by one or more R3 radicals. Most preferably, Ar1 is a divalent group derived from benzene that may be substituted in each case by one or more R3 radicals. Ar1 groups may be selected identically or differently at each instance.

Preferably, k is selected from 0 or 1; more preferably, k is 0.

Preferred -(Ar1)$_k$- groups in the case that k=1 conform to the following formulae:
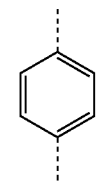
Ar1-1
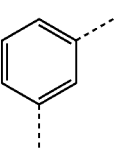
Ar1-2
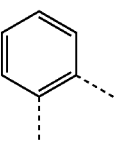
Ar1-3
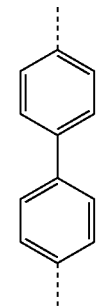
Ar1-4
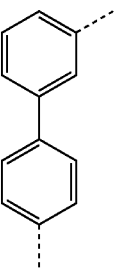
Ar1-5
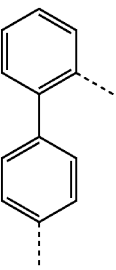
Ar1-6
-continued
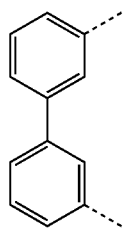
Ar1-7
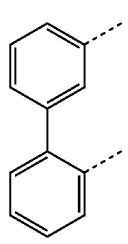
Ar1-8
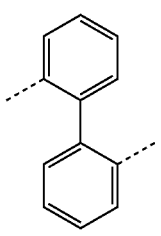
Ar1-9
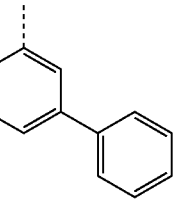
Ar1-10
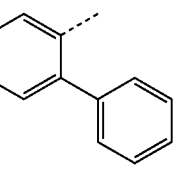
Ar1-11
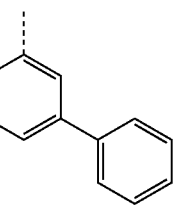
Ar1-12
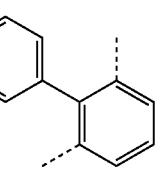
Ar1-13

Ar1-14
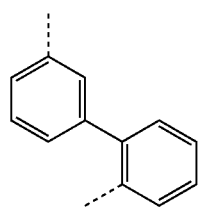
Ar1-15
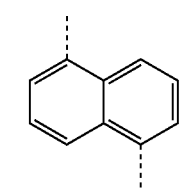
Ar1-16
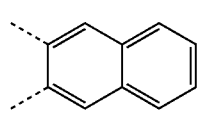
Ar1-17
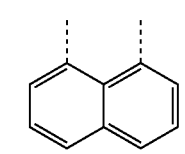
Ar1-18
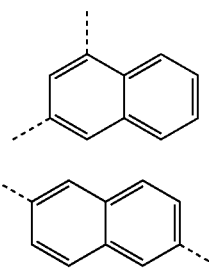
Ar1-19
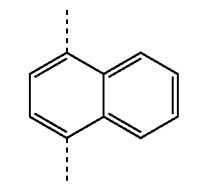
Ar1-20
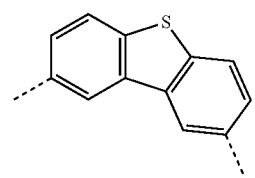
Ar1-21
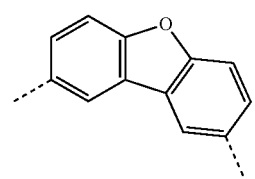
Ar1-22
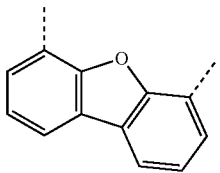
Ar1-23
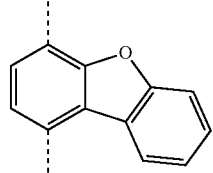
Ar1-24
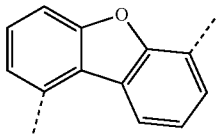
Ar1-25
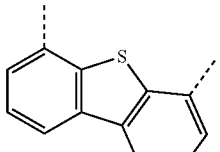
Ar1-26
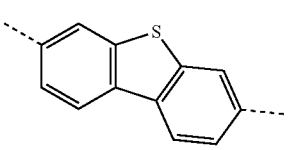
Ar1-27
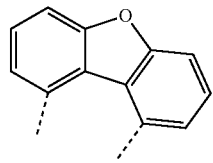
Ar1-28
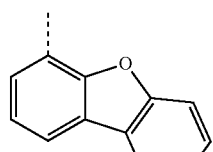
Ar1-29
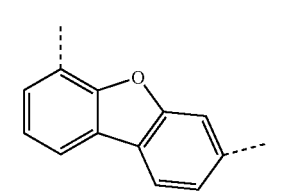
Ar1-30
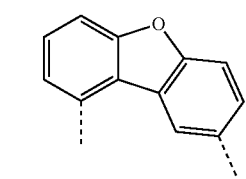
Ar1-31

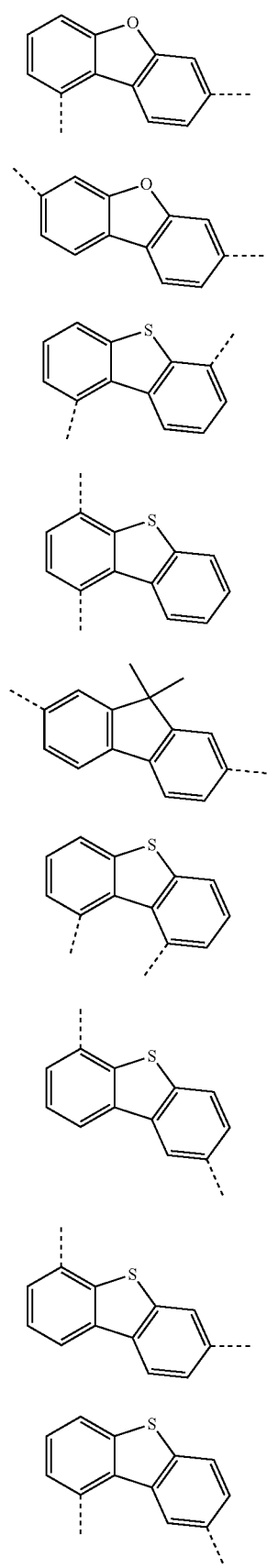
Ar1-32
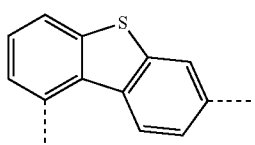
Ar1-41
Ar1-33
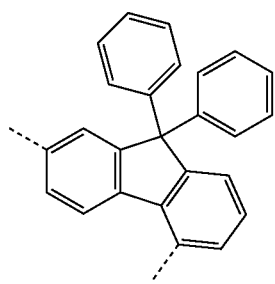
Ar1-42
Ar1-34
Ar1-35
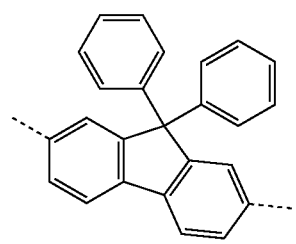
Ar1-43
Ar1-36
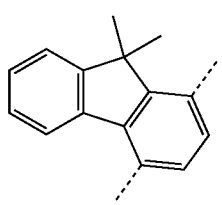
Ar1-44
Ar1-37
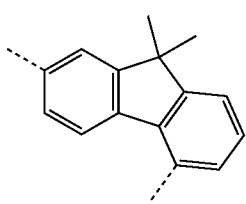
Ar1-45
Ar1-38
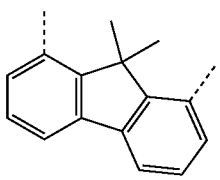
Ar1-46
Ar1-39
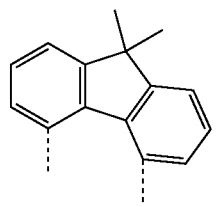
Ar1-47
Ar1-40

-continued
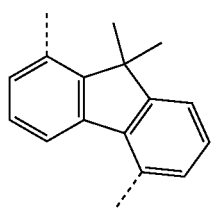
Ar1-48
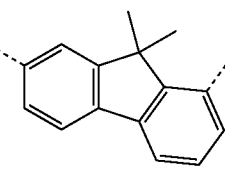
Ar1-49
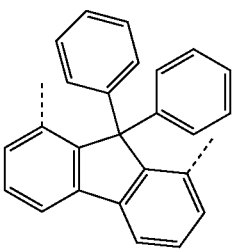
Ar1-50
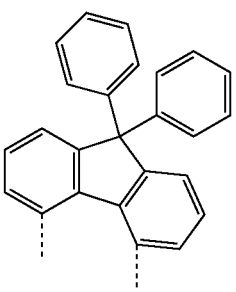
Ar1-51
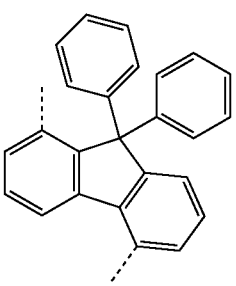
Ar1-52
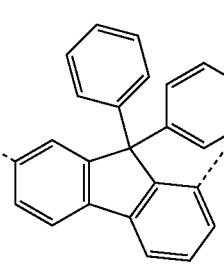
Ar1-53
-continued
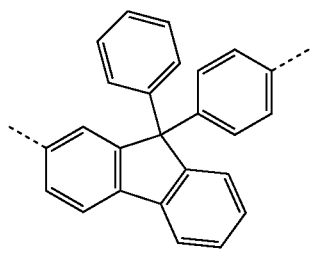
Ar1-54
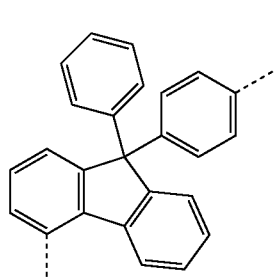
Ar1-55
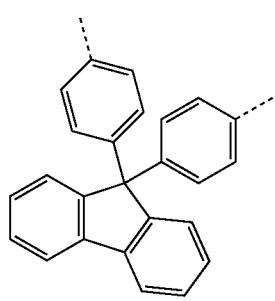
Ar1-56
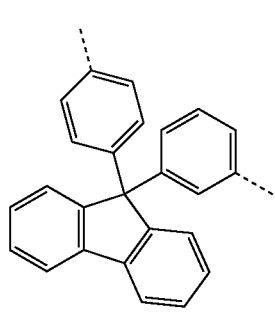
Ar1-57
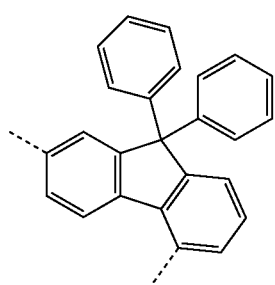
Ar1-58

Ar1-59
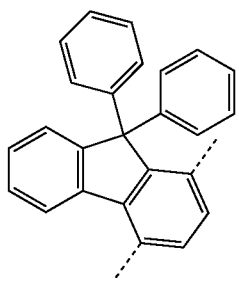
Ar1-60
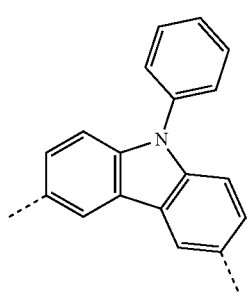
Ar1-61
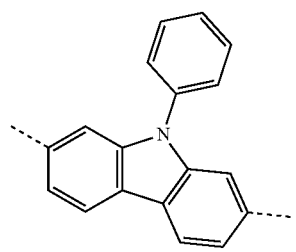
Ar1-62
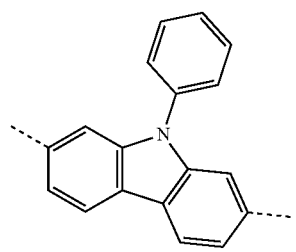
Ar1-63
Ar1-64
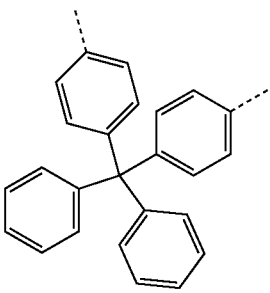
Ar1-65
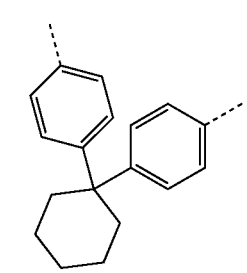
Ar1-66
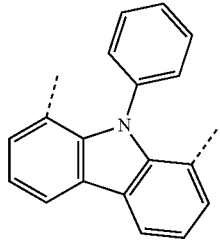
Ar1-67
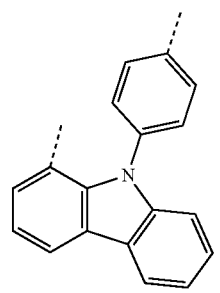
Ar1-68
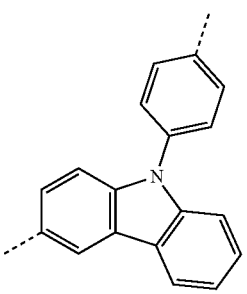

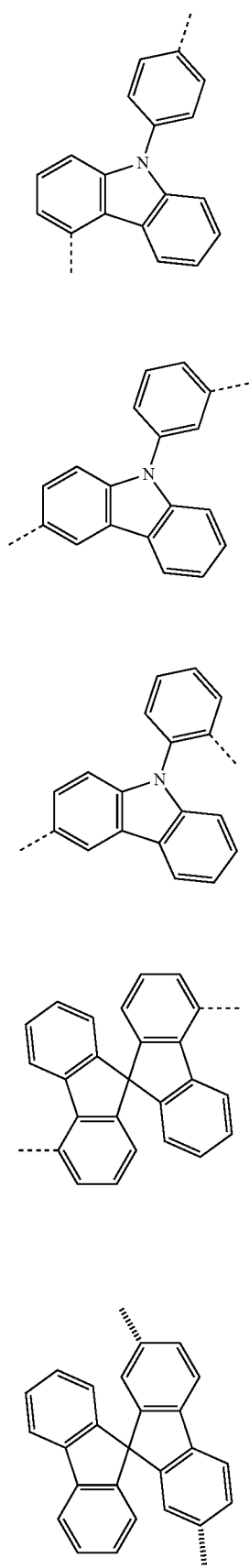
Ar1-69
Ar1-70
Ar1-71
Ar1-72
Ar1-73
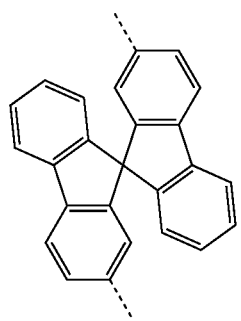
Ar1-74
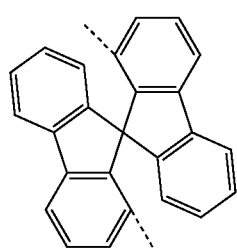
Ar1-75
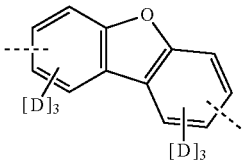
Ar1-76
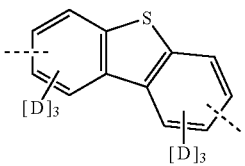
Ar1-77
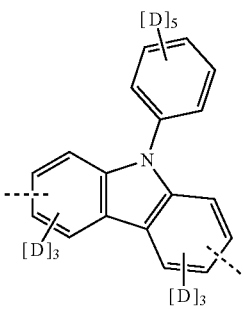
Ar1-78
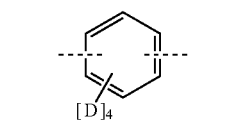
Ar1-79
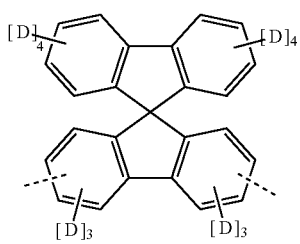
Ar1-80

Ar1-81

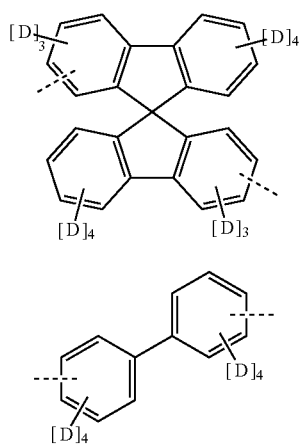

Ar1-82 where the dotted lines represent the bonds to the rest of the formula (I), and where the groups at the positions shown as unsubstituted are each substituted by R3 radicals, where the R3 radicals in these positions are preferably H.

Preferably, Ar2 and Ar3 groups are the same or different at each instance and are selected from monovalent groups derived from benzene, biphenyl, terphenyl, quaterphenyl, naphthalene, fluorene, especially 9,9'-dimethylfluorene and 9,9'-diphenylfluorene, 9-silafluorene, especially 9,9'-dimethyl-9-silafluorene and 9,9'-diphenyl-9-silafluorene, benzofluorene, spirobifluorene, indenofluorene, indenocarbazole, dibenzofuran, dibenzothiophene, benzocarbazole, carbazole, benzofuran, benzothiophene, indole, quinoline, pyridine, pyrimidine, pyrazine, pyridazine and triazine, where the monovalent groups are each substituted by one or more R4 radicals. Alternatively, the Ar2 and Ar3 groups are the same or different at each instance and may preferably be selected from combinations of groups derived from benzene, biphenyl, terphenyl, quaterphenyl, naphthalene, fluorene, especially 9,9'-dimethylfluorene and 9,9'-diphenylfluorene, 9-silafluorene, especially 9,9'-dimethyl-9-silafluorene and 9,9'-diphenyl-9-silafluorene, benzofluorene, spirobifluorene, indenofluorene, indenocarbazole, dibenzofuran, dibenzothiophene, carbazole, benzofuran, benzothiophene, indole, quinoline, pyridine, pyrimidine, pyrazine, pyridazine and triazine, where the groups are each substituted by one or more R4 radicals.

Particularly preferred Ar2 and Ar3 groups are the same or different at each instance and are selected from phenyl, biphenyl, terphenyl, quaterphenyl, naphthyl, fluorenyl, especially 9,9'-dimethylfluorenyl and 9,9'-diphenylfluorenyl, benzofluorenyl, spirobifluorenyl, indenofluorenyl, indenocarbazolyl, dibenzofuranyl, dibenzothiophenyl, carbazolyl, benzofuranyl, benzothiophenyl, benzofused dibenzofuranyl, benzofused dibenzothiophenyl, naphthyl-substituted phenyl, fluorenyl-substituted phenyl, spirobifluorenyl-substituted phenyl, dibenzofuranyl-substituted phenyl, dibenzothiophenyl-substituted phenyl, carbazolyl-substituted phenyl, pyridyl-substituted phenyl, pyrimidyl-substituted phenyl, and triazinyl-substituted phenyl, where the groups mentioned are each substituted by one or more R4 radicals.

In a preferred embodiment, exactly one group selected from the Ar2 and Ar3 groups is phenyl substituted by R4 radicals that are preferably selected from H, D, F, CN and alkyl groups having 1 to 10 carbon atoms, and are more preferably H. Such compounds have particularly good hole transport properties.

Particularly preferred Ar2 and Ar3 groups are the same or different and are selected from the following formulae:

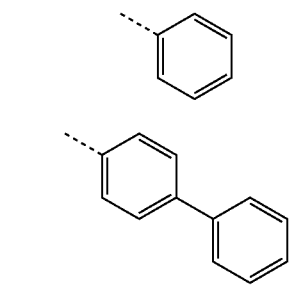

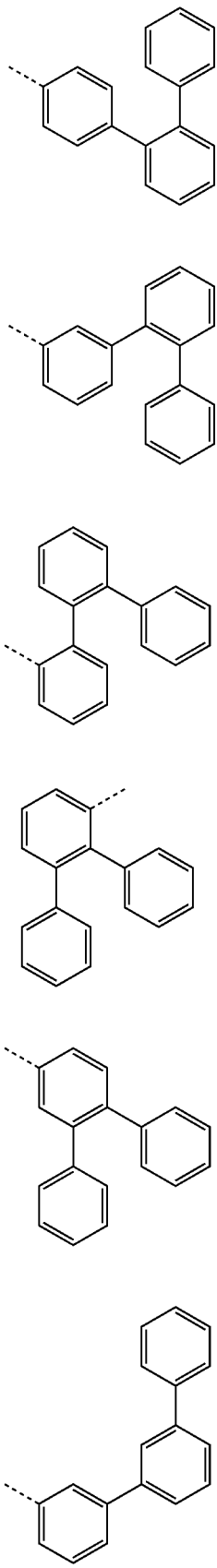
Ar-8
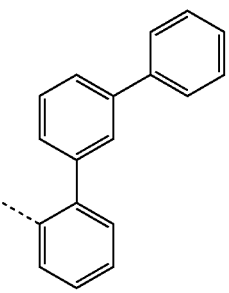
Ar-9
Ar-10
Ar-11
Ar-12
Ar-13
Ar-14
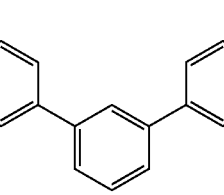
Ar-15
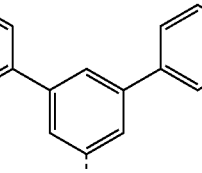
Ar-16
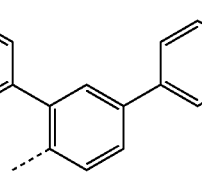
Ar-17
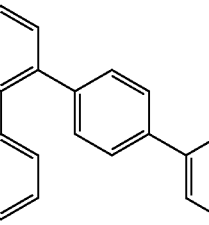
Ar-18
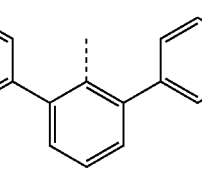
Ar-19
Ar-20
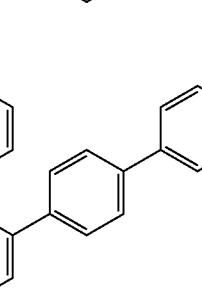

Ar-21
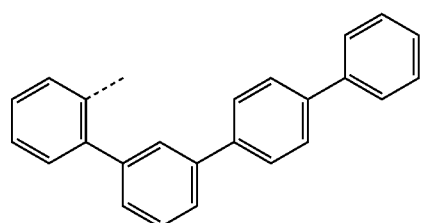
Ar-22
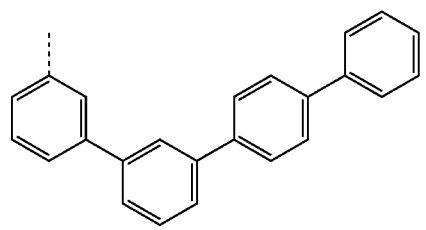
Ar-23
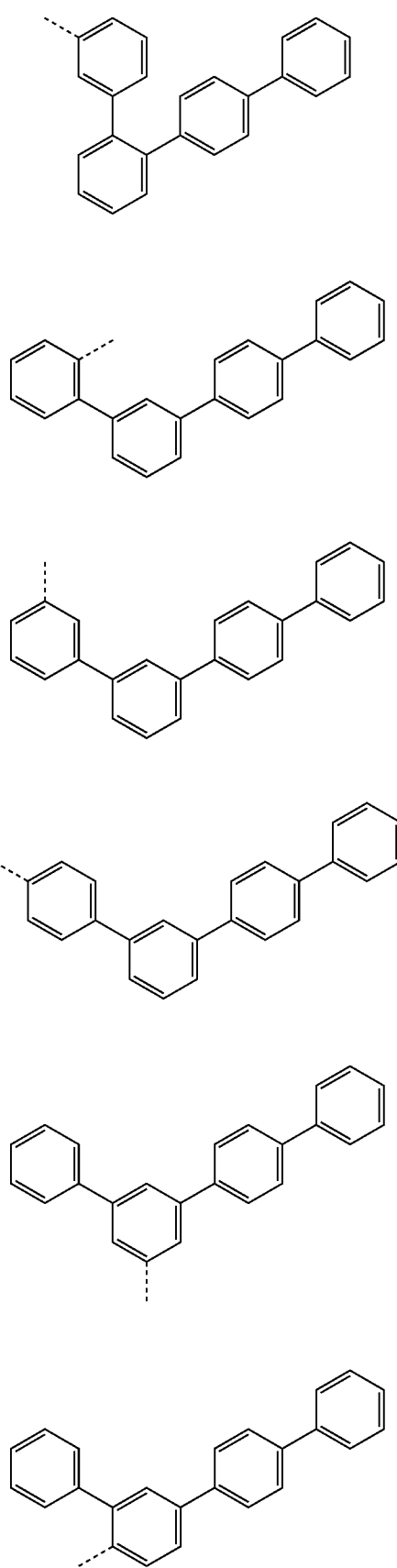
Ar-24
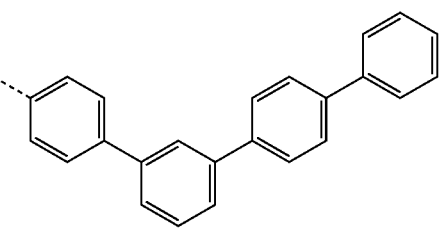
Ar-25
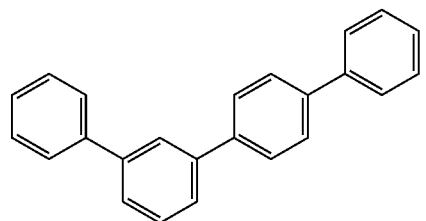
Ar-26
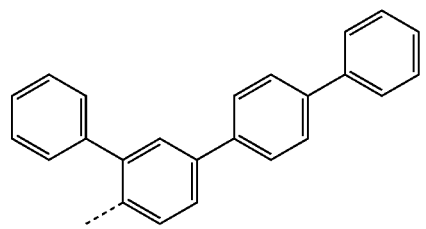
Ar-27
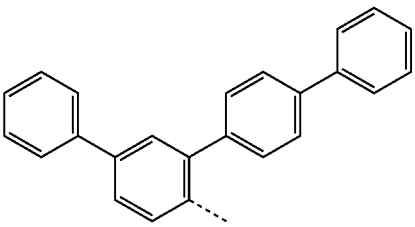
Ar-28
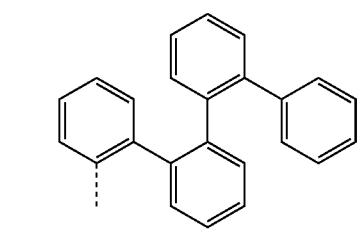
Ar-29
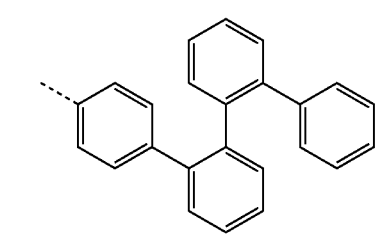
Ar-30
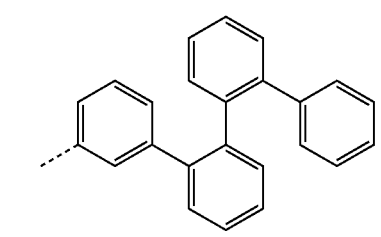
Ar-31
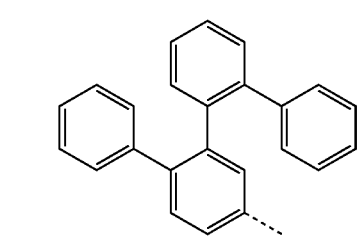
Ar-32
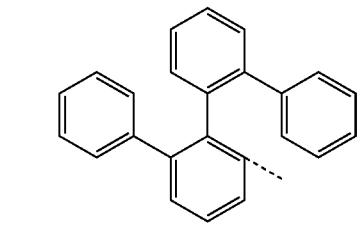

Ar-33
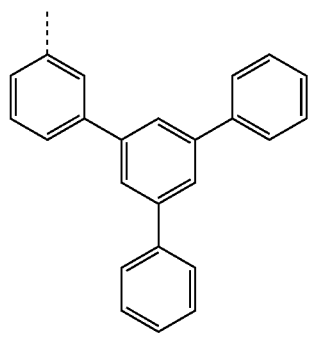
Ar-34
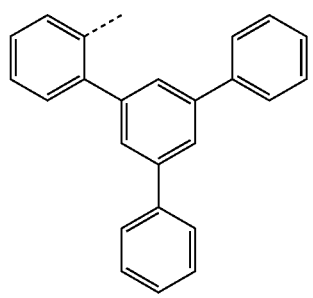
Ar-35
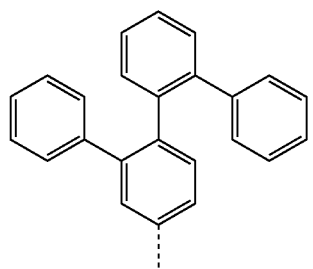
Ar-36
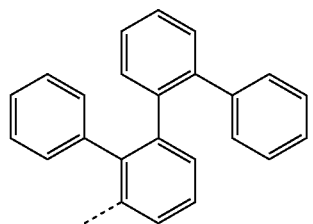
Ar-37
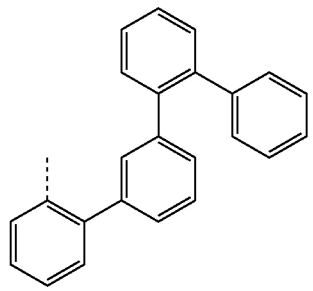
Ar-38
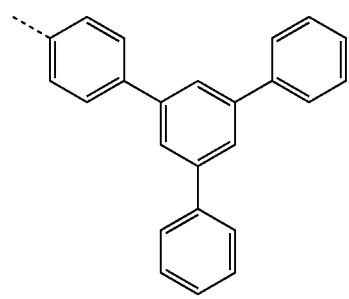
Ar-39
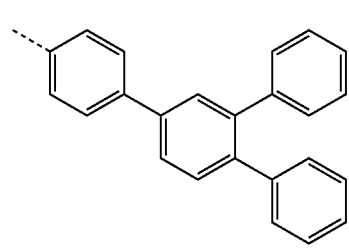
Ar-40
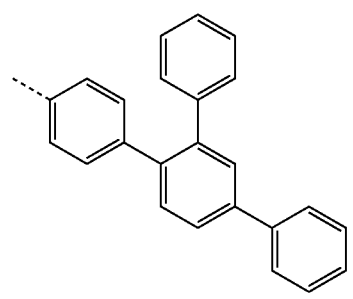
Ar-41
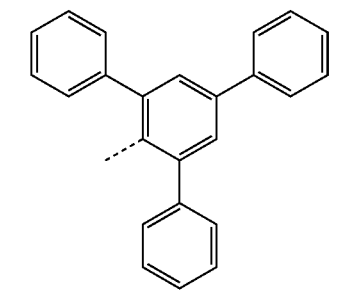
Ar-42
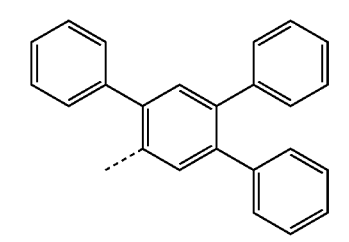
Ar-43
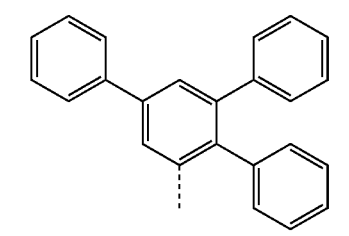

Ar-44
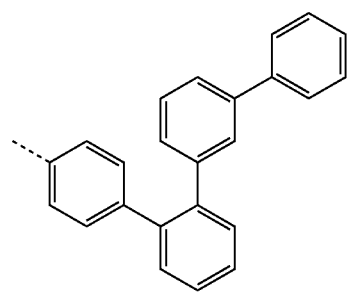
Ar-45
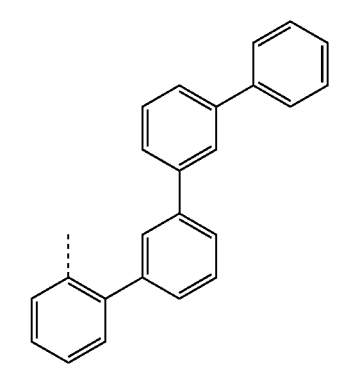
Ar-46
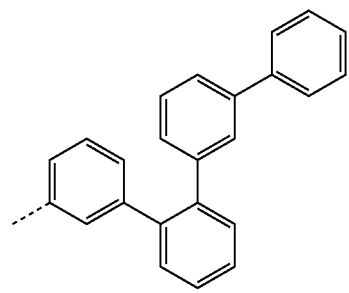
Ar-47
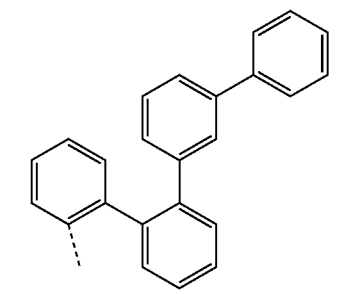
Ar-48
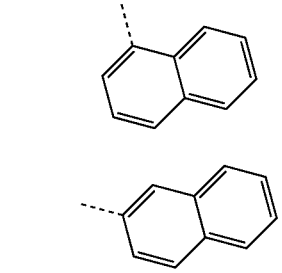
Ar-49
Ar-50
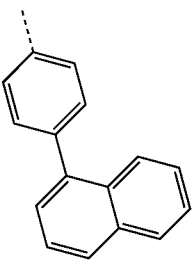
Ar-51
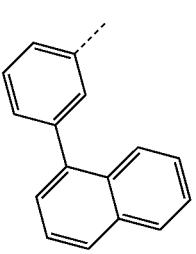
Ar-52
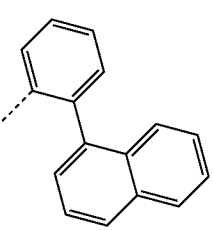
Ar-53
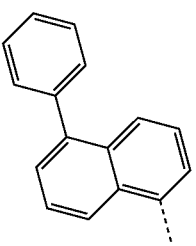
Ar-54
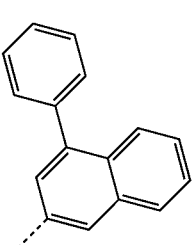
Ar-55
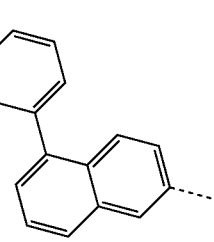

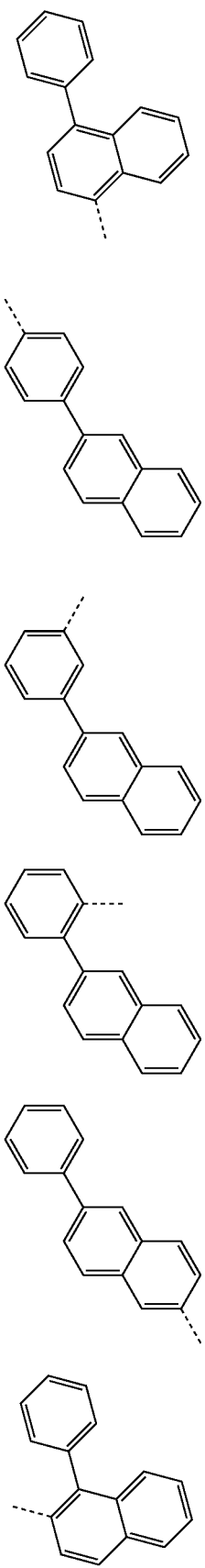 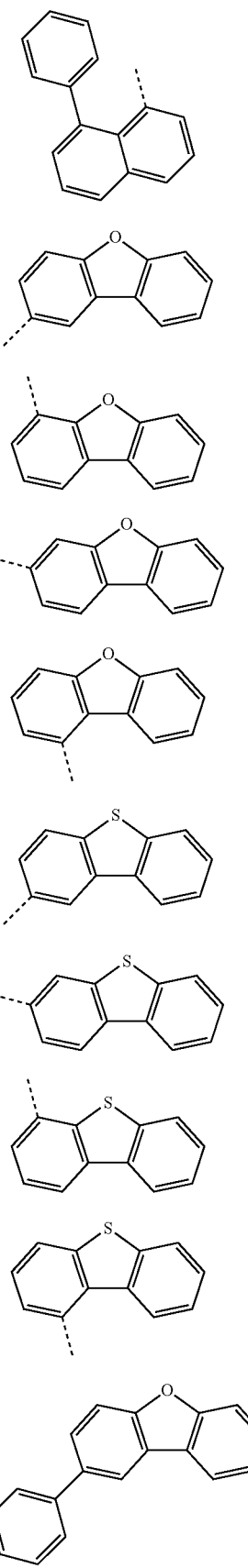

Ar-72
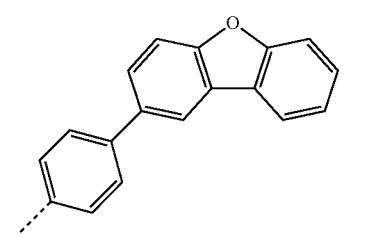
Ar-73
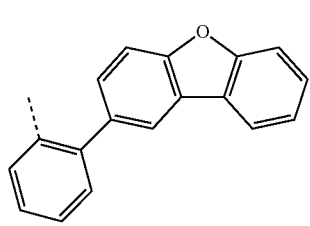
Ar-74
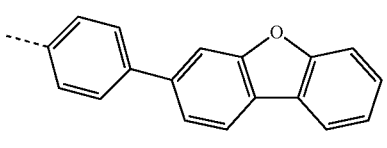
Ar-75
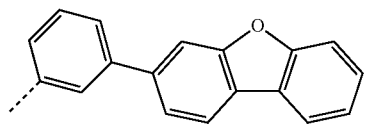
Ar-76
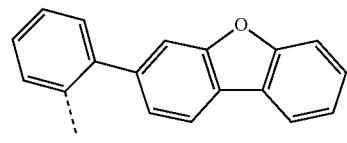
Ar-77
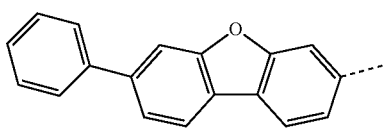
Ar-78
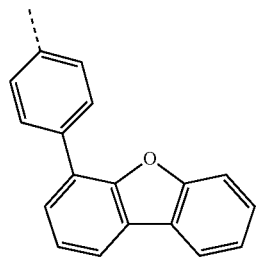
Ar-79
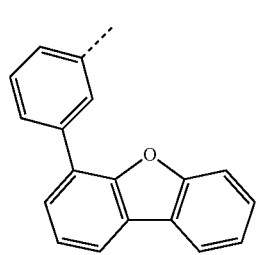
Ar-80
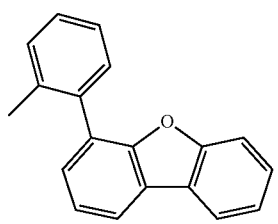
Ar-81
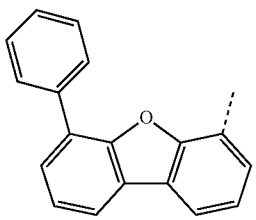
Ar-82
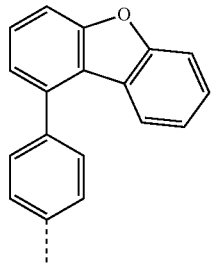
Ar-83
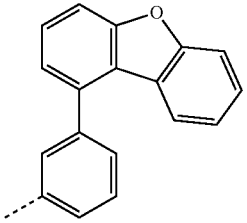
Ar-84
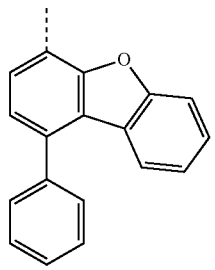
Ar-85
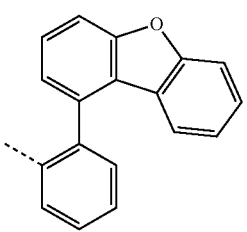

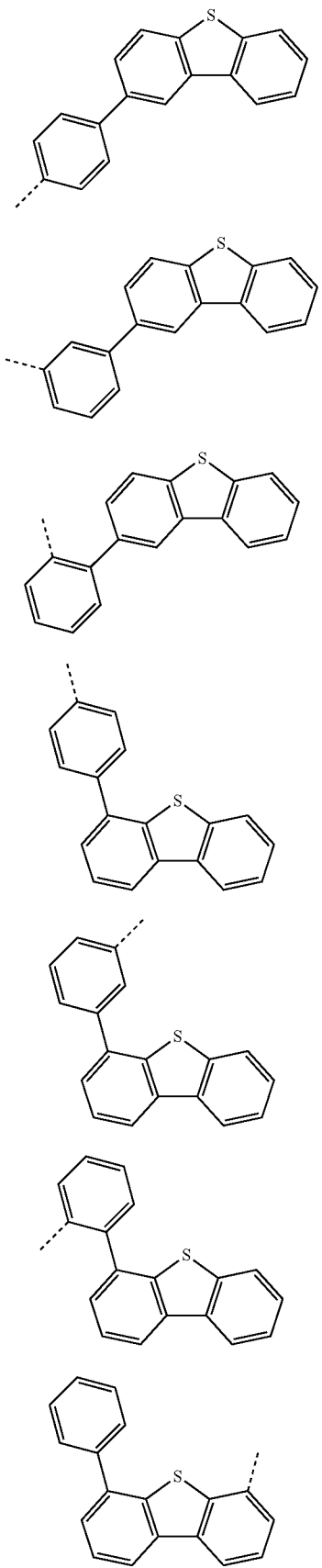
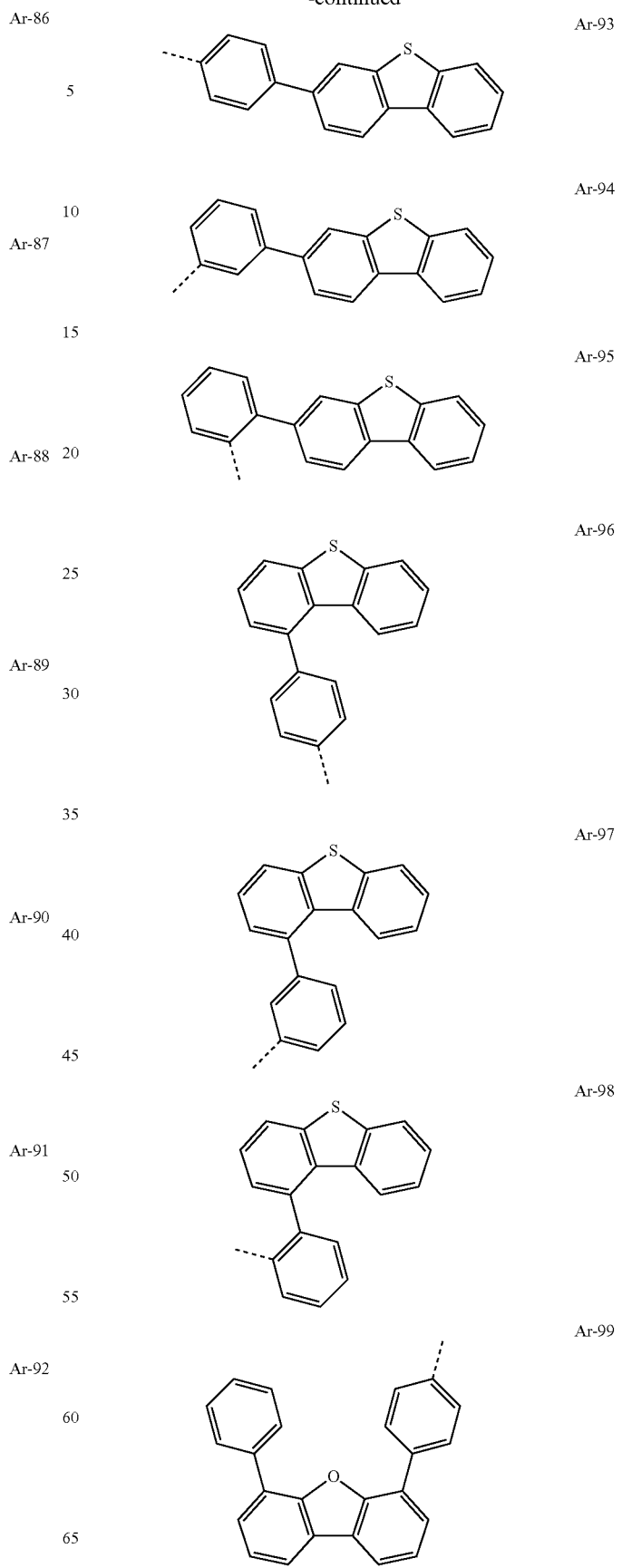

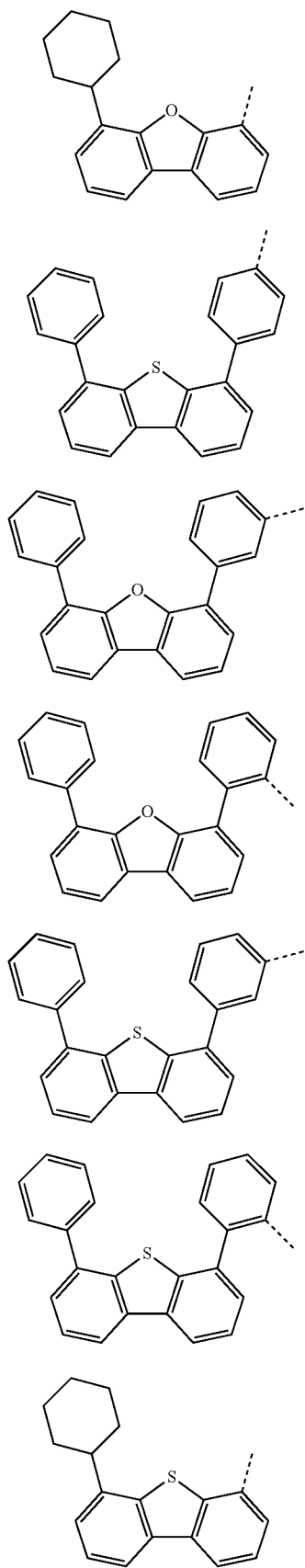
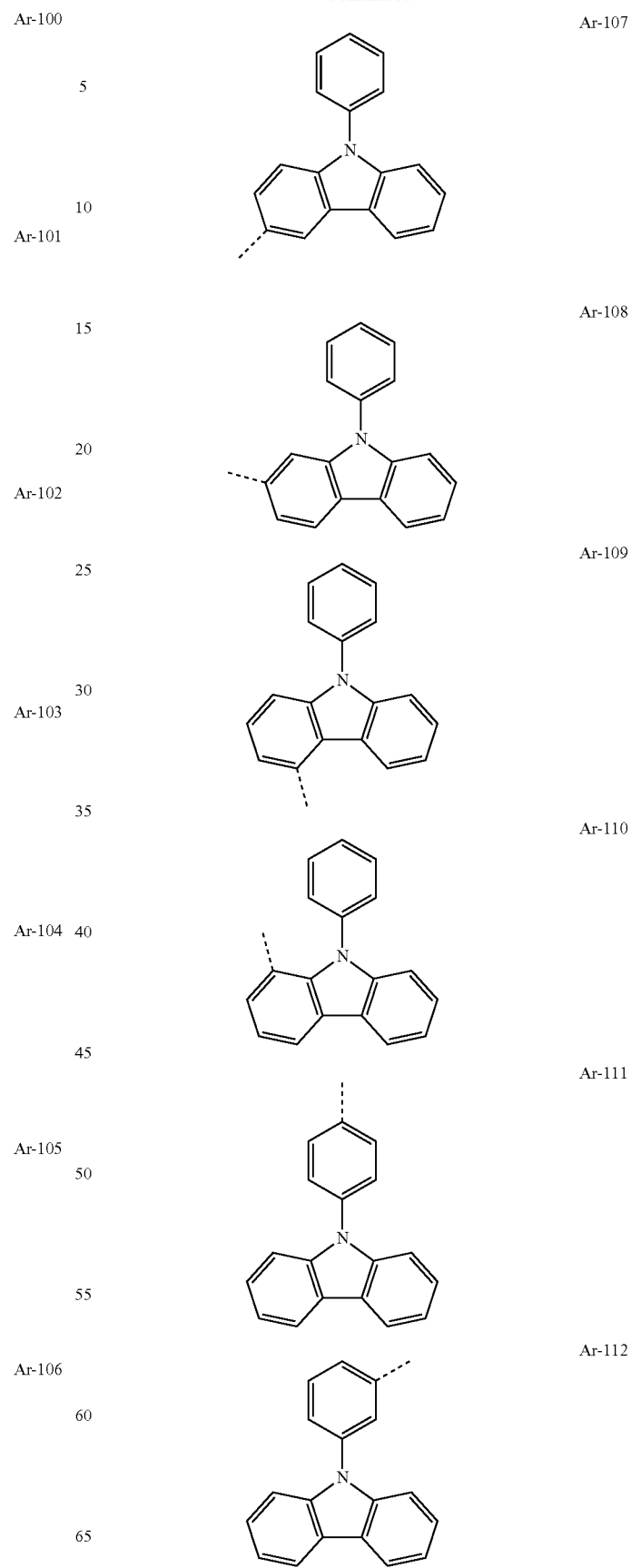

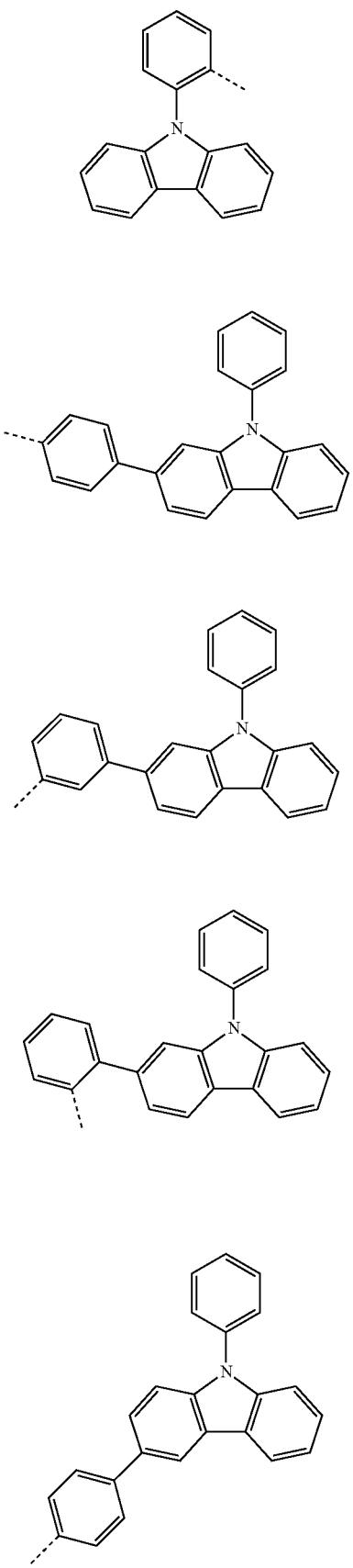
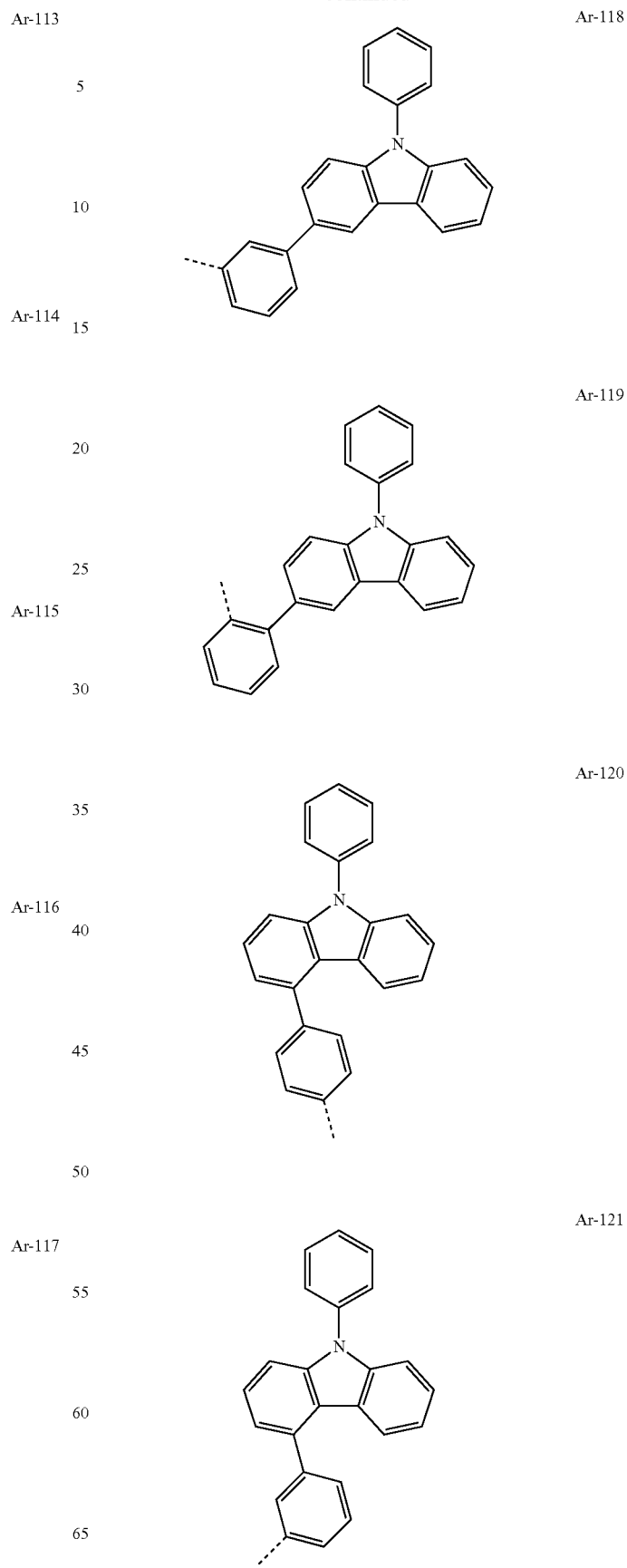

Ar-122
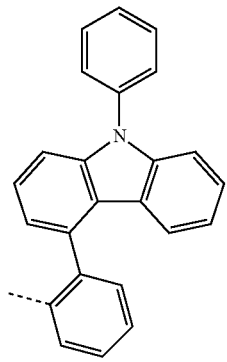
Ar-123
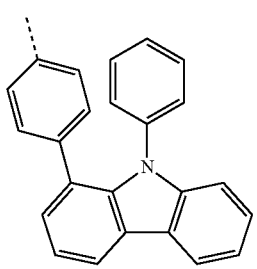
Ar-124
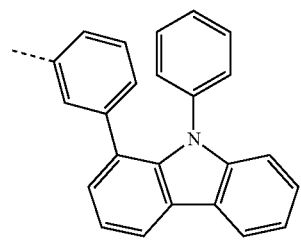
Ar-125
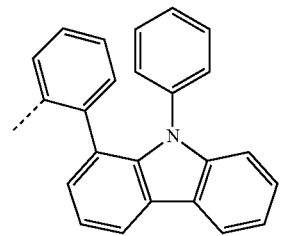
Ar-126
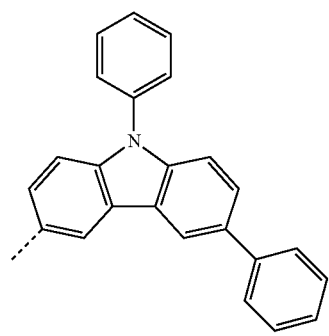
Ar-127
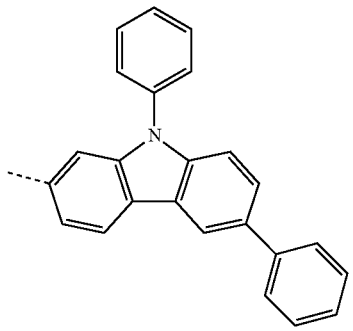
Ar-128
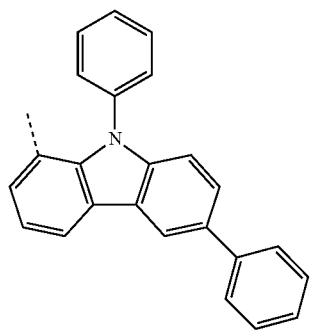
Ar-129
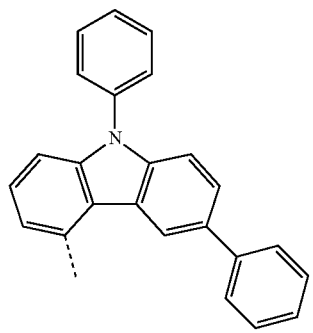
Ar-130
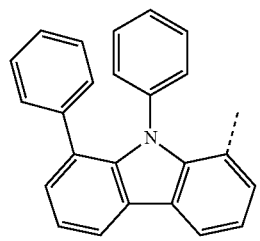
Ar-131
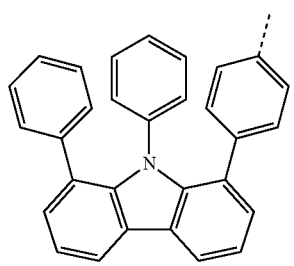

Ar-132
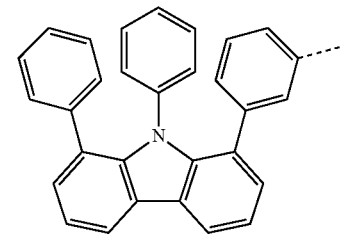
Ar-133
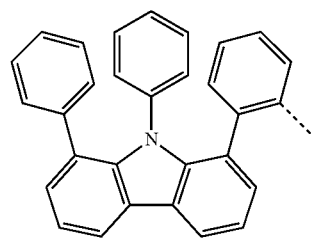
Ar-134
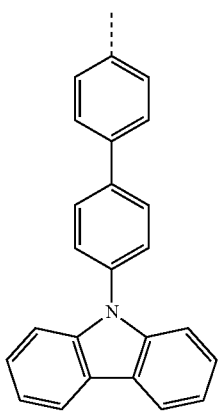
Ar-135
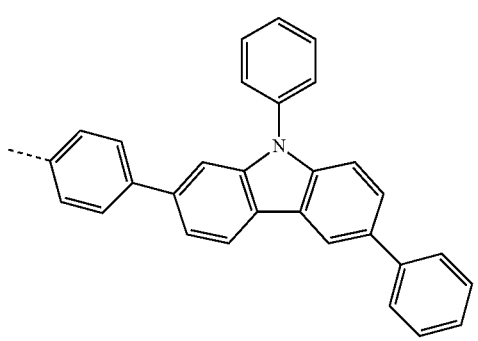
Ar-136
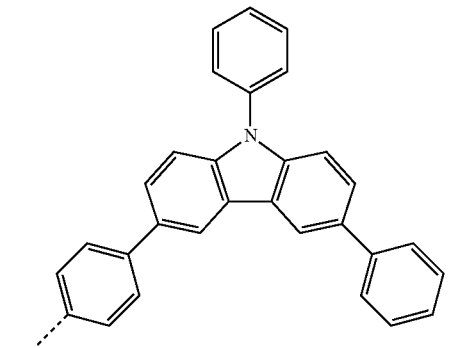
Ar-137
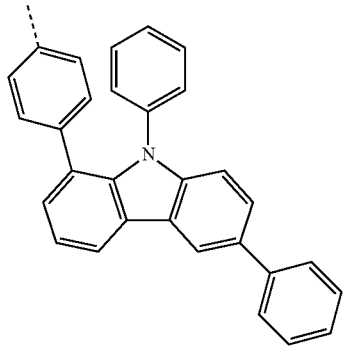
Ar-138
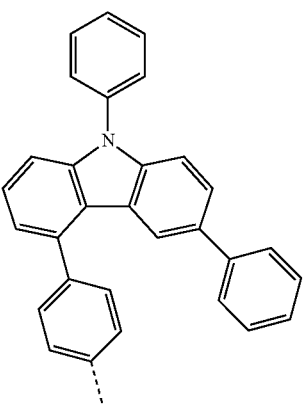
Ar-139
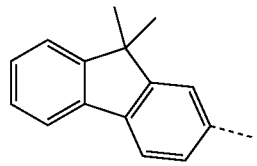
Ar-140
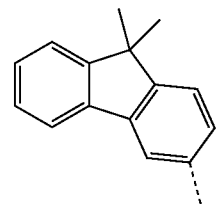
Ar-141
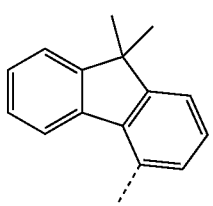
Ar-142
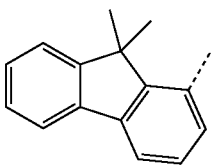

Ar-143

Ar-144

Ar-145

Ar-146

Ar-147

Ar-148

Ar-149

Ar-150

Ar-151

Ar-152

Ar-153

Ar-154

Ar-155

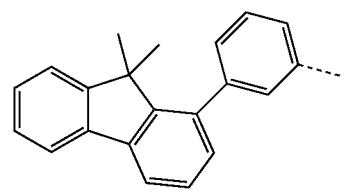
Ar-156
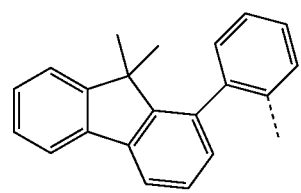
Ar-157
Ar-158
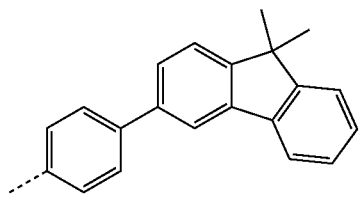
Ar-159
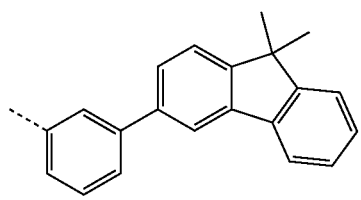
Ar-160
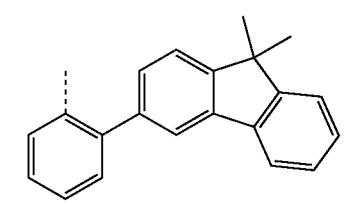
Ar-161
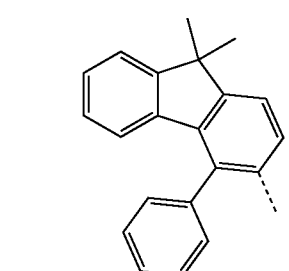
Ar-162
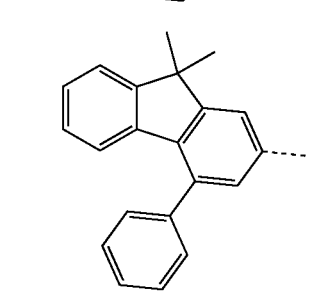
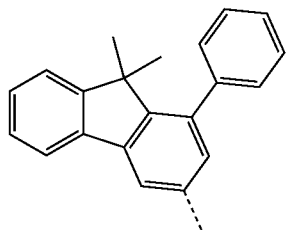
Ar-163
Ar-164
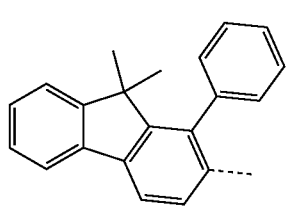
Ar-165
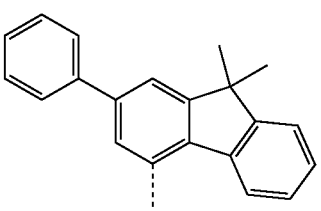
Ar-166
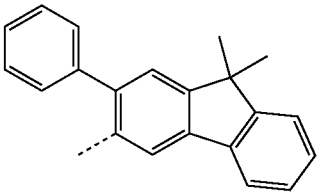
Ar-167
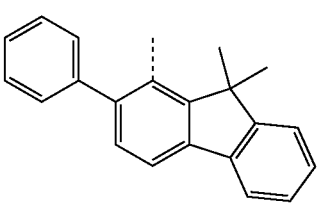
Ar-168
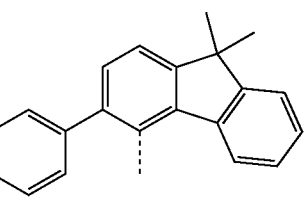
Ar-169
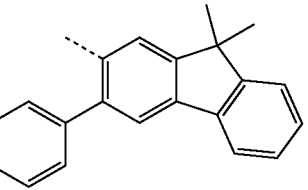

Ar-170
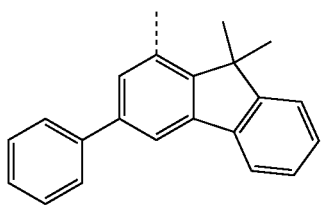
Ar-171
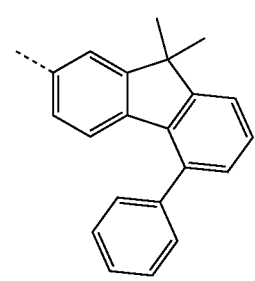
Ar-172
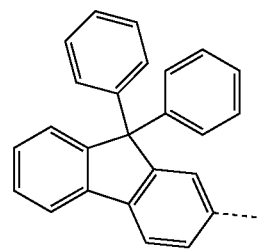
Ar-173
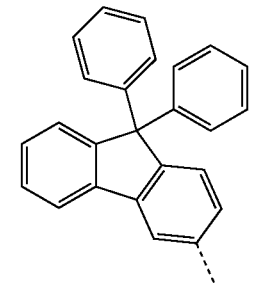
Ar-174
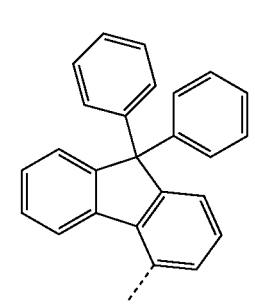
Ar-175
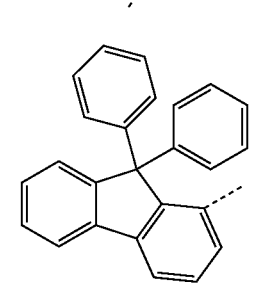
Ar-176
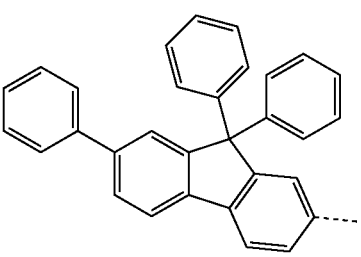
Ar-177
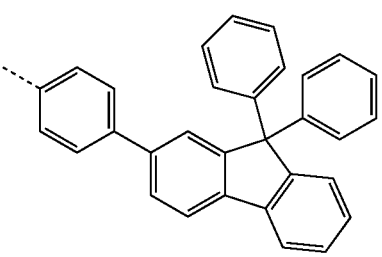
Ar-178
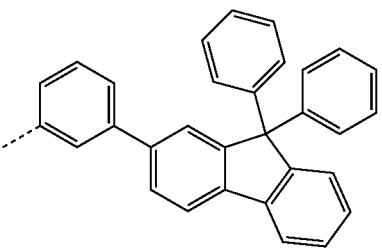
Ar-179
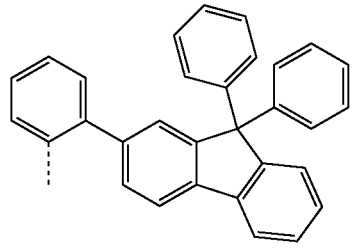
Ar-180
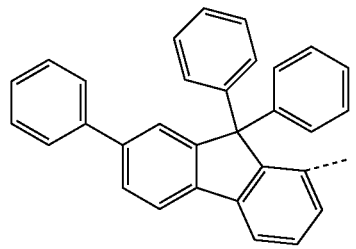
Ar-181
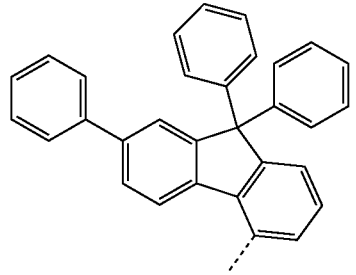

-continued
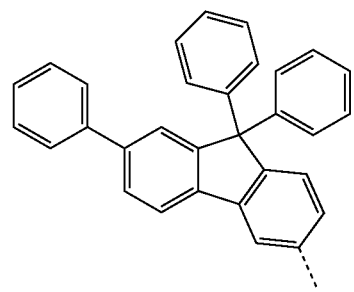
Ar-182
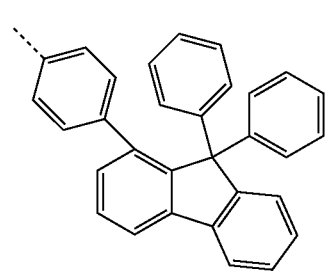
Ar-183
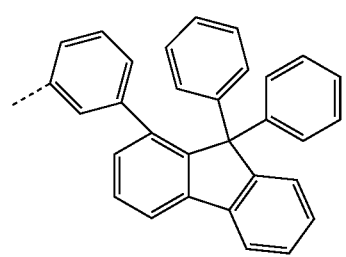
Ar-184
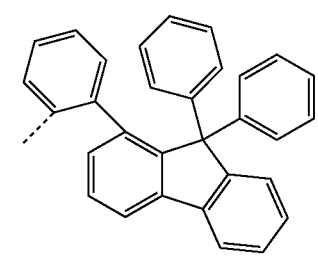
Ar-185
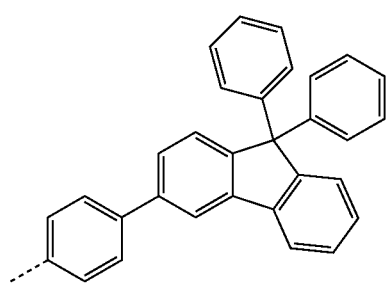
Ar-186
-continued
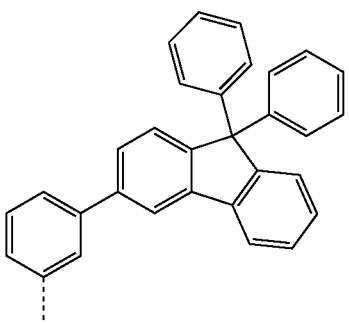
Ar-187
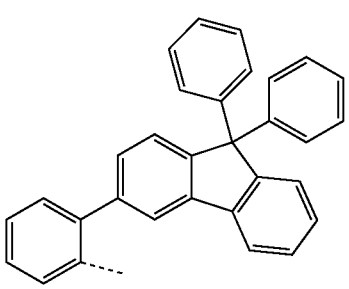
Ar-188
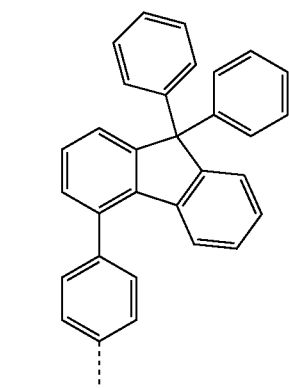
Ar-189
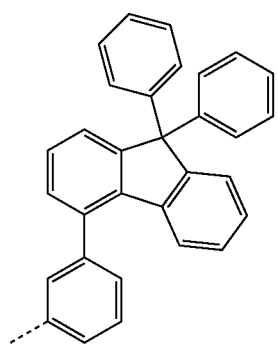
Ar-190

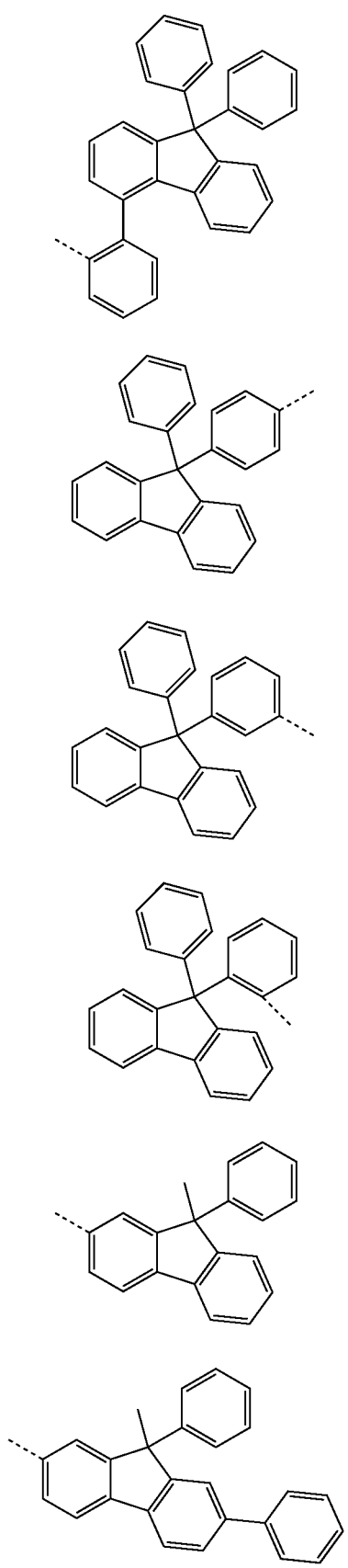
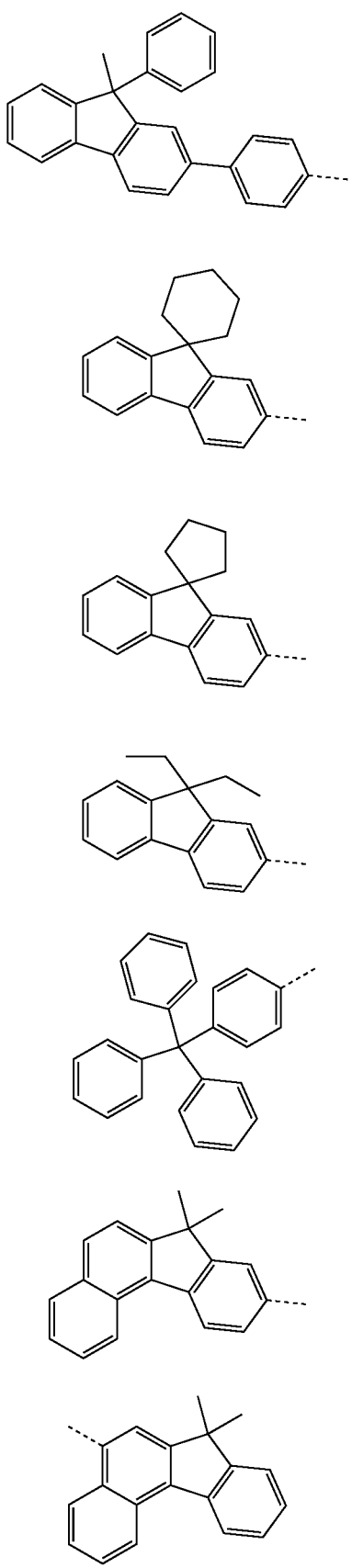

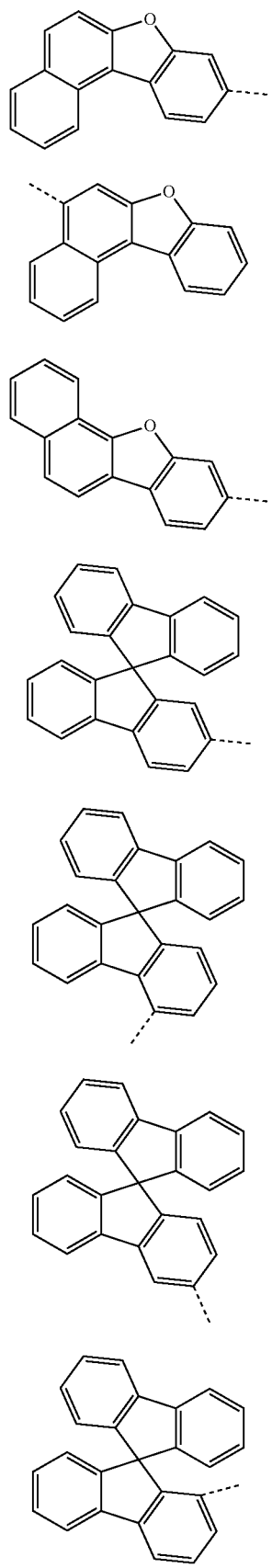
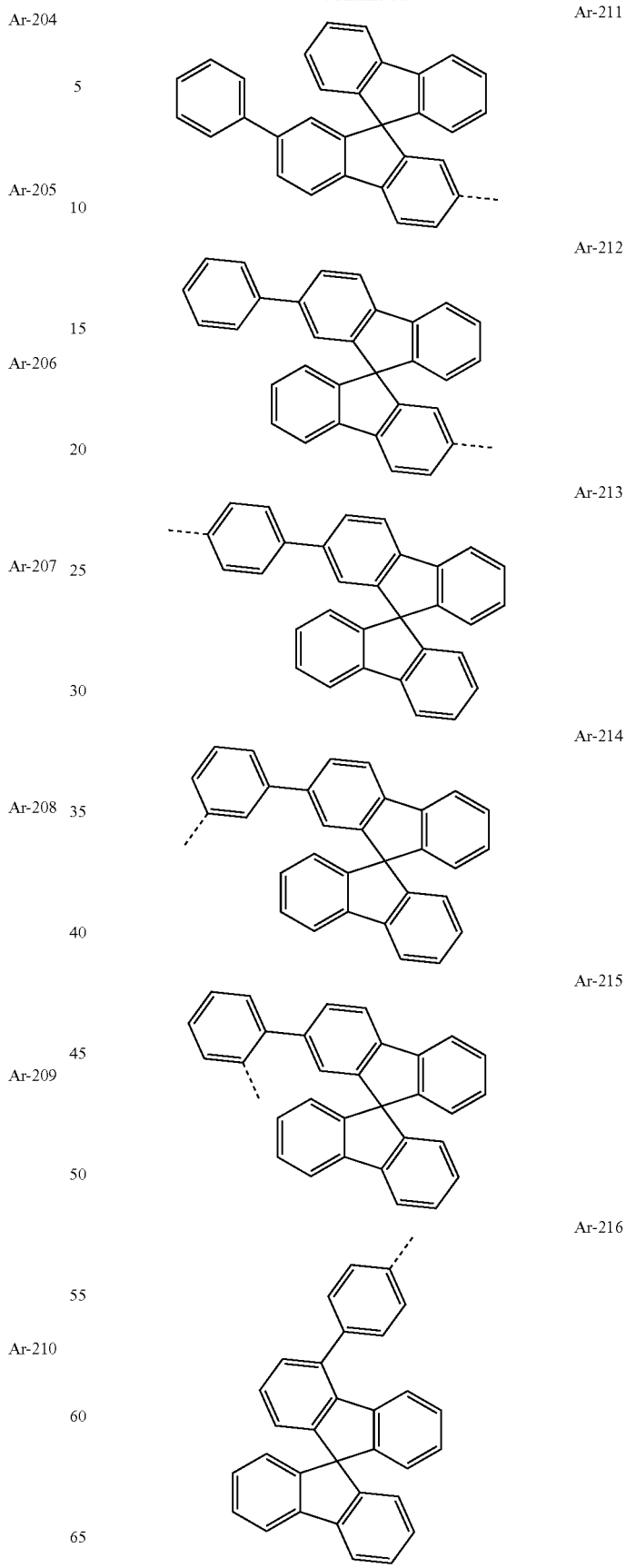

Ar-217 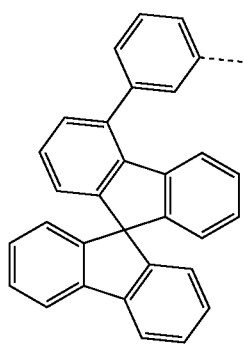
Ar-218 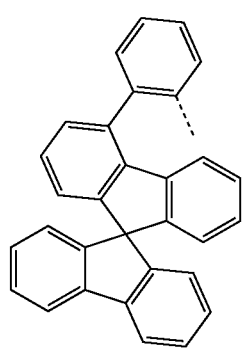
Ar-219 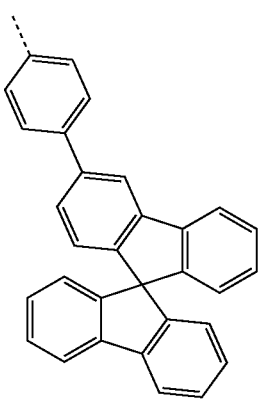
Ar-220 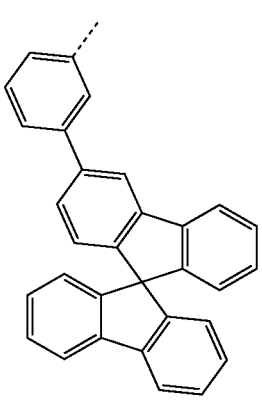
Ar-221 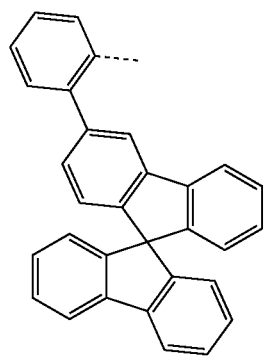
Ar-222 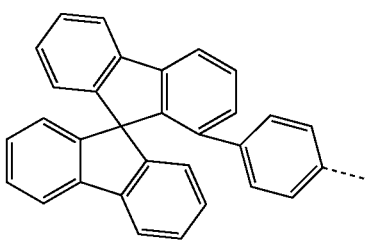
Ar-223 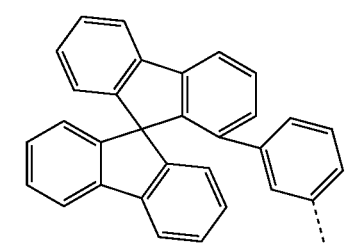
Ar-224 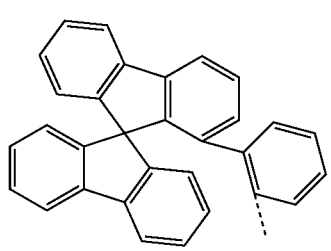
Ar-225 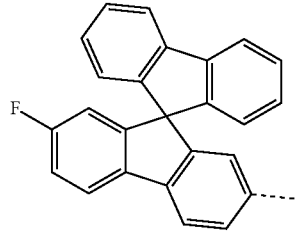
Ar-226 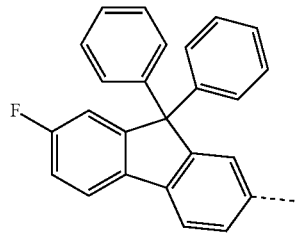

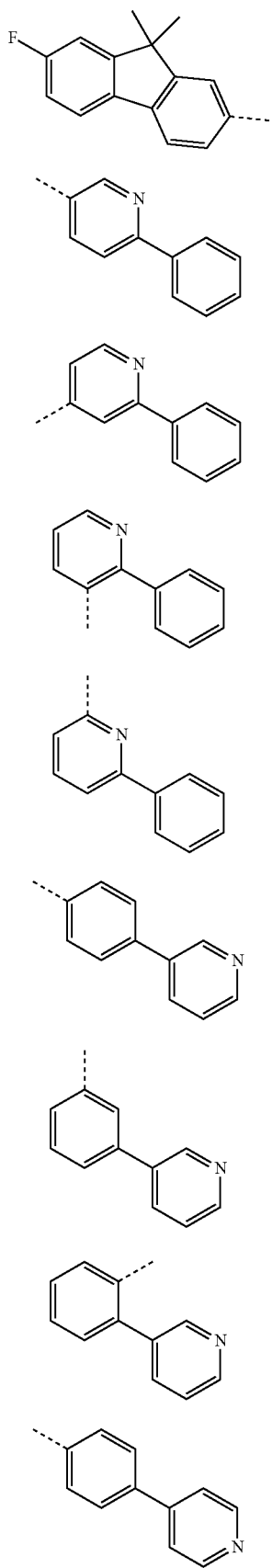

Ar-246 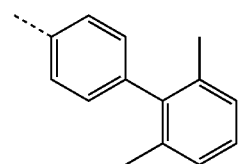
Ar-247 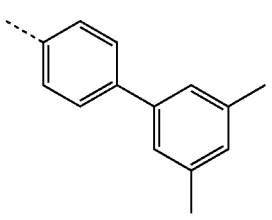
Ar-248 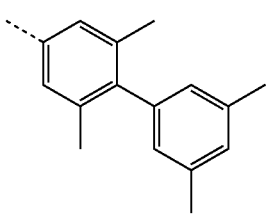
Ar-250 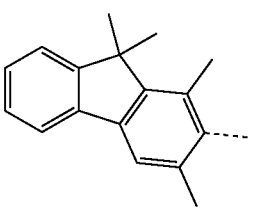
Ar-251 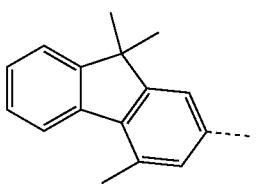
Ar-252 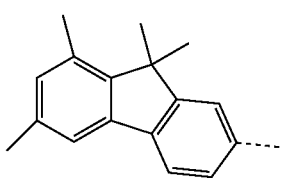
Ar-253 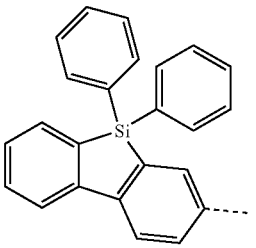
Ar-254
Ar-255
Ar-256
Ar-257
Ar-258
Ar-259
Ar-260

Ar-261
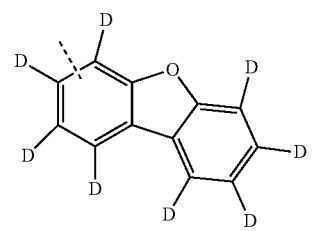
Ar-262
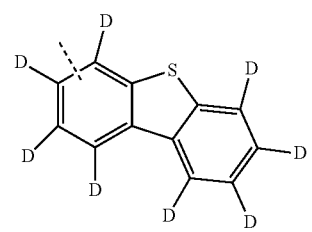
Ar-263
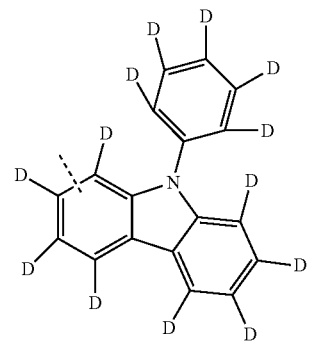
Ar-264
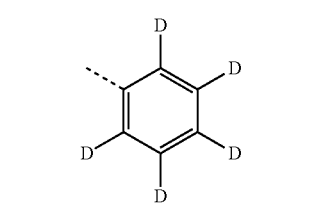
Ar-265
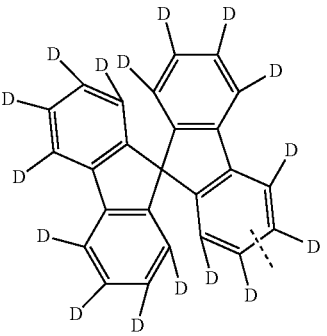
Ar-266
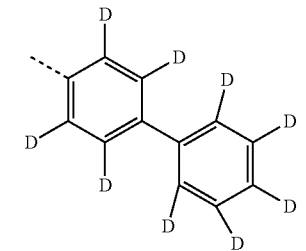
Ar-267
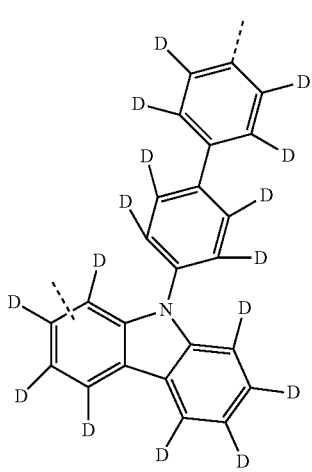
Ar-268
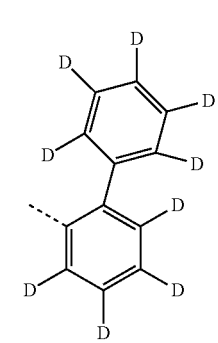
Ar-269
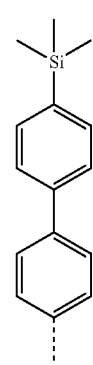
Ar-270
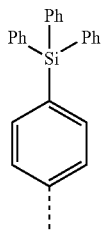

Ar-271

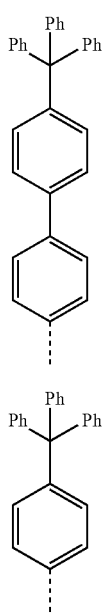

Ar-272 where the groups at the positions shown as unsubstituted are substituted by R4 radicals, where R4 in these positions is preferably H, and where the dotted bond is the bond to the amine nitrogen atom.

In a preferred embodiment, Ar2 and Ar3 in formula (I) are selected differently.

Ar4 is preferably phenyl which may be substituted by R2 radicals or 1-naphthyl which may be substituted by R2 radicals, more preferably phenyl which may be substituted by R2 radicals. Most preferably, Ar4 is unsubstituted phenyl or 1-naphthyl, most preferably unsubstituted phenyl.

R1 is preferably the same or different at each instance and is selected from H, D, F, CN, $Si(R5)_3$, $N(R5)_2$, straight-chain alkyl or alkoxy groups having 1 to 20 carbon atoms, branched or cyclic alkyl or alkoxy groups having 3 to 20 carbon atoms, aromatic ring systems having 6 to 40 aromatic ring atoms and heteroaromatic ring systems having 5 to 40 aromatic ring atoms; where the alkyl and alkoxy groups mentioned, the aromatic ring systems mentioned and the heteroaromatic ring systems mentioned are each substituted by R5 radicals; and where one or more $CH_2$ groups in the alkyl or alkoxy groups mentioned may be replaced by —C≡C—, —R5C=CR5-, $Si(R5)_2$, C=O, C=NR5, —NR5-, —O—, —S—, —C(=O)O— or —C(=O)NR5-. More preferably, R1 is the same or different at each instance and is selected from H, aromatic ring systems having 6 to 40 aromatic ring atoms and heteroaromatic ring systems having 5 to 40 aromatic ring atoms, where the aromatic ring systems and the heteroaromatic ring systems are each substituted by R5 radicals. Most preferably, R1 is H.

In a preferred embodiment, one or two and preferably one R1 radical is/are selected from aromatic ring systems which have 6 to 40 aromatic ring atoms and are substituted by R5 radicals, and heteroaromatic ring systems which have 5 to 40 aromatic ring atoms and are substituted by R5 radicals, and the other R1 radicals are H. Particularly preferred embodiments of aromatic and heteroaromatic ring systems as R1 radicals in this case are phenyl, biphenyl, terphenyl, fluorenyl, naphthyl, dibenzofuranyl, dibenzothiophenyl and N-phenylcarbazolyl, each substituted by R5 radicals, where these R5 radicals are preferably H. Preferably, the R1 radicals selected from aromatic or heteroaromatic ring systems in formula (I) are bonded to the fluorene in formula (I) in a position selected from positions 5 to 8, more preferably in position 5.

Preferably, R1 is not $N(R5)_2$. More preferably, R1 radicals including substituents do not contain an amino group.

R2 is preferably the same or different at each instance and is selected from aromatic ring systems which have 6 to 40 aromatic ring atoms and are substituted by R5 radicals, and heteroaromatic ring systems which have 5 to 40 aromatic ring atoms and are substituted by R5 radicals. More preferably, R2 is selected from aromatic ring systems which have 6 to 40 aromatic ring atoms and are substituted by R5 radicals; most preferably, R2 is selected from phenyl, fluorenyl, especially 9,9'-dimethylfluorenyl and 9,9'-diphenylfluorenyl, and naphthyl, where the groups mentioned are each substituted by R5 radicals, in which case R5 is preferably H.

R3 is preferably the same or different at each instance and is selected from H, D, F, CN, $Si(R5)_3$, $N(R5)_2$, straight-chain alkyl or alkoxy groups having 1 to 20 carbon atoms, branched or cyclic alkyl or alkoxy groups having 3 to 20 carbon atoms, aromatic ring systems having 6 to 40 aromatic ring atoms and heteroaromatic ring systems having 5 to 40 aromatic ring atoms; where the alkyl and alkoxy groups mentioned, the aromatic ring systems mentioned and the heteroaromatic ring systems mentioned are each substituted by R5 radicals; and where one or more $CH_2$ groups in the alkyl or alkoxy groups mentioned may be replaced by —C≡C—, —R5C=CR5-, $Si(R5)_2$, C=O, C=NR5, —NR5-, —O—, —S—, —C(=O)O— or —C(=O)NR5-. More preferably, R3 is the same or different at each instance and is selected from H, $N(R5)_2$, straight-chain alkyl groups having 1 to 20 carbon atoms, branched or cyclic alkyl groups having 3 to 20 carbon atoms, aromatic ring systems having 6 to 40 aromatic ring atoms and heteroaromatic ring systems having 5 to 40 aromatic ring atoms, where the alkyl groups, the aromatic ring systems and the heteroaromatic ring systems are each substituted by R5 radicals. Most preferably, R3 is H.

R4 is preferably the same or different at each instance and is selected from H, D, F, CN, $Si(R5)_3$, $N(R5)_2$, straight-chain alkyl or alkoxy groups having 1 to 20 carbon atoms, branched or cyclic alkyl or alkoxy groups having 3 to 20 carbon atoms, aromatic ring systems having 6 to 40 aromatic ring atoms and heteroaromatic ring systems having 5 to 40 aromatic ring atoms; where the alkyl and alkoxy groups mentioned, the aromatic ring systems mentioned and the heteroaromatic ring systems mentioned are each substituted by R5 radicals; and where one or more $CH_2$ groups in the alkyl or alkoxy groups mentioned may be replaced by —C≡C—, —R5C=CR5-, $Si(R5)_2$, C=O, C=NR5, —NR5-, —O—, —S—, —C(=O)O— or —C(=O)NR5-. More preferably, R4 is the same or different at each instance and is selected from H, $N(R5)_2$, straight-chain alkyl groups having 1 to 20 carbon atoms, branched or cyclic alkyl groups having 3 to 20 carbon atoms, aromatic ring systems having 6 to 40 aromatic ring atoms and heteroaromatic ring systems having 5 to 40 aromatic ring atoms, where the alkyl groups, the aromatic ring systems and the heteroaromatic ring systems are each substituted by R5 radicals. Most preferably, R4 is H.

R5 is preferably the same or different at each instance and is selected from H, D, F, CN, $Si(R6)_3$, $N(R6)_2$, straight-chain alkyl or alkoxy groups having 1 to 20 carbon atoms, branched or cyclic alkyl or alkoxy groups having 3 to 20 carbon atoms, aromatic ring systems having 6 to 40 aromatic ring atoms and heteroaromatic ring systems having 5 to 40 aromatic ring atoms; where the alkyl and alkoxy groups mentioned, the aromatic ring systems mentioned and the heteroaromatic ring systems mentioned are each substituted by R6 radicals; and where one or more $CH_2$ groups in the alkyl or alkoxy groups mentioned may be replaced by —C≡C—, —R6C=CR6-, $Si(R6)_2$, C=O, C=NR6, —NR6-, —O—, —S—, —C(=O)O— or —C(=O)NR6-. More preferably, R5 is the same or different at each instance and is selected from H, straight-chain alkyl groups having 1 to 20 carbon atoms, branched or cyclic alkyl groups having 3 to 20 carbon atoms, aromatic ring systems having 6 to 40 aromatic ring atoms and heteroaromatic ring systems having 5 to 40 aromatic ring atoms, where the alkyl groups, the aromatic ring systems and the heteroaromatic ring systems are each substituted by R6 radicals. Most preferably, R5 is H.

In a preferred embodiment, i=0. In a preferred embodiment, n=0. More preferably, i and n are each 0.

It is preferable that the -[Ar1]$_k$-N(Ar2)(Ar3) group is bonded to the fluorenyl group in formula (I) in the 1 position, in the 2 position or in the 4 position. It is more preferably bonded in the 2 position or in the 4 position, most preferably in the 4 position.

Preferred embodiments of the formula (I) conform to the following formulae:

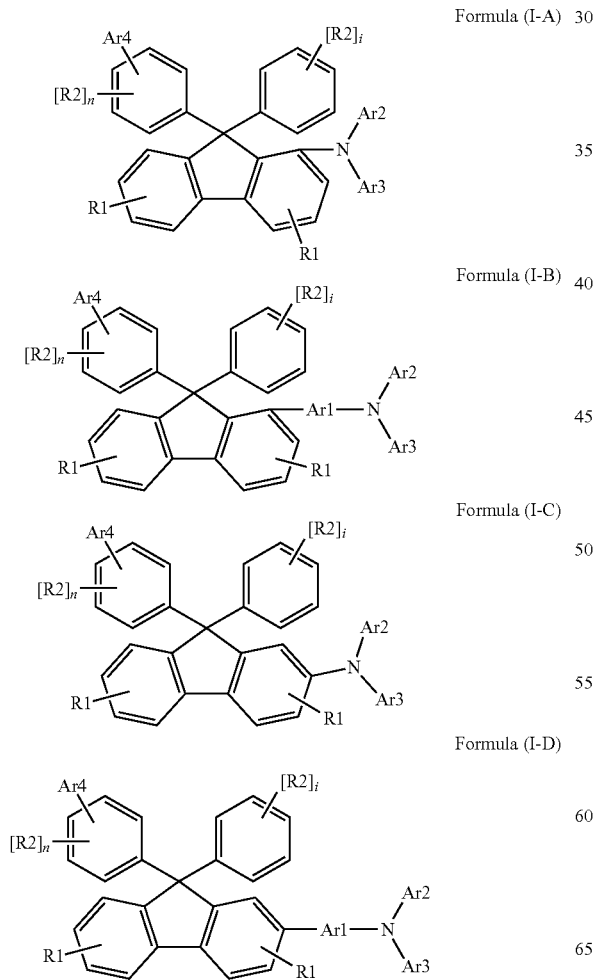

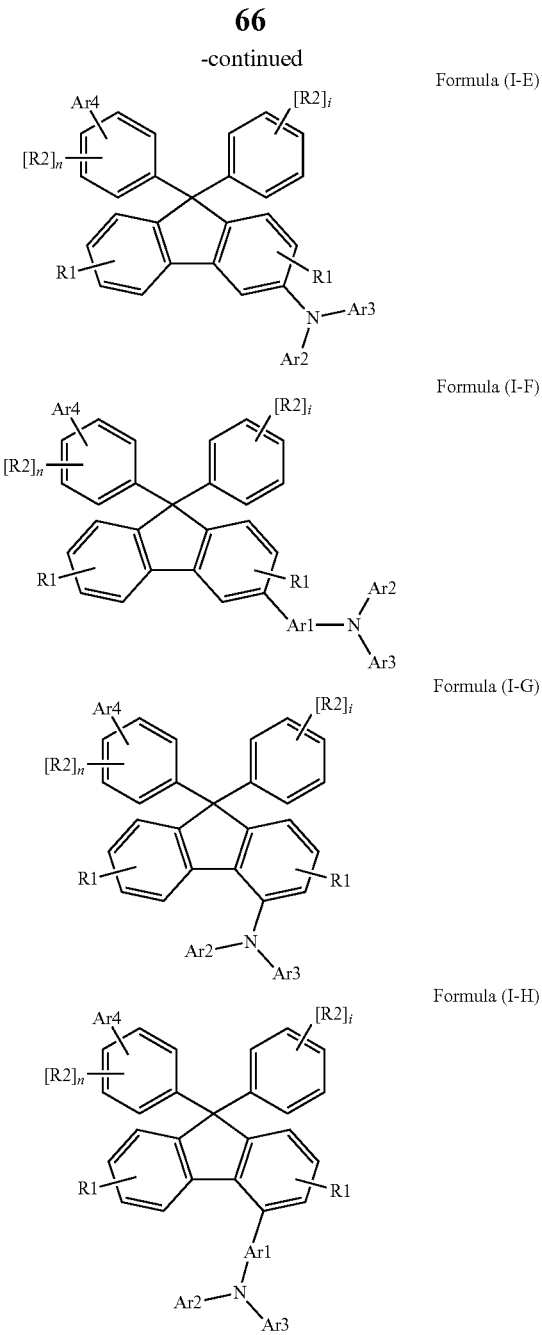

where the symbols and indices that occur are as defined above, and where the bonded R1 radical means that all positions shown as unsubstituted on the benzene ring in question are substituted by R1 radicals. Especially preferably, in the abovementioned formulae, i=0 and n=0. It is further preferable when R2 is selected from aromatic ring systems which have 6 to 40 aromatic ring atoms and are substituted by R5 radicals. It is further preferable again when R1 is H. It is further preferable again when Ar4 is phenyl or 1-naphthyl, preferably phenyl, each of which may be substituted by R2 radicals, and are preferably unsubstituted.

Among the abovementioned formulae (I-A) to (I-H), preference is given to formulae (I-A) to (I-D) and (I-G) and (I-H), even greater preference to formulae (I-C), (I-D), (I-G) and (I-H). Most preferred are formulae (I-C) and (I-D).

Preferred embodiments of the formula (I) conform to the following formulae:

Formula (I-1)

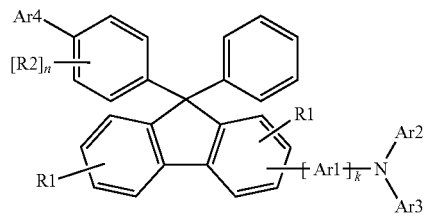

Formula (I-2)

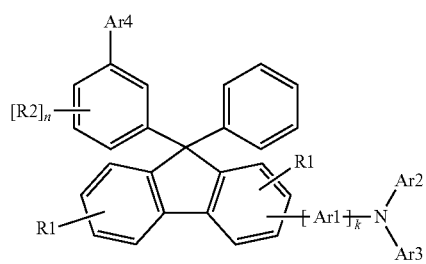

Formula (I-3)

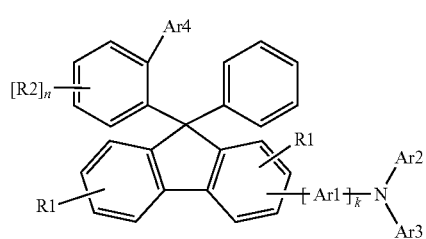

where the symbols and indices that occur are as defined above, and where the bonded R1 radical means that all positions shown as unsubstituted on the benzene ring in question are substituted by R1 radicals. Especially preferably, in the abovementioned formulae, n=0. It is further preferable when R2 is selected from aromatic ring systems which have 6 to 40 aromatic ring atoms and are substituted by R5 radicals. It is further preferable that R1 is H. It is further preferable when Ar4 is phenyl or 1-naphthyl, preferably phenyl, each of which may be substituted by R2 radicals, and are preferably unsubstituted.

Among the abovementioned formulae (I-1) to (I-3), preference is given to formulae (I-1) and (I-2).

Preferred embodiments of the formula (I) conform to the following formulae:

Formula (I-A-1)

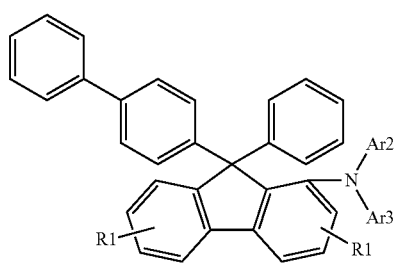

Formula (I-A-2)

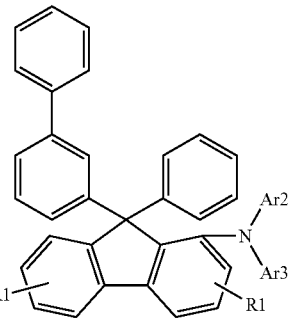

Formula (I-A-3)

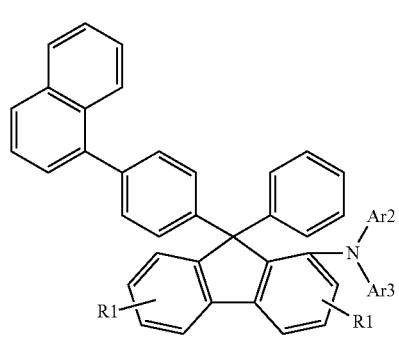

Formula (I-A-4)

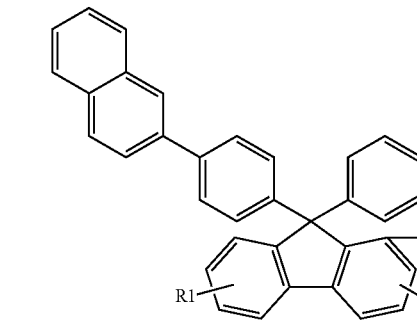

Formula (I-B-1)

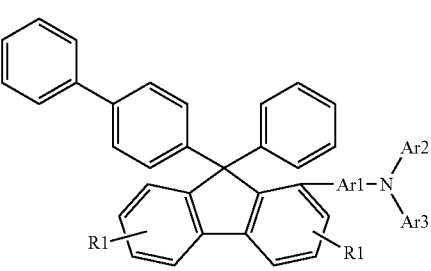

Formula (I-B-2)

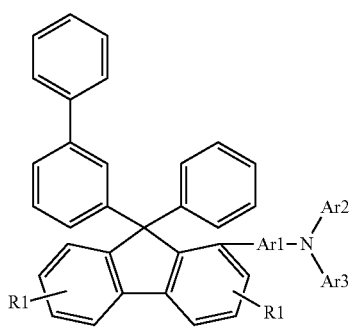

Formula (I-B-3)
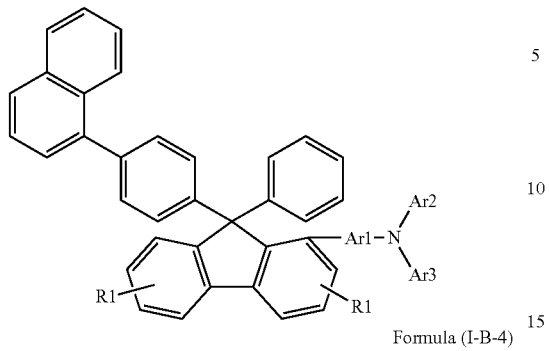
Formula (I-B-4)
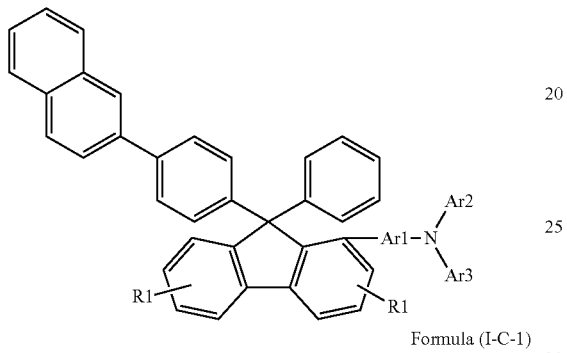
Formula (I-C-1)
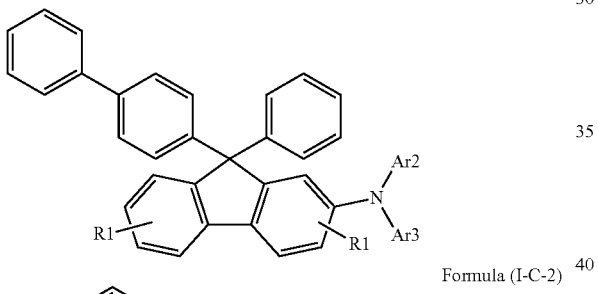
Formula (I-C-2)
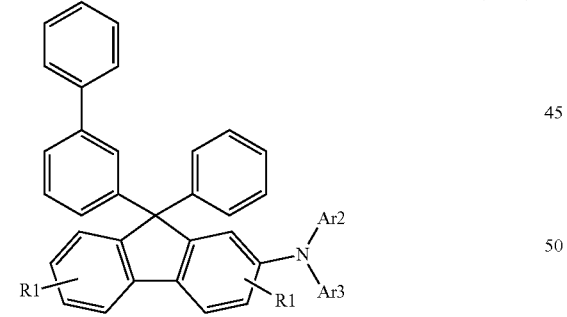
Formula (I-C-3)
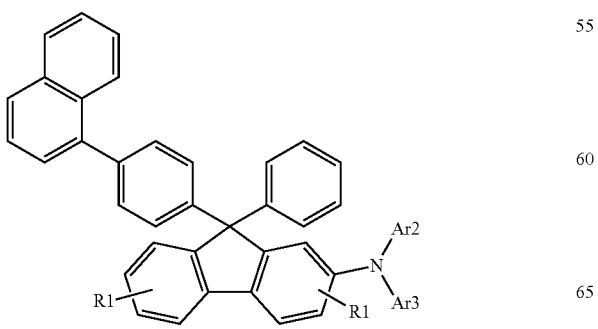
Formula (I-C-4)
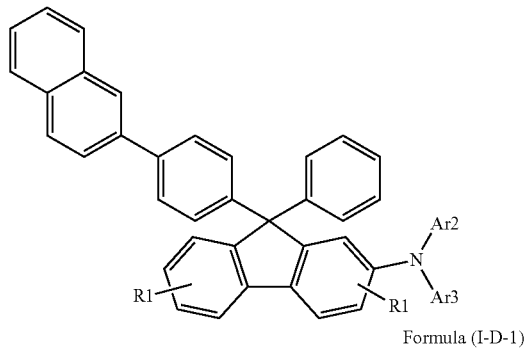
Formula (I-D-1)
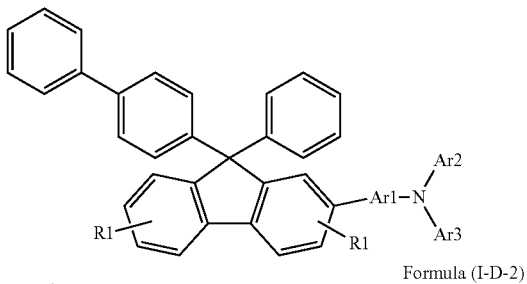
Formula (I-D-2)
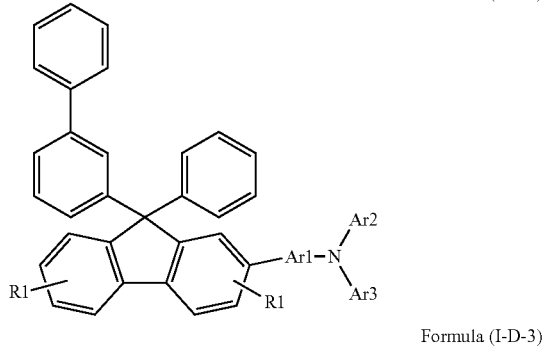
Formula (I-D-3)
Formula (I-D-4)

Formula (I-E-1)
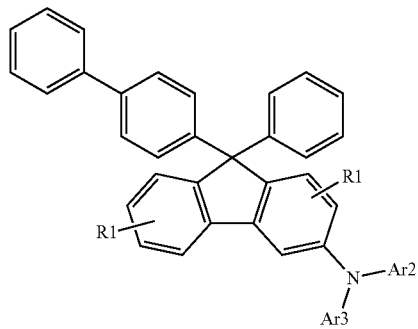
Formula (I-F-1)
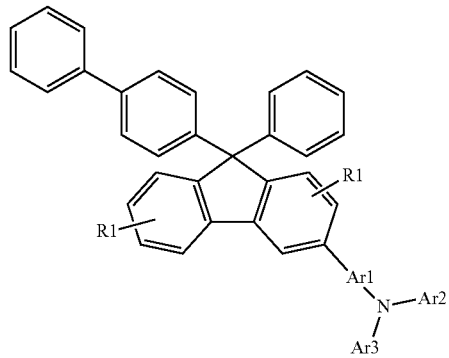
Formula (I-E-2)
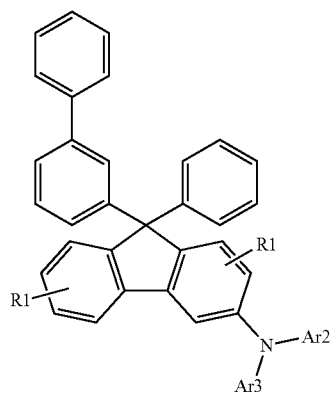
Formula (I-F-2)
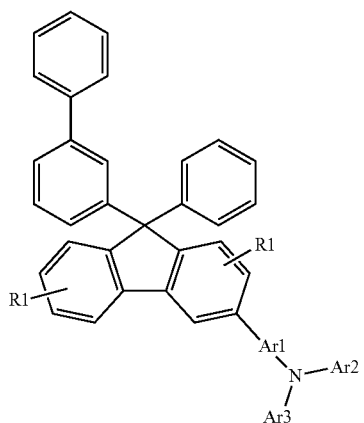
Formula (I-E-3)
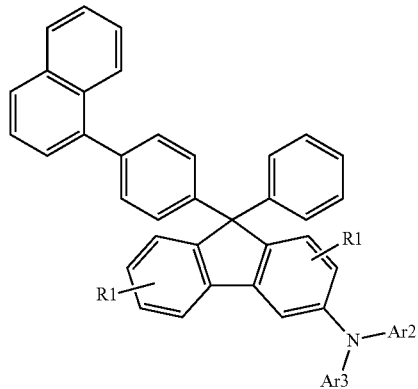
Formula (I-E-4)
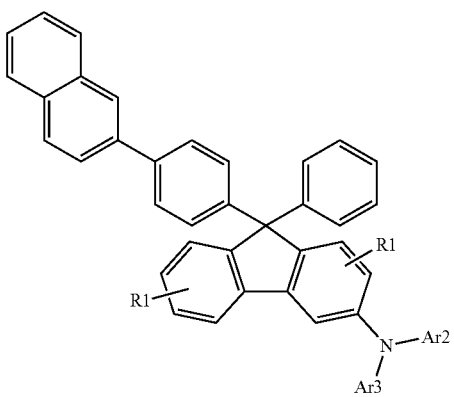
Formula (I-F-3)
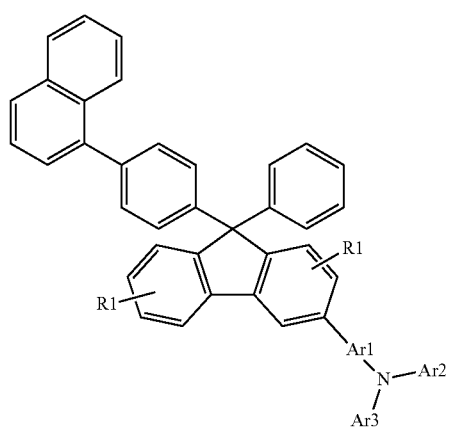

Formula (I-F-4)
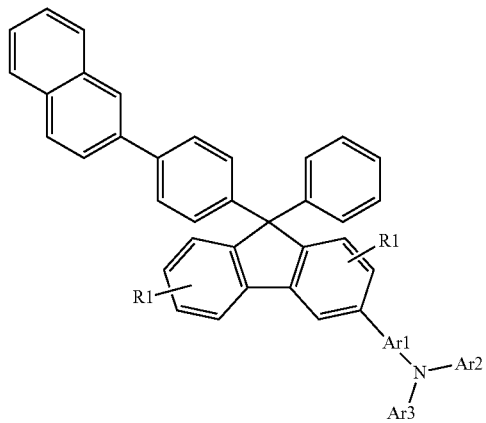
Formula (I-G-1)
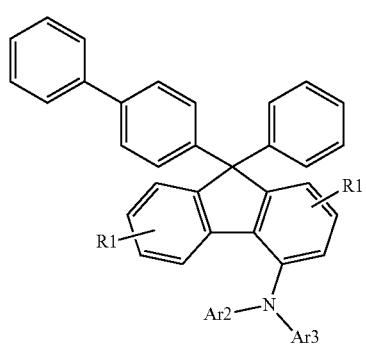
Formula (I-G-2)
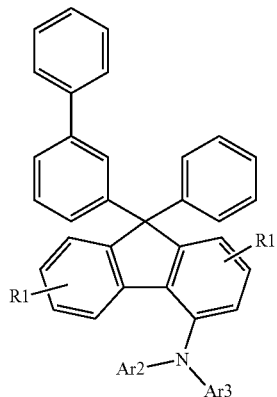
Formula (I-G-3)
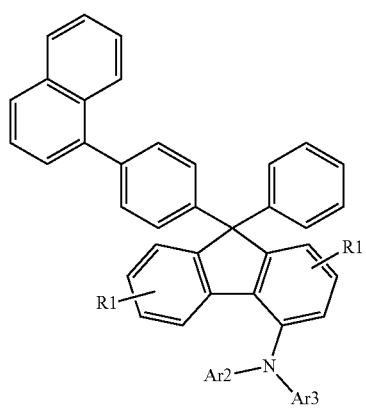
Formula (I-G-4)
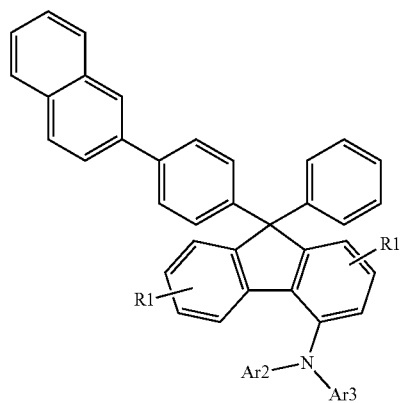
Formula (I-H-1)
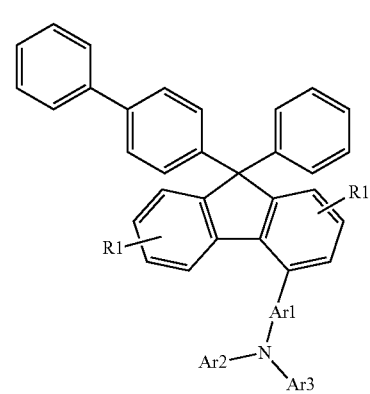
Formula (I-H-2)
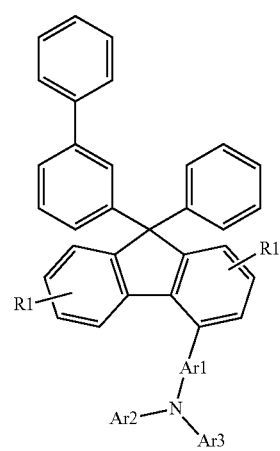

Formula (I-H-3)

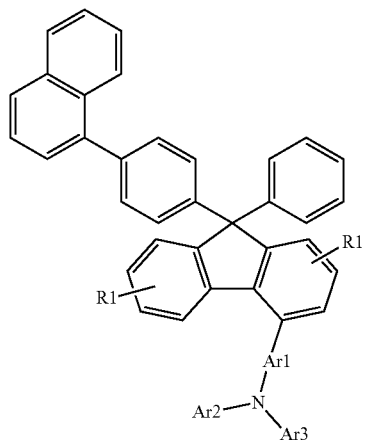

Formula (I-H-4)

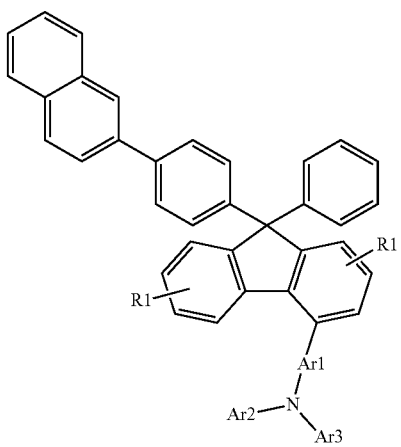

where the symbols and indices that occur are as defined above, and where the bonded R1 radical means that all positions shown as unsubstituted on the benzene ring in question are substituted by R1 radicals. Preferably, R1 is H. It is especially preferable that Ar1 is selected from divalent groups derived from benzene, biphenyl, terphenyl, naphthalene, fluorene, indenofluorene, indenocarbazole, spirobifluorene, dibenzofuran, dibenzothiophene, and carbazole, each of which may be substituted by one or more R3 radicals. It is further preferable that Ar2 and Ar3 are the same or different at each instance and are selected from groups of the formulae (Ar-1) to (Ar-256) as defined above.

Among the abovementioned formulae, particular preference is given to the formulae (I-A-1), (I-A-2), (I-B-1), (I-B-2), (I-C-1), (I-C-2), (I-D-1), (I-D-2), (I-E-1), (I-E-2), (I-F-1), (I-F-2), (I-G-1), (I-G-2), (I-H-1) and (I-H-2).

Preferred embodiments of compounds of formula (I) are shown below:

1

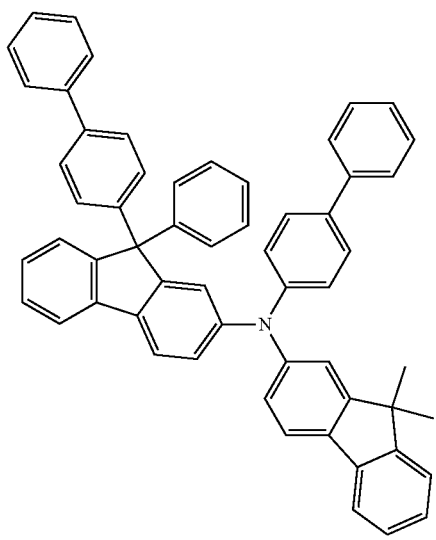

2

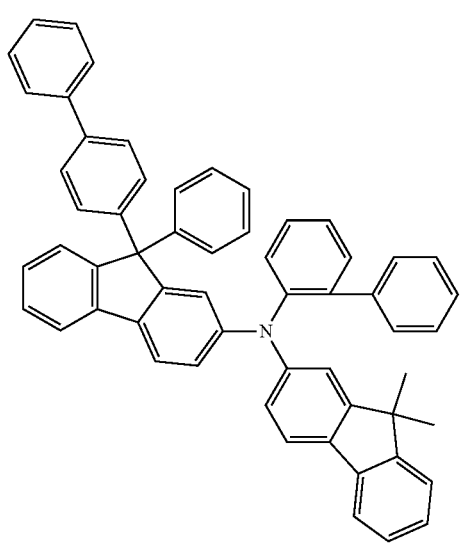

3

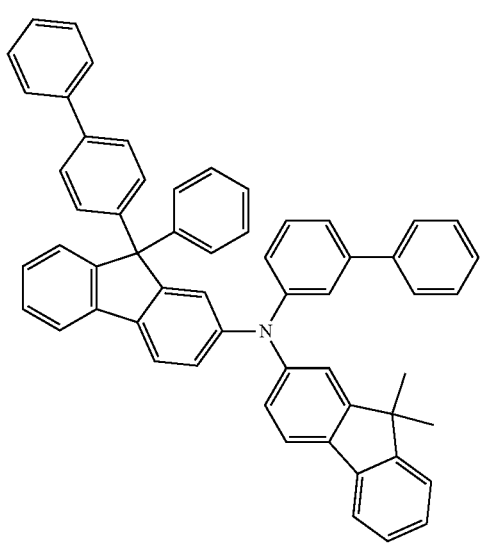

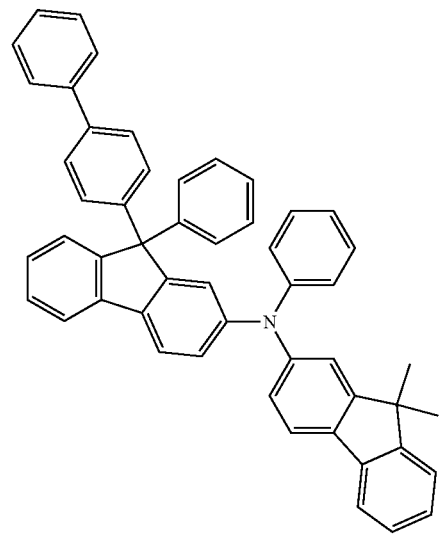
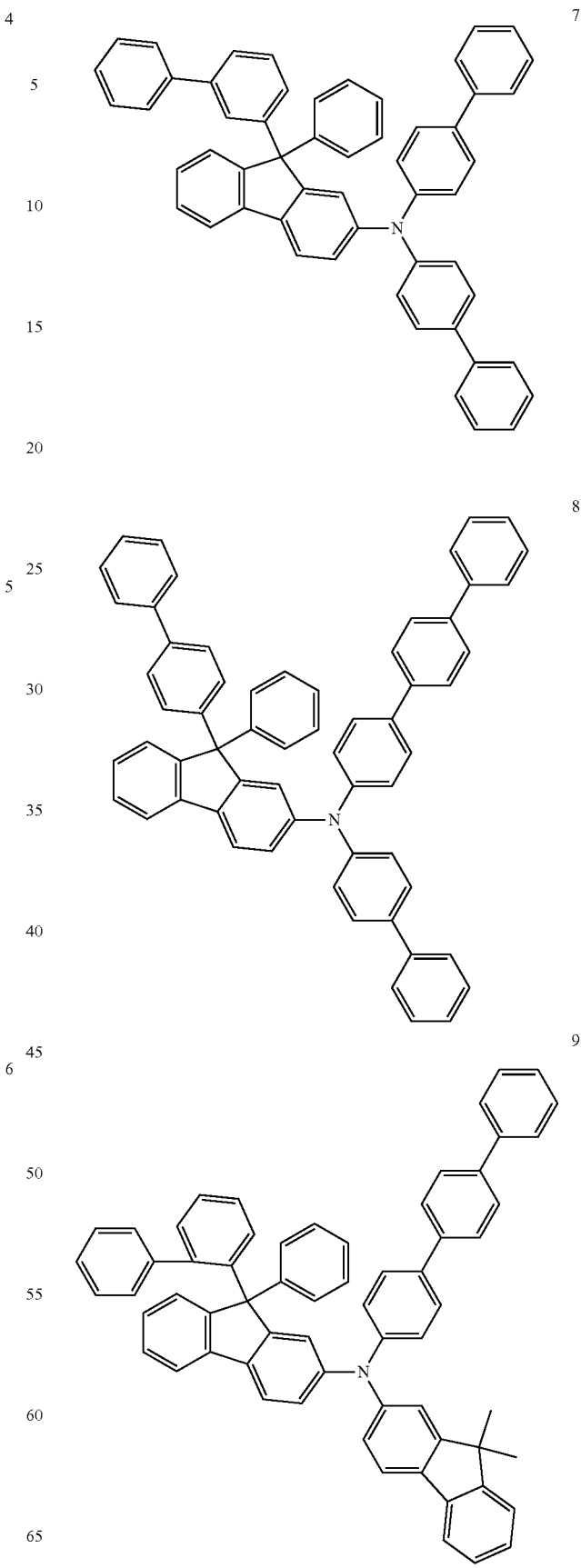

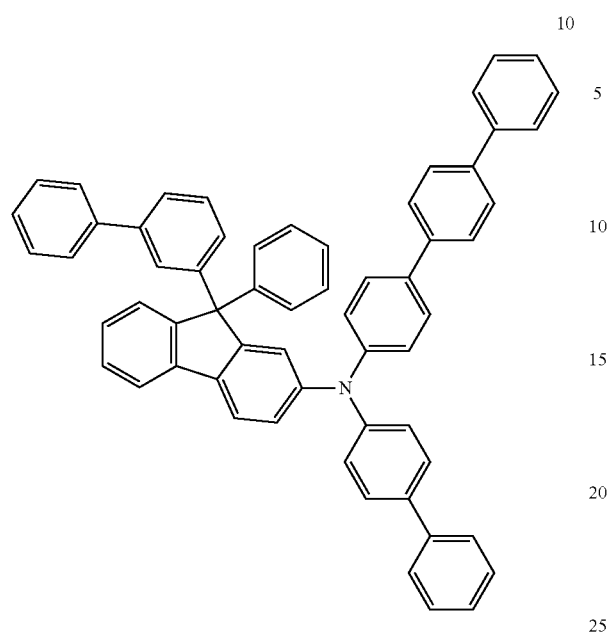
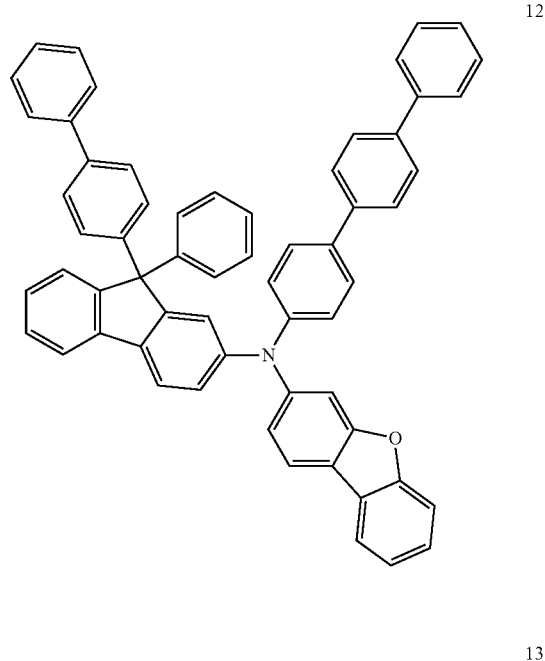
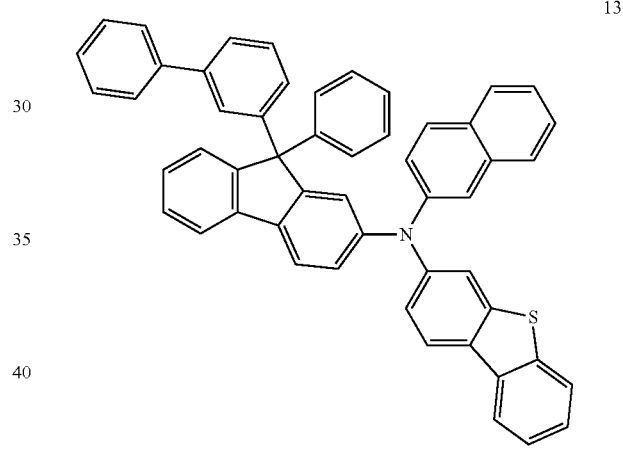
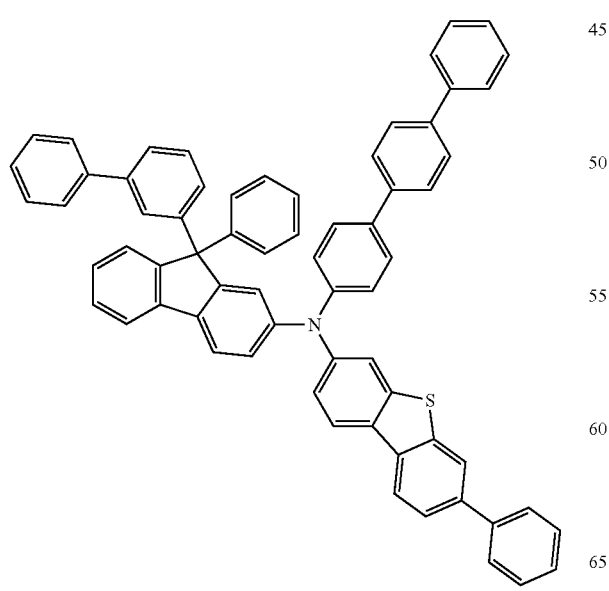
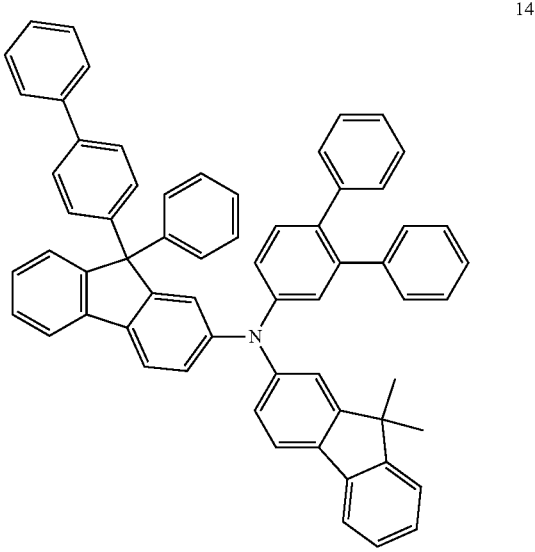

15
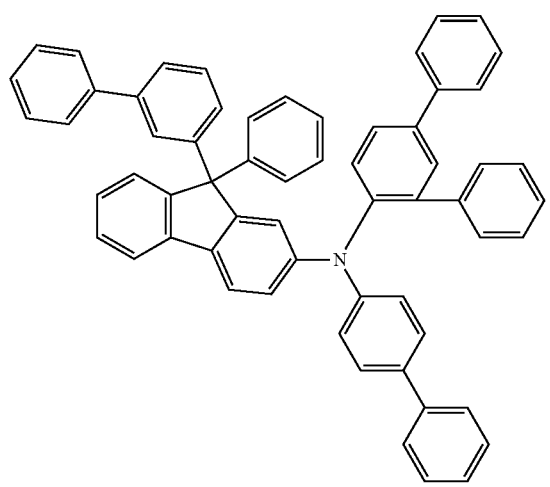
16
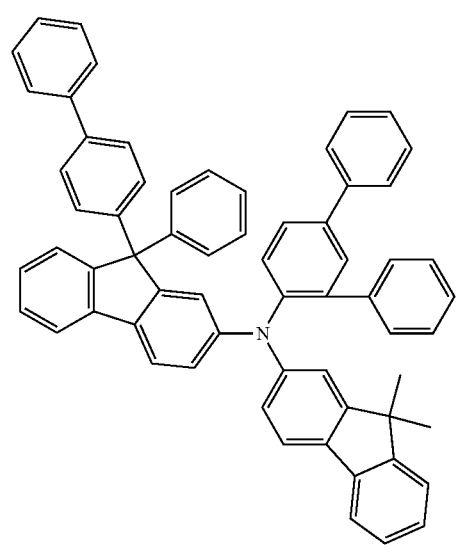
17
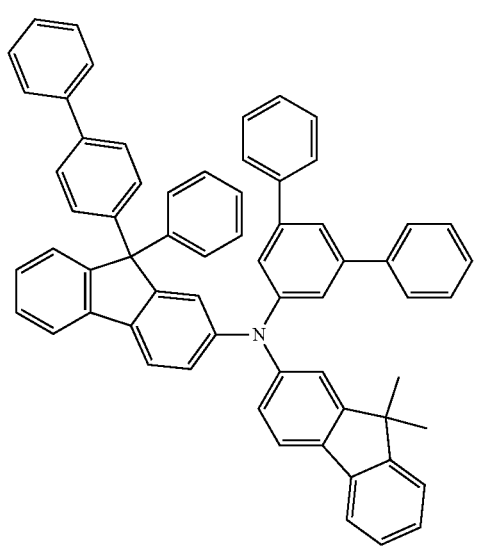
18
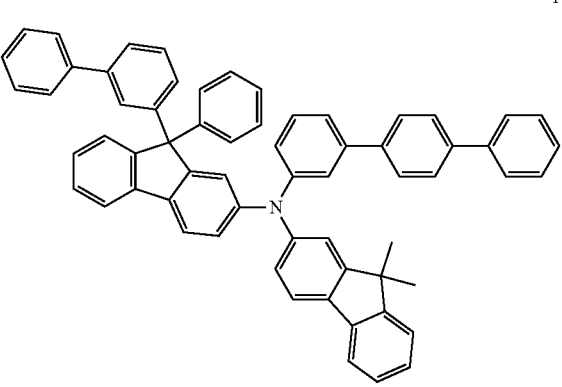
19
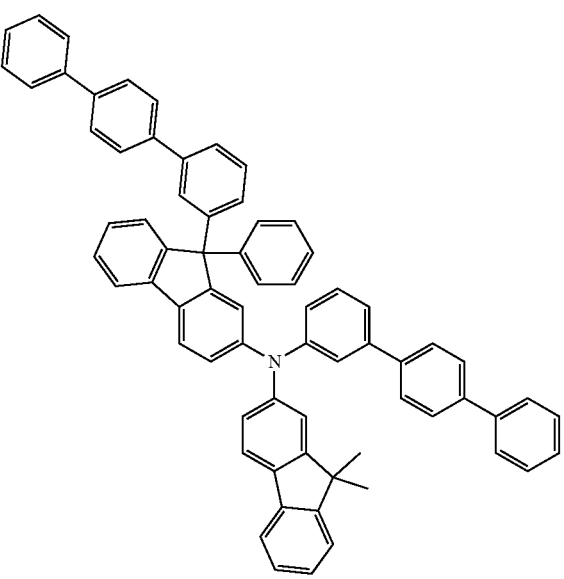
20

21
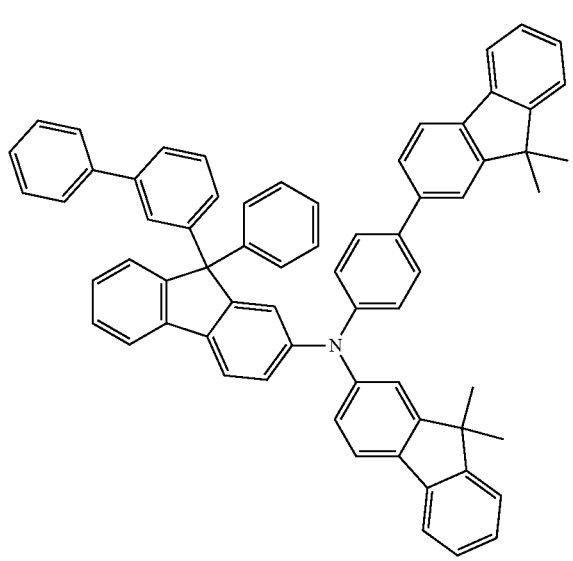
22
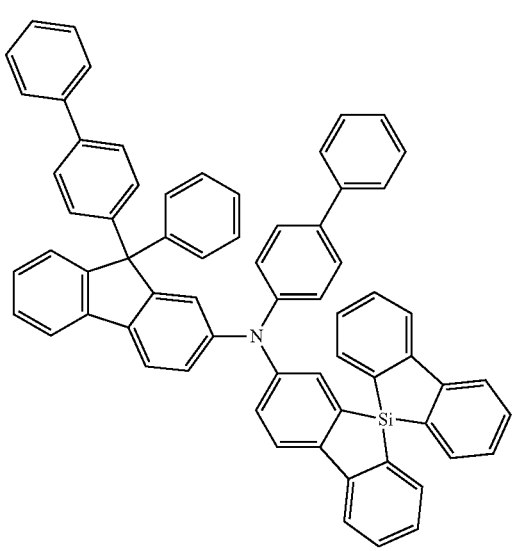
23
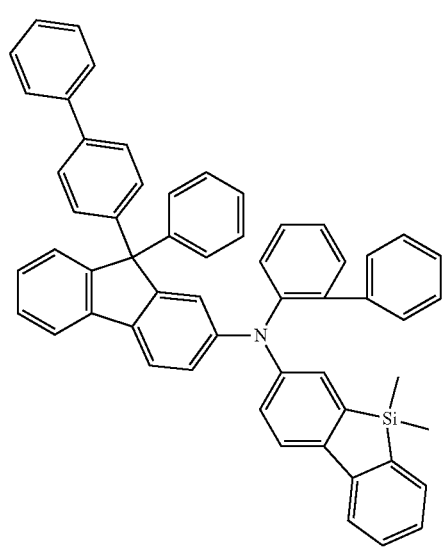
24
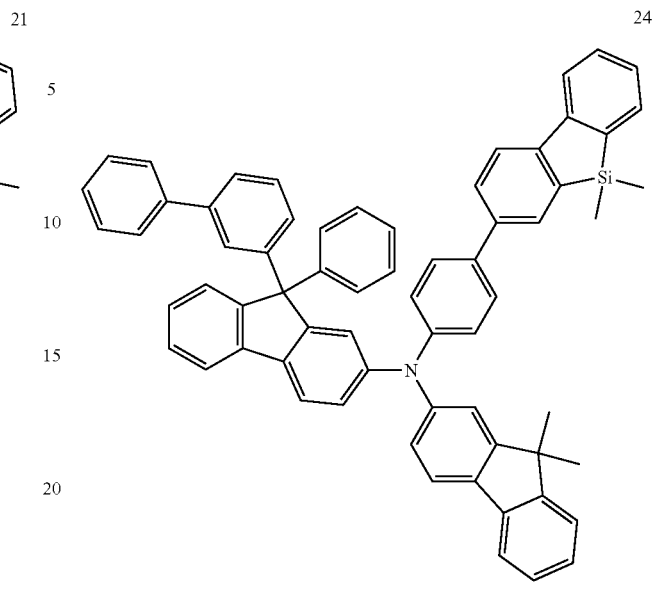
25
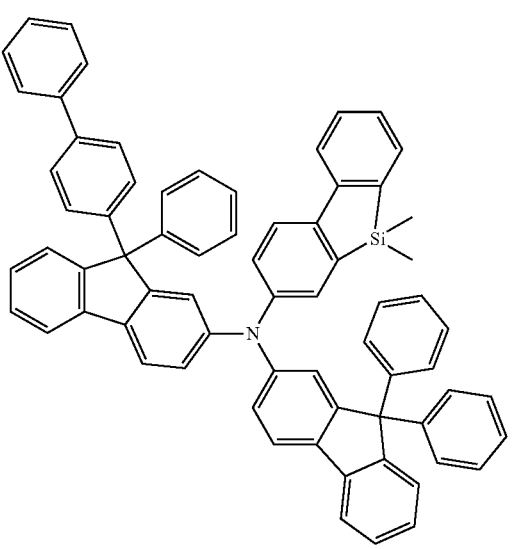
26
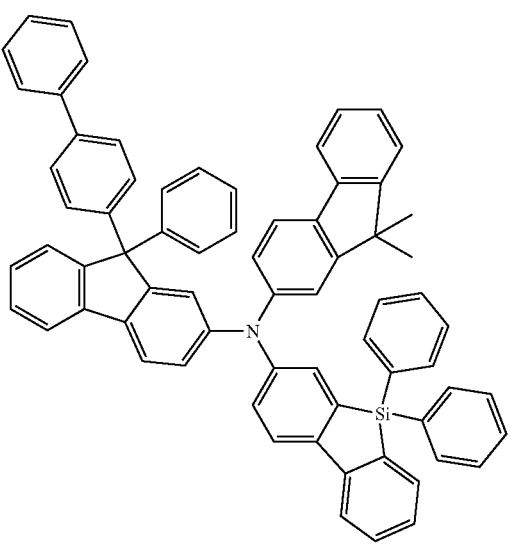

27
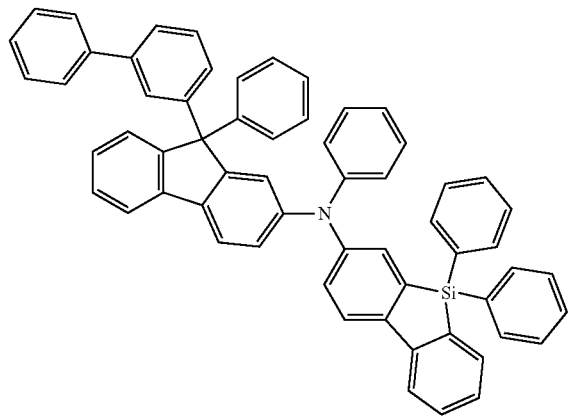
28
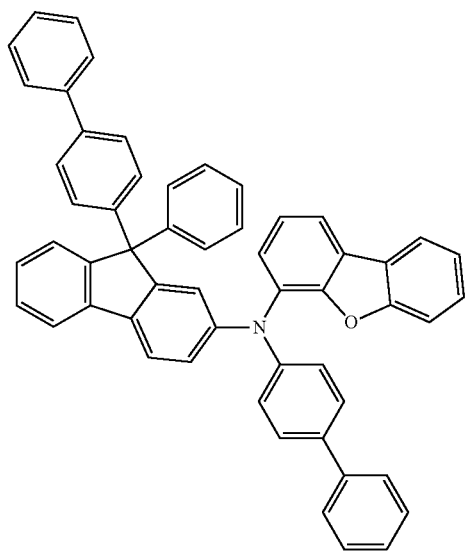
29
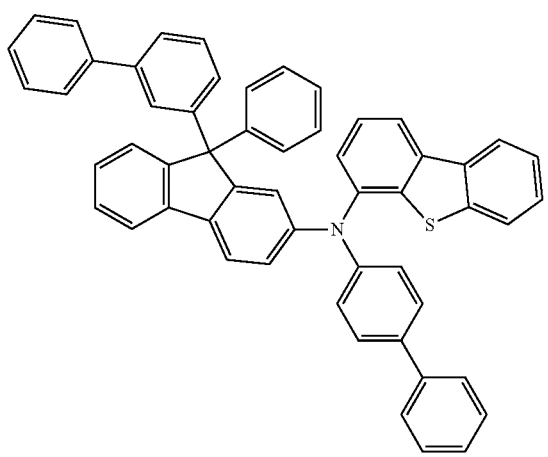
30
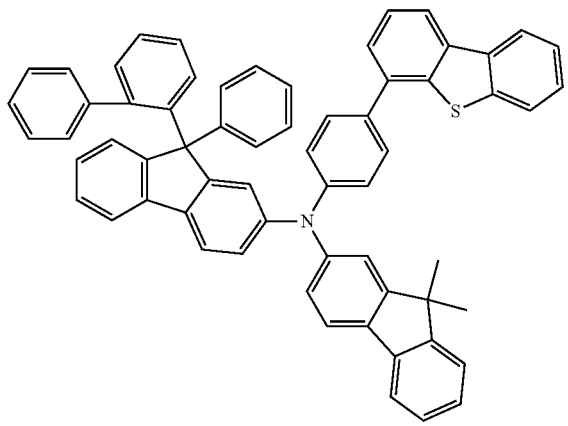
31
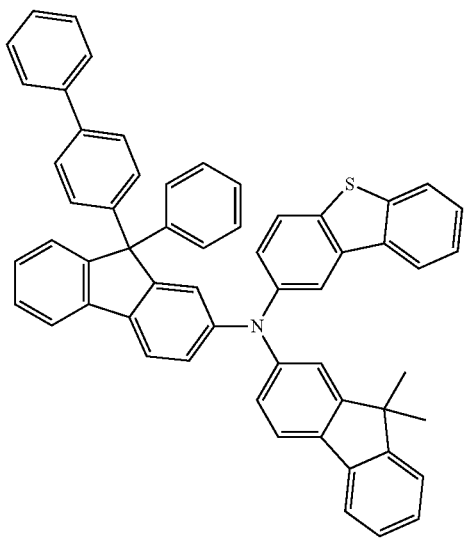
32
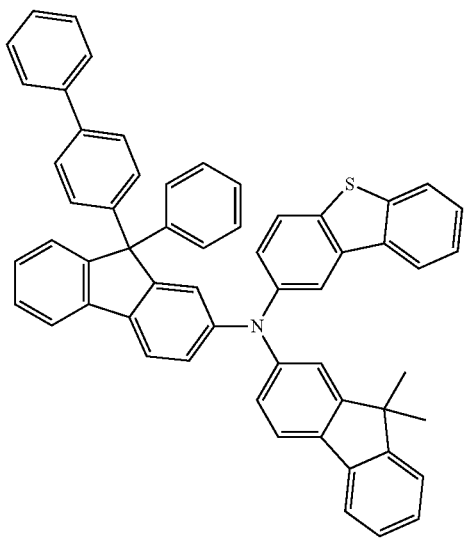

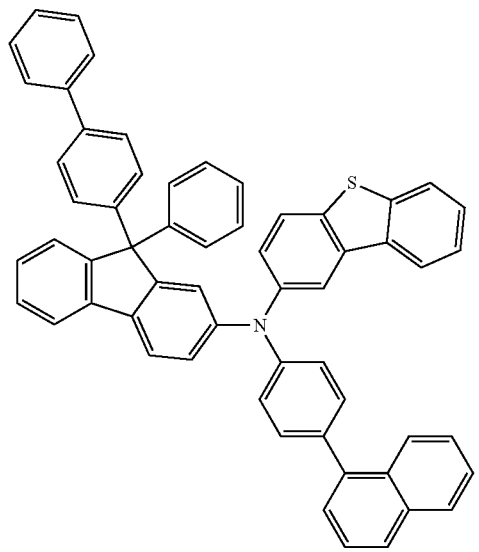
33
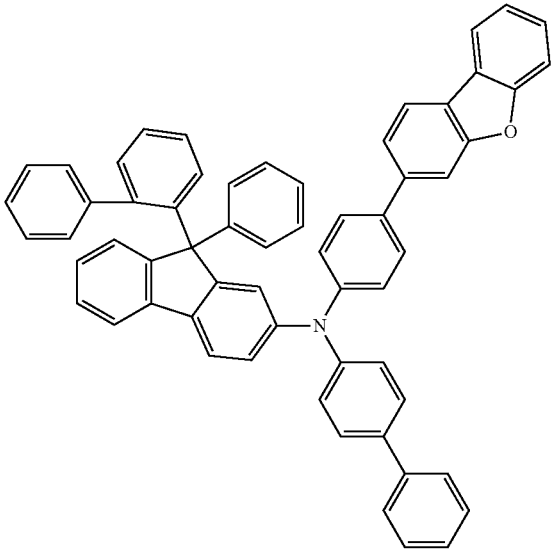
36
34
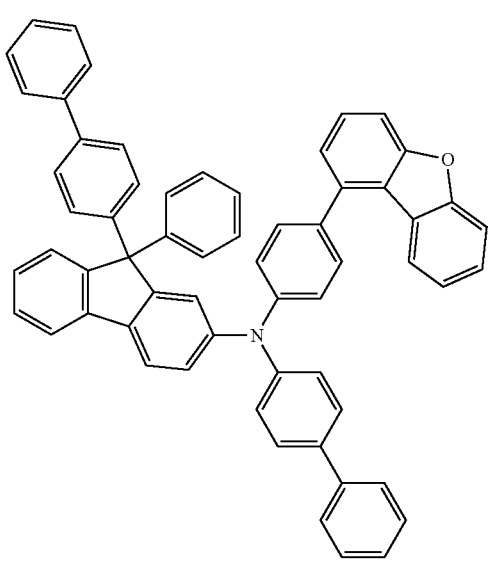
37
35
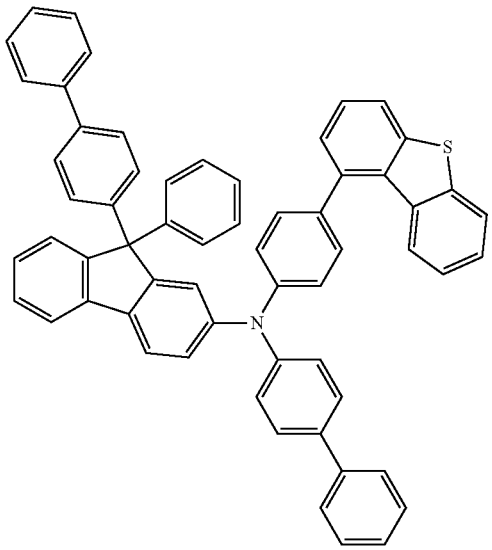
38

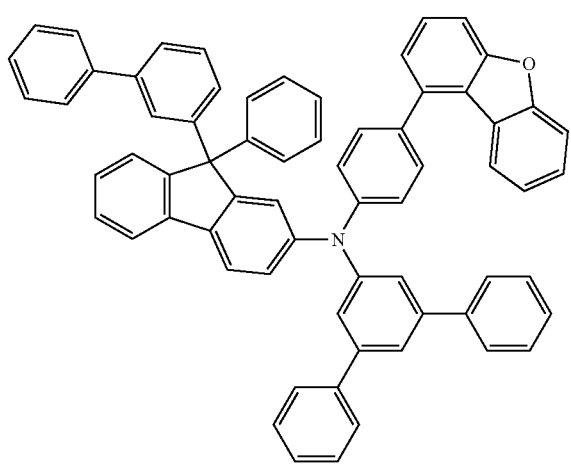
39
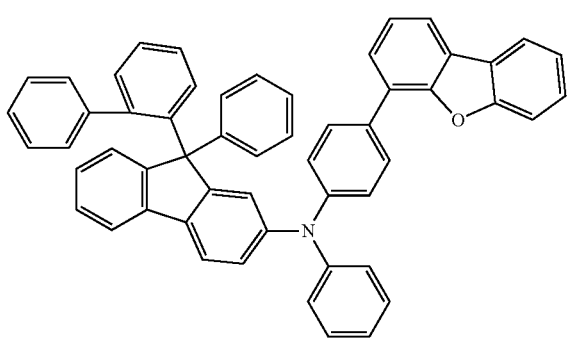
42
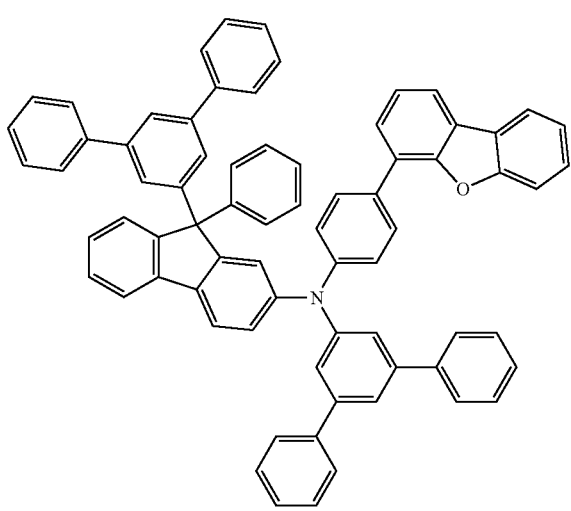
40
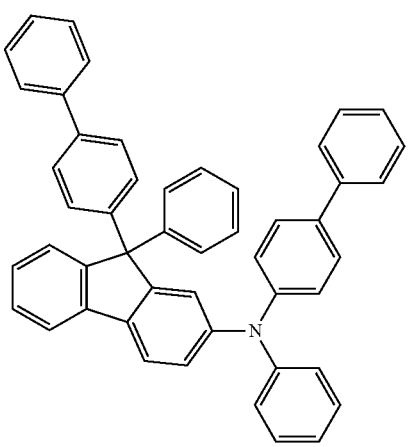
43
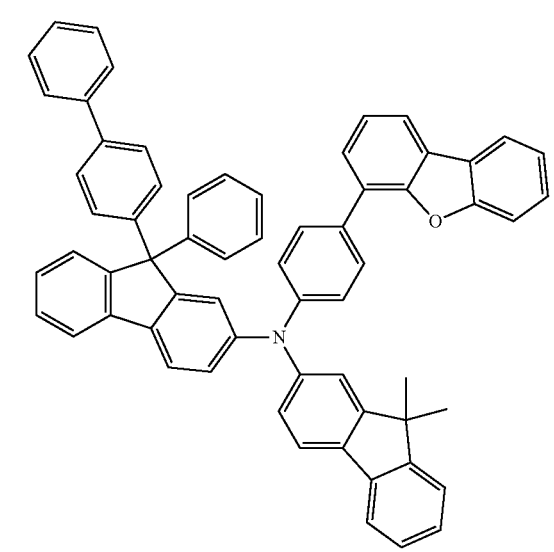
41
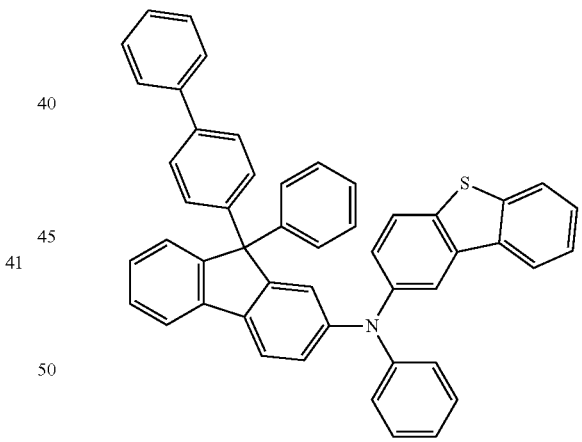
44
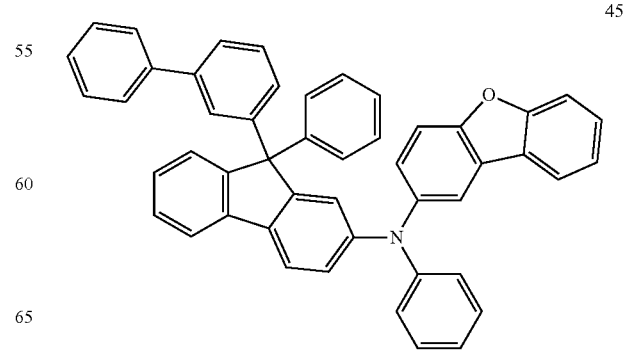
45

46
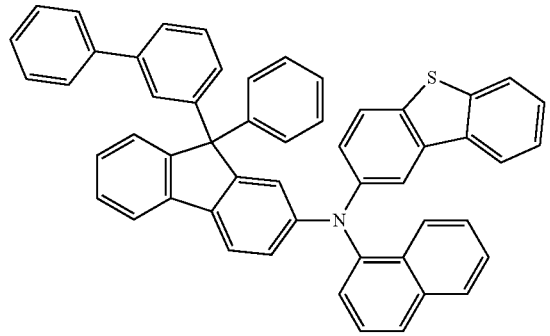
47
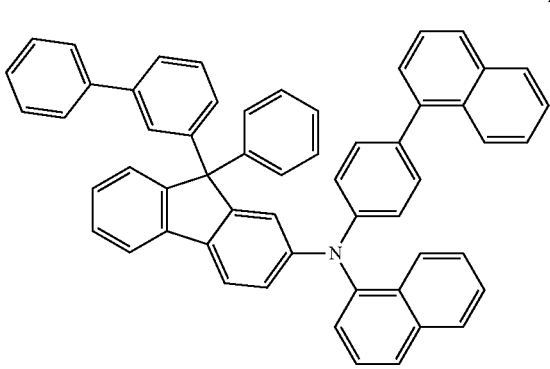
48
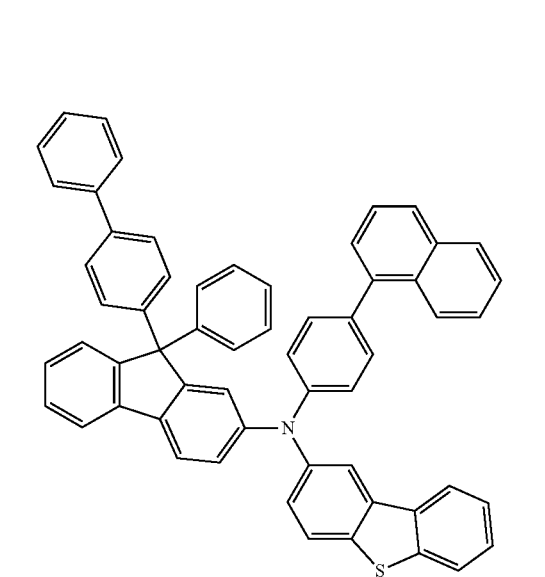
49
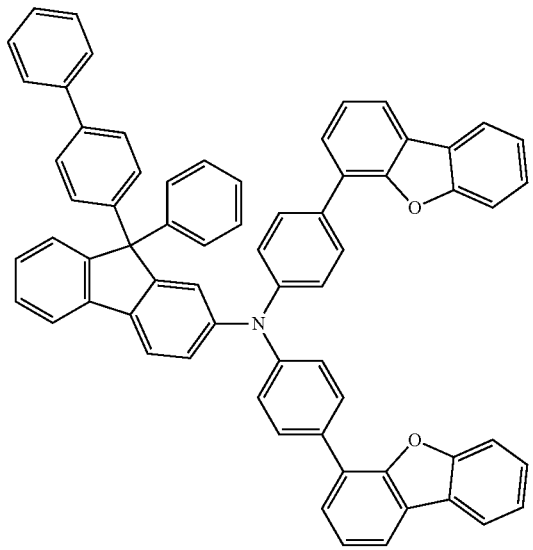
50
51
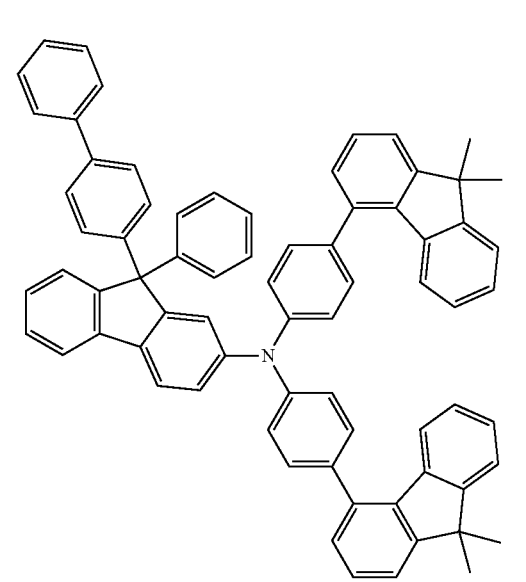

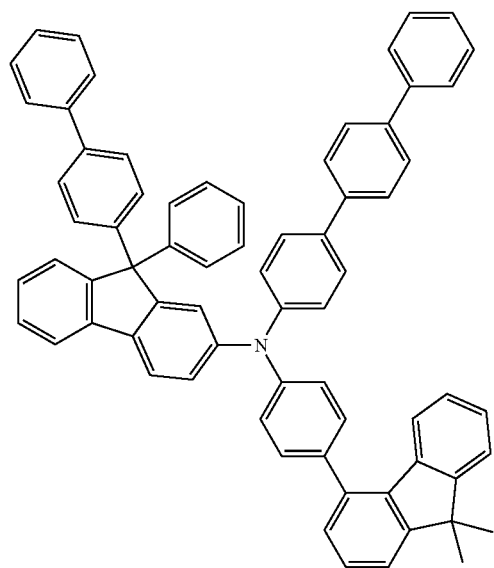
52
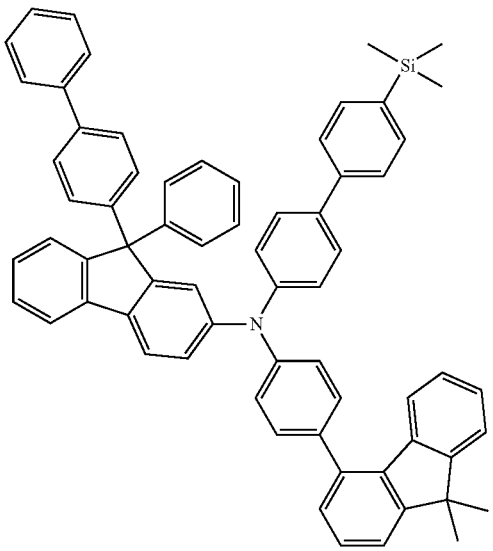
54
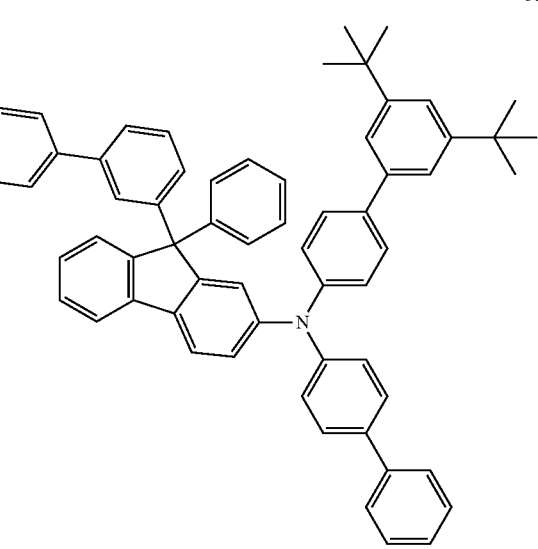
55
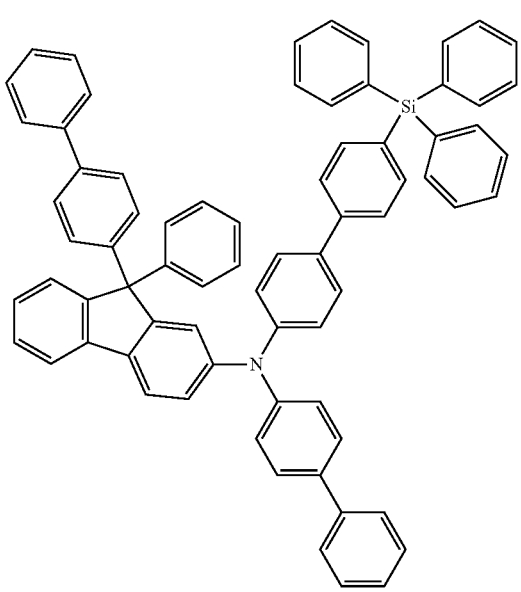
53
56

57
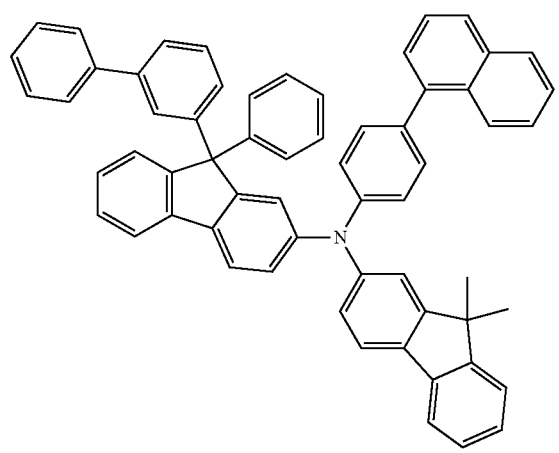
58
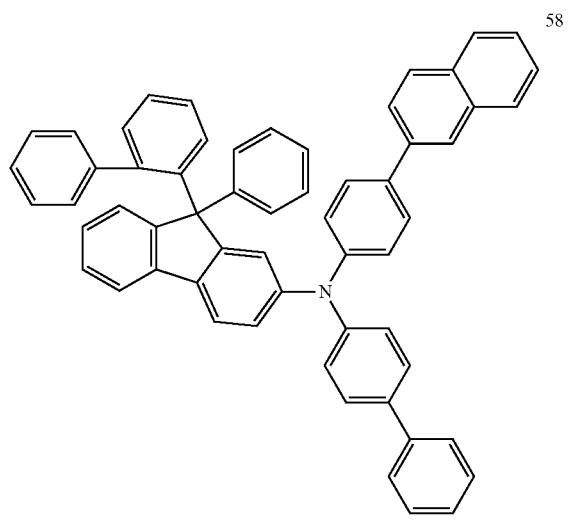
59
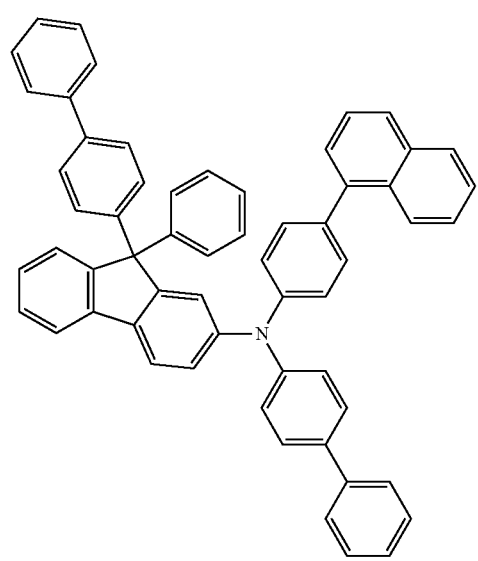
60
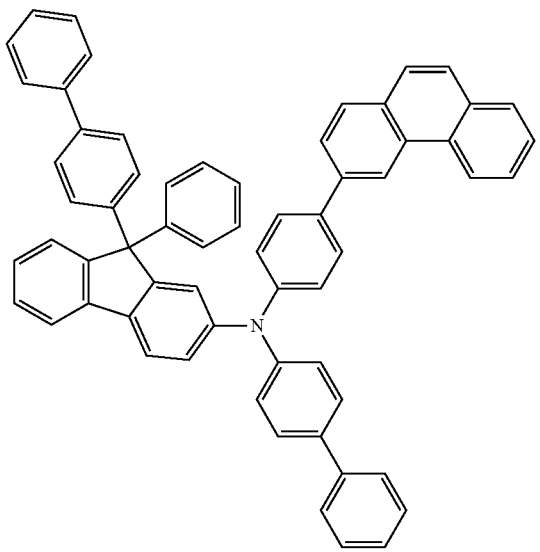
61
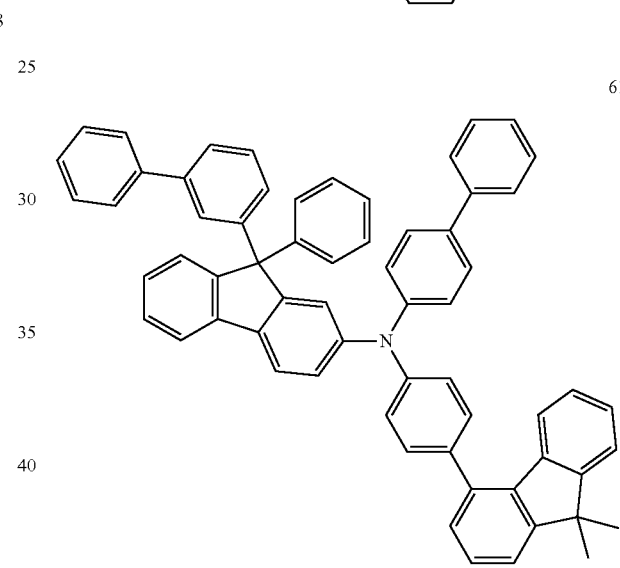
62
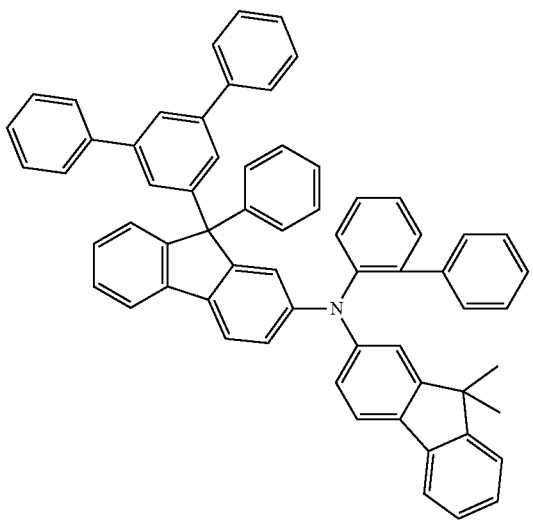

-continued
63
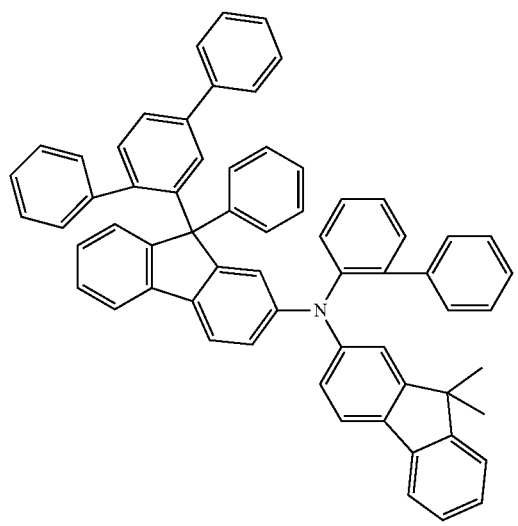
64
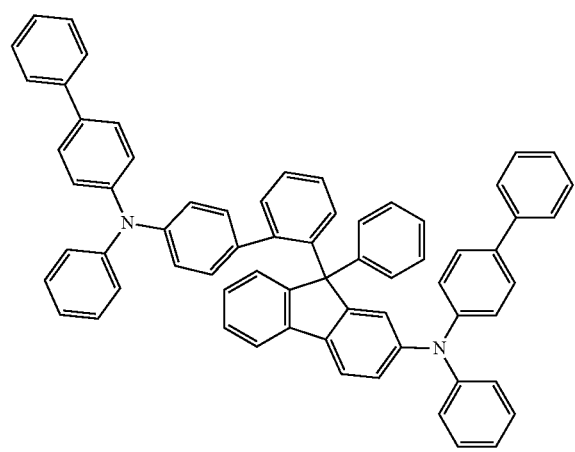
65
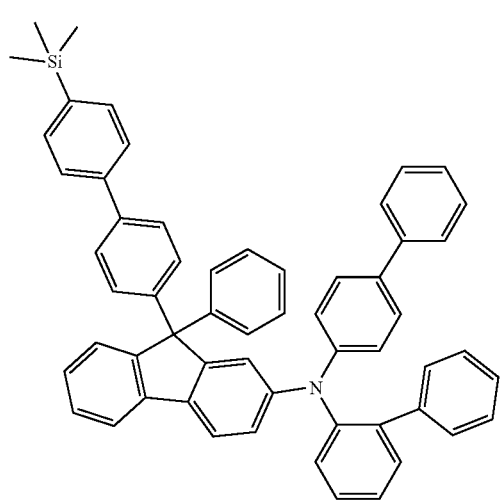
-continued
66
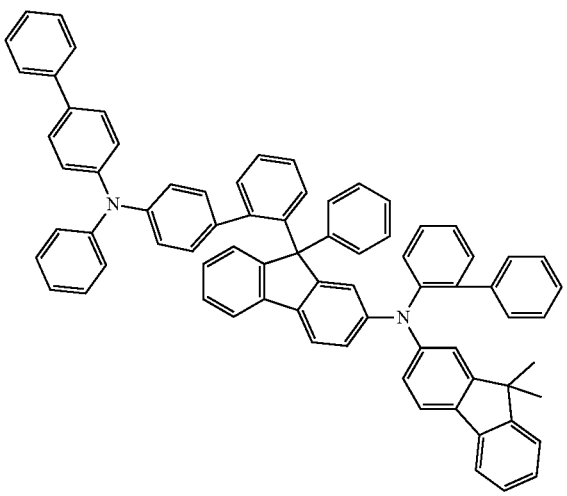
67
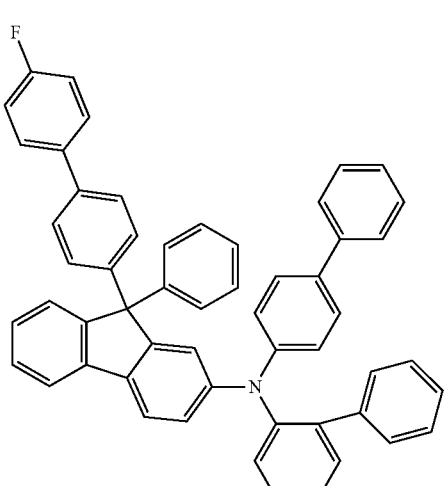
68
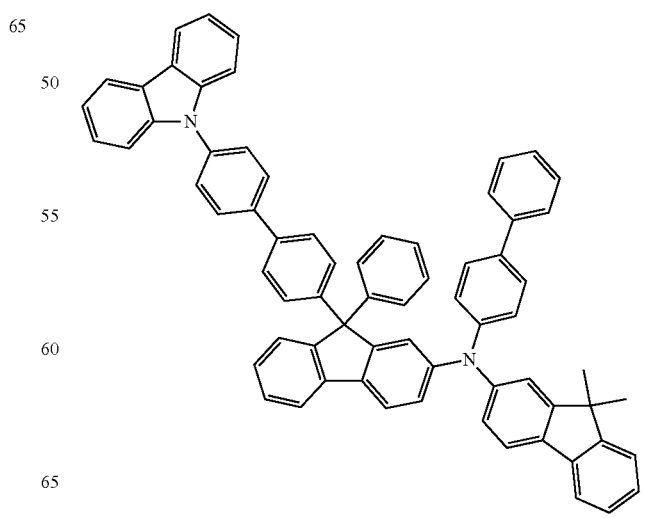

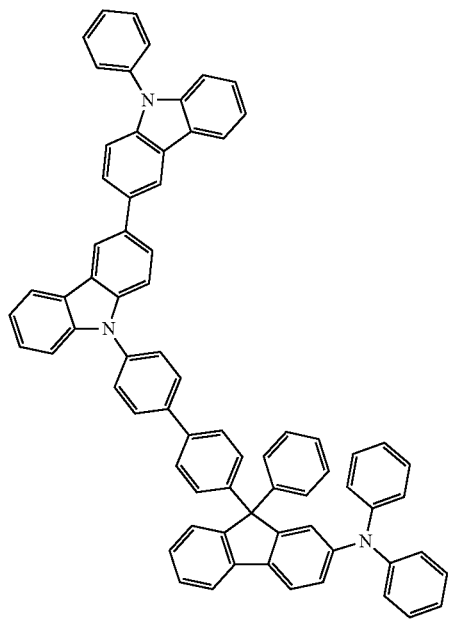
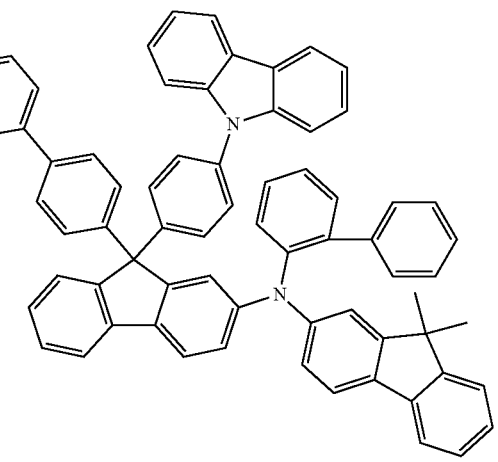
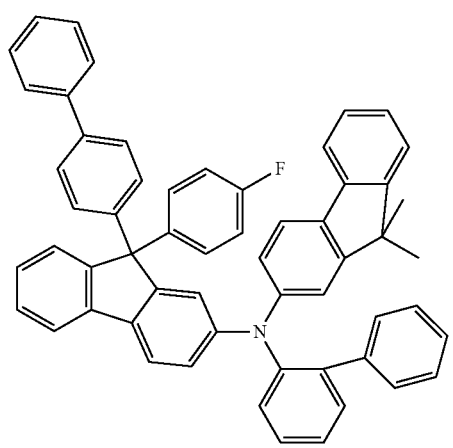
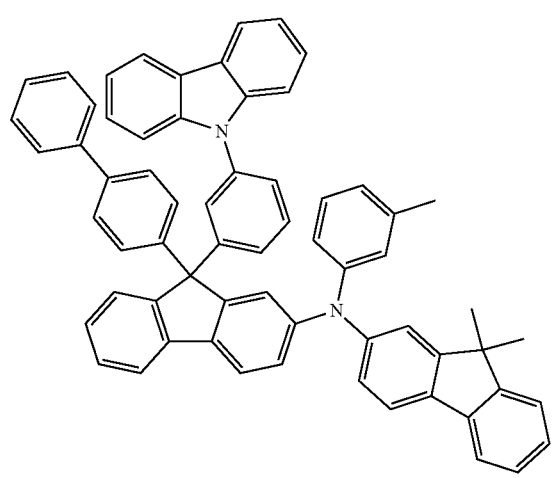
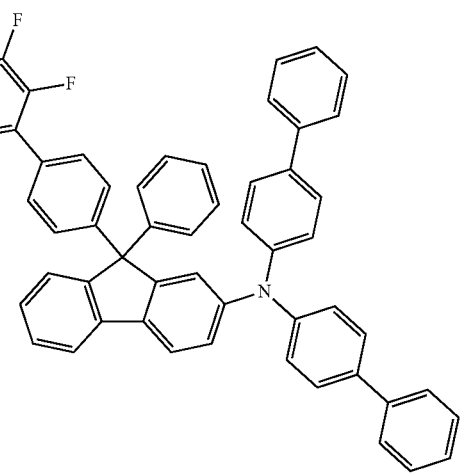

75
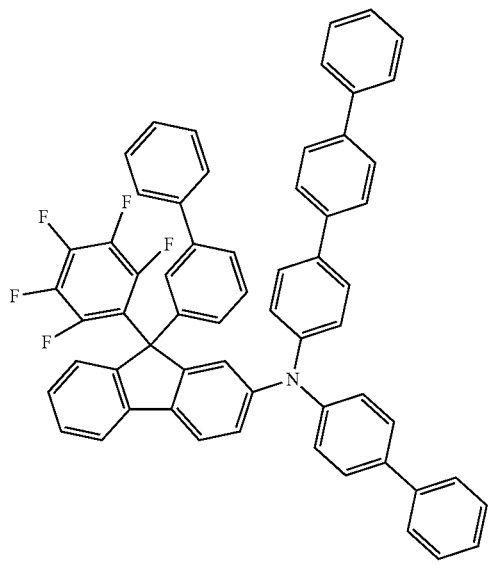
76
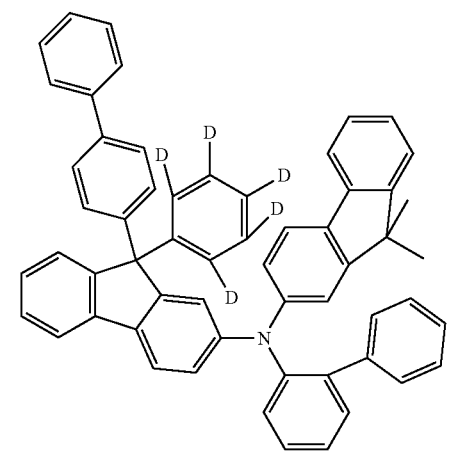
77
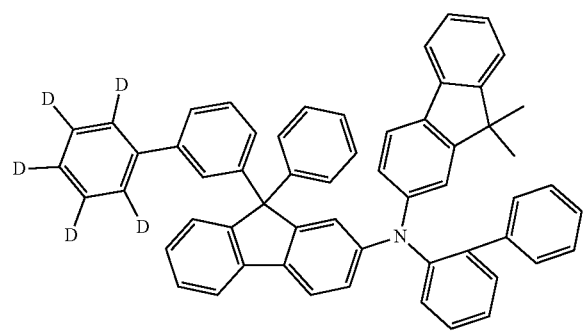
78
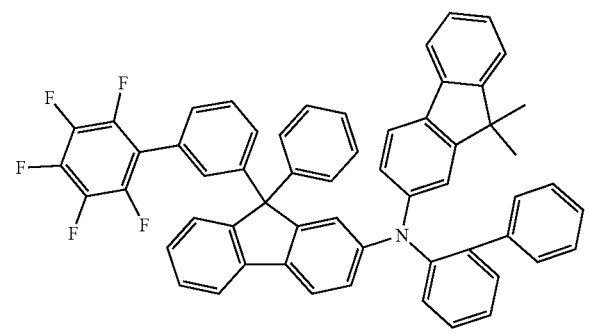
79
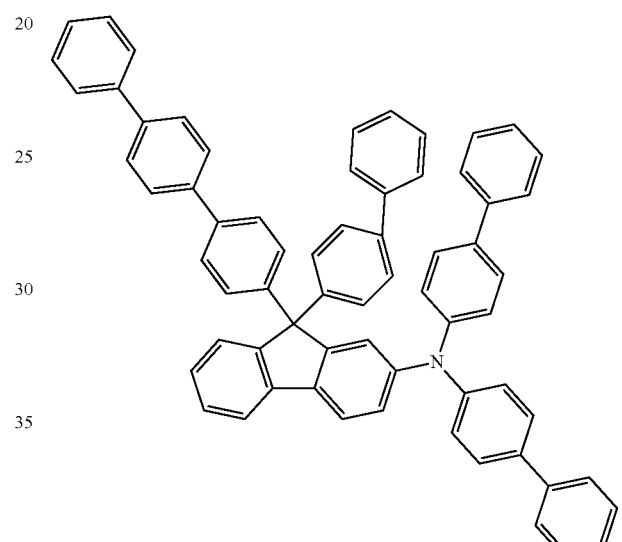
80
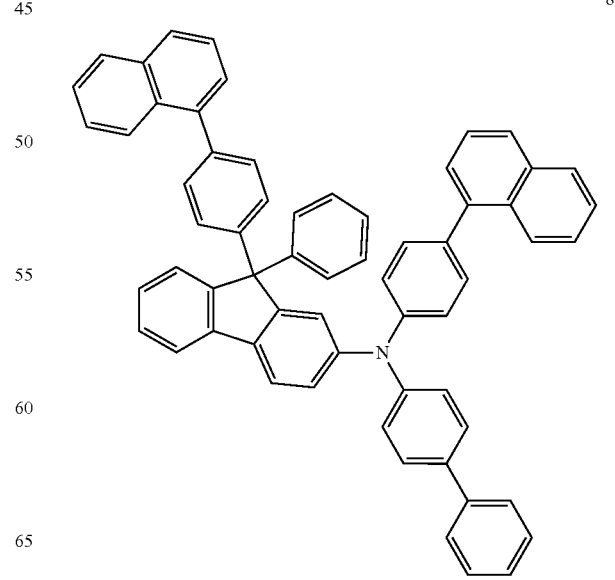

81
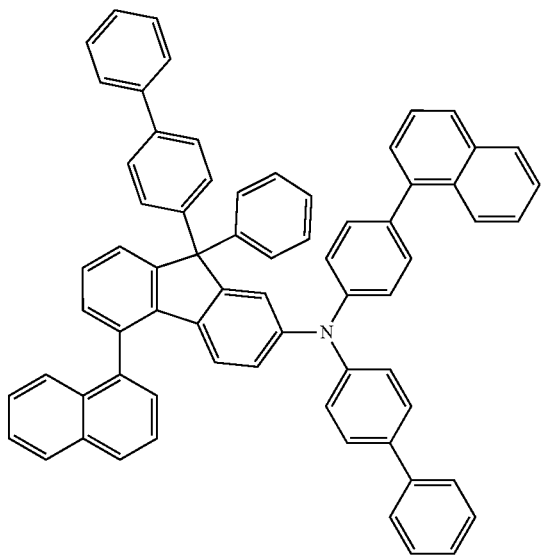
82
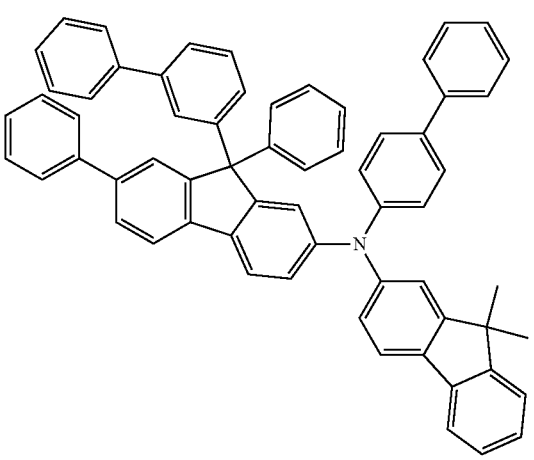
83
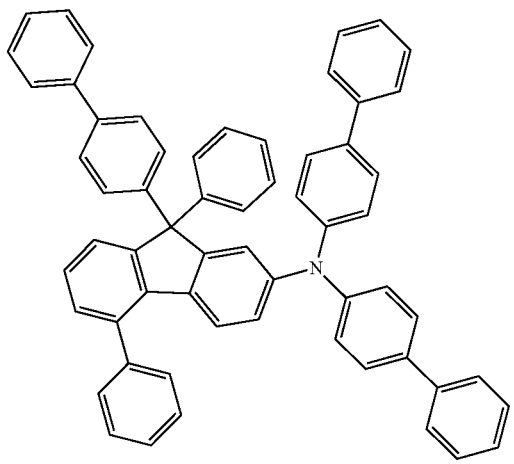
84
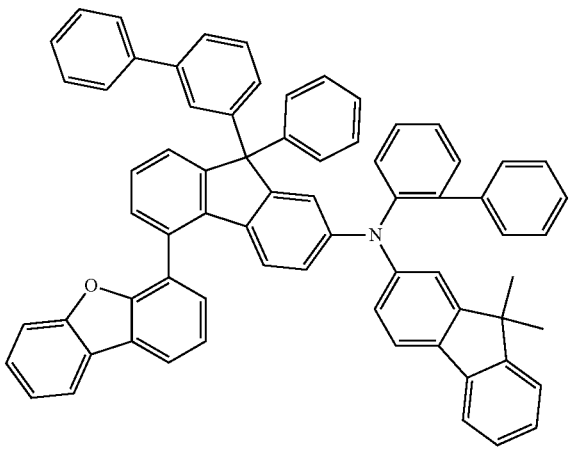
85
86
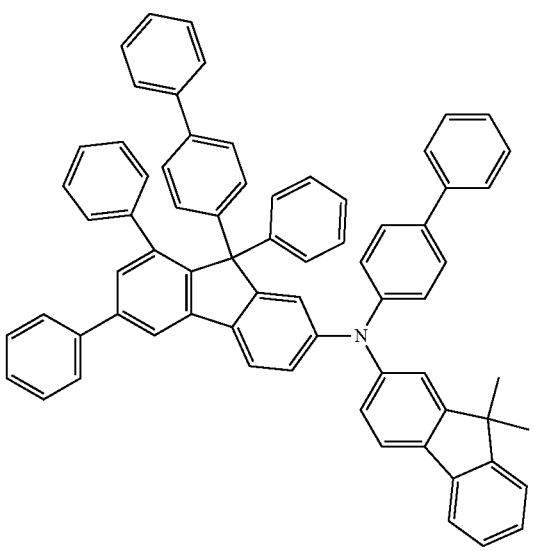

87
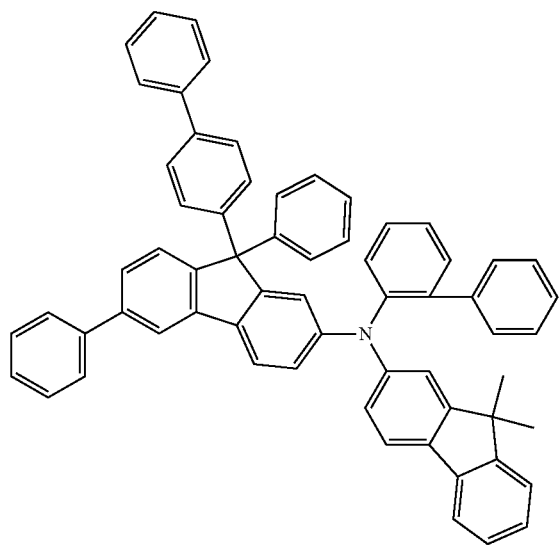
88
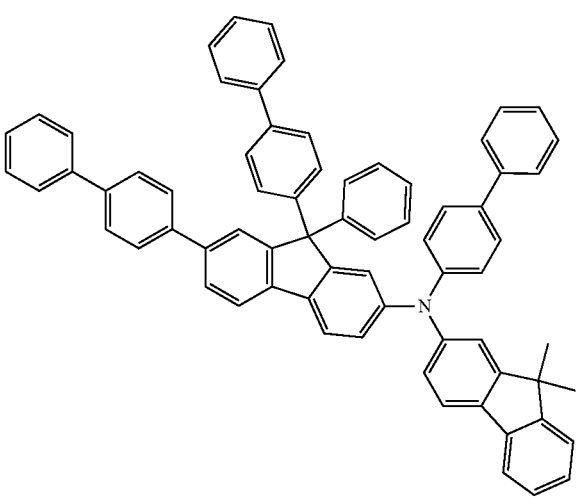
89
90
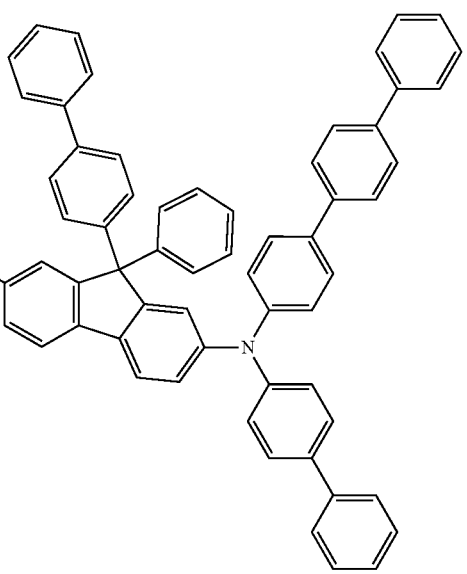
91
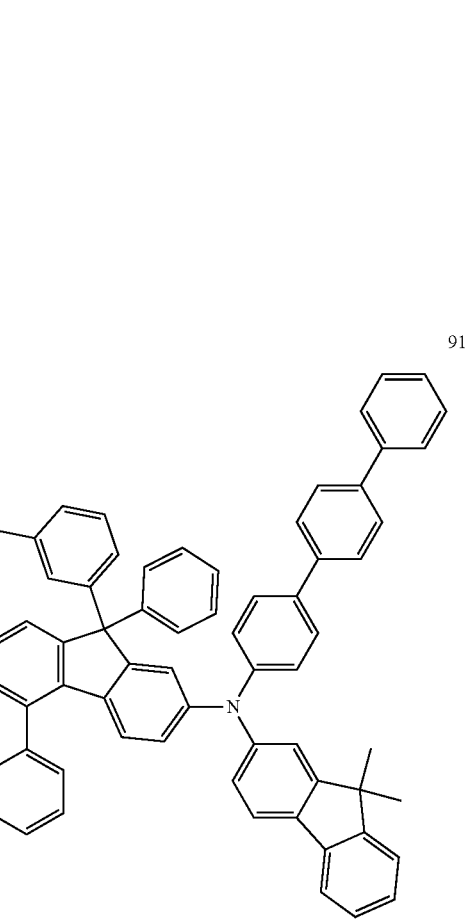

92
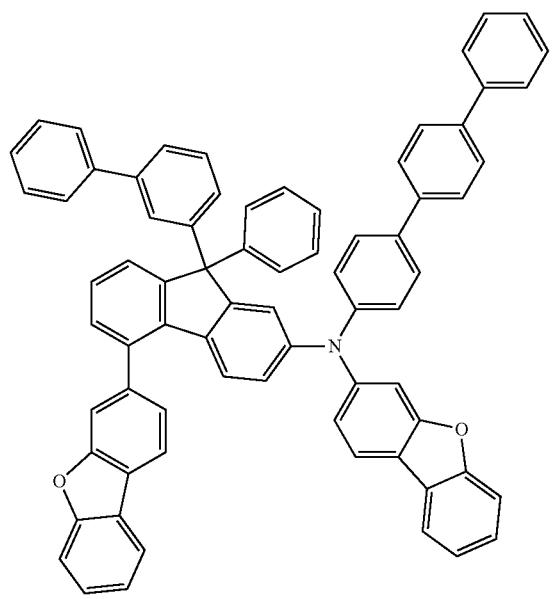
93
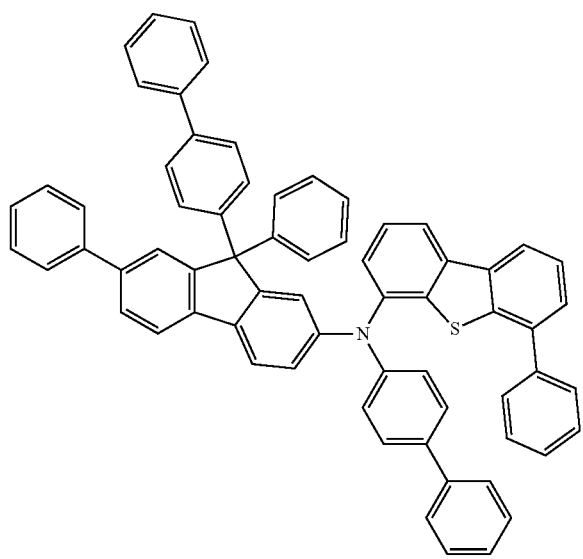
94
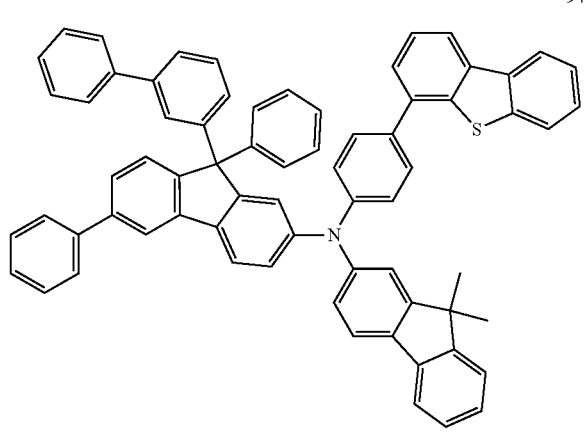
95
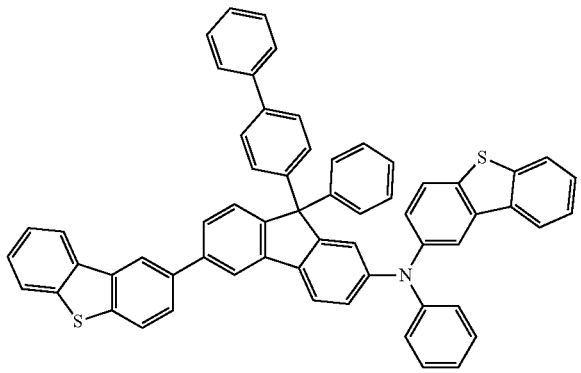
96
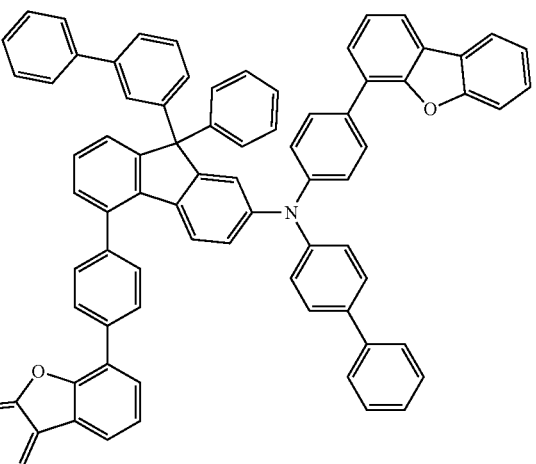
97
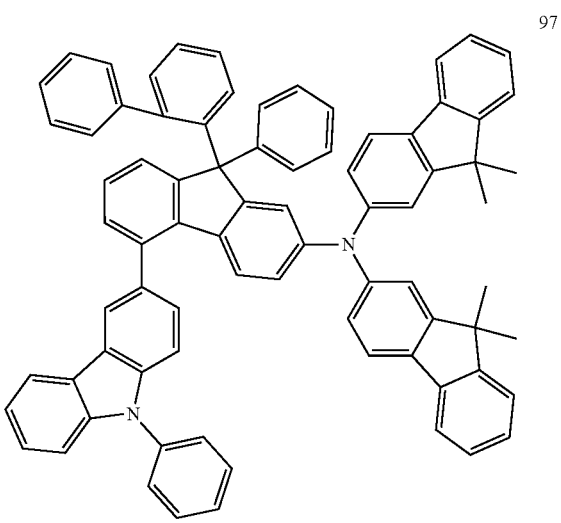

98
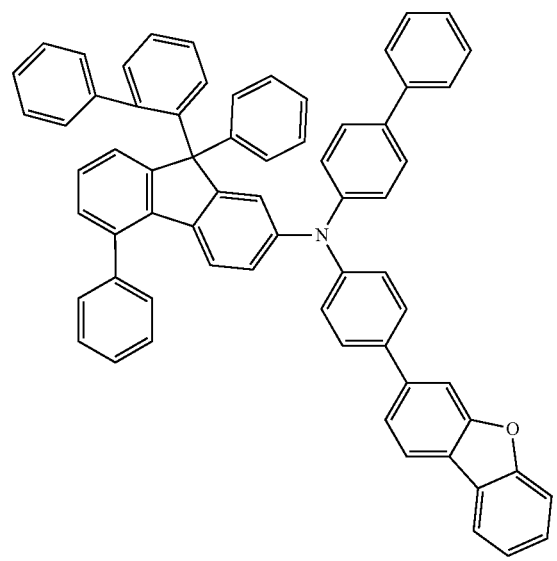
99
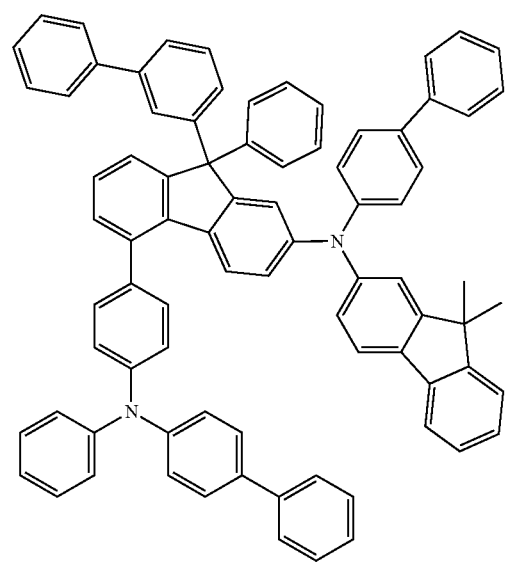
100
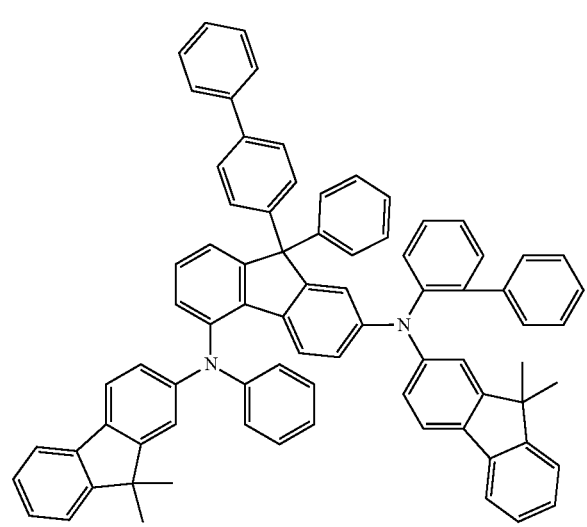
101
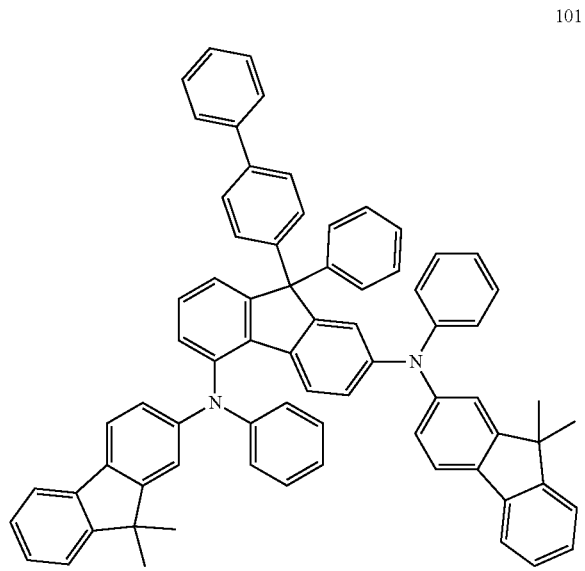
102
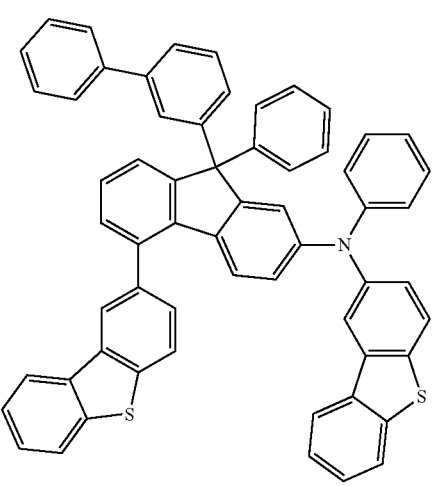
103
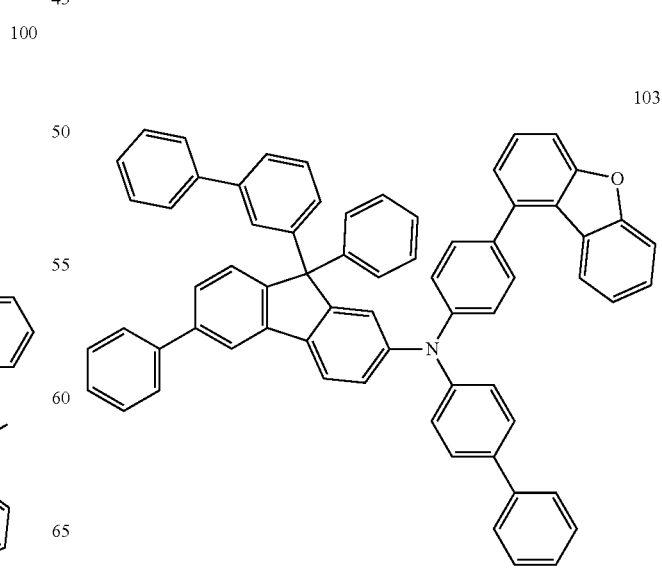

104
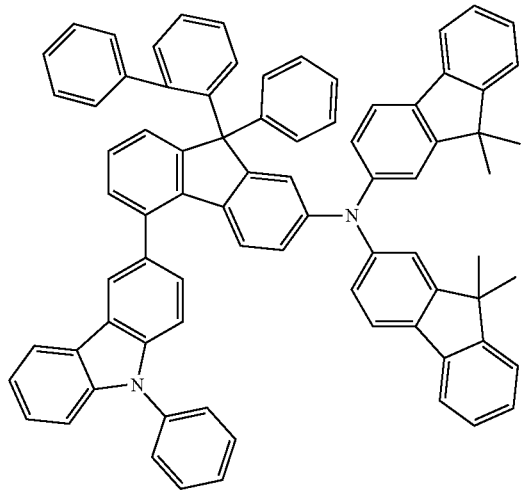
105
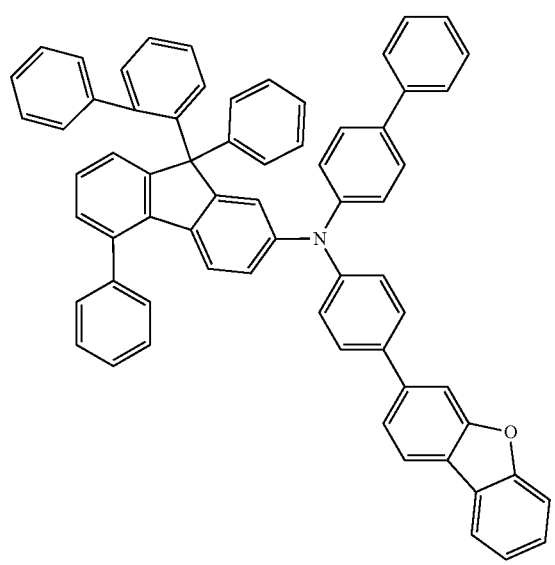
106
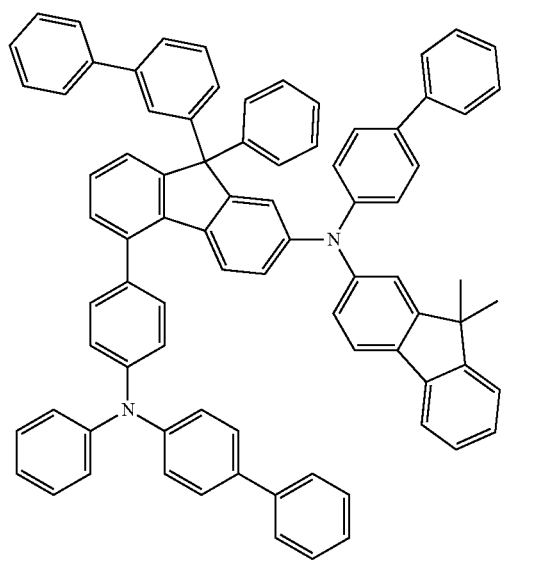
107
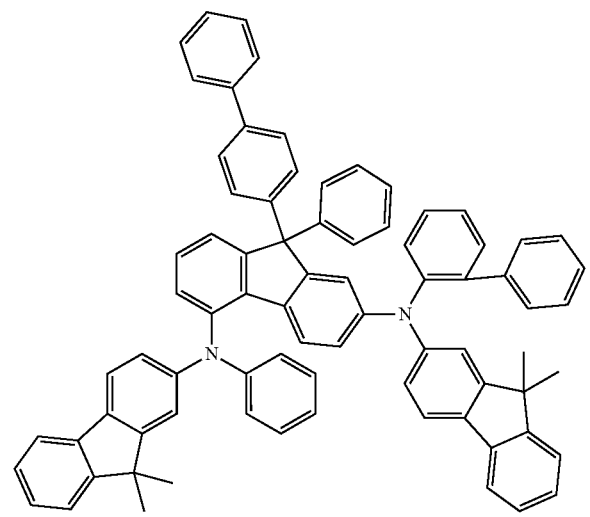
108
109
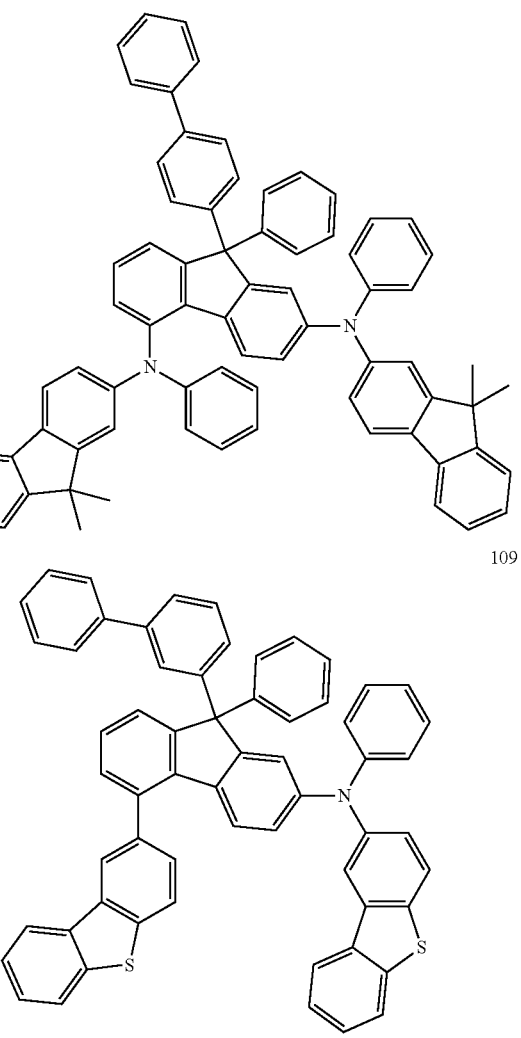

113
-continued
110
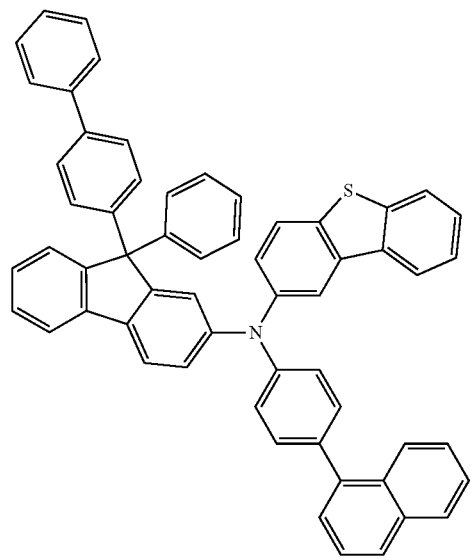
111
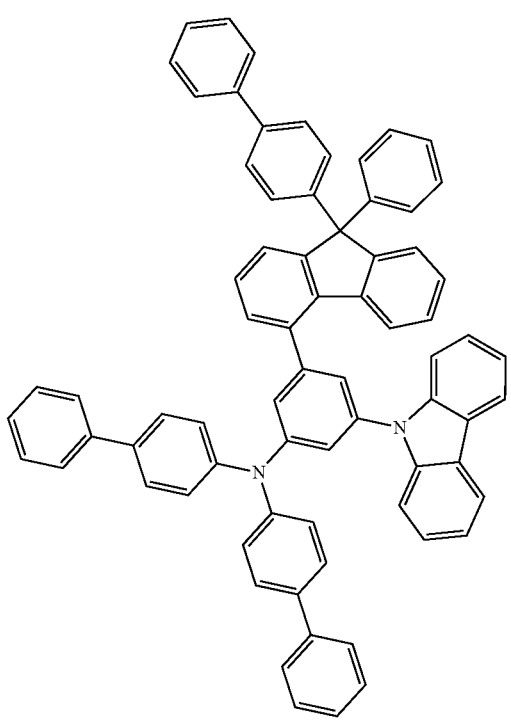
114
-continued
112
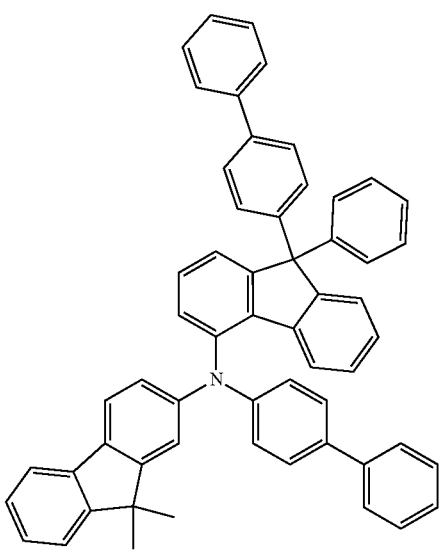
113
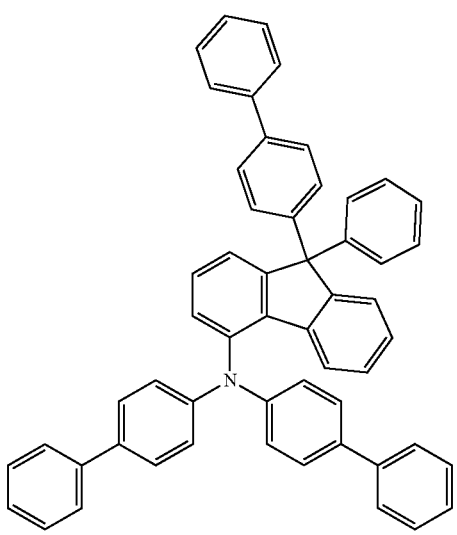

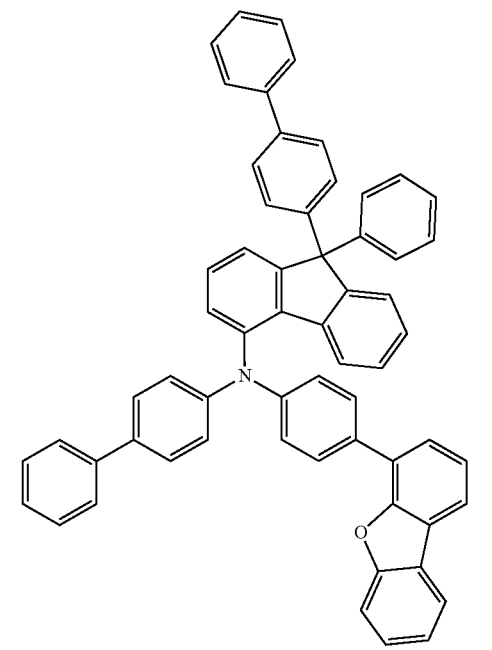
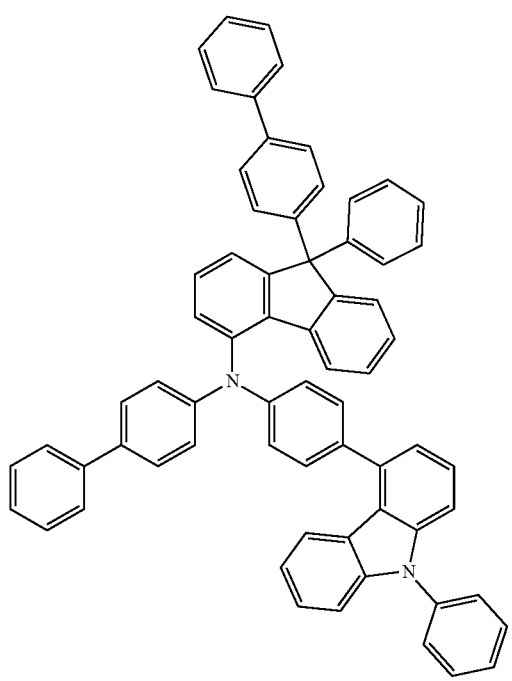
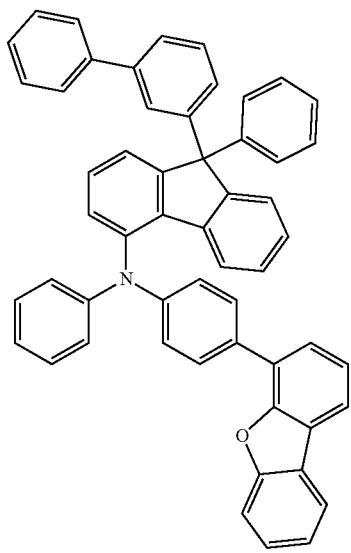
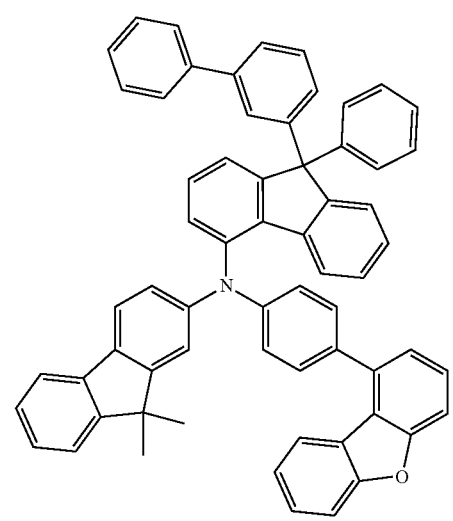
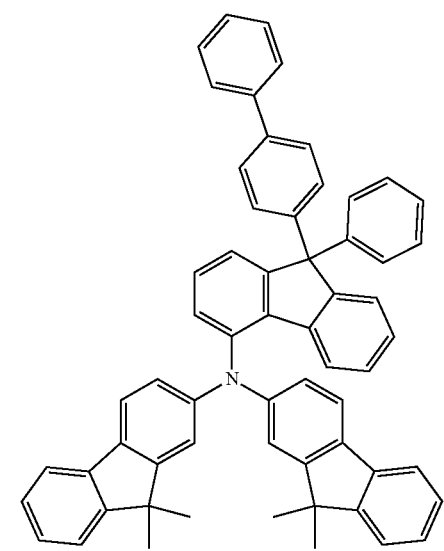

119
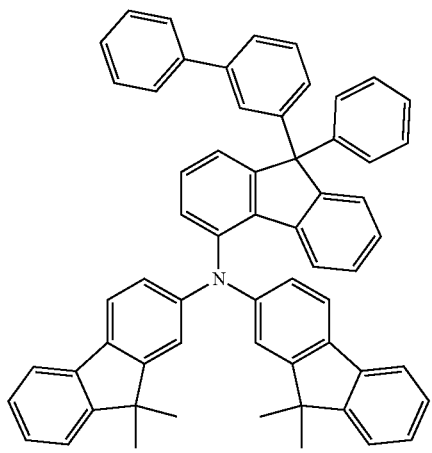
120
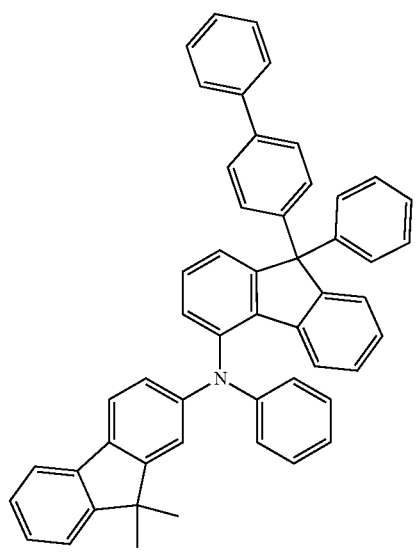
121
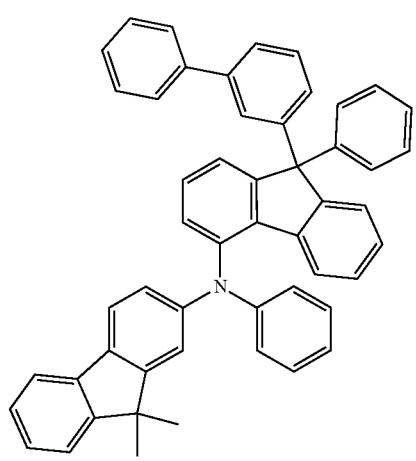
122
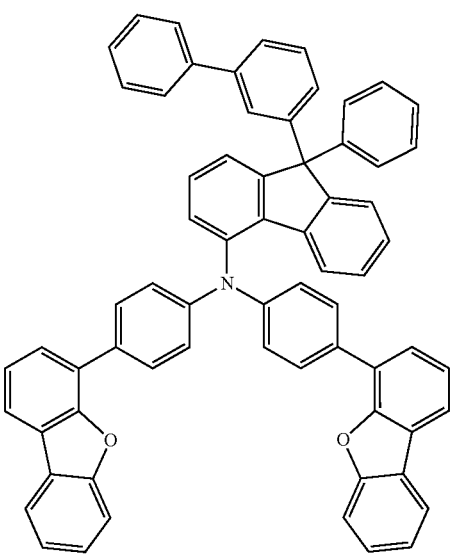
123
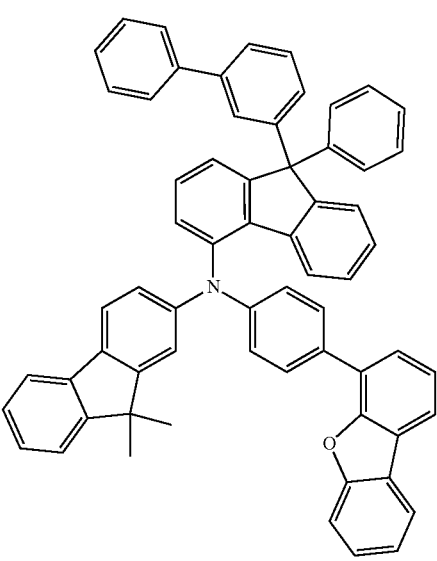
124
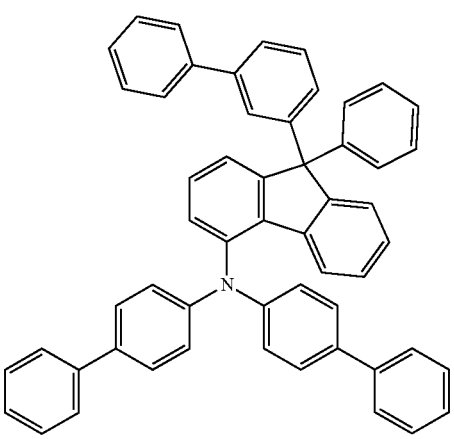

125
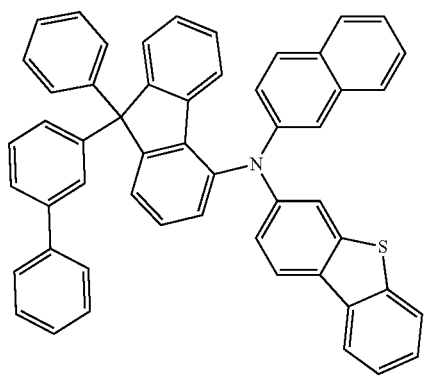
126
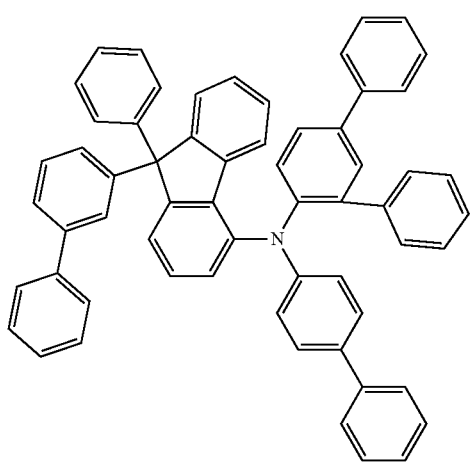
127
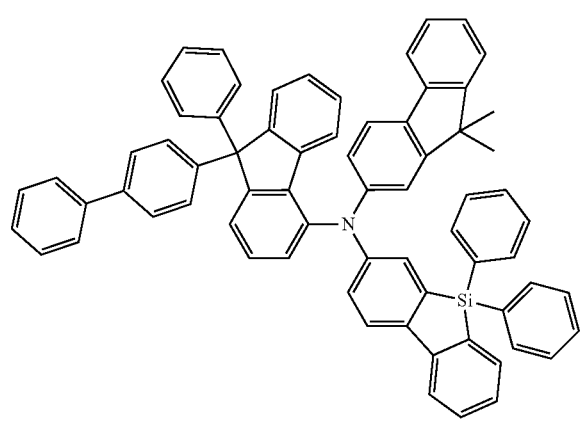
128
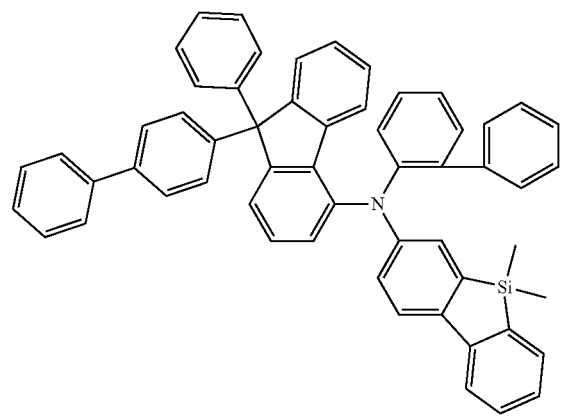
129
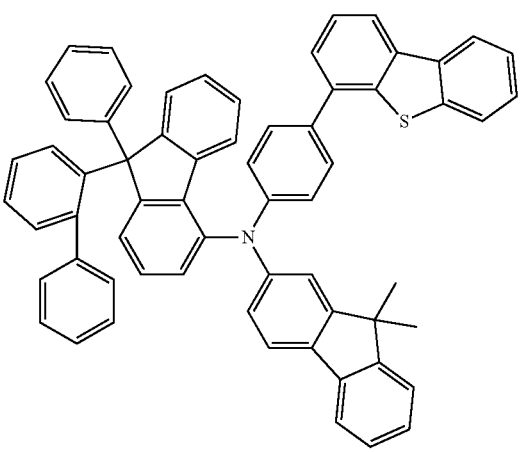
130
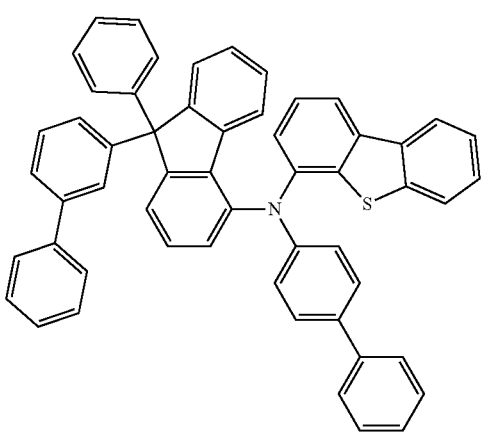

-continued
131
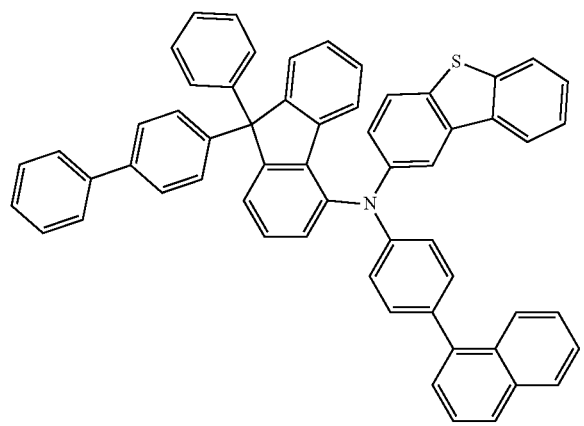
132
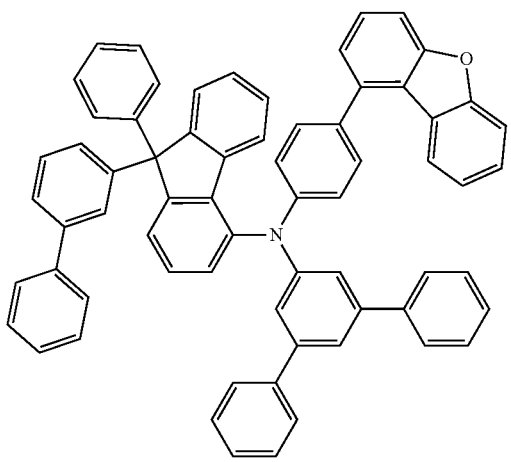
133
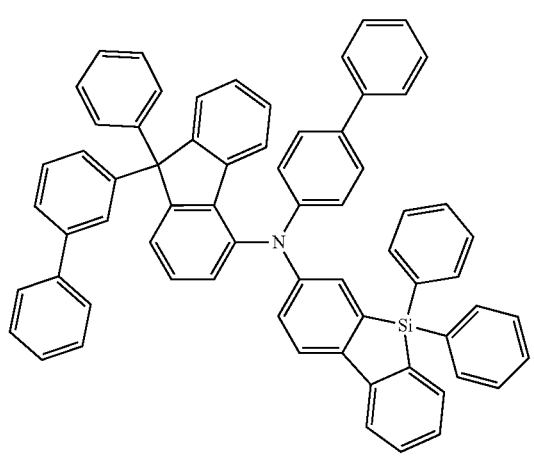
-continued
134
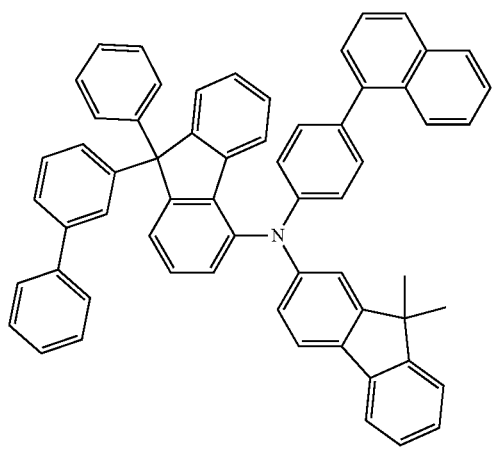
135
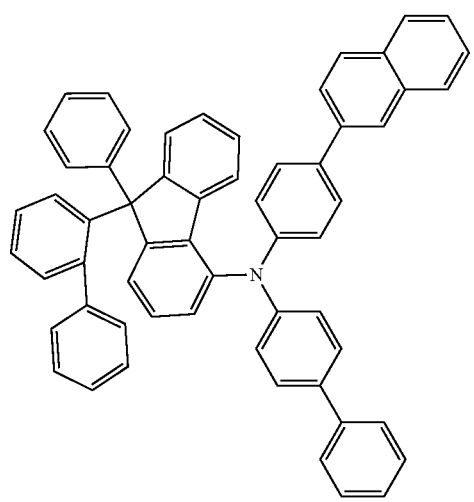
136
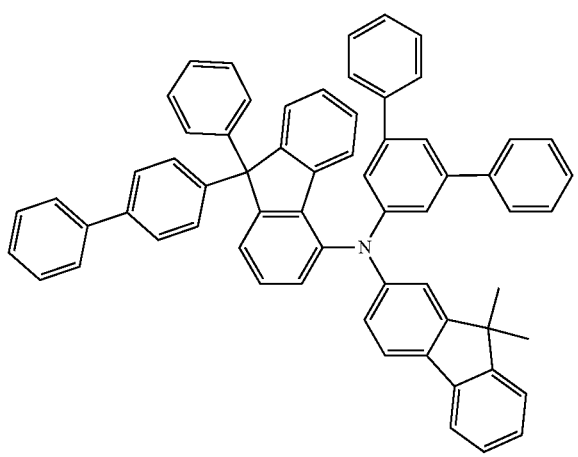

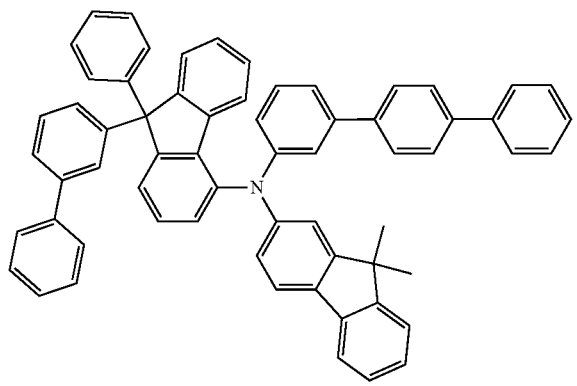
137
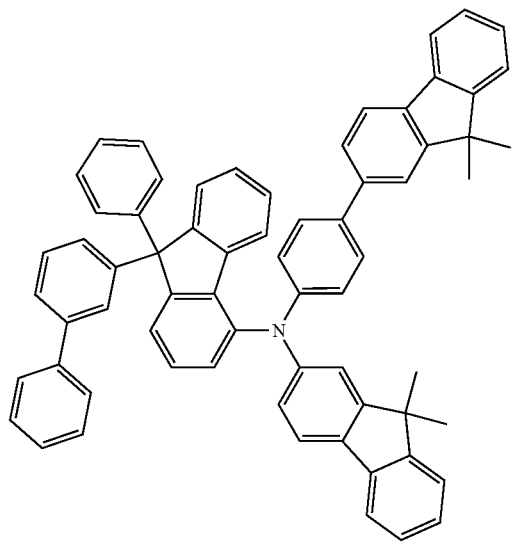
140
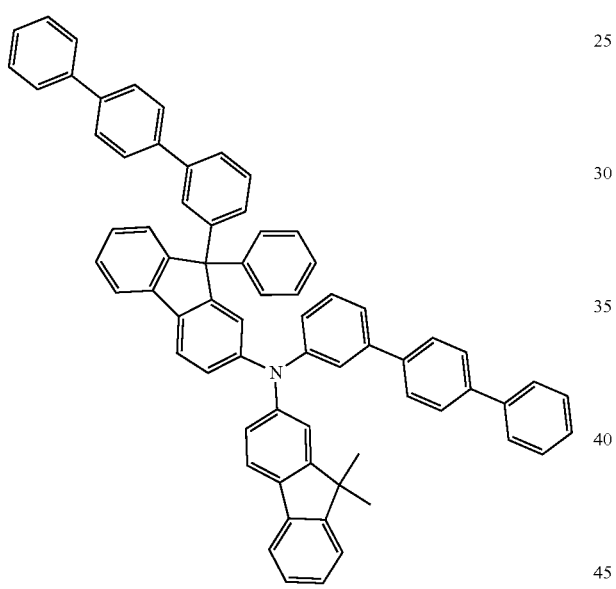
138
141
139
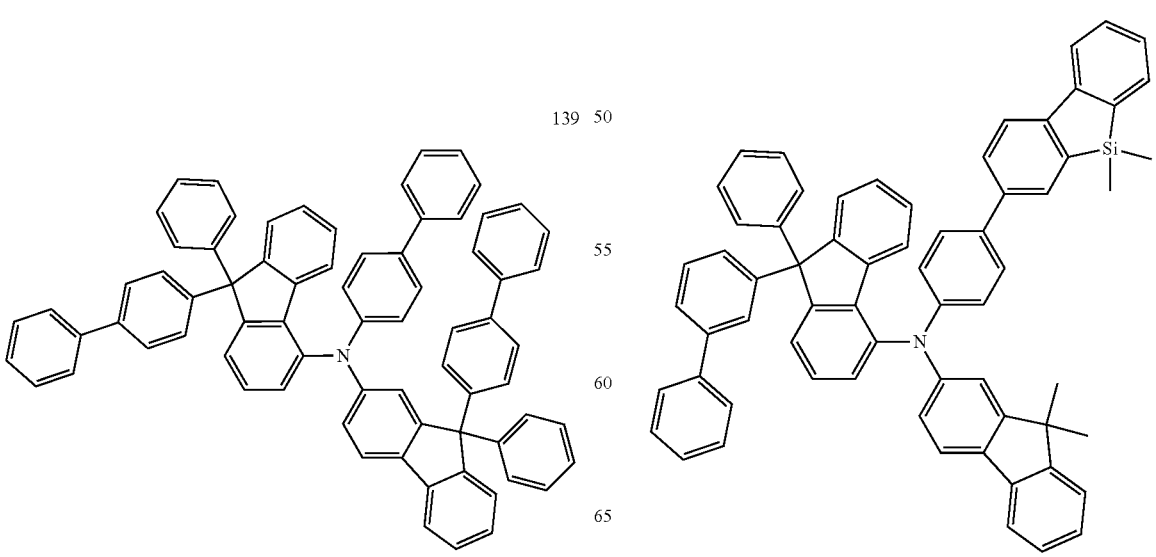
142

143
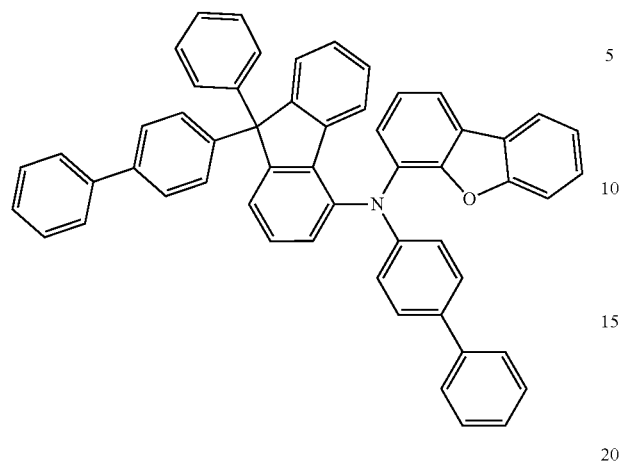
144
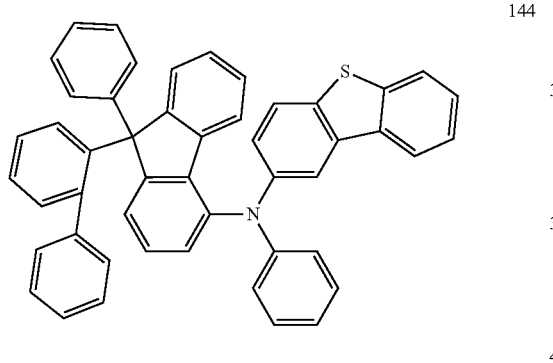
145
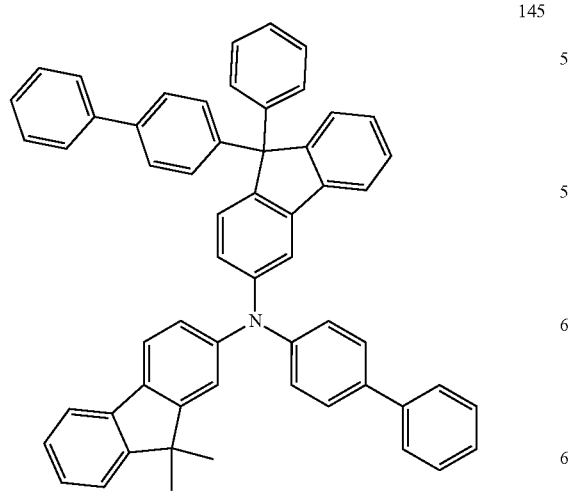
146
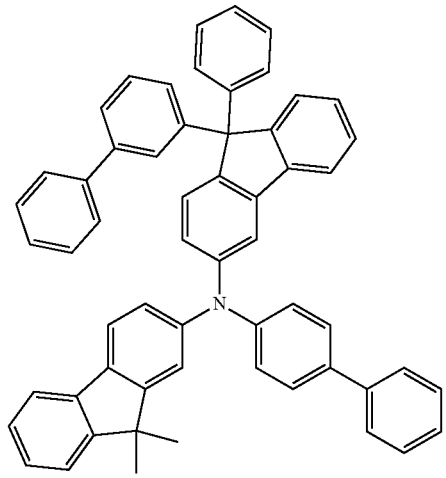
147
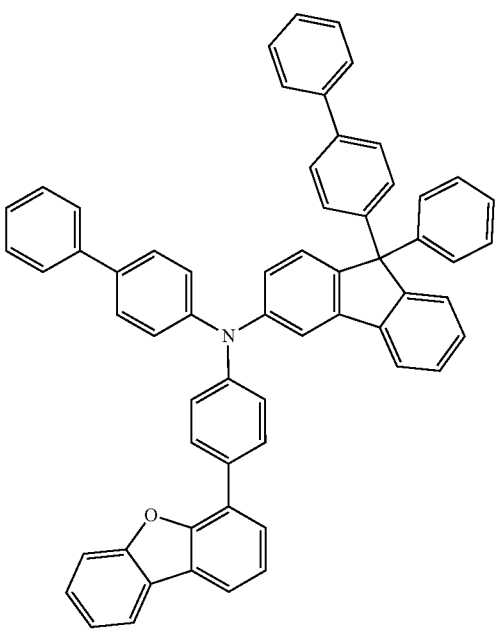

127
-continued
148
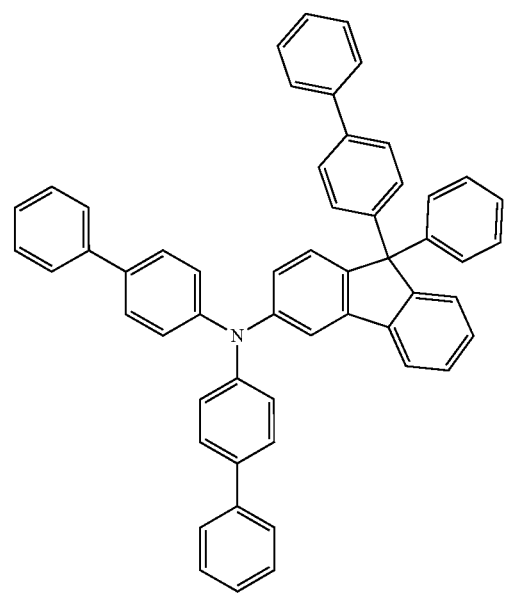
149
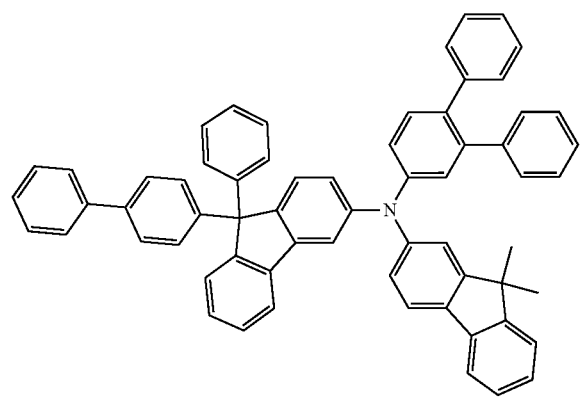
150
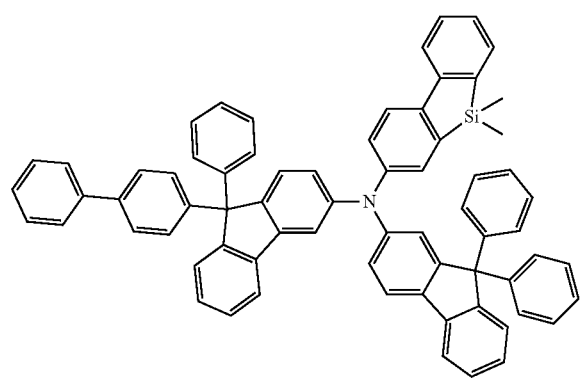
128
-continued
151
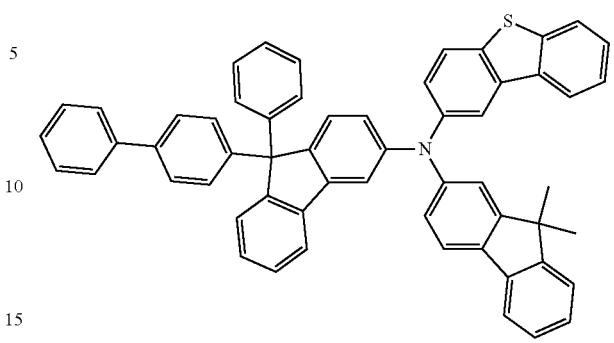
152
153
154

-continued
155
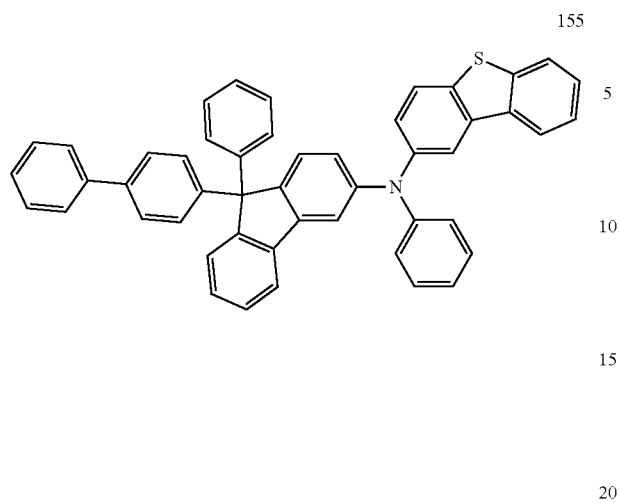
156
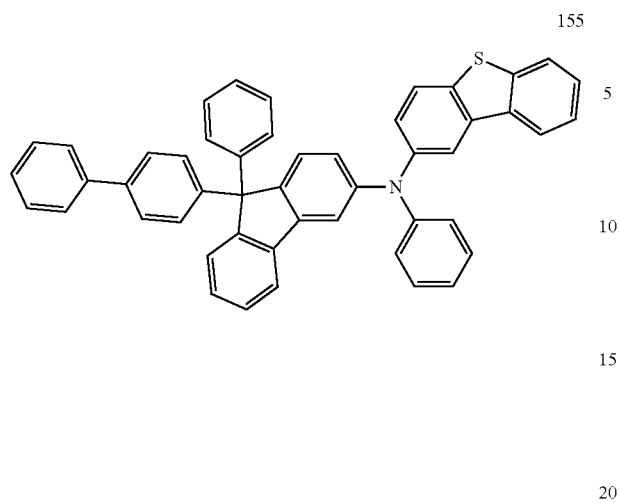
157
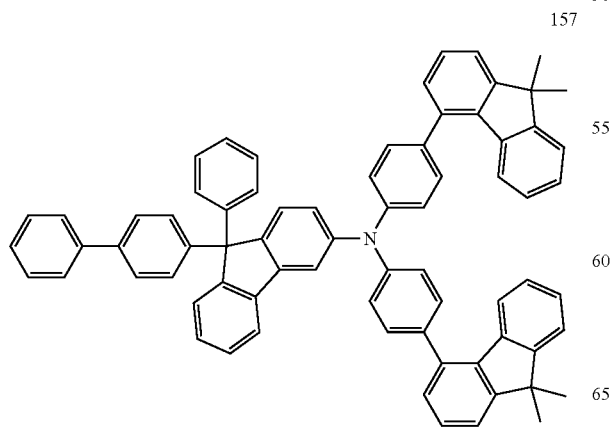
-continued
158
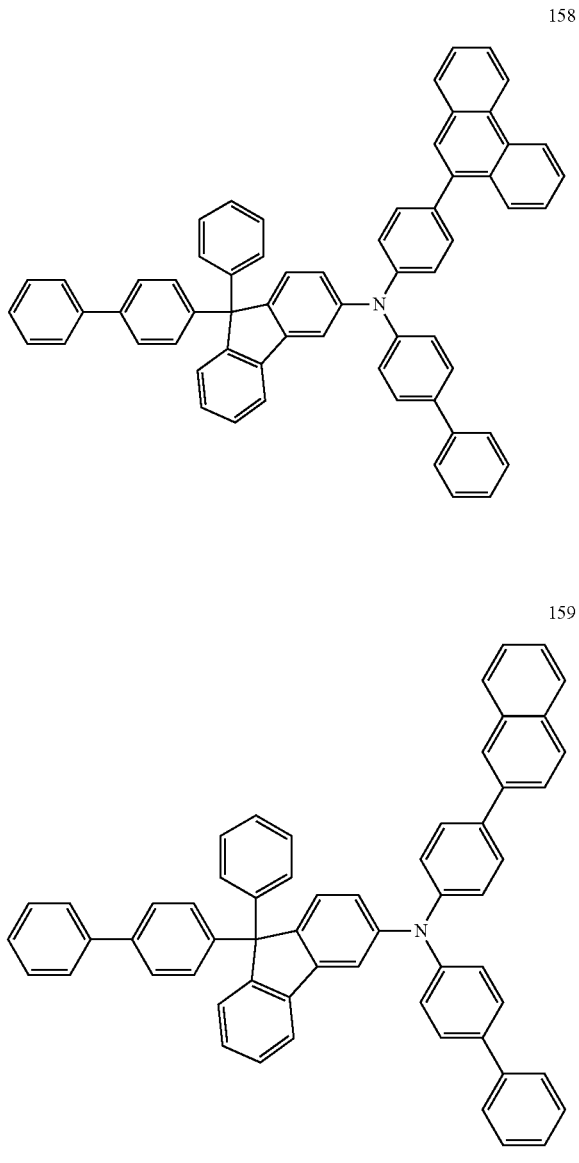
159
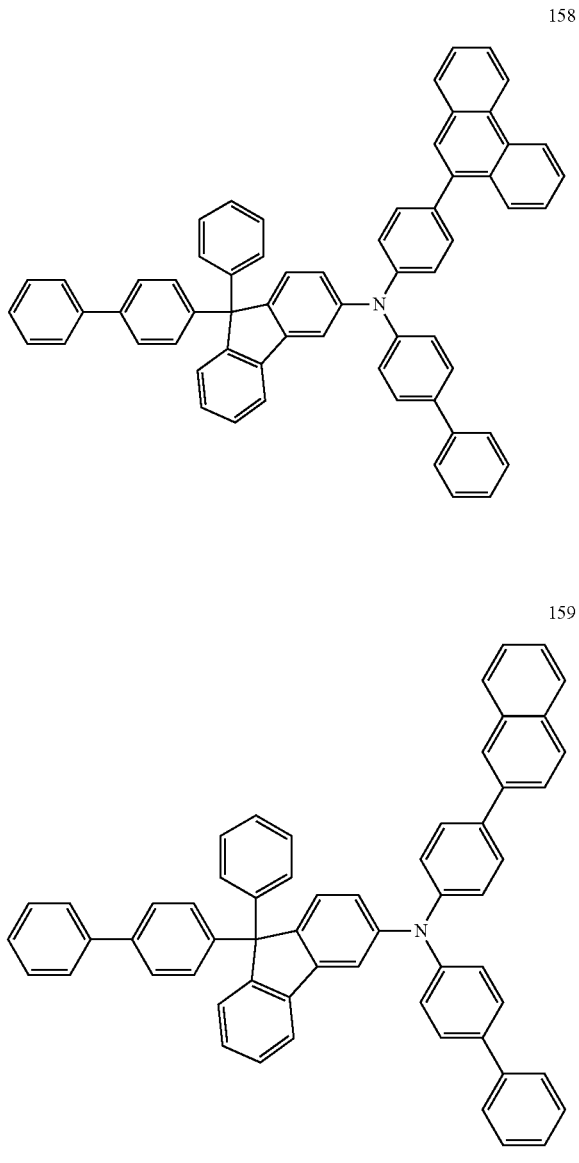
160
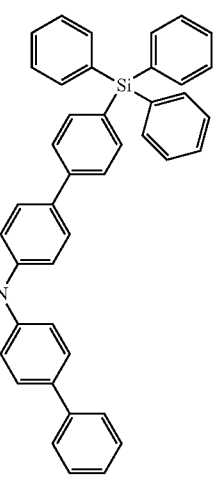

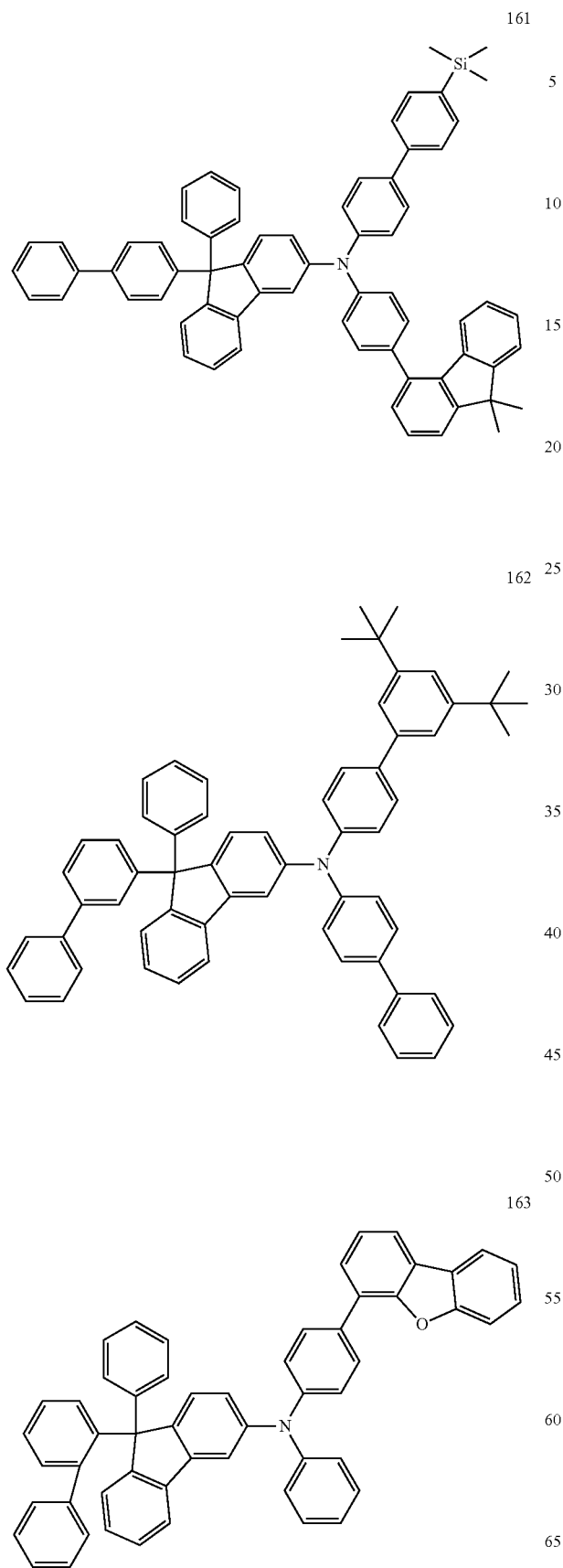
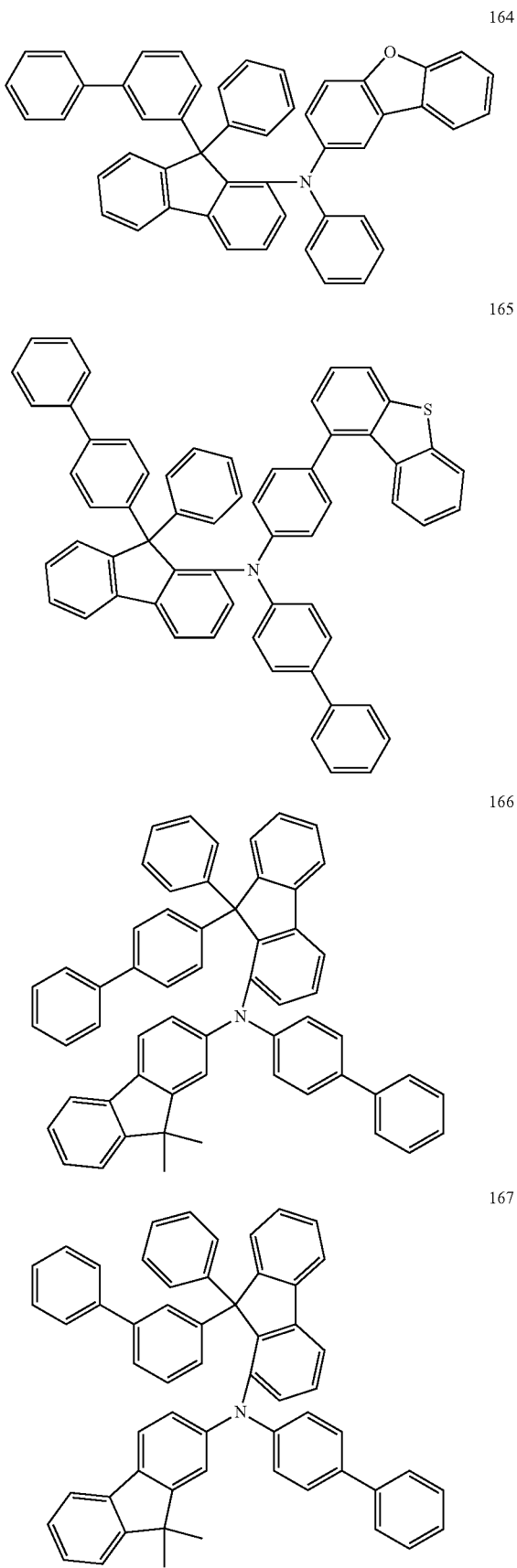

168
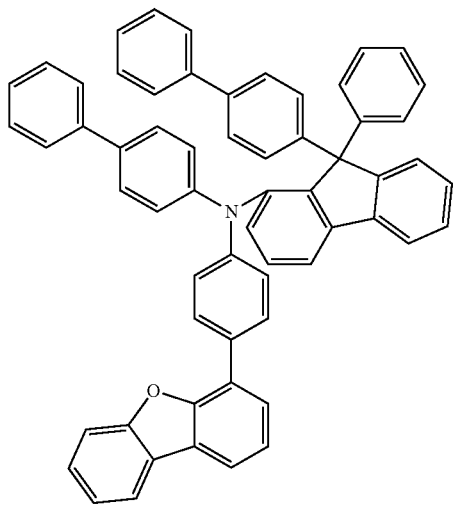
169
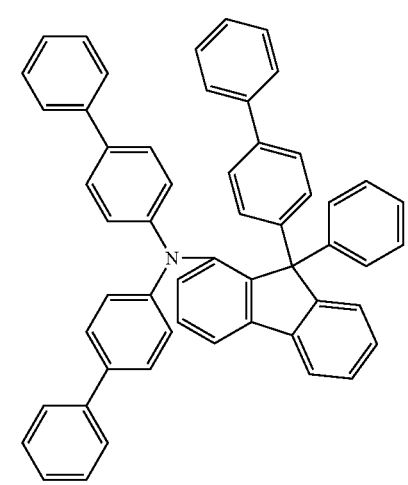
170
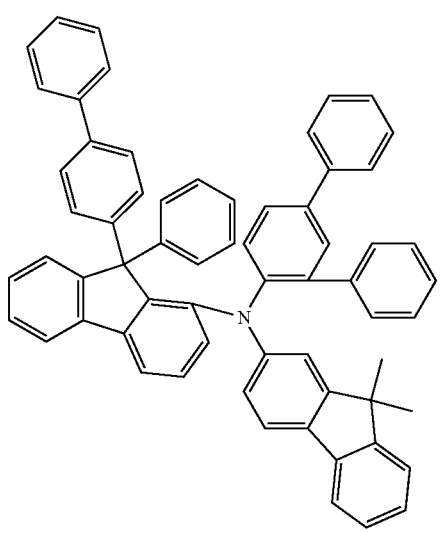
171
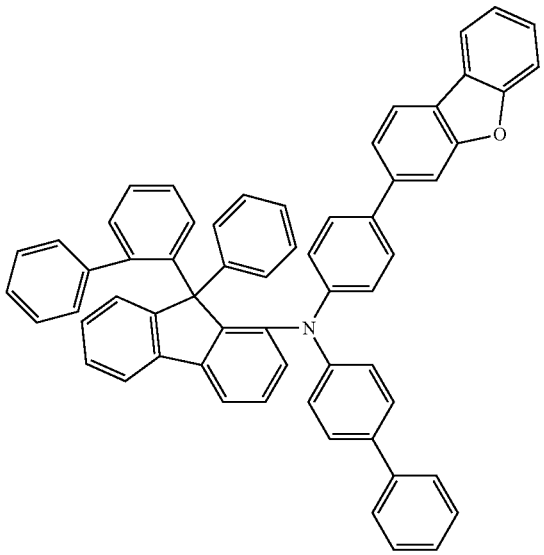
172
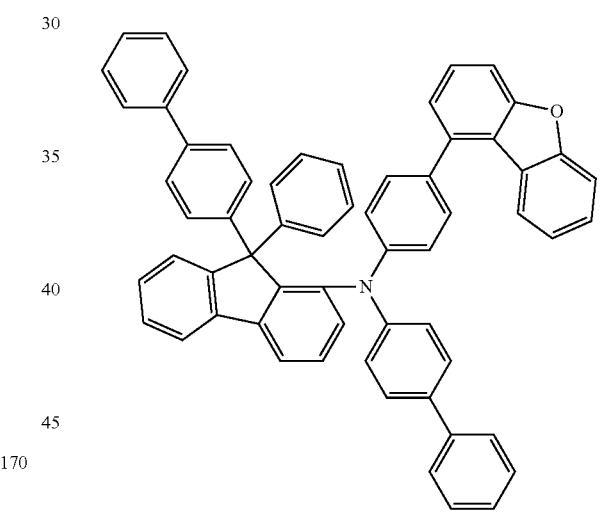
173
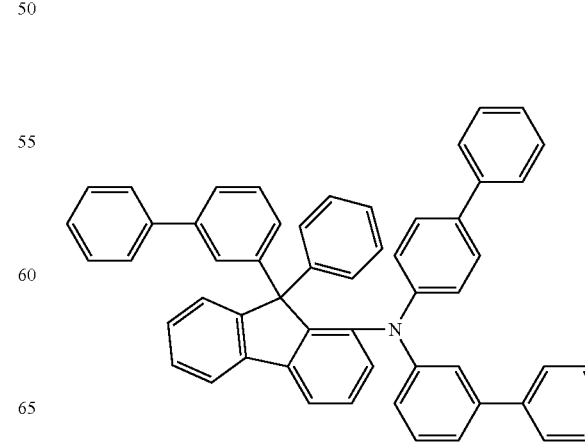

174
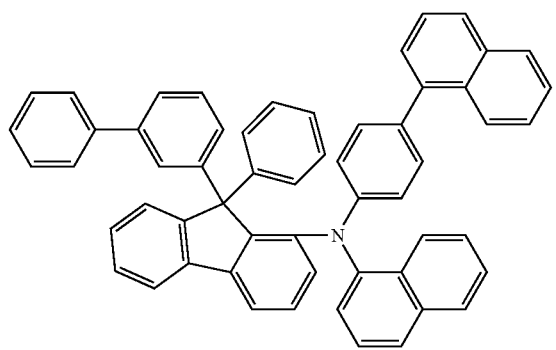
175
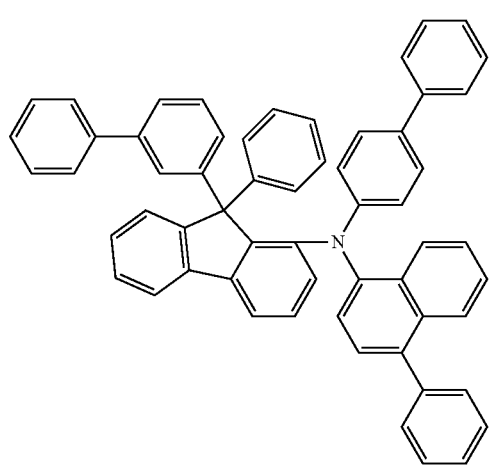
176
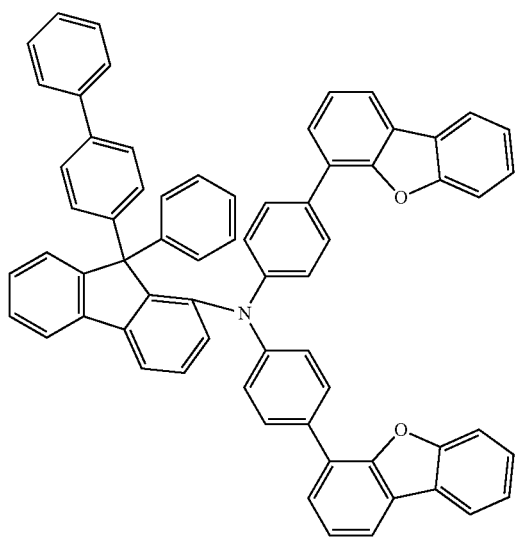
177
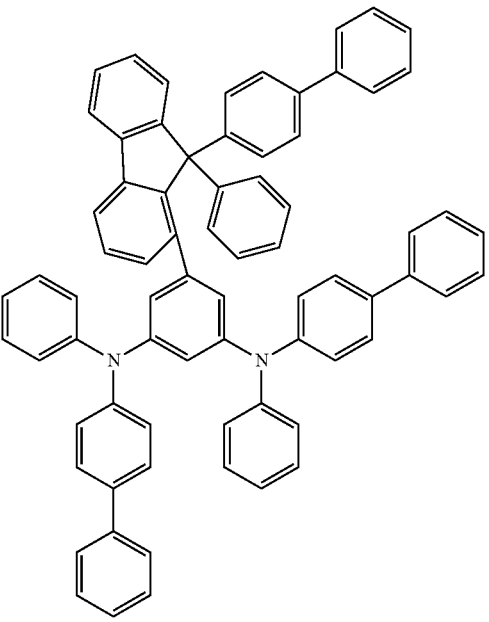
178
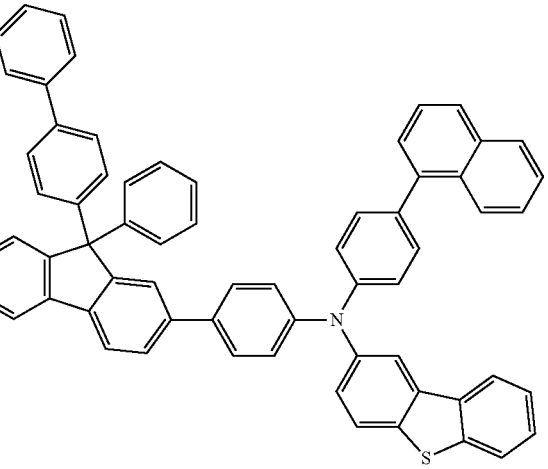
179
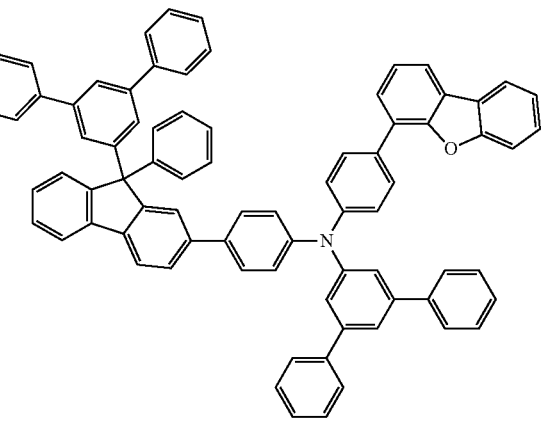

180
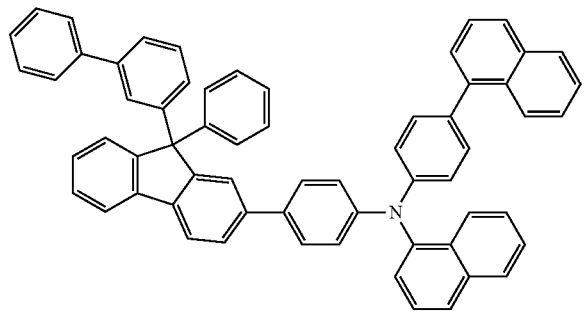
181
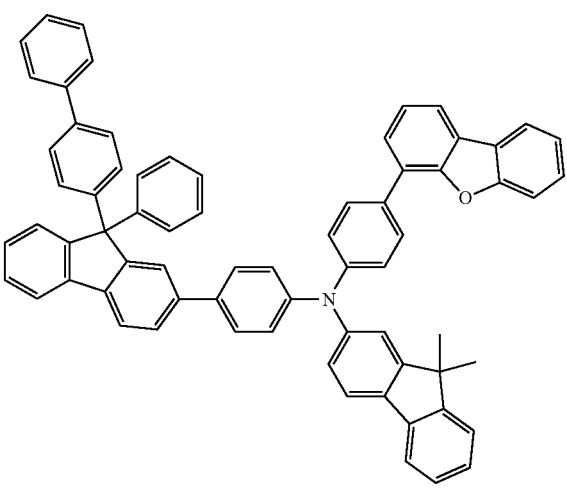
182
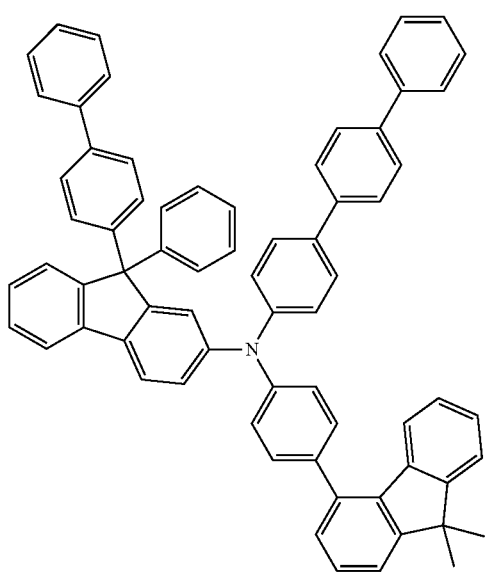
183
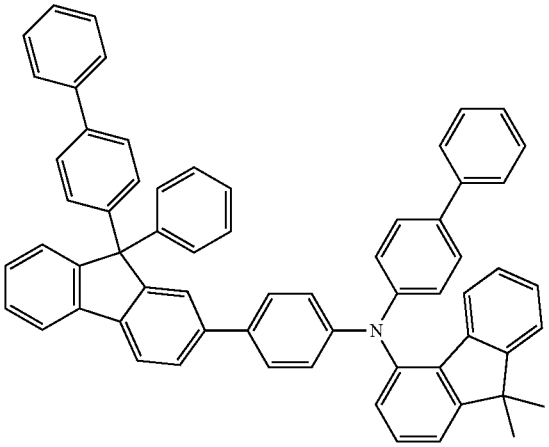
184
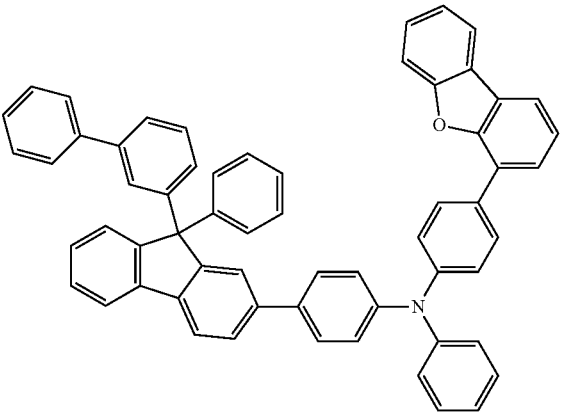
185
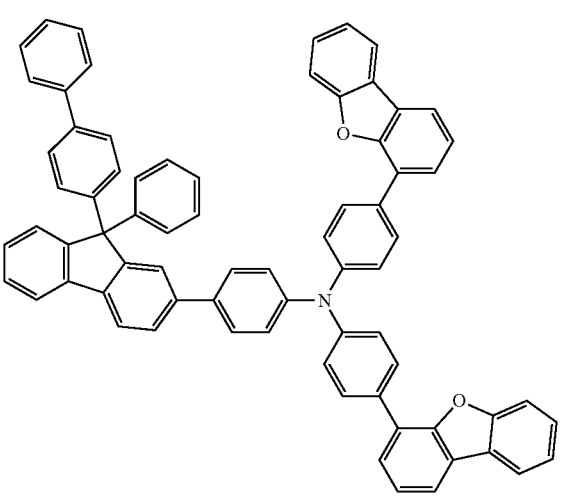

186
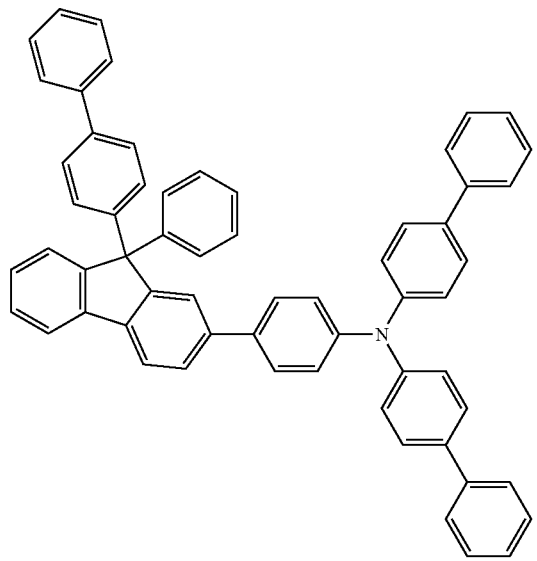
187
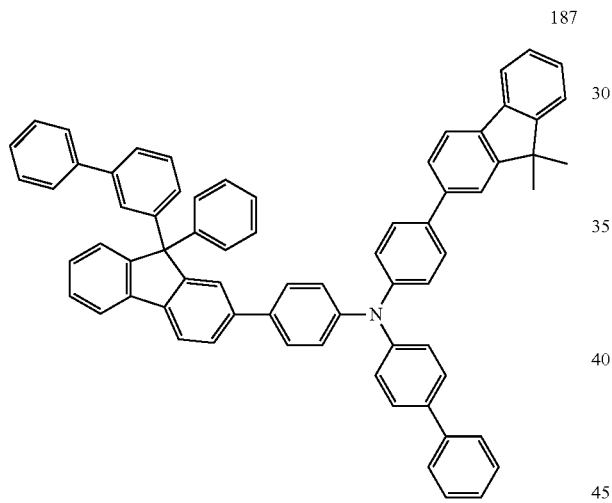
188
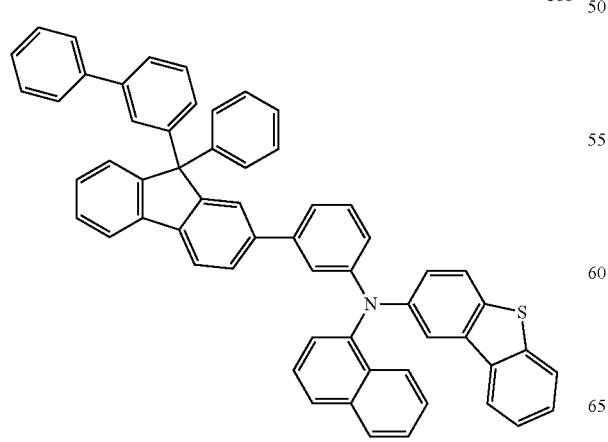
189
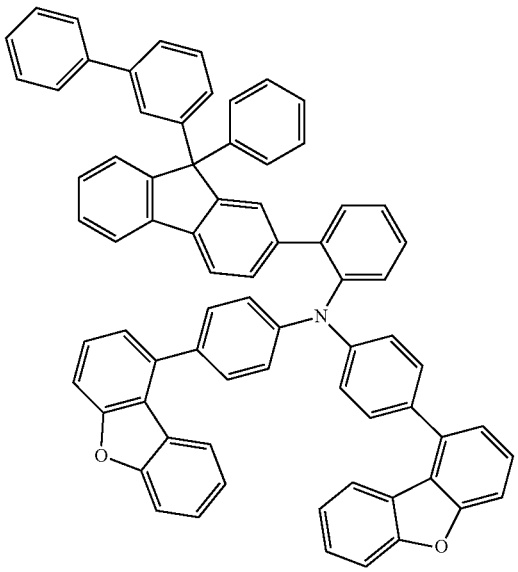
190
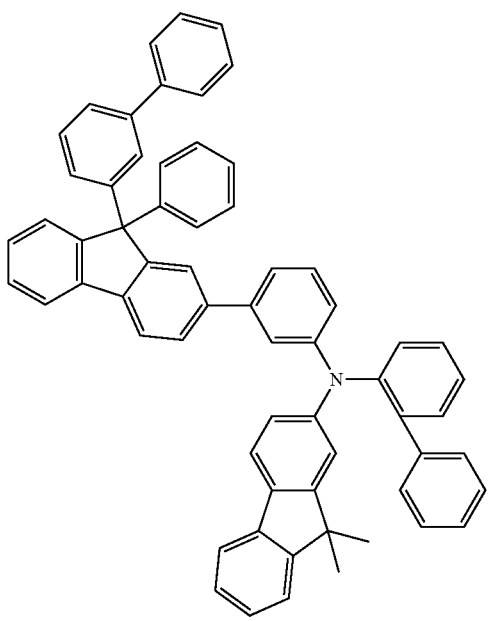

191
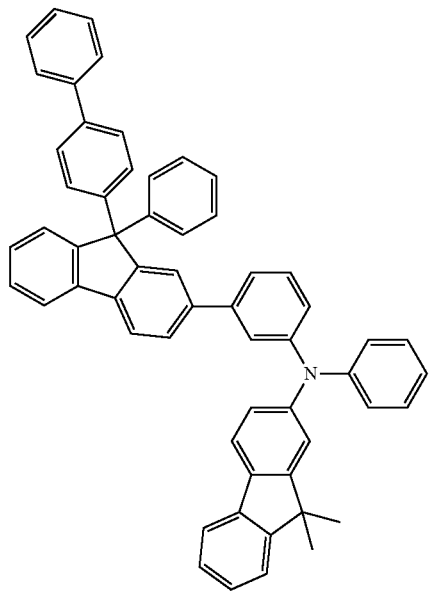
192
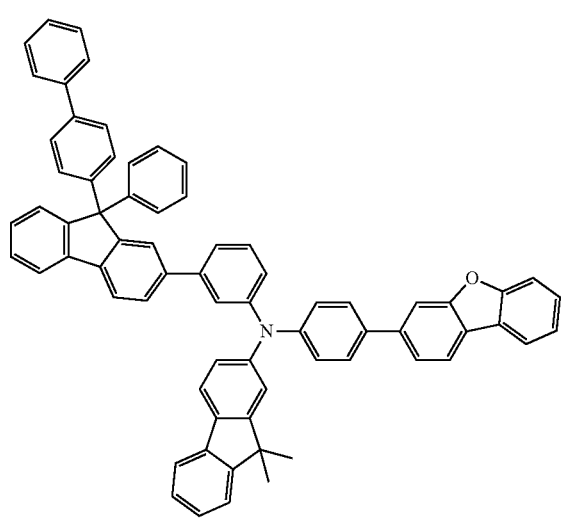
194
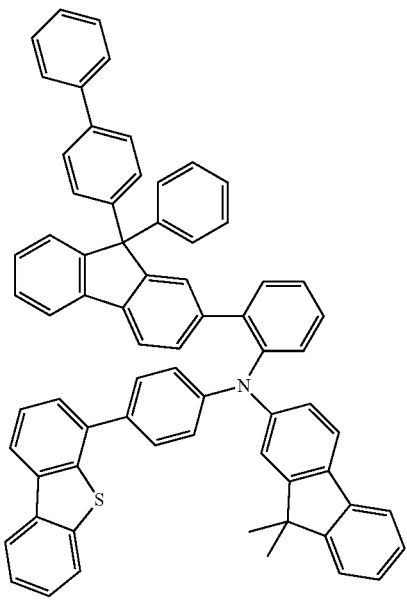
193
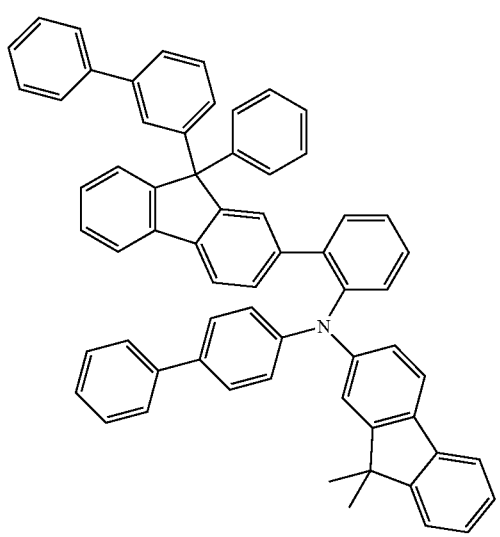
195
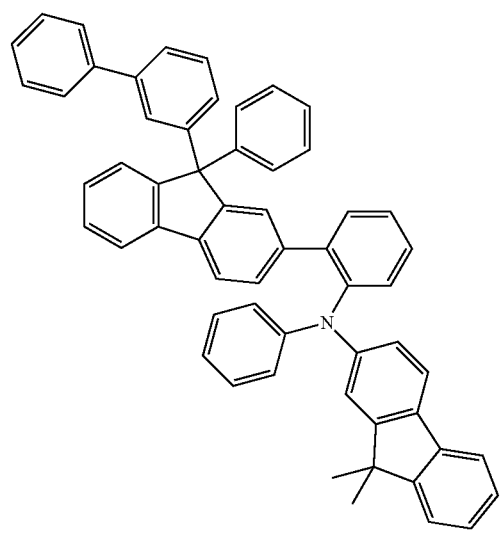

196
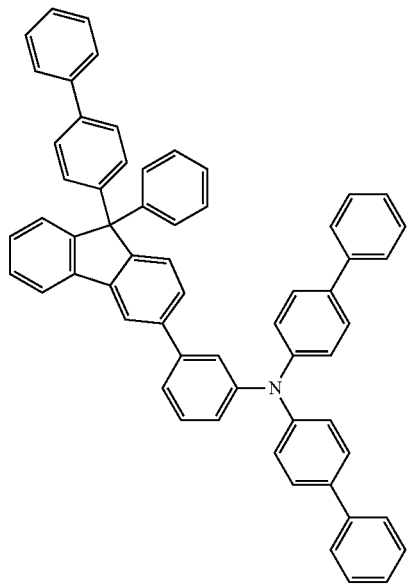
197
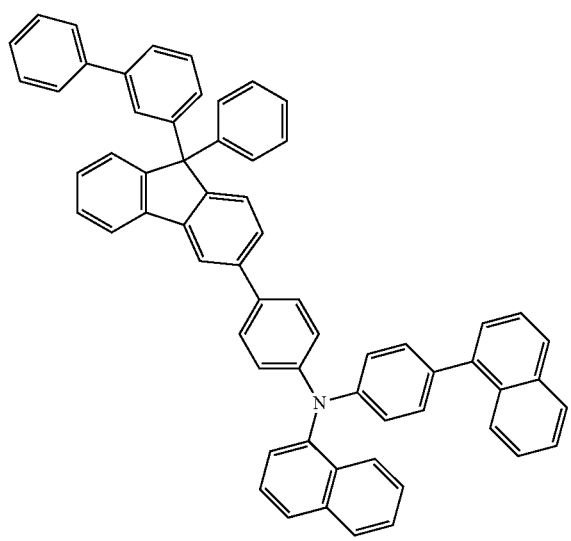
198
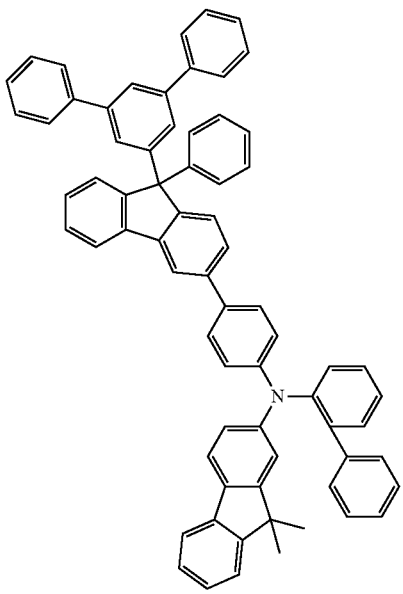
199
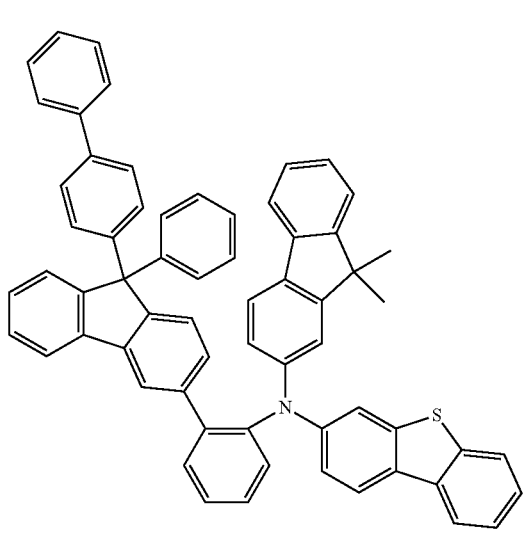

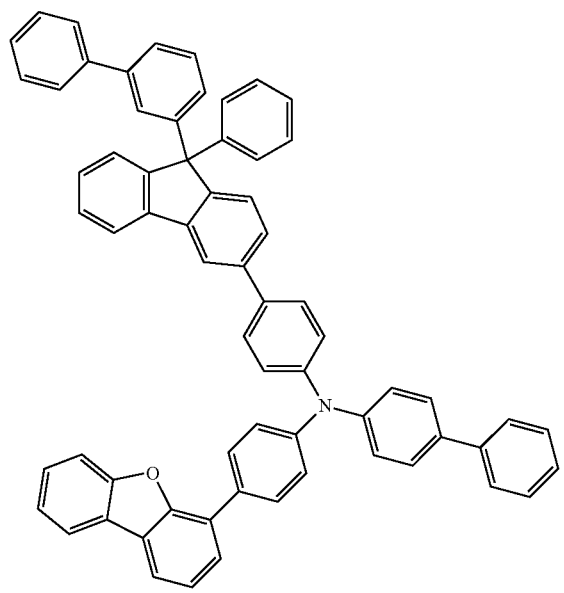
200
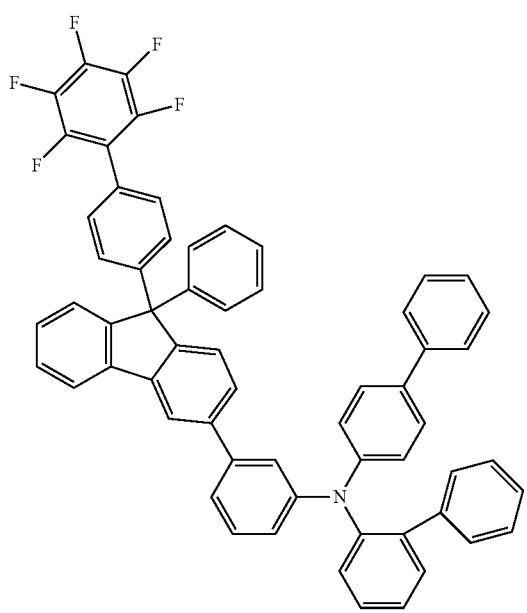
201
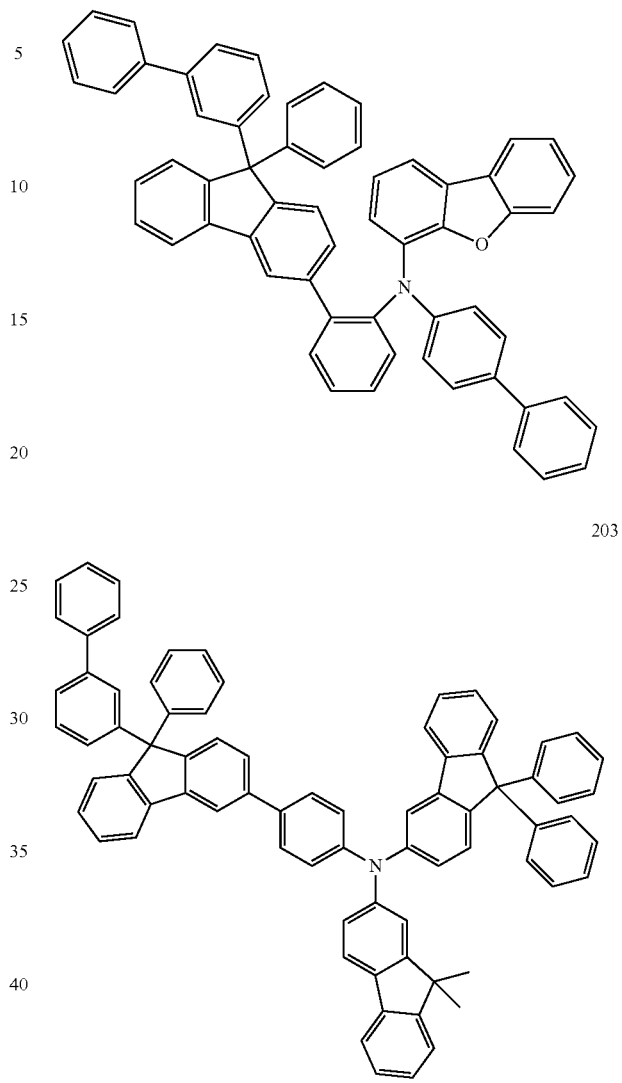
202
203
204

205
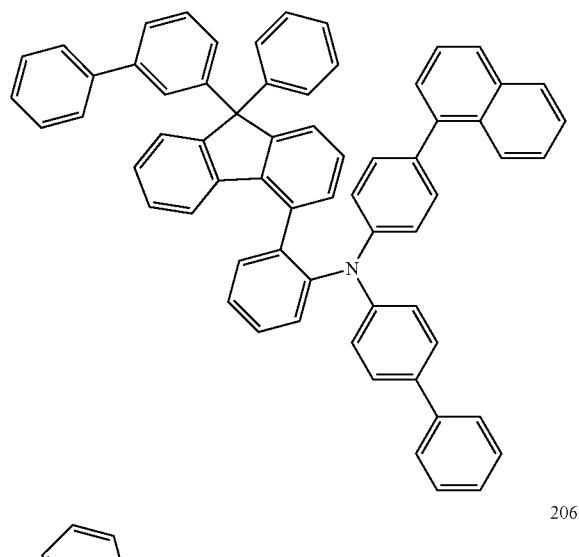
206
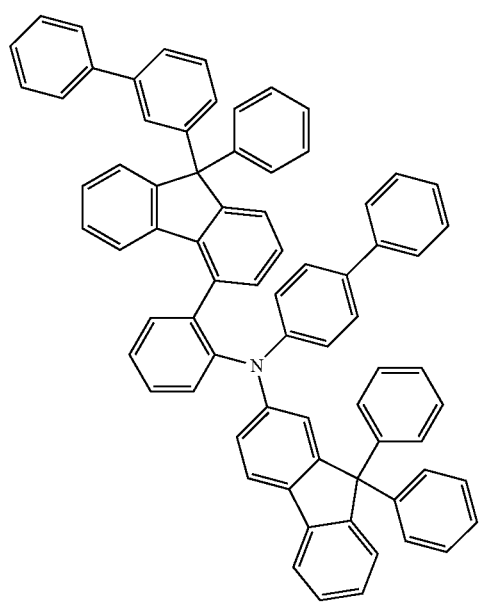
207
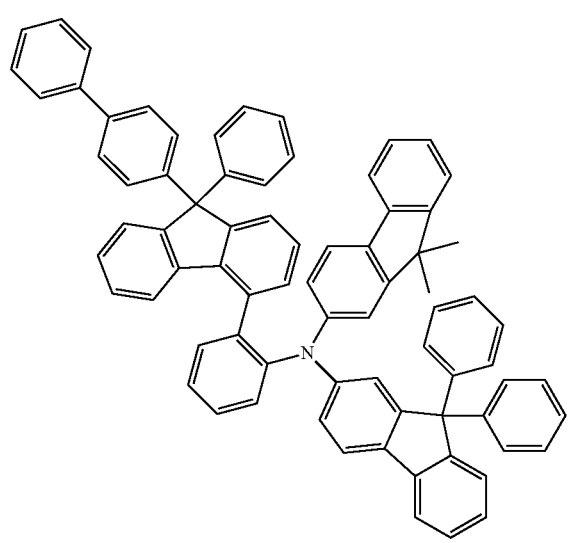
208
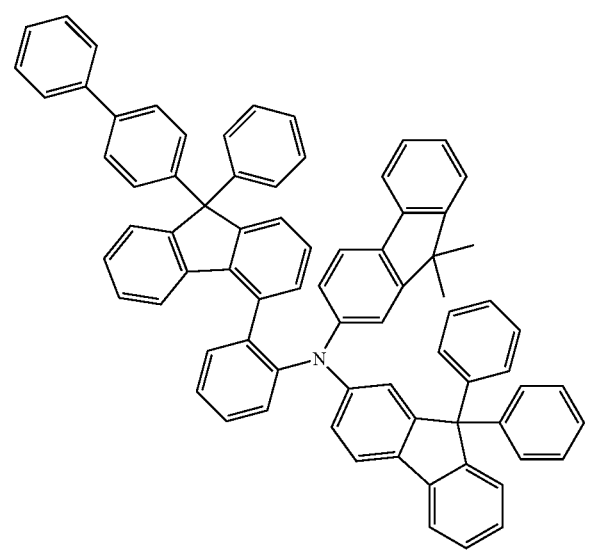
209
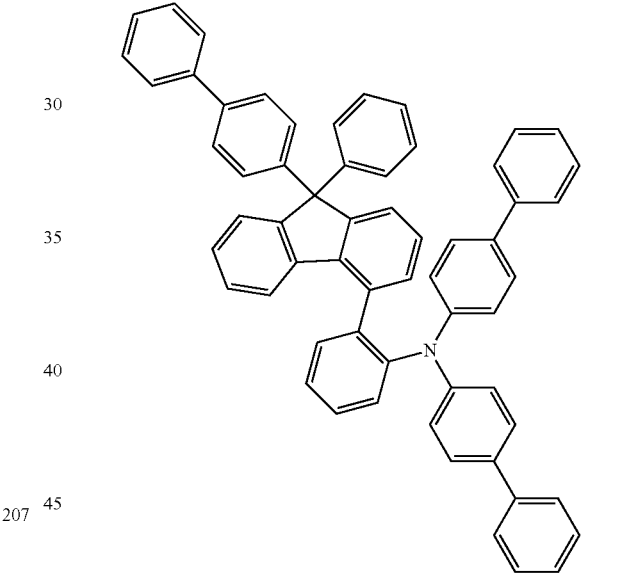
210
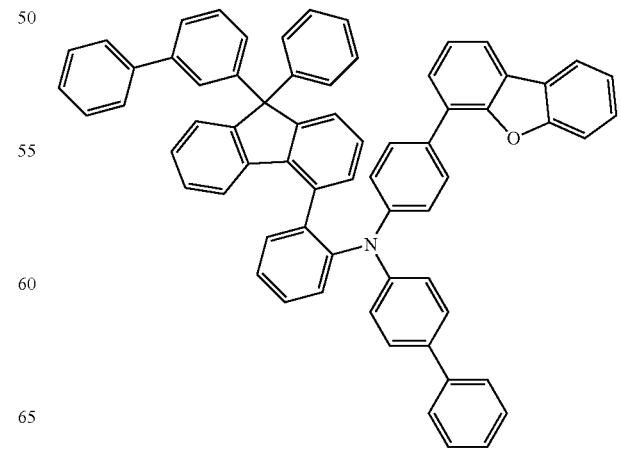

149
-continued
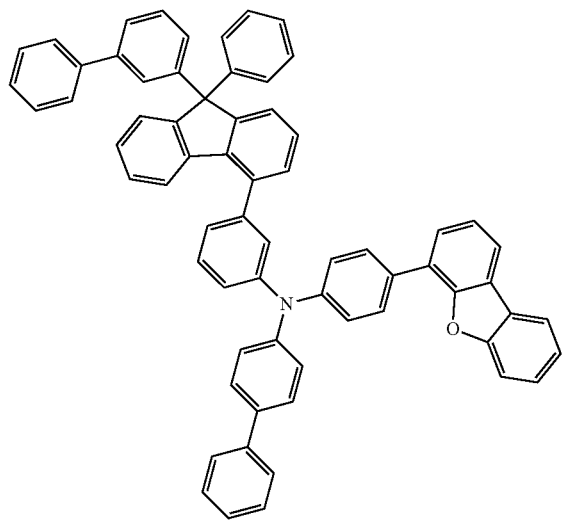
211
150
-continued
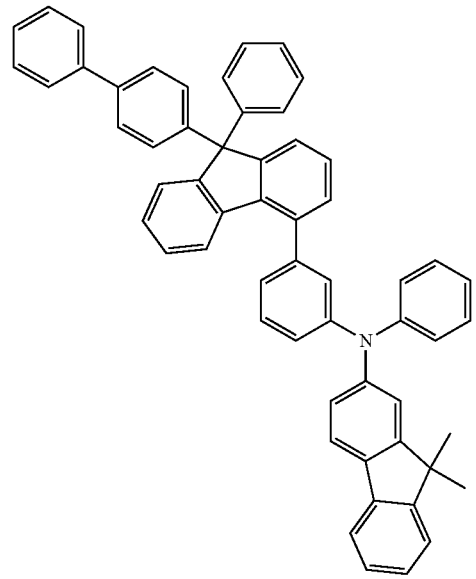
213
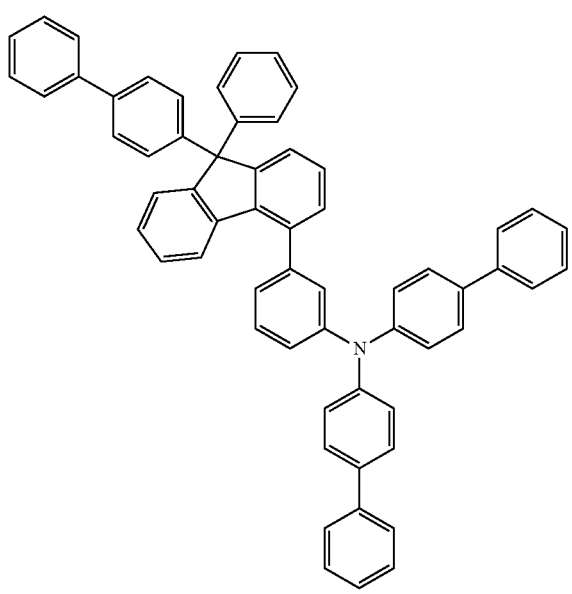
212
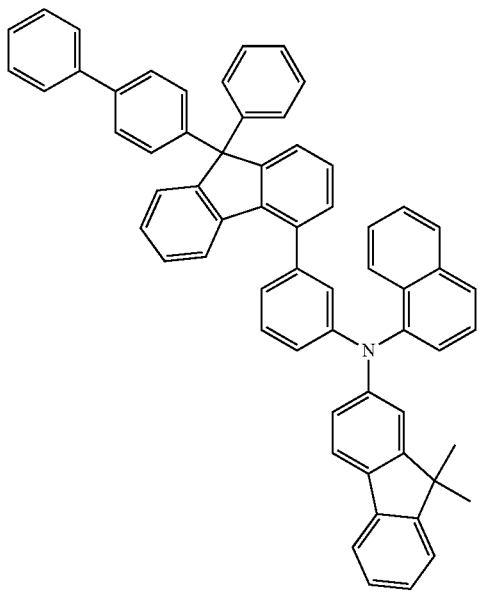
214

215
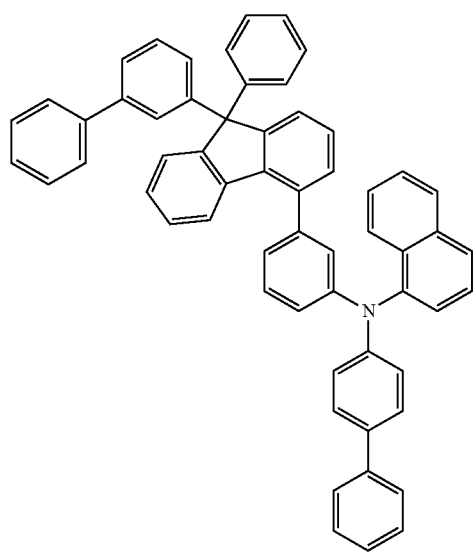
216
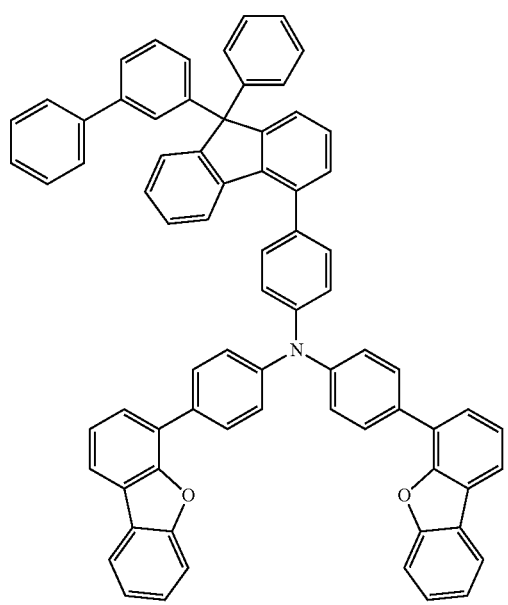
217
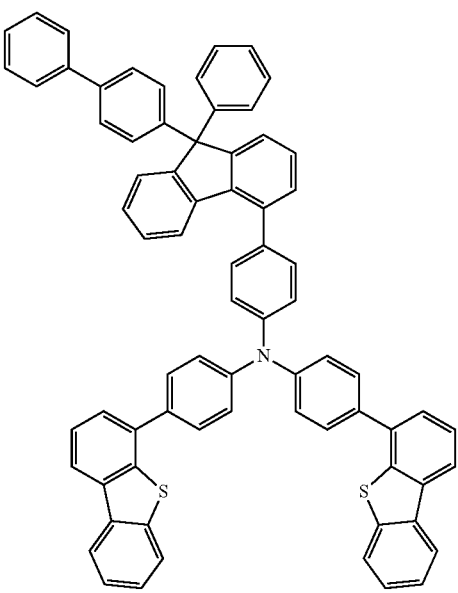
218
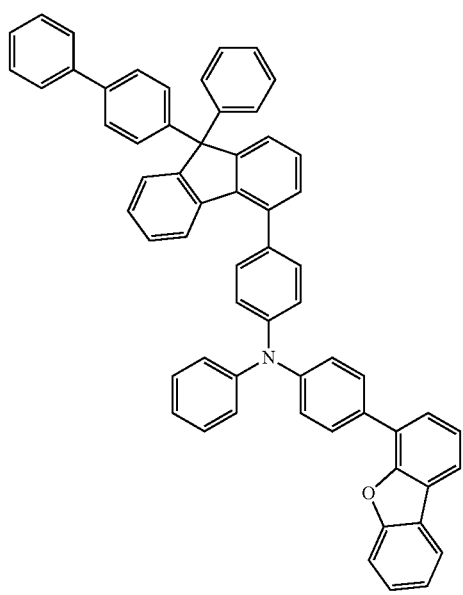

219
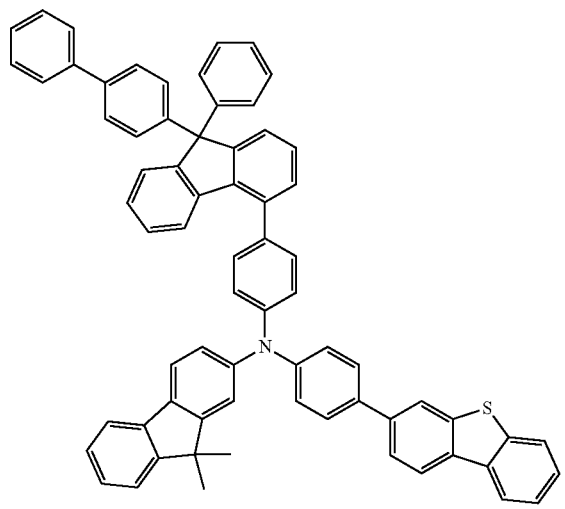
220
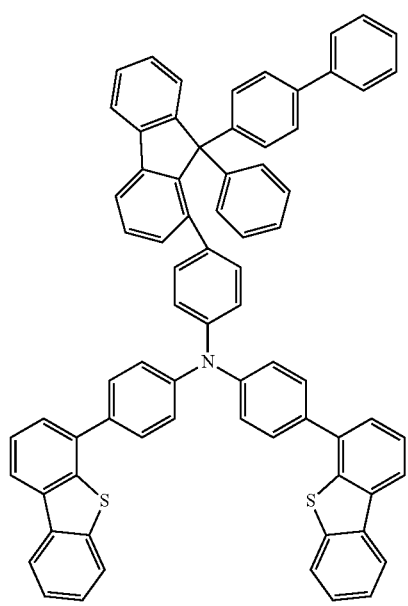
221
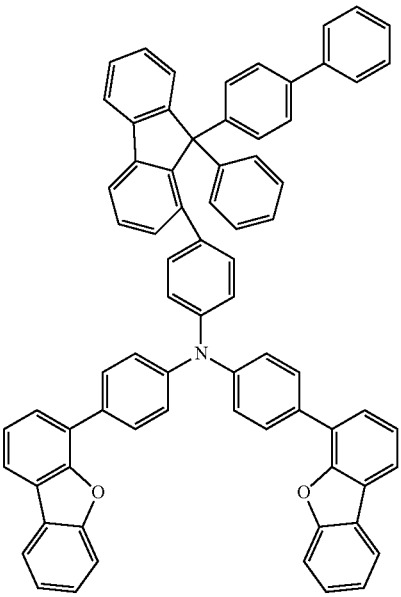
222
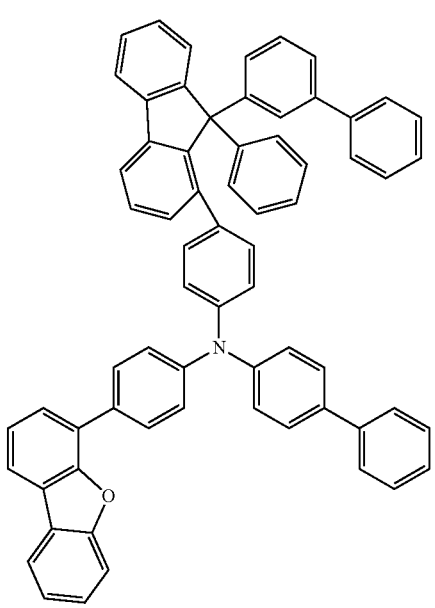

223
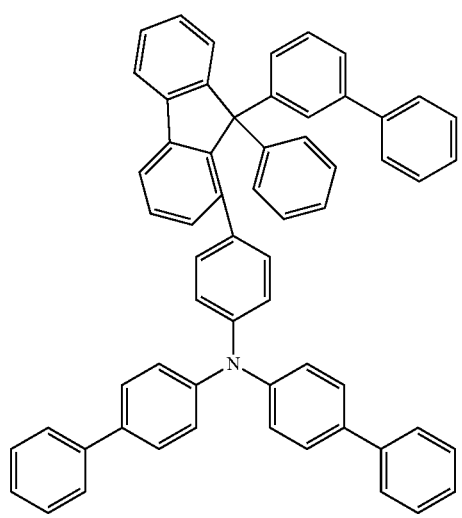
224
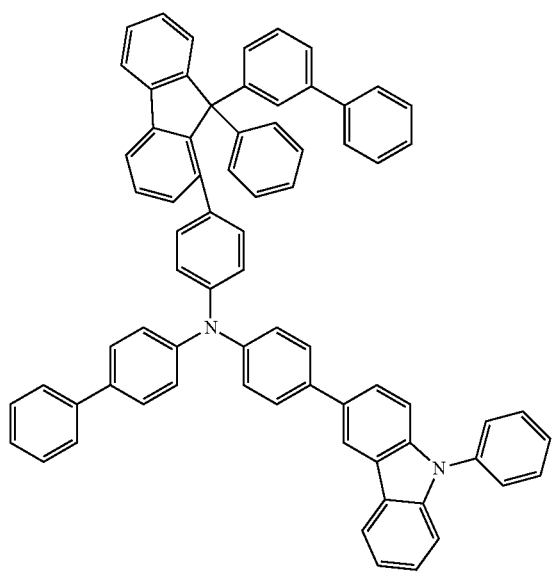
225
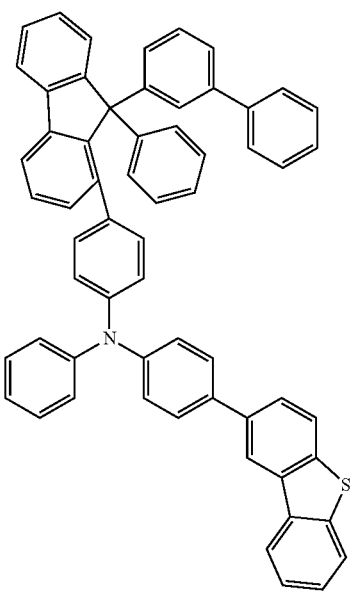
226
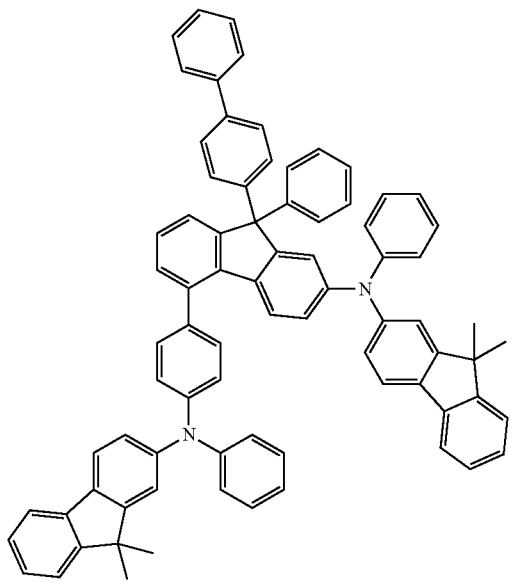

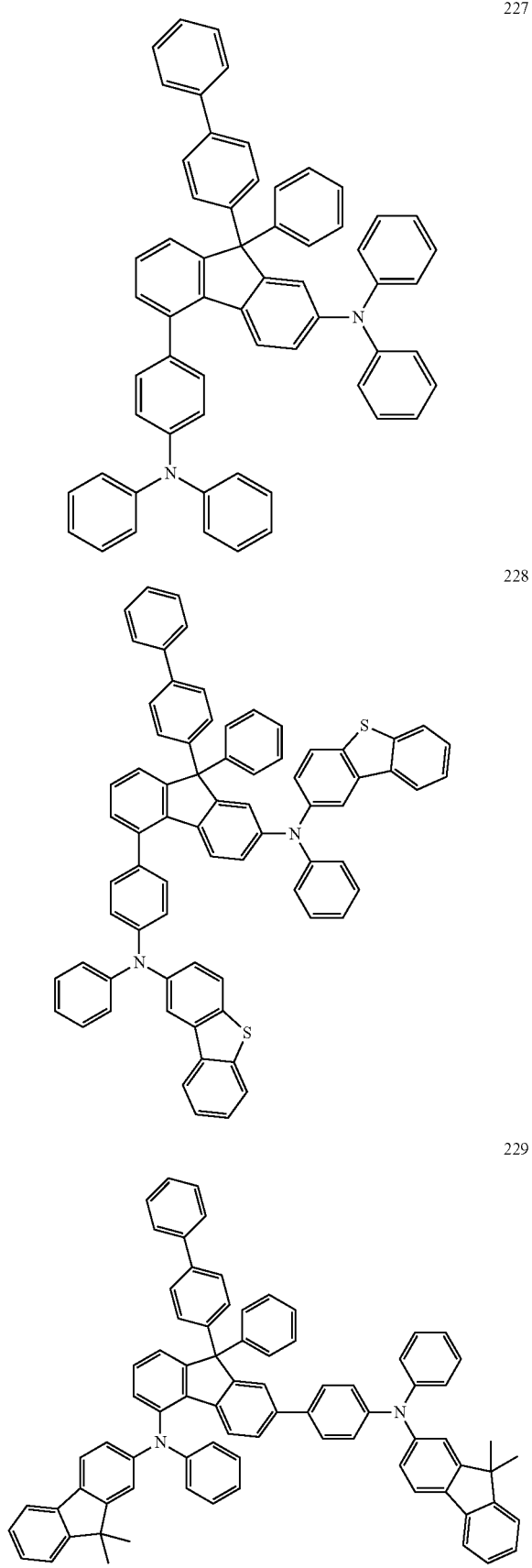
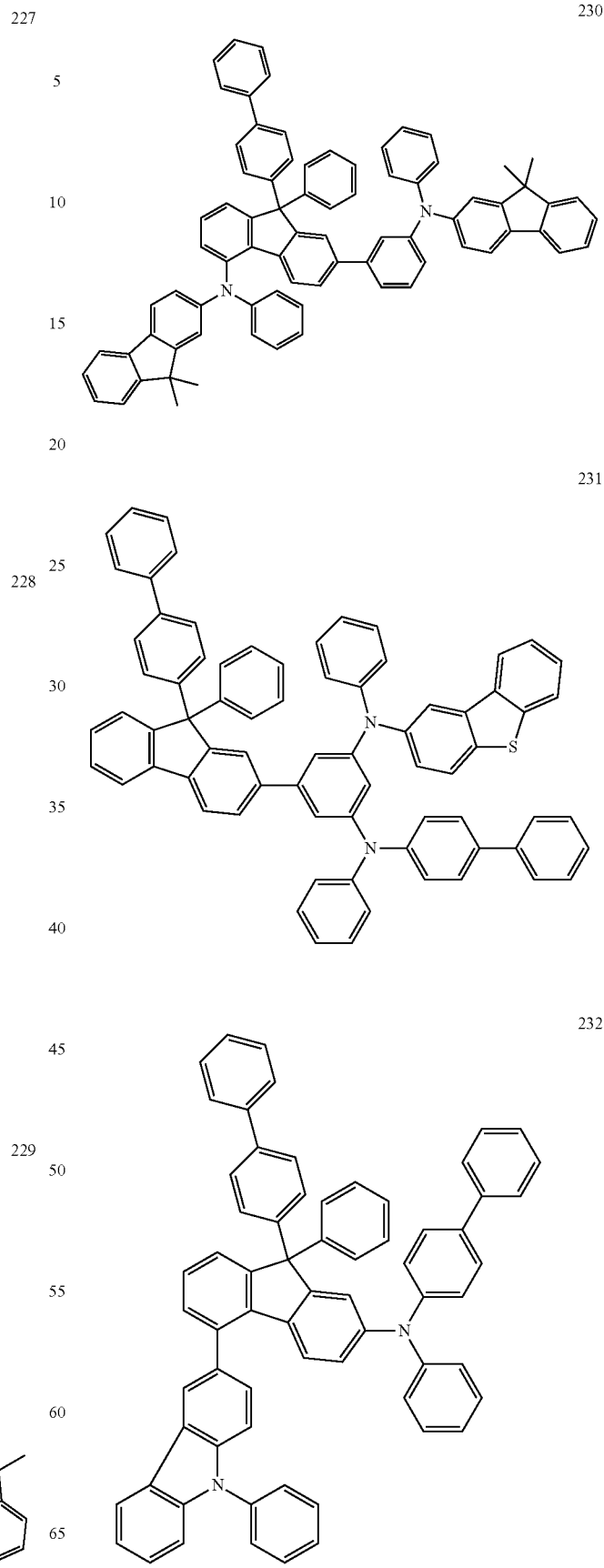

233
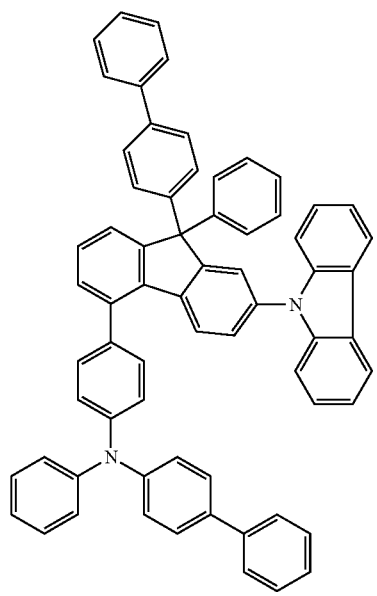
235
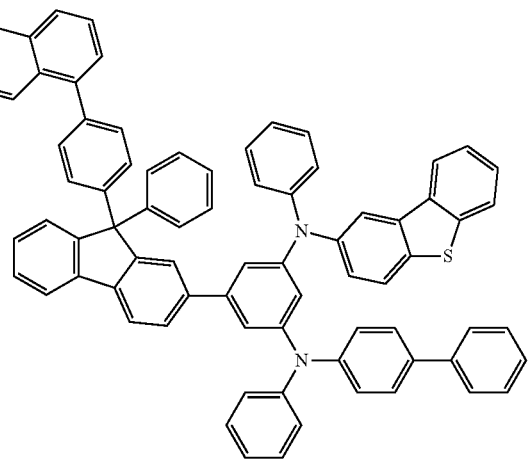
236
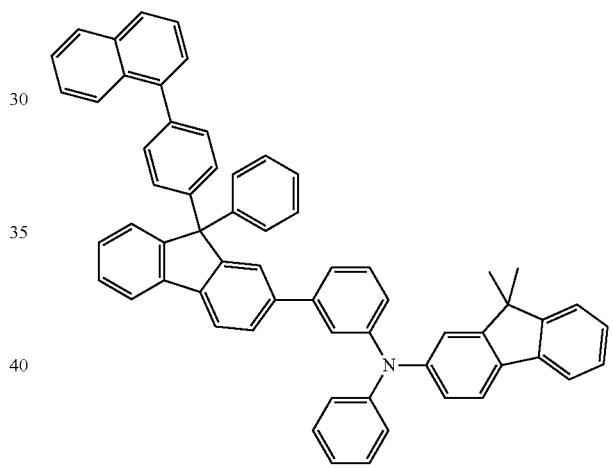
234
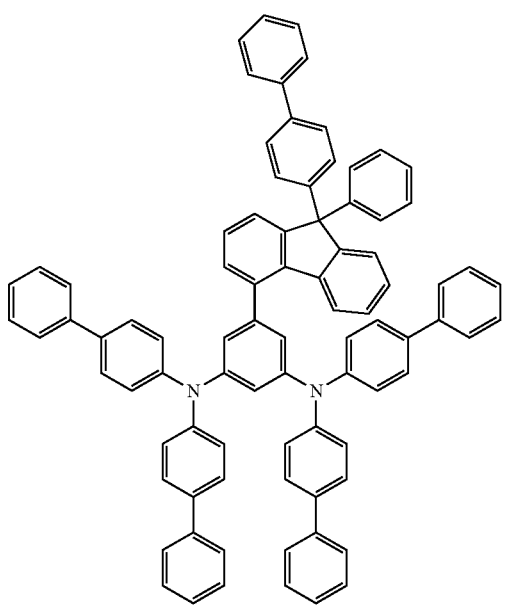
237
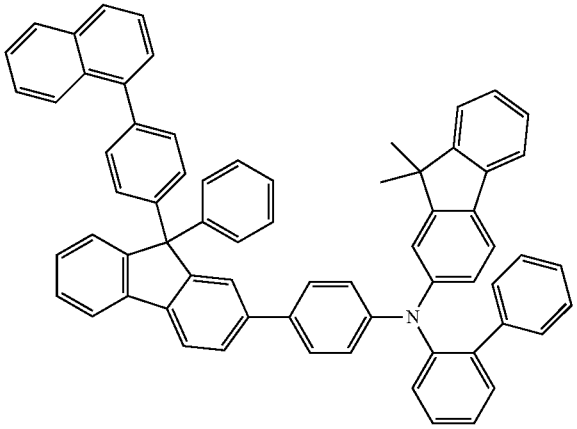

-continued
238
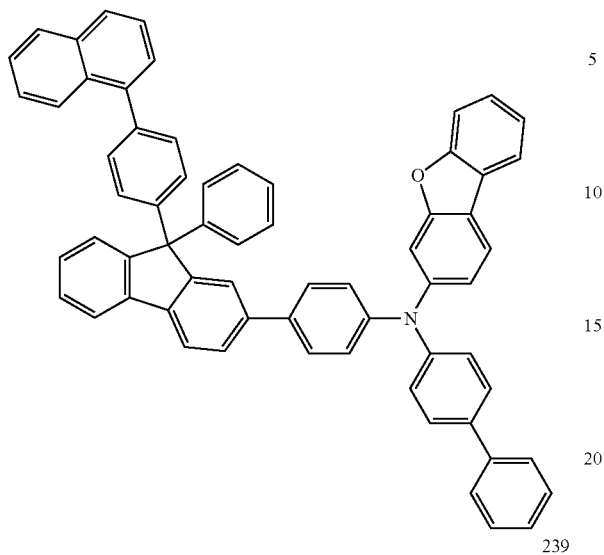
239
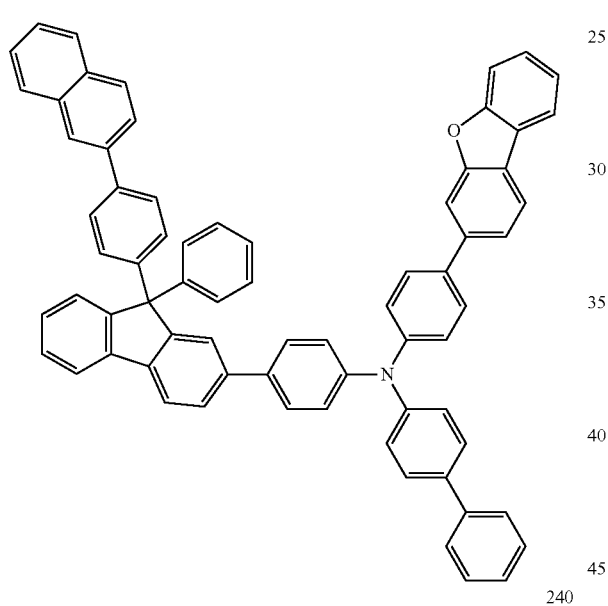
240
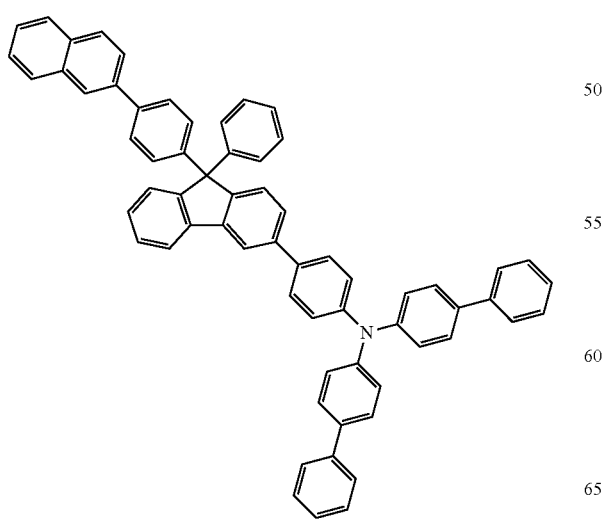
-continued
241
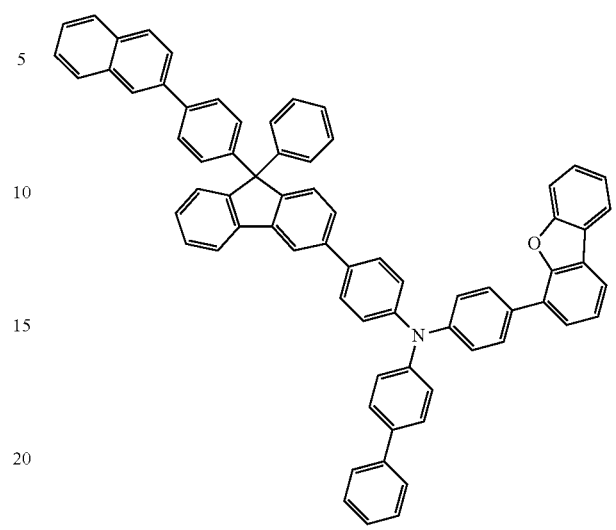
242
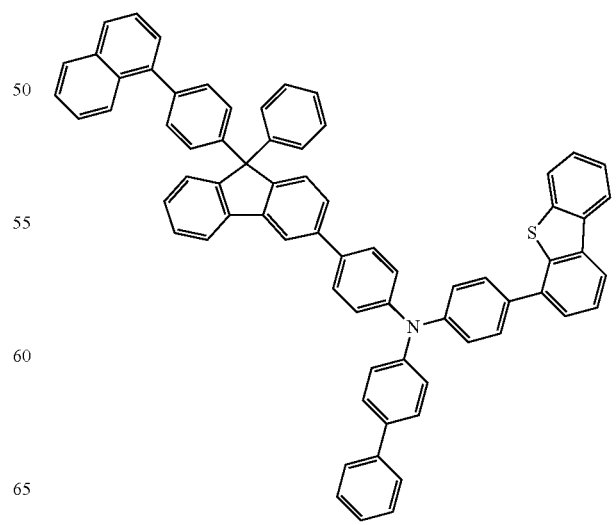

243
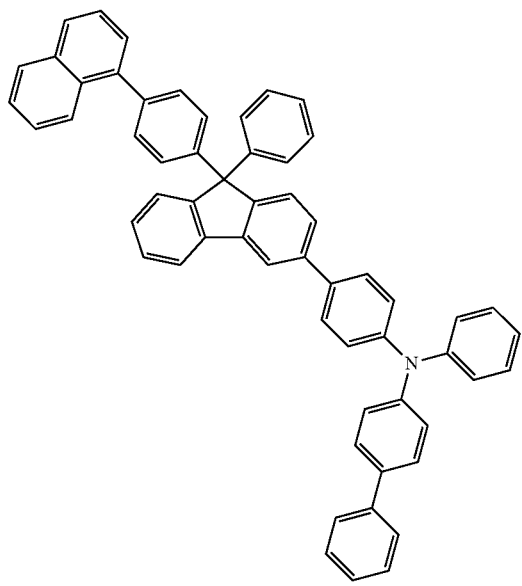
244
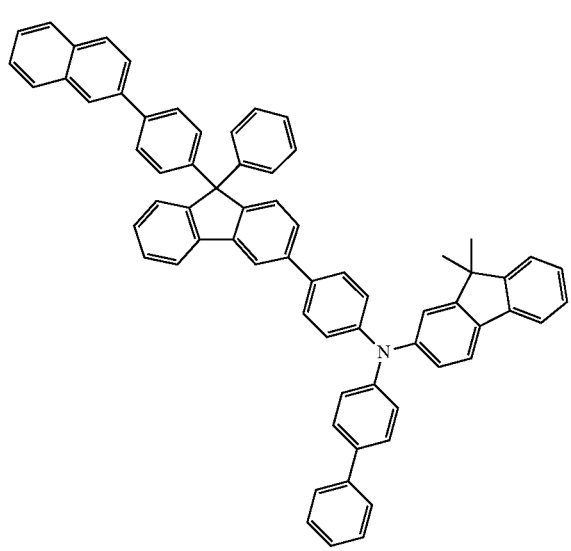
245
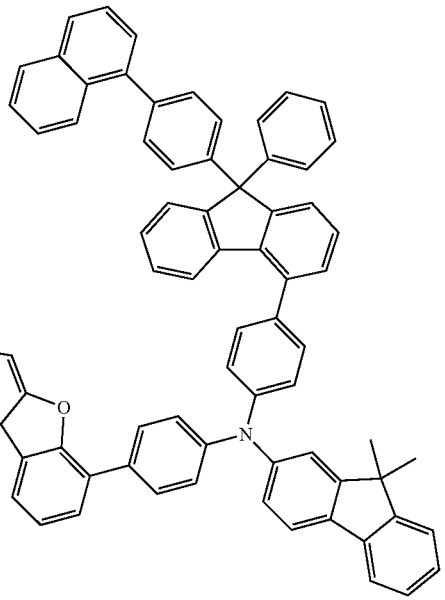
246
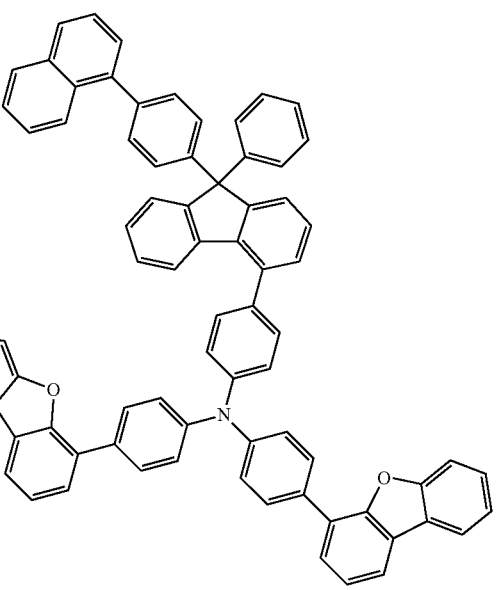
247
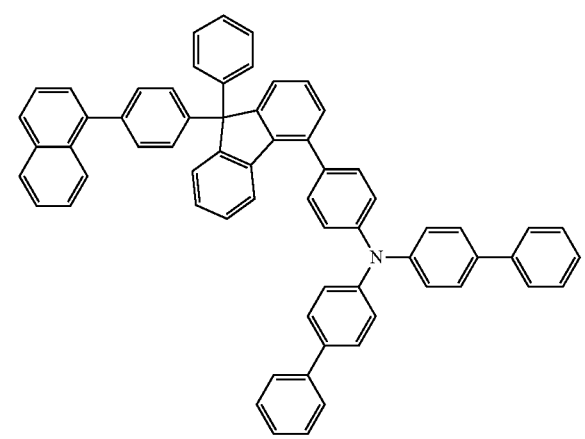

-continued
248
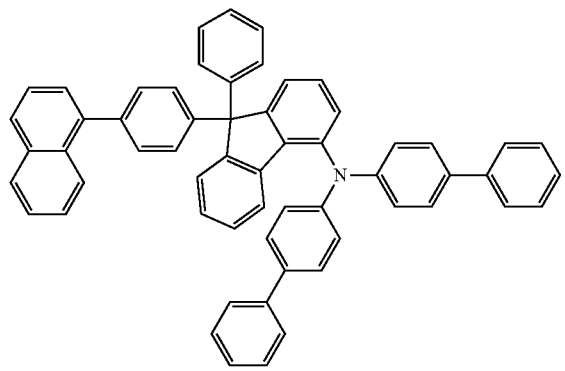
249
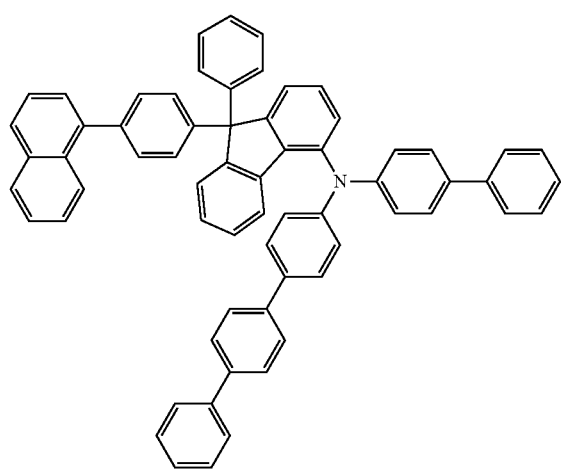
250
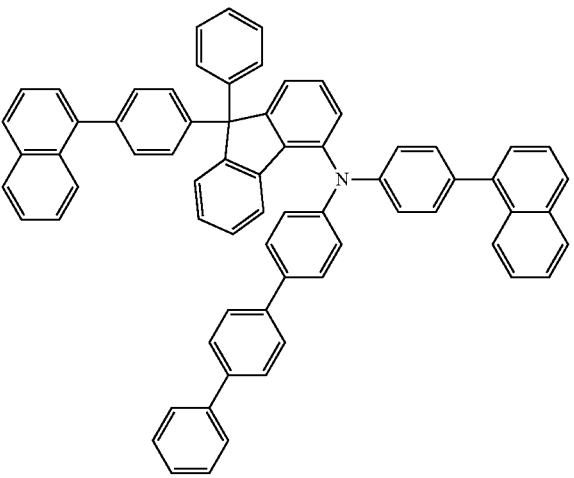
-continued
251
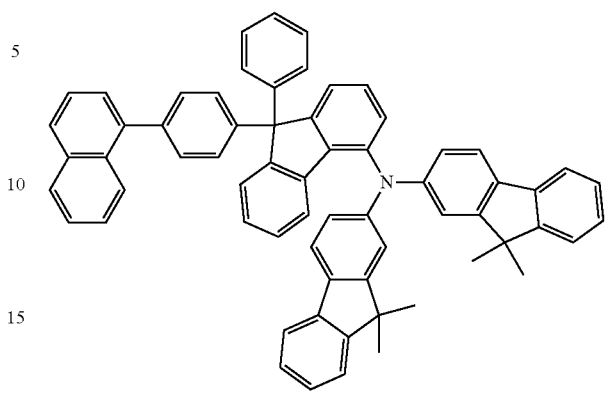
252
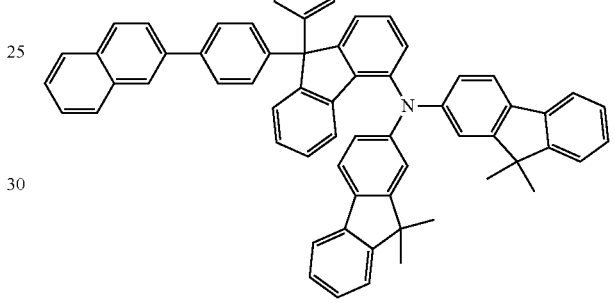
253
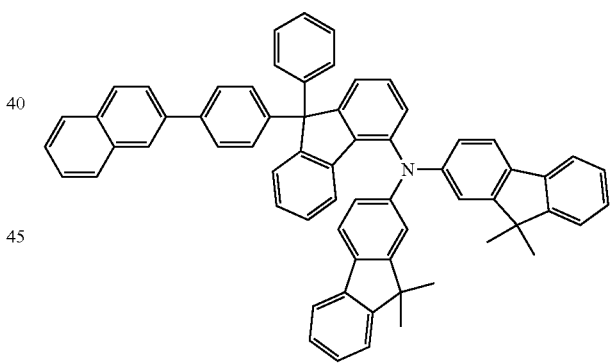
254
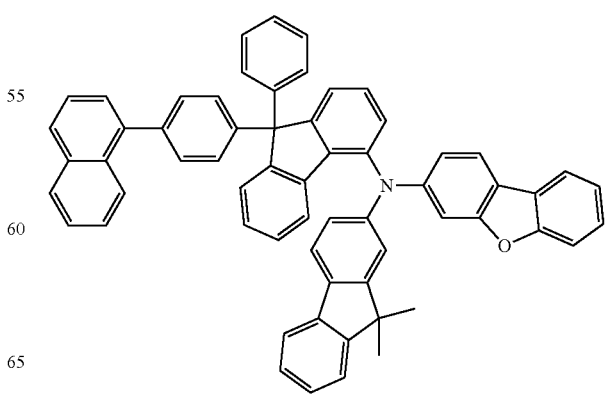

167
-continued
255
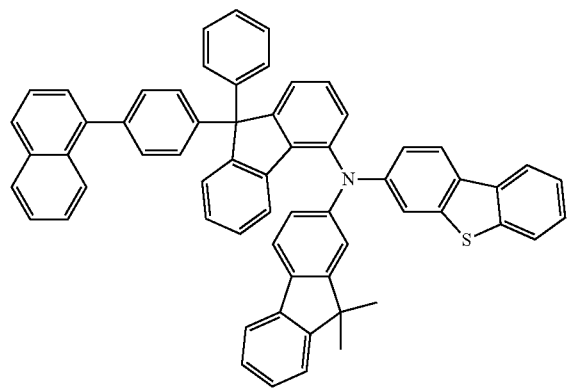
256
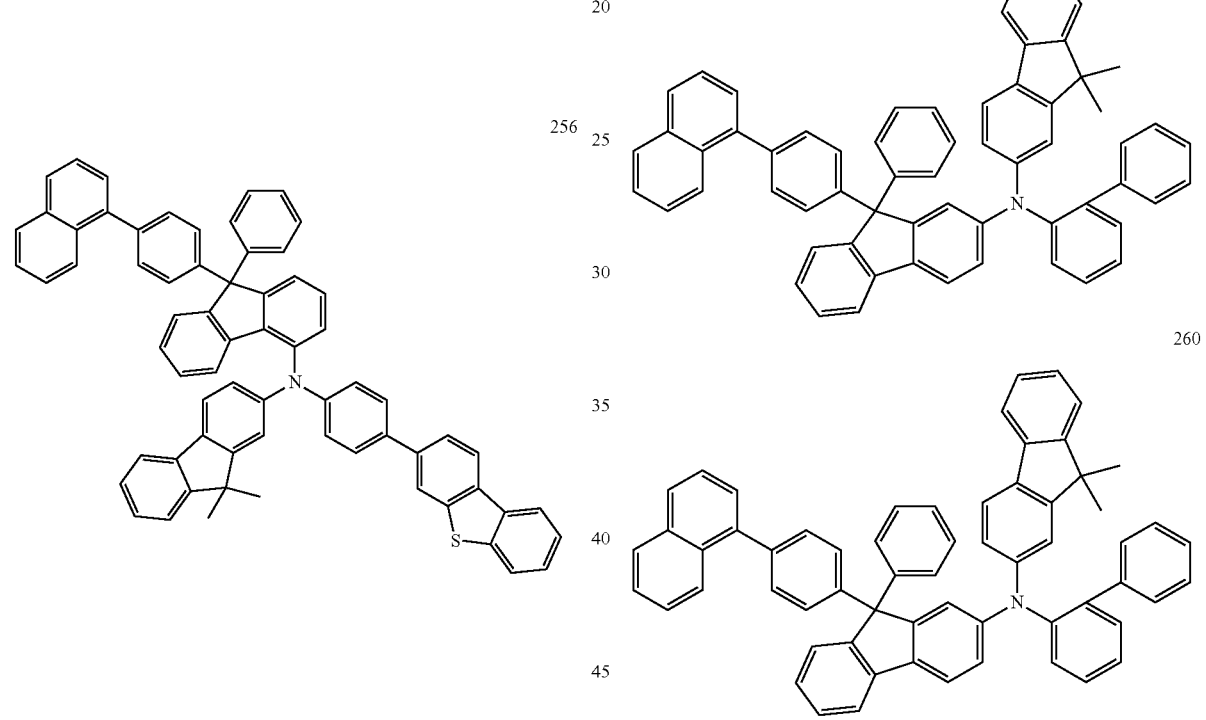
257
168
-continued
258
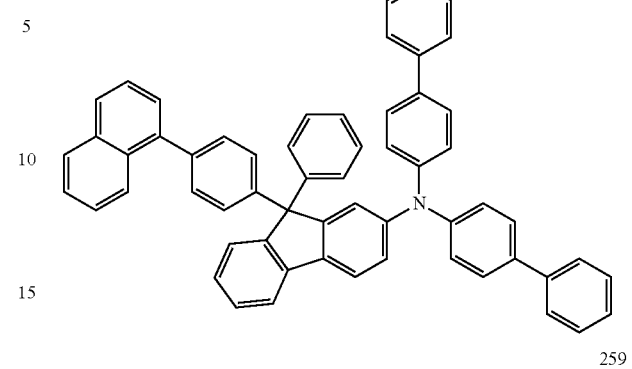
259
260
261
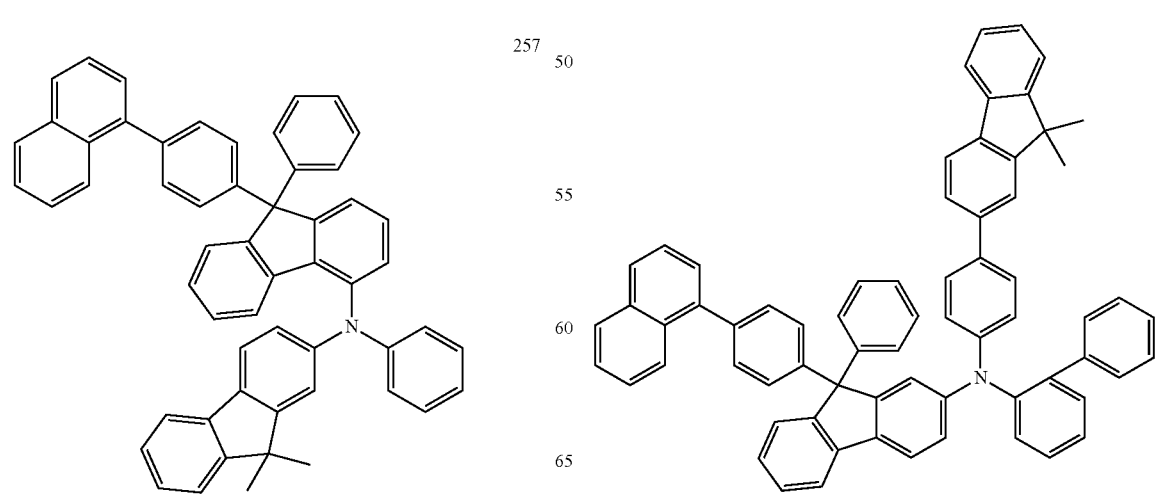

262
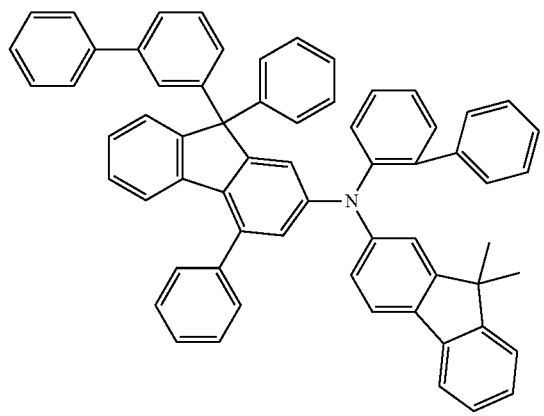
263
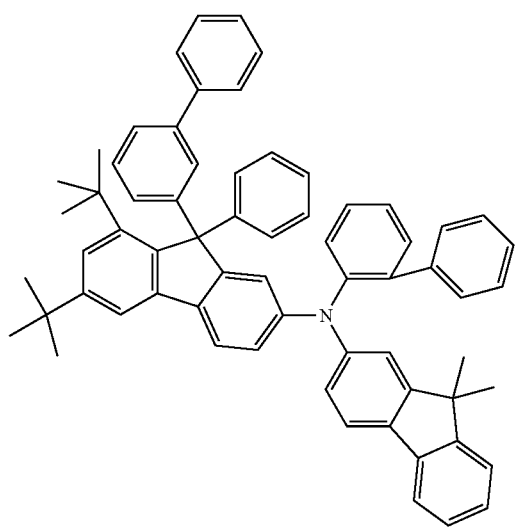
264
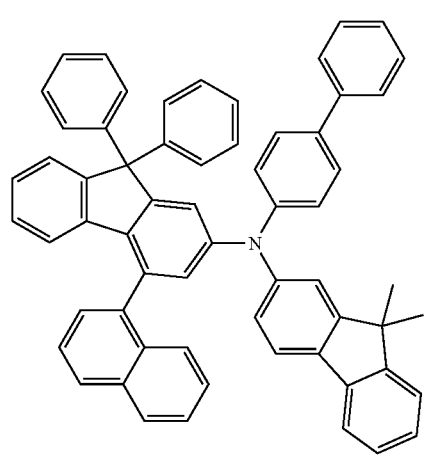
265
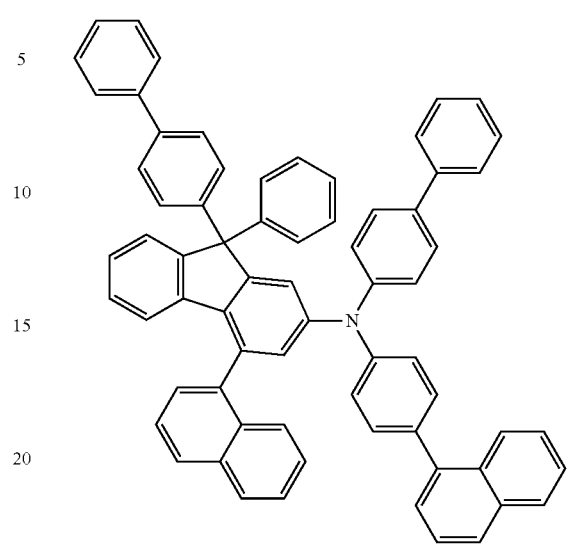
266
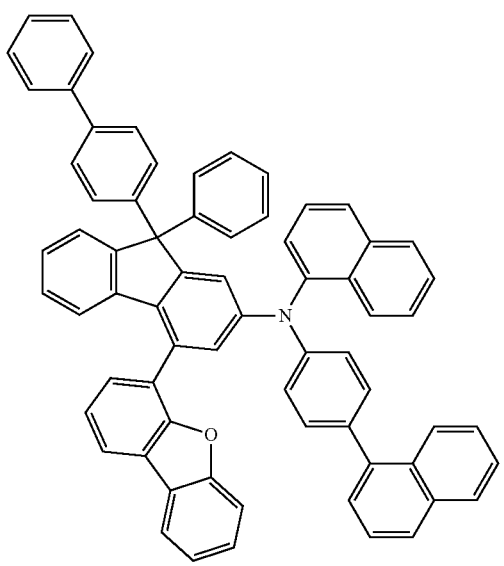

267
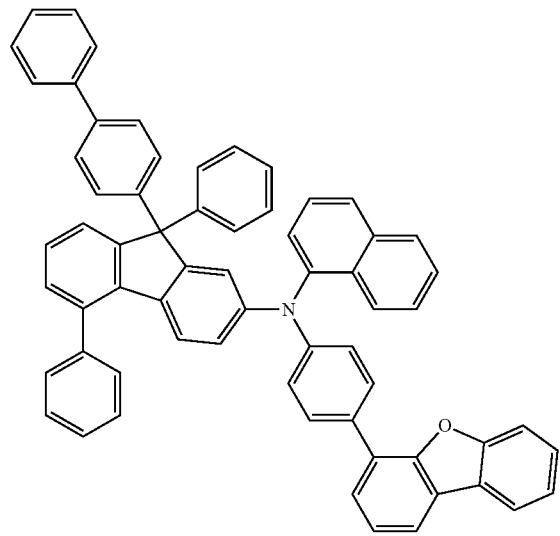
268
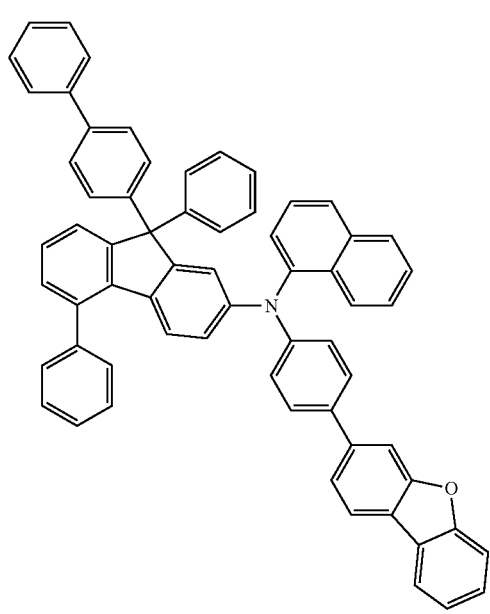
269
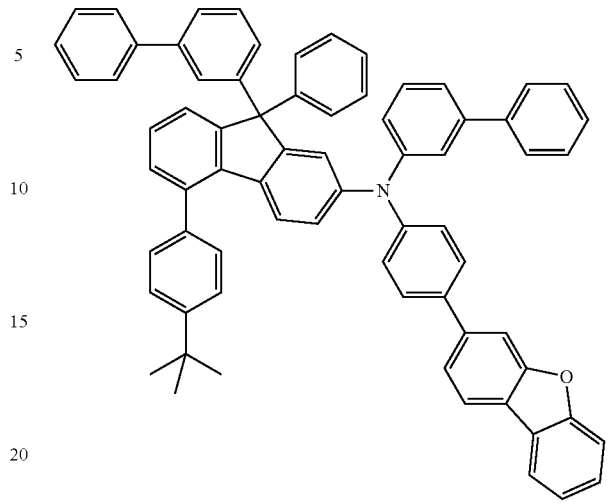
270
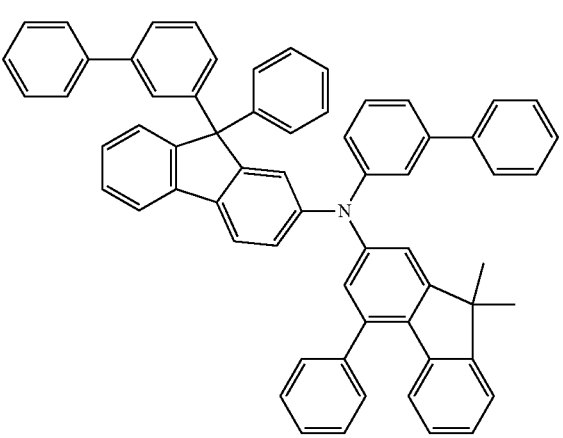
271

272
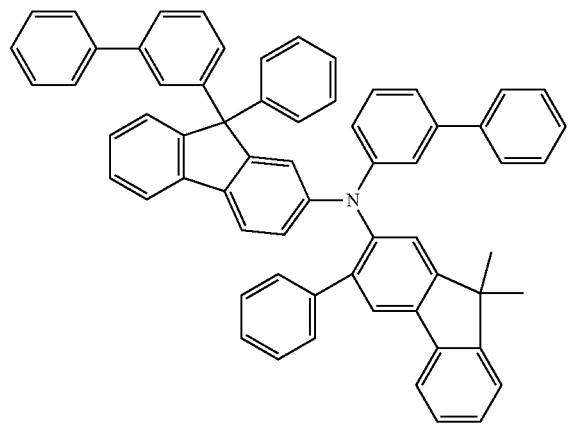
273
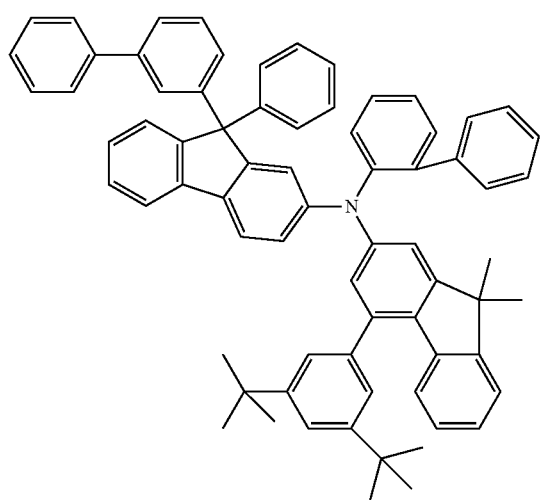
274
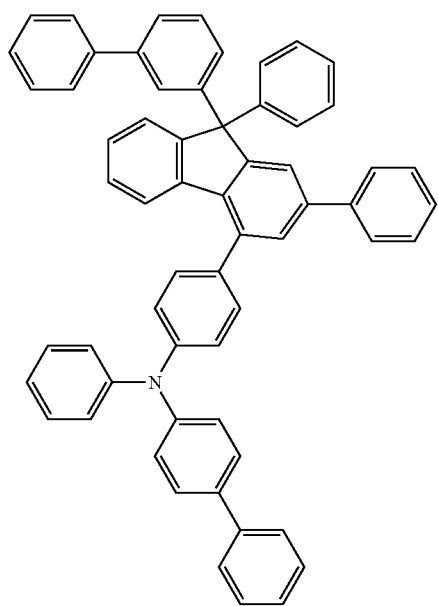
275
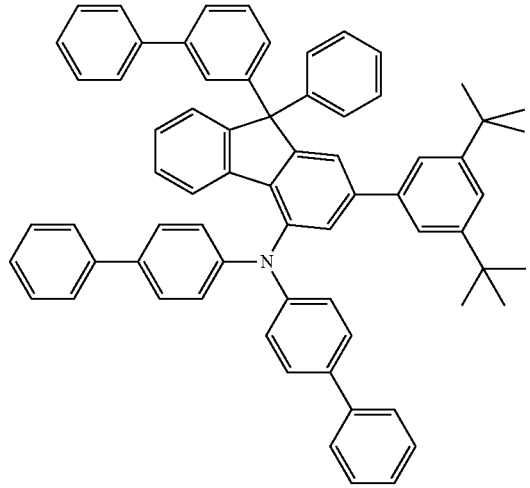
276
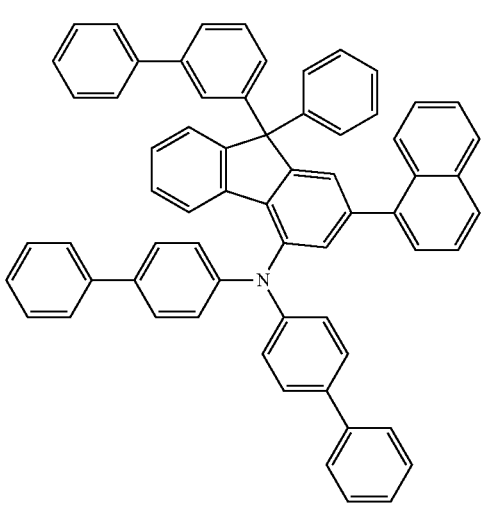
277
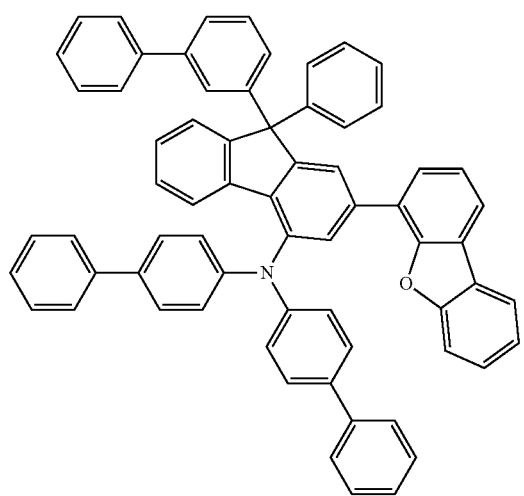

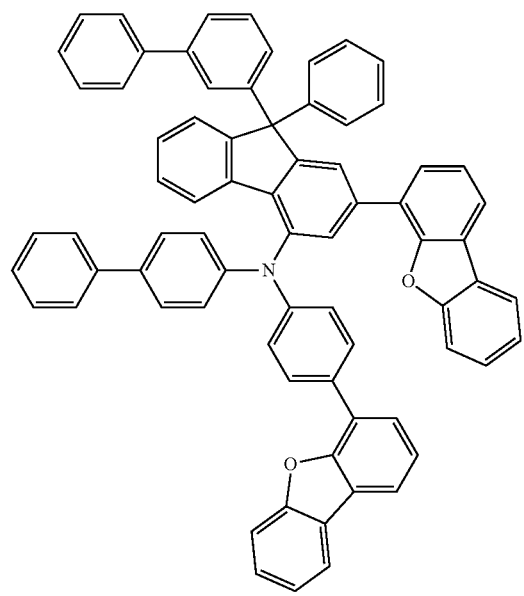
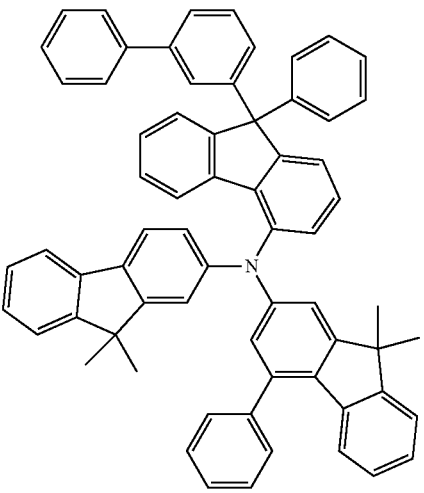
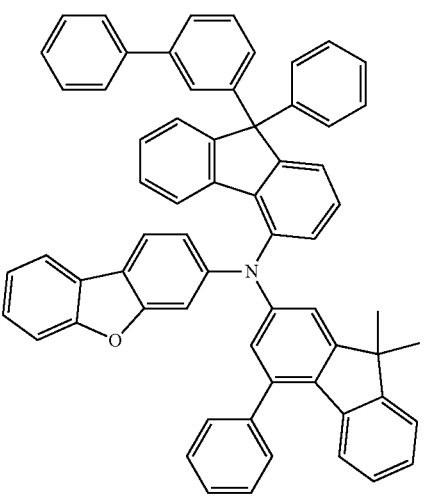
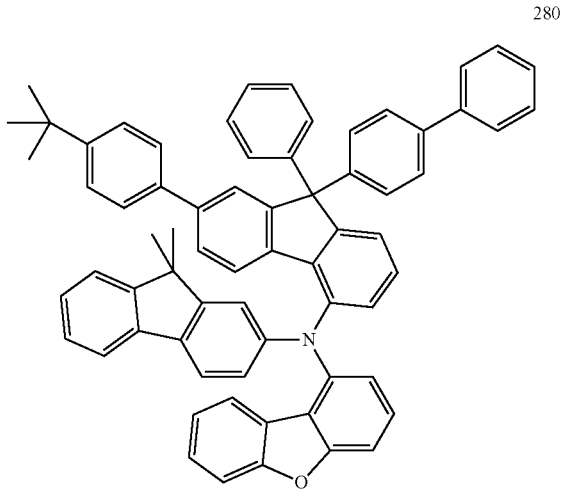

284
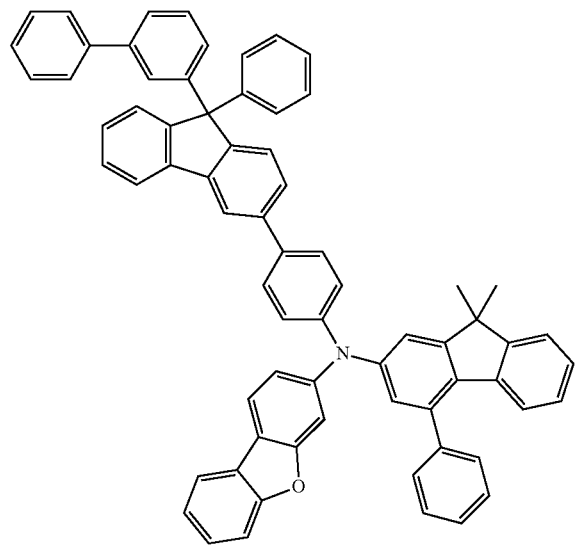
285
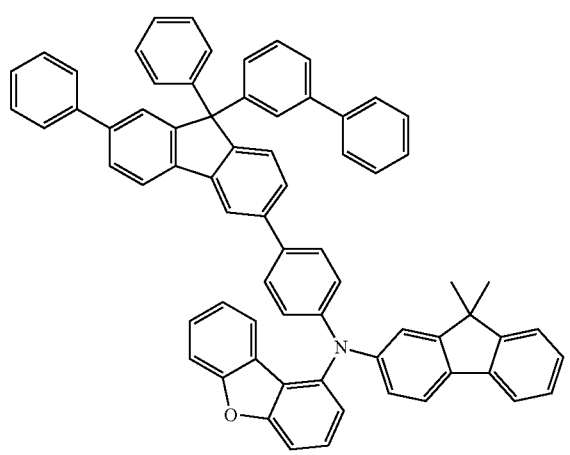
286
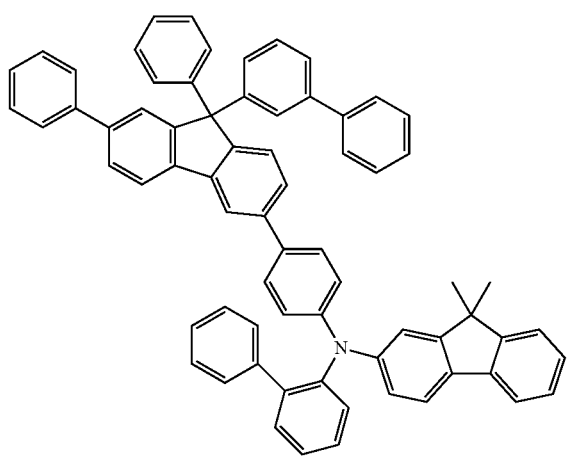
287
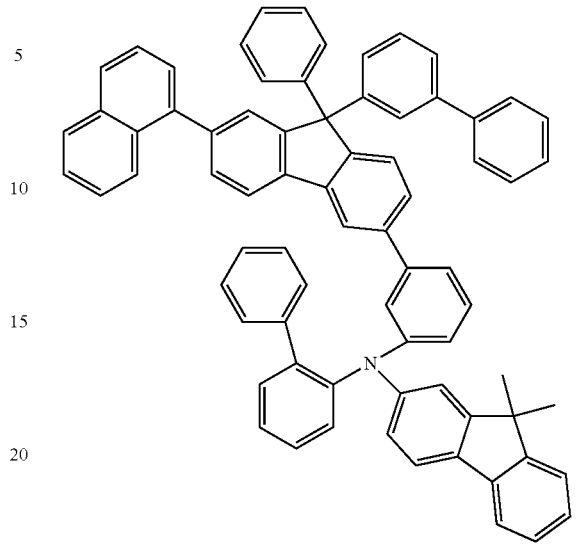
288
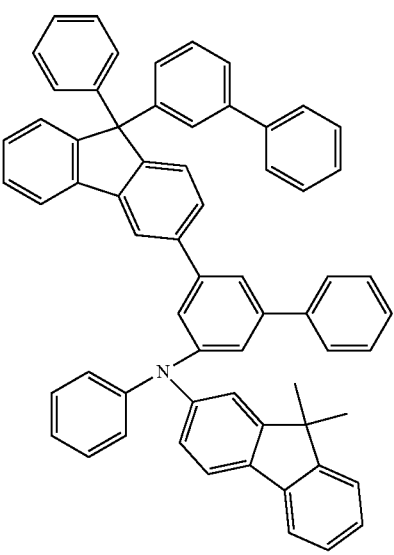
289
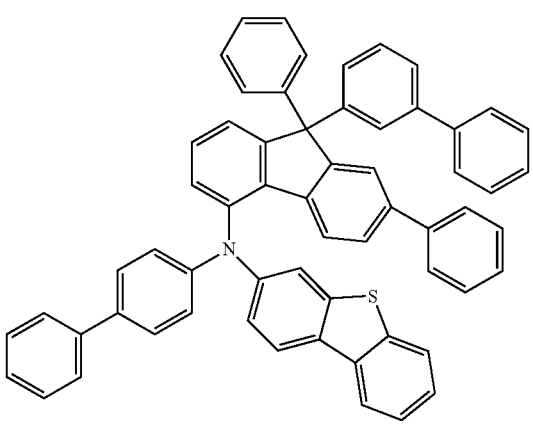

290

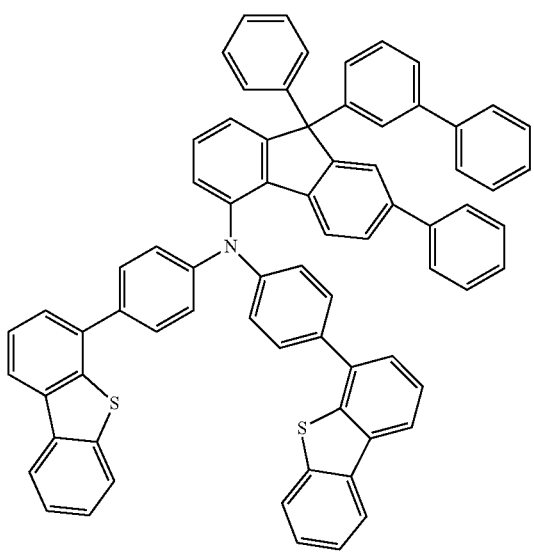

291

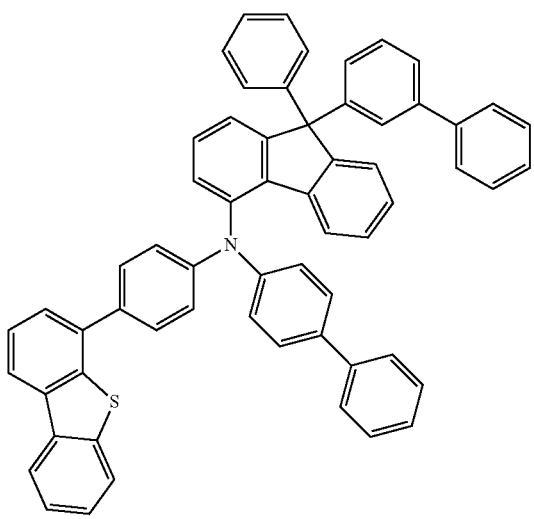

292

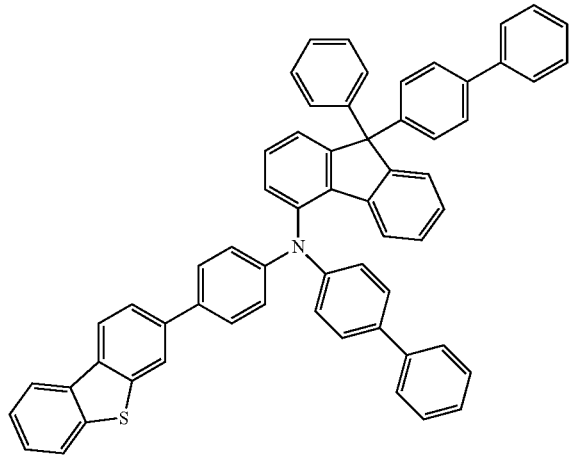

293

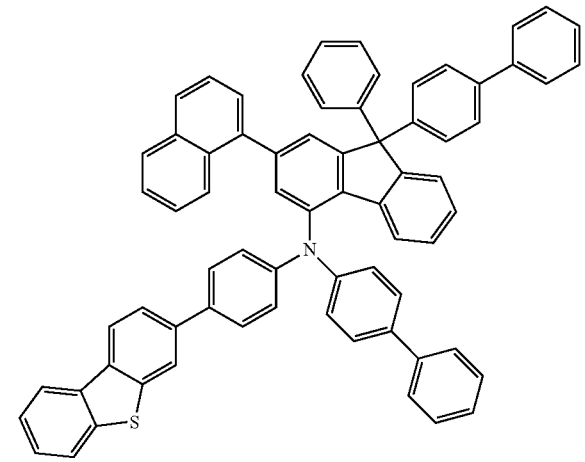

294

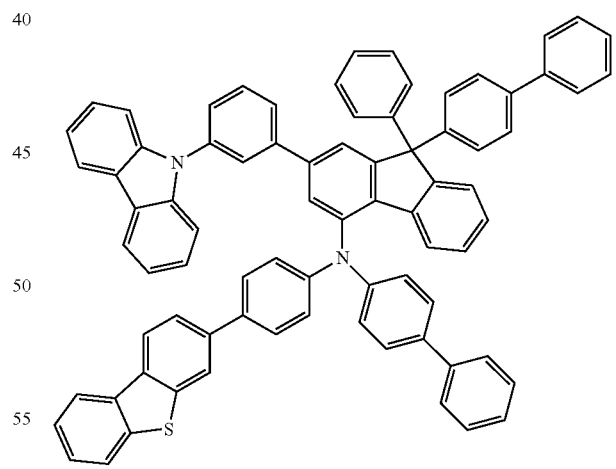

The compounds of the formula (I) can be prepared by means of customary synthesis methods in organic chemistry, for example Buchwald coupling reactions and Suzuki coupling reactions.

A preferred synthesis route for the compounds according to the present application is shown below. The person skilled in the art will be able to modify this synthesis route within the scope of his common art knowledge.

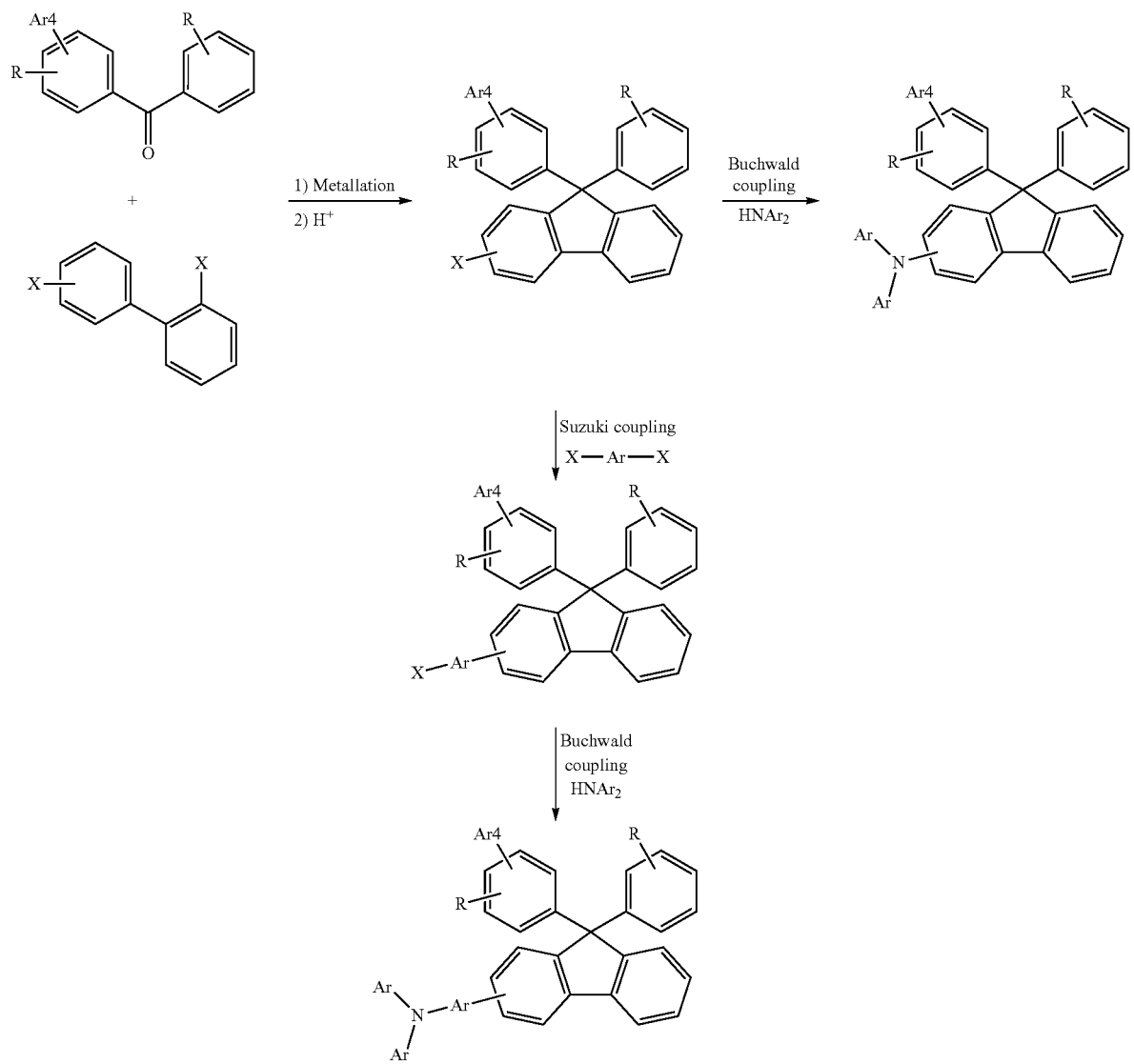

X = reactive group, preferably Cl, Br or I
R = organic radical or H
Ar = Aromatic or heteroaromatic ring system
Ar4 = phenyl or naphthyl, each of which may be substituted In a first step, a metal organyl is added here onto a carbonyl derivative bearing a phenyl- or naphthyl-substituted phenyl group and a phenyl group. This metal organyl has been formed from a biphenyl substituted by two reactive groups, where at least one of the reactive groups is bonded to the biphenyl in the ortho position. After the addition, a cyclization is conducted under acidic conditions. This affords a fluorenyl derivative containing a phenyl group at the bridgehead carbon atom and a phenyl- or naphthyl-substituted phenyl group, and bearing a reactive group on one of its benzene rings. A diarylamino group can be introduced via this reactive group in a Buchwald reaction, or an aromatic or heteroaromatic ring system to which a diarylamino group has been bonded can be introduced in a two-step reaction. The two-step reaction comprises a Suzuki reaction in which an aromatic or heteroaromatic ring system bearing a reactive group is introduced at the position of the reactive group, and a Buchwald reaction in which a diarylamino group is introduced at the position of the reactive group in the aromatic or heteroaromatic ring system.

The reactive group is preferably selected from Cl, Br and I, and is more preferably Br.

The R group is preferably the same or different at each instance and is selected from H, F, heteroaryl groups having 5 to 40 aromatic ring atoms and aryl groups having 6 to 40 aromatic ring atoms. It is possible for one or more R groups to be present on the benzene rings.

The aryl group Ar4 in the scheme shown above is preferably selected from phenyl which is preferably unsubstituted.

The application thus provides a process for preparing a compound of the formula (I), characterized in that a biphenyl derivative bearing two reactive groups, at least one of which is in the ortho position, is metallated and then is added onto a carbonyl derivative containing a phenyl- or naphthyl-substituted phenyl group and a phenyl group bonded to the carbonyl group. The process is preferably characterized in that a cyclization is subsequently effected under acidic conditions, which affords a fluorenyl derivative bearing a phenyl group on its bridgehead carbon atom and a phenyl- or naphthyl-substituted phenyl group and substituted by a reactive group. Preferably, this fluorenyl derivative is then reacted in a Buchwald reaction with a secondary amine having two substituents selected from aromatic and heteroaromatic ring systems to obtain a compound of the formula (I). In an alternative, likewise preferred embodiment, the fluorenyl derivative is reacted in a Suzuki reaction with an aromatic or heteroaromatic ring system having two reactive groups. In this embodiment, the fluorenyl derivative is then reacted in a Buchwald reaction with a secondary amine having two substituents selected from aromatic and heteroaromatic ring systems to obtain a compound of the formula (I).

The above-described compounds of the invention, especially compounds substituted by reactive leaving groups, such as bromine, iodine, chlorine, boronic acid or boronic ester, may find use as monomers for production of corresponding oligomers, dendrimers or polymers. Suitable reactive leaving groups are, for example, bromine, iodine, chlorine, boronic acids, boronic esters, amines, alkenyl or alkynyl groups having a terminal C═C double bond or C—C triple bond, oxiranes, oxetanes, groups which enter into a cycloaddition, for example a 1,3-dipolar cycloaddition, for example dienes or azides, carboxylic acid derivatives, alcohols and silanes.

The invention therefore further provides oligomers, polymers or dendrimers containing one or more compounds of formula (I), wherein the bond(s) to the polymer, oligomer or dendrimer may be localized at any desired positions substituted by R1, R2, R3 or R4 in formula (I). According to the linkage of the compound of formula (I), the compound is part of a side chain of the oligomer or polymer or part of the main chain. An oligomer in the context of this invention is understood to mean a compound formed from at least three monomer units. A polymer in the context of the invention is understood to mean a compound formed from at least ten monomer units. The polymers, oligomers or dendrimers of the invention may be conjugated, partly conjugated or nonconjugated. The oligomers or polymers of the invention may be linear, branched or dendritic. In the structures having linear linkage, the units of formula (I) may be joined directly to one another, or they may be joined to one another via a bivalent group, for example via a substituted or unsubstituted alkylene group, via a heteroatom or via a bivalent aromatic or heteroaromatic group. In branched and dendritic structures, it is possible, for example, for three or more units of formula (I) to be joined via a trivalent or higher-valency group, for example via a trivalent or higher-valency aromatic or heteroaromatic group, to give a branched or dendritic oligomer or polymer. For the repeat units of formula (I) in oligomers, dendrimers and polymers, the same preferences apply as described above for compounds of formula (I).

For preparation of the oligomers or polymers, the monomers of the invention are homopolymerized or copolymerized with further monomers. Suitable and preferred comonomers are selected from fluorenes, spirobifluorenes, paraphenylenes, carbazoles, thiophenes, dihydrophenanthrenes, cis- and trans-indenofluorenes, ketones, phenanthrenes or else two or more of these units. The polymers, oligomers and dendrimers typically contain still further units, for example emitting (fluorescent or phosphorescent) units, for example vinyltriarylamines or phosphorescent metal complexes, and/or charge transport units, especially those based on triarylamines.

The polymers, oligomers and dendrimers of the invention have advantageous properties, especially high lifetimes, high efficiencies and good colour coordinates.

The polymers and oligomers of the invention are generally prepared by polymerization of one or more monomer types, of which at least one monomer leads to repeat units of the formula (I) in the polymer. Suitable polymerization reactions are known to those skilled in the art and are described in the literature. Particularly suitable and preferred polymerization reactions which lead to C—C and C—N couplings are as follows:

(A) SUZUKI polymerization;
(B) YAMAMOTO polymerization;
(C) STILLE polymerization; and
(D) HARTWIG-BUCHWALD polymerization.

How the polymerization can be conducted by these methods and how the polymers can then be separated from the reaction medium and purified is known to those skilled in the art and is described in detail in the literature.

For the processing of the compounds of the invention from a liquid phase, for example by spin-coating or by printing methods, formulations of the compounds of the invention are required. These formulations may, for example, be solutions, dispersions or emulsions. For this purpose, it may be preferable to use mixtures of two or more solvents. Suitable and preferred solvents are, for example, toluene, anisole, o-, m- or p-xylene, methyl benzoate, mesitylene, tetralin, veratrole, THF, methyl-THF, THP, chlorobenzene, dioxane, phenoxytoluene, especially 3-phenoxytoluene, (−)-fenchone, 1,2,3,5-tetramethylbenzene, 1,2,4,5-tetramethylbenzene, 1-methylnaphthalene, 2-methylbenzothiazole, 2-phenoxyethanol, 2-pyrrolidinone, 3-methylanisole, 4-methylanisole, 3,4-dimethylanisole, 3,5-dimethylanisole, acetophenone, alpha-terpineol, benzothiazole, butyl benzoate, cumene, cyclohexanol, cyclohexanone, cyclohexylbenzene, decalin, dodecylbenzene, ethyl benzoate, indane, methyl benzoate, NMP, p-cymene, phenetole, 1,4-diisopropylbenzene, dibenzyl ether, diethylene glycol butyl methyl ether, triethylene glycol butyl methyl ether, diethylene glycol dibutyl ether, triethylene glycol dimethyl ether, diethylene glycol monobutyl ether, tripropylene glycol dimethyl ether, tetraethylene glycol dimethyl ether, 2-isopropylnaphthalene, pentylbenzene, hexylbenzene, heptylbenzene, octylbenzene, 1,1-bis(3,4-dimethylphenyl)ethane, or mixtures of these solvents.

The invention therefore further provides a formulation, especially a solution, dispersion or emulsion, comprising at least one compound of formula (I) or at least one polymer, oligomer or dendrimer containing at least one unit of formula (I) and at least one solvent, preferably an organic solvent. The way in which such solutions can be prepared is known to those skilled in the art. The compound of formula (I) is suitable for use in an electronic device, especially an organic electroluminescent device (OLED). Depending on the substitution, the compound of the formula (I) can be used in different functions and layers. Preference is given to use as a hole-transporting material in a hole-transporting layer and/or as matrix material in an emitting layer, more preferably in combination with a phosphorescent emitter.

The invention therefore further provides for the use of a compound of formula (I) in an electronic device. This electronic device is preferably selected from the group consisting of organic integrated circuits (OICs), organic field-effect transistors (OFETs), organic thin-film transistors (OTFTs), organic light-emitting transistors (OLETs), organic solar cells (OSCs), organic optical detectors, organic photoreceptors, organic field-quench devices (OFQDs), organic light-emitting electrochemical cells (OLECs), organic laser diodes (O-lasers) and more preferably organic electroluminescent devices (OLEDs).

The invention further provides an electronic device comprising at least one compound of formula (I). This electronic device is preferably selected from the abovementioned devices.

Particular preference is given to an organic electroluminescent device comprising anode, cathode and at least one emitting layer, characterized in that at least one organic layer comprising at least one compound of formula (I) is present in the device. Preference is given to an organic electroluminescent device comprising anode, cathode and at least one emitting layer, characterized in that at least one organic layer in the device, selected from hole-transporting and emitting layers, comprises at least one compound of formula (I).

A hole-transporting layer is understood here to mean all layers disposed between anode and emitting layer, preferably hole injection layer, hole transport layer and electron blocker layer. A hole injection layer is understood here to mean a layer that directly adjoins the anode. A hole transport layer is understood here to mean a layer which is between the anode and emitting layer but does not directly adjoin the anode, and preferably does not directly adjoin the emitting layer either. An electron blocker layer is understood here to mean a layer which is between the anode and emitting layer and directly adjoins the emitting layer. An electron blocker layer preferably has a high-energy LUMO and hence prevents electrons from exiting from the emitting layer.

Apart from the cathode, anode and emitting layer, the electronic device may comprise further layers. These are selected, for example, from in each case one or more hole injection layers, hole transport layers, hole blocker layers, electron transport layers, electron injection layers, electron blocker layers, exciton blocker layers, interlayers, charge generation layers and/or organic or inorganic p/n junctions. However, it should be pointed out that not every one of these layers need necessarily be present and the choice of layers always depends on the compounds used and especially also on whether the device is a fluorescent or phosphorescent electroluminescent device.

The sequence of layers in the electronic device is preferably as follows:
—anode—
—hole injection layer—
—hole transport layer—
—optionally further hole transport layers—
—emitting layer—
—optionally hole blocker layer—
—electron transport layer—
—electron injection layer—
—cathode—.

At the same time, it should be pointed out again that not all the layers mentioned need be present and/or that further layers may additionally be present.

The organic electroluminescent device of the invention may contain two or more emitting layers. More preferably, these emission layers have several emission maxima between 380 nm and 750 nm overall, such that the overall result is white emission; in other words, various emitting compounds which may fluoresce or phosphoresce and which emit blue, green yellow, orange or red light are used in the emitting layers. Especially preferred are three-layer systems, i.e. systems having three emitting layers, wherein one of the three layers in each case shows blue emission, one of the three layers in each case shows green emission, and one of the three layers in each case shows orange or red emission. The compounds of the invention here are preferably present in a hole-transporting layer or in the emitting layer. It should be noted that, for the production of white light, rather than a plurality of colour-emitting emitter compounds, an emitter compound used individually which emits over a broad wavelength range may also be suitable.

It is preferable that the compound of the formula (I) is used as hole transport material. The emitting layer here may be a fluorescent emitting layer, or it may be a phosphorescent emitting layer. The emitting layer is preferably a blue-fluorescing layer or a green-phosphorescing layer.

When the device containing the compound of the formula (I) contains a phosphorescent emitting layer, it is preferable that this layer contains two or more, preferably exactly two, different matrix materials (mixed matrix system). Preferred embodiments of mixed matrix systems are described in detail further down.

If the compound of formula (I) is used as hole transport material in a hole transport layer, a hole injection layer or an electron blocker layer, the compound can be used as pure material, i.e. in a proportion of 100%, in the hole transport layer, or it can be used in combination with one or more further compounds.

In a preferred embodiment, a hole-transporting layer comprising the compound of the formula (I) additionally comprises one or more further hole-transporting compounds. These further hole-transporting compounds are preferably selected from triarylamine compounds, more preferably from monotriarylamine compounds. With very particular preference they are selected from the preferred embodiments of hole transport materials that are indicated later on below. In the preferred embodiment described, the compound of the formula (I) and the one or more further hole-transporting compounds are preferably each present in a proportion of at least 10%, more preferably each in a proportion of at least 20%.

In a preferred embodiment, a hole-transporting layer comprising the compound of the formula (I) additionally contains one or more p-dopants. p-Dopants used according to the present invention are preferably those organic electron acceptor compounds capable of oxidizing one or more of the other compounds in the mixture.

Particularly preferred as p-dopants are quinodimethane compounds, azaindenofluorenediones, azaphenalenes, azatriphenylenes, $I_2$, metal halides, preferably transition metal halides, metal oxides, preferably metal oxides comprising at least one transition metal or a metal from main group 3, and transition metal complexes, preferably complexes of Cu, Co, Ni, Pd and Pt with ligands containing at least one oxygen atom as binding site. Preference is further given to transition metal oxides as dopants, preferably oxides of rhenium, molybdenum and tungsten, more preferably $Re_2O_7$, $MoO_3$, $WO_3$ and $ReO_3$. Still further preference is given to complexes of bismuth in the (III) oxidation state, more particularly bismuth(III) complexes with electron-deficient ligands, more particularly carboxylate ligands.

The p-dopants are preferably in substantially homogeneous distribution in the p-doped layers. This can be achieved, for example, by coevaporation of the p-dopant and the hole transport material matrix. The p-dopant is preferably present in a proportion of 1% to 10% in the p-doped layer.

Preferred p-dopants are especially the following compounds:
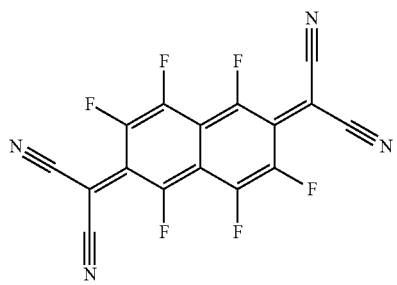
(D-1)
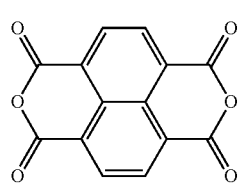
(D-2)
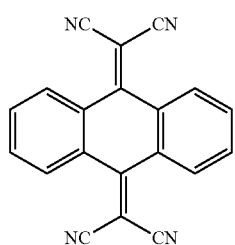
(D-3)
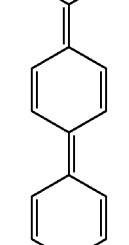
(D-4)
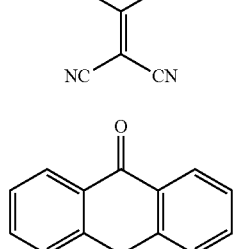
(D-5)
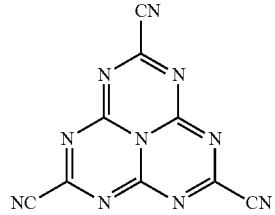
(D-6)
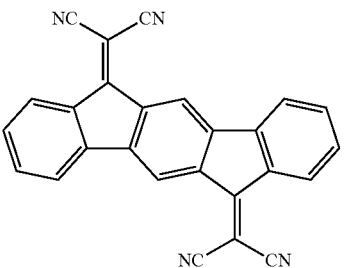
(D-7)
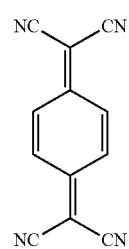
(D-8)
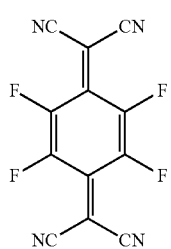
(D-9)
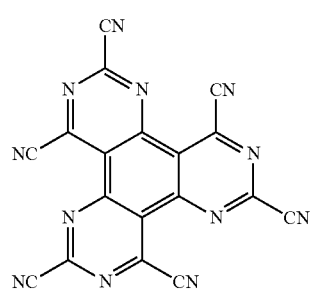
(D-10)
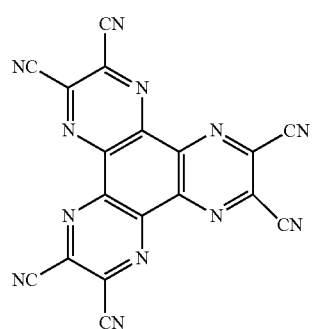
(D-11)

-continued

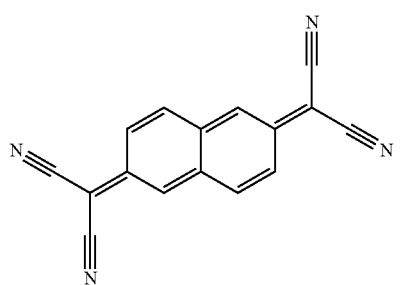
(D-12)

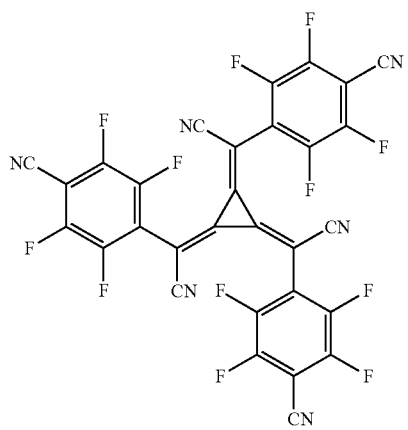
(D-13)

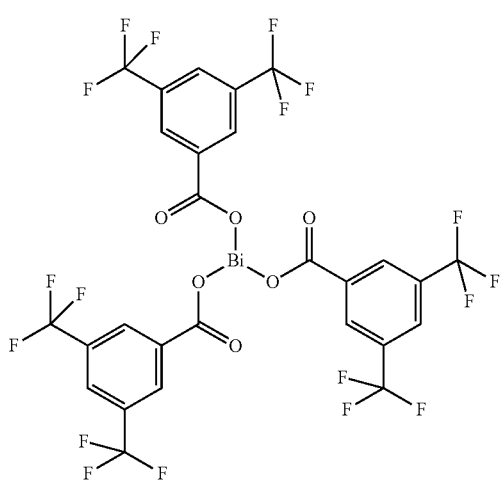
(D-14)

In a preferred embodiment, a hole injection layer that conforms to one of the following embodiments is present in the device: a) it contains a triarylamine and a p-dopant; or b) it contains a single electron-deficient material (electron acceptor). In a preferred embodiment of embodiment a), the triarylamine is a monotriarylamine, especially one of the preferred triarylamine derivatives mentioned further down. In a preferred embodiment of embodiment b), the electron-deficient material is a hexaazatriphenylene derivative as described in US 2007/0092755.

The compound of the formula (I) may be present in a hole injection layer, in a hole transport layer and/or in an electron blocker layer of the device. When the compound is present in a hole injection layer or in a hole transport layer, it has preferably been p-doped, meaning that it is in mixed form with a p-dopant, as described above, in the layer.

More preferably, the compound of the formula (I) is present in an electron blocker layer. In this case, it is preferably not p-doped. Further preferably, in this case, it is preferably in the form of a single compound in the layer without addition of a further compound.

In an alternative preferred embodiment, the compound of the formula (I) is used in an emitting layer as matrix material in combination with one or more emitting compounds, preferably phosphorescent emitting compounds. The phosphorescent emitting compounds here are preferably selected from red-phosphorescing and green-phosphorescing compounds.

The proportion of the matrix material in the emitting layer in this case is between 50.0% and 99.9% by volume, preferably between 80.0% and 99.5% by volume, and more preferably between 85.0% and 97.0% by volume.

Correspondingly, the proportion of the emitting compound is between 0.1% and 50.0% by volume, preferably between 0.5% and 20.0% by volume, and more preferably between 3.0% and 15.0% by volume.

An emitting layer of an organic electroluminescent device may also contain systems comprising a plurality of matrix materials (mixed matrix systems) and/or a plurality of emitting compounds. In this case too, the emitting compounds are generally those compounds having the smaller proportion in the system and the matrix materials are those compounds having the greater proportion in the system. In individual cases, however, the proportion of a single matrix material in the system may be less than the proportion of a single emitting compound.

It is preferable that the compounds of formula (I) are used as a component of mixed matrix systems, preferably for phosphorescent emitters. The mixed matrix systems preferably comprise two or three different matrix materials, more preferably two different matrix materials. Preferably, in this case, one of the two materials is a material having hole-transporting properties and the other material is a material having electron-transporting properties. It is further preferable when one of the materials is selected from compounds having a large energy differential between HOMO and LUMO (wide-bandgap materials). The compound of the formula (I) in a mixed matrix system is preferably the matrix material having hole-transporting properties. Correspondingly, when the compound of the formula (I) is used as matrix material for a phosphorescent emitter in the emitting layer of an OLED, a second matrix compound having electron-transporting properties is present in the emitting layer. The two different matrix materials may be present here in a ratio of 1:50 to 1:1, preferably 1:20 to 1:1, more preferably 1:10 to 1:1 and most preferably 1:4 to 1:1.

The desired electron-transporting and hole-transporting properties of the mixed matrix components may, however, also be combined mainly or entirely in a single mixed matrix component, in which case the further mixed matrix component(s) fulfill(s) other functions.

Preference is given to using the following material classes in the abovementioned layers of the device:
Phosphorescent Emitters:

The term "phosphorescent emitters" typically encompasses compounds where the emission of light is effected through a spin-forbidden transition, for example a transition from an excited triplet state or a state having a higher spin quantum number, for example a quintet state.

Suitable phosphorescent emitters are especially compounds which, when suitably excited, emit light, preferably in the visible region, and also contain at least one atom of atomic number greater than 20, preferably greater than 38, and less than 84, more preferably greater than 56 and less than 80. Preference is given to using, as phosphorescent emitters, compounds containing copper, molybdenum, tungsten, rhenium, ruthenium, osmium, rhodium, iridium, palladium, platinum, silver, gold or europium, especially compounds containing iridium, platinum or copper.

In the context of the present invention, all luminescent iridium, platinum or copper complexes are considered to be phosphorescent compounds.

In general, all phosphorescent complexes as used for phosphorescent OLEDs according to the prior art and as known to those skilled in the art in the field of organic electroluminescent devices are suitable for use in the devices of the invention. Further examples of suitable phosphorescent emitters are shown in the following table:

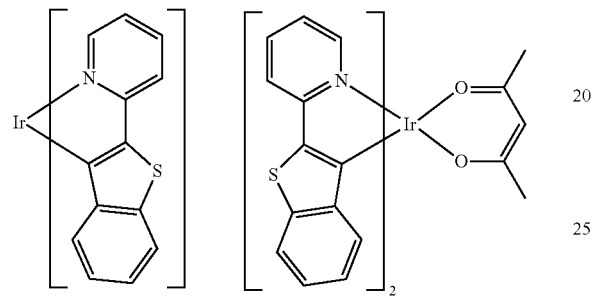
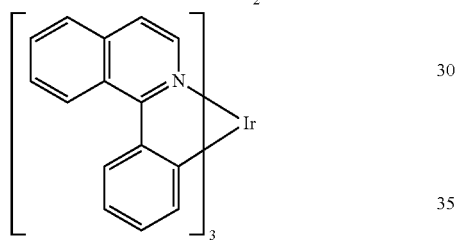
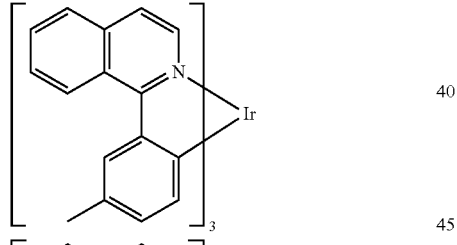

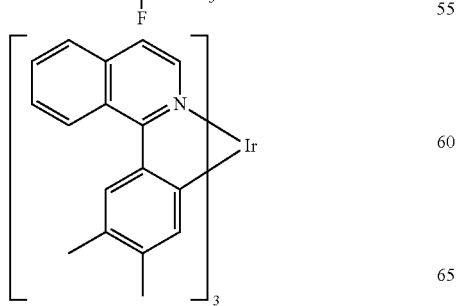
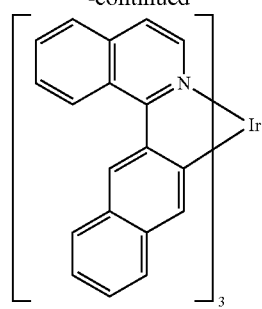
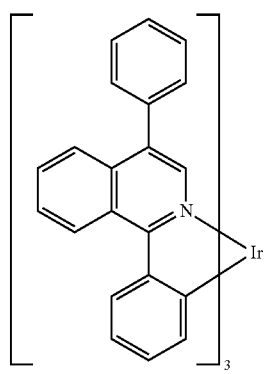
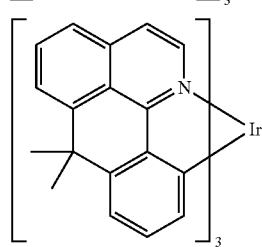
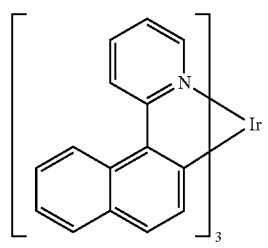
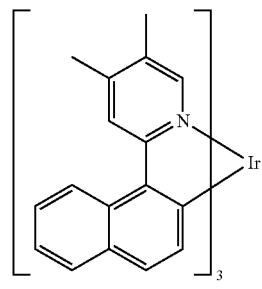
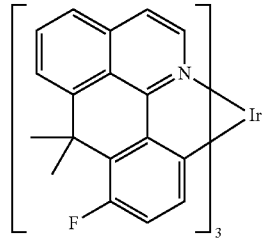

193
-continued
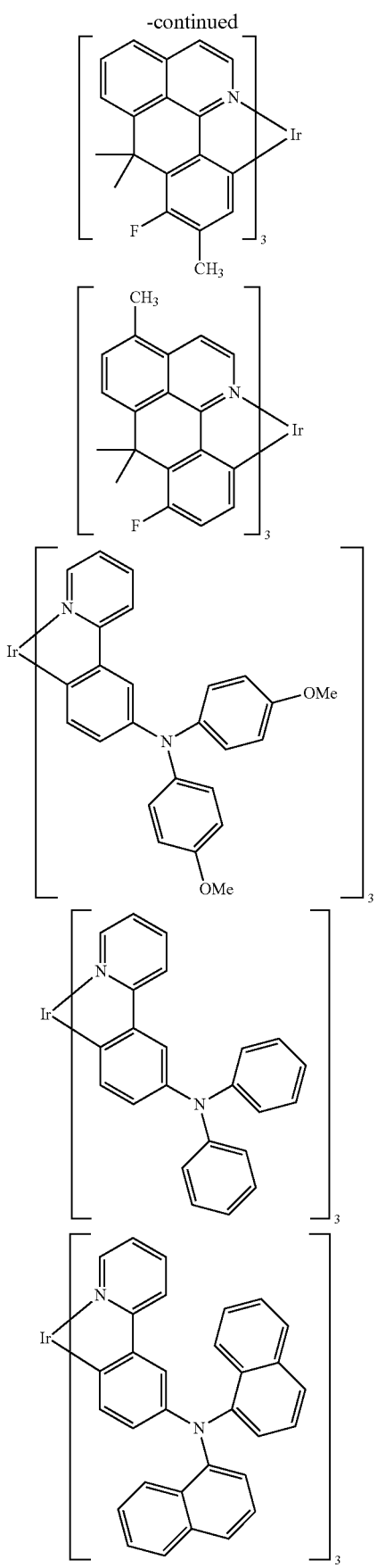
194
-continued
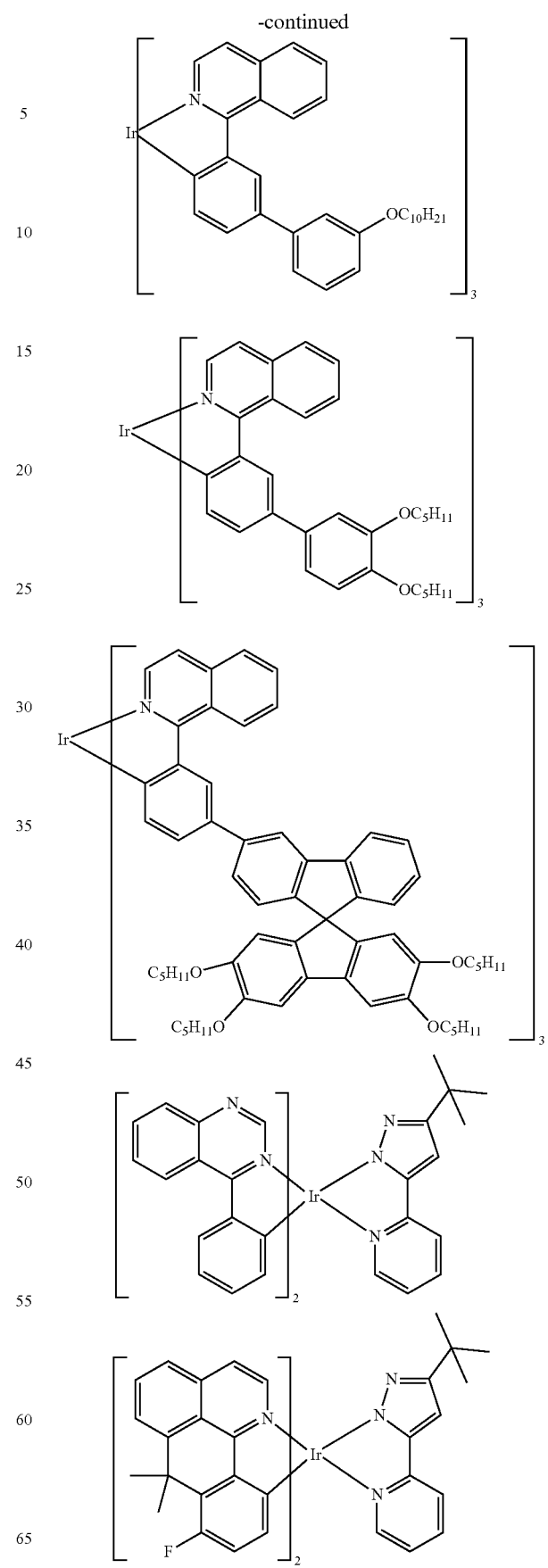

-continued
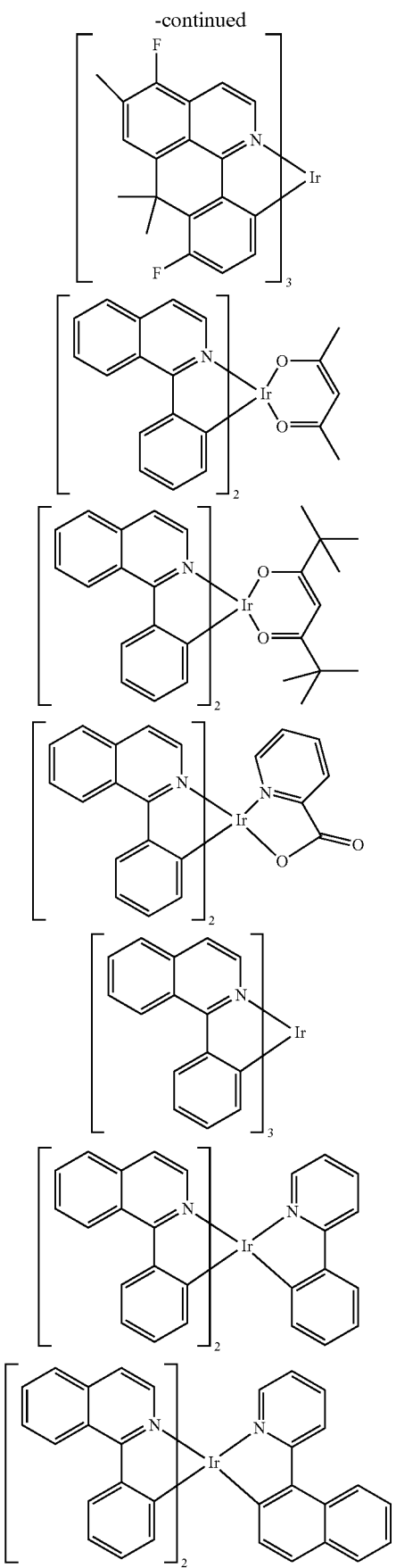
-continued
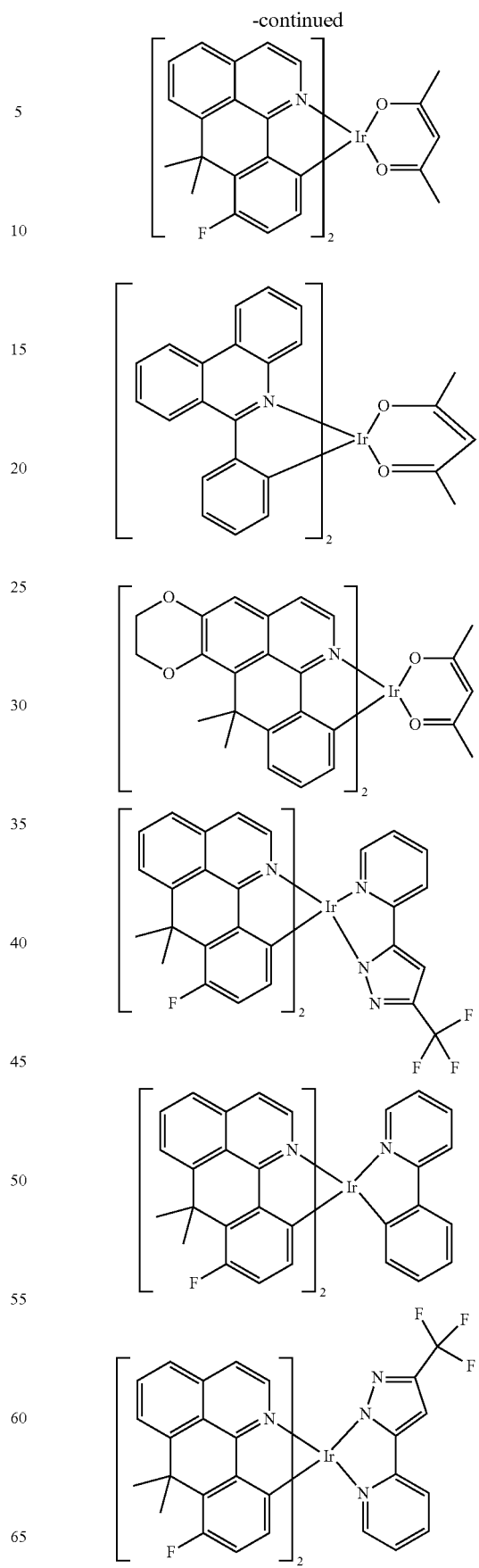

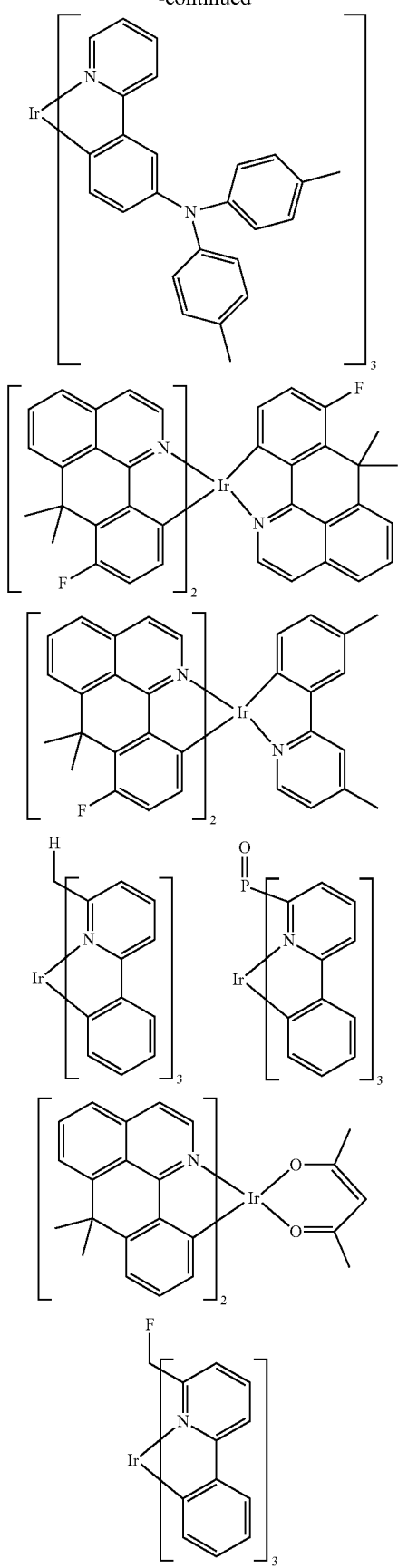
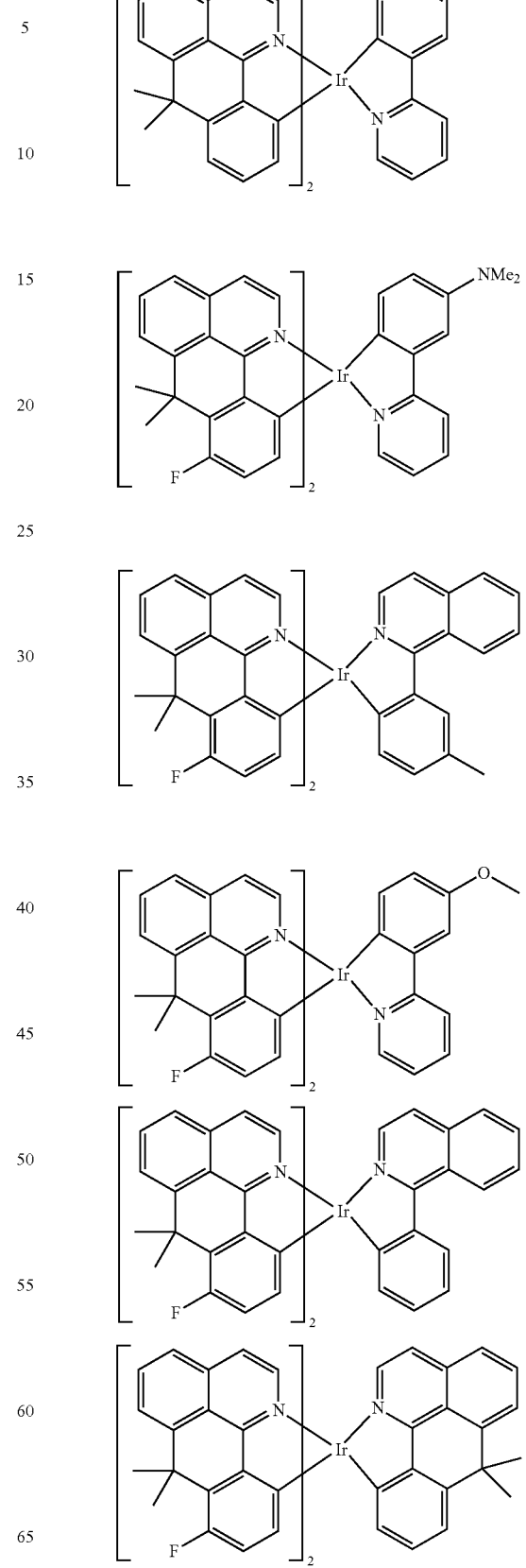

199
-continued
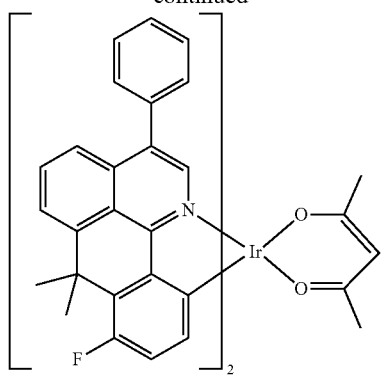
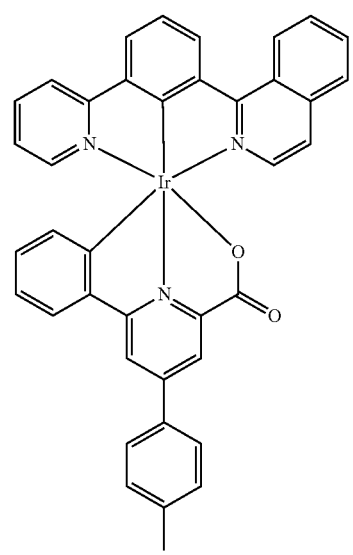
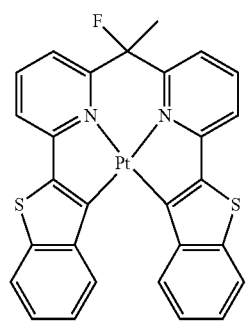
200
-continued
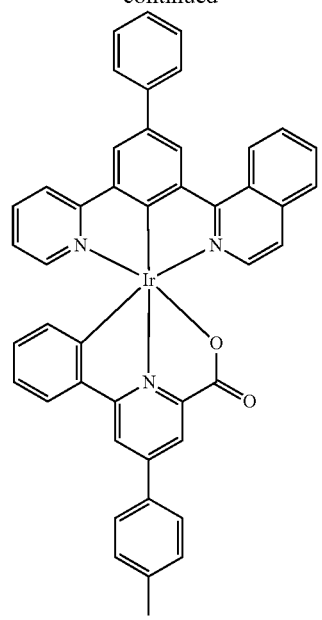
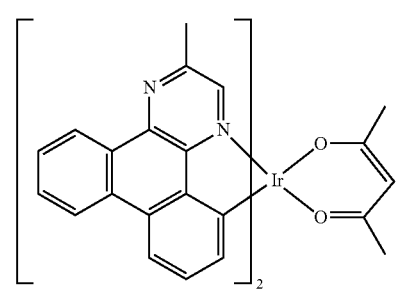
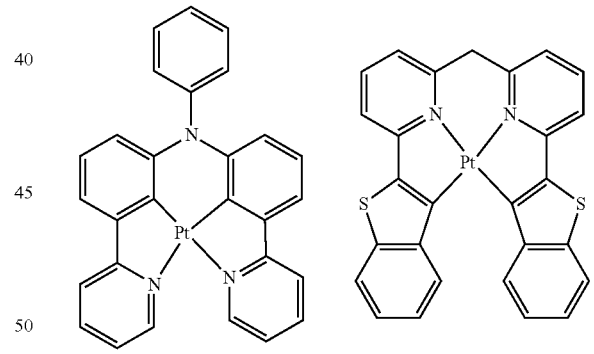
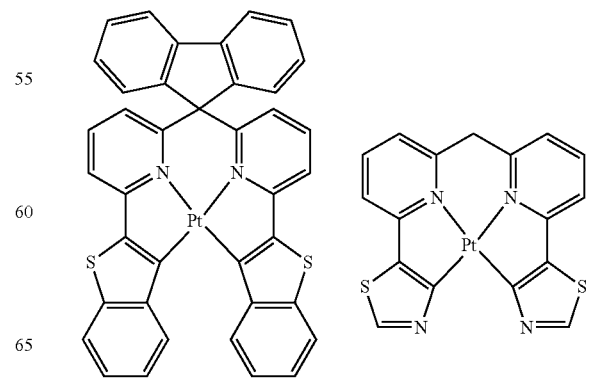

201
-continued
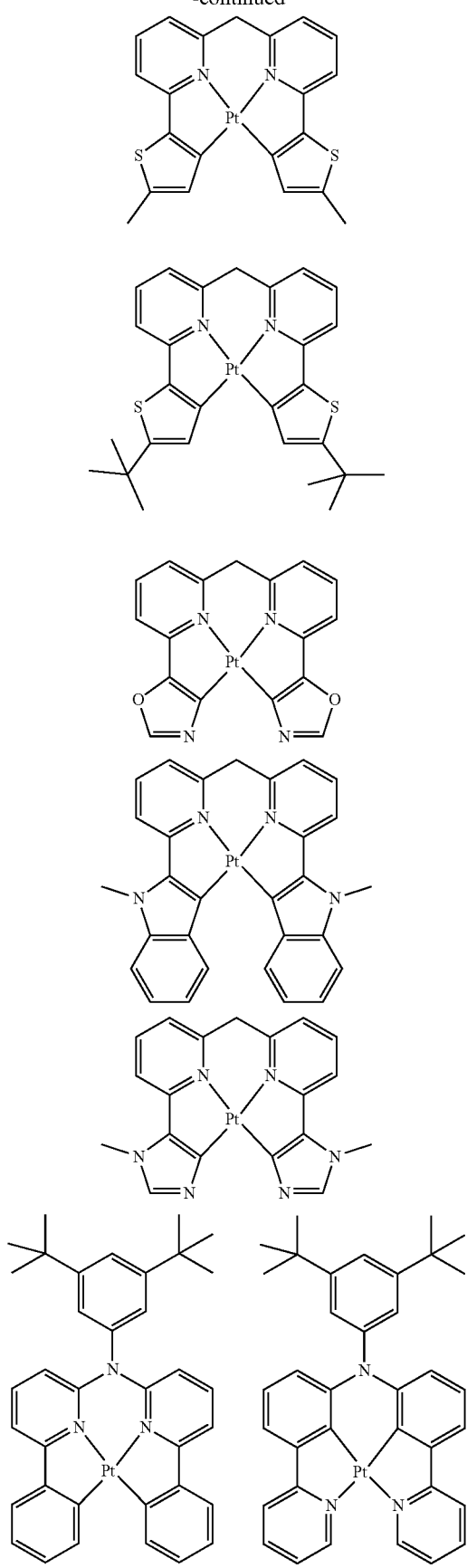
202
-continued
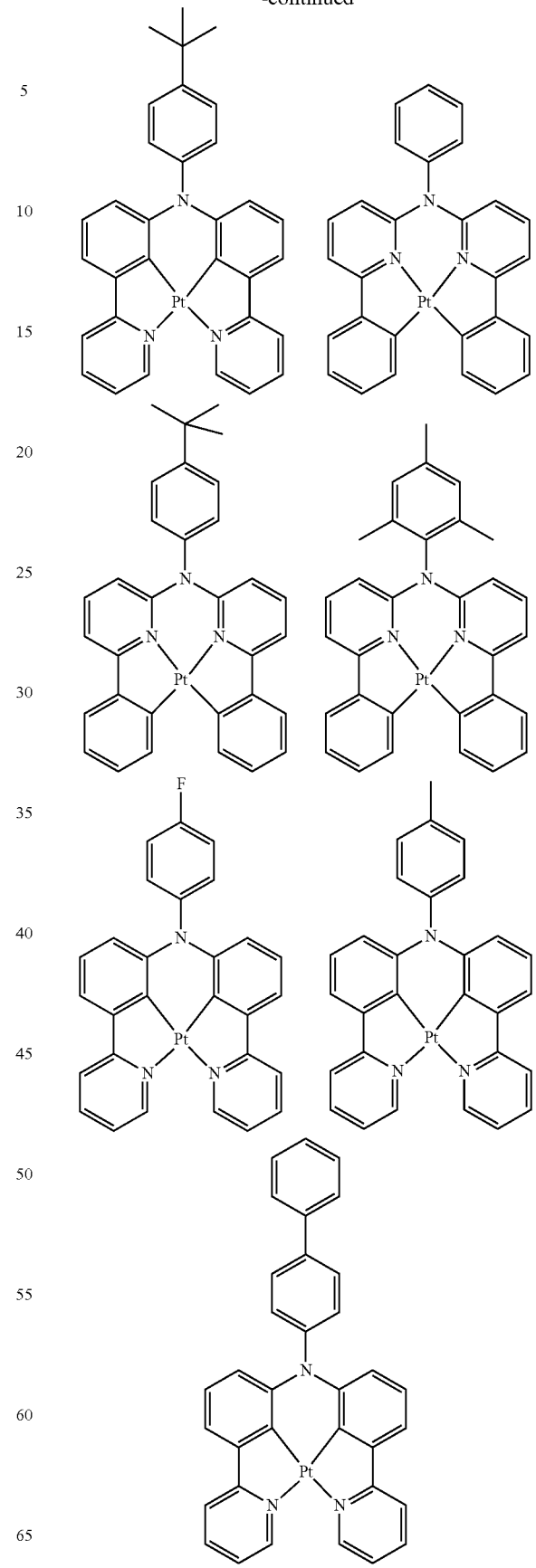

203
-continued
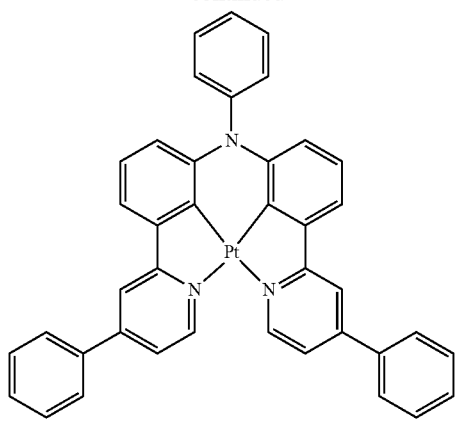
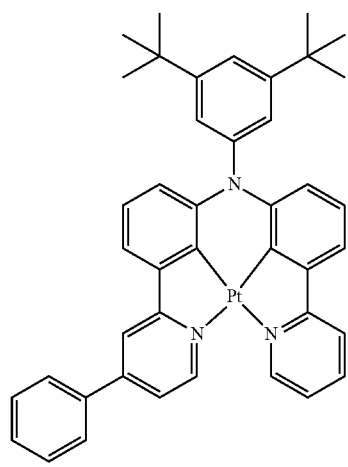
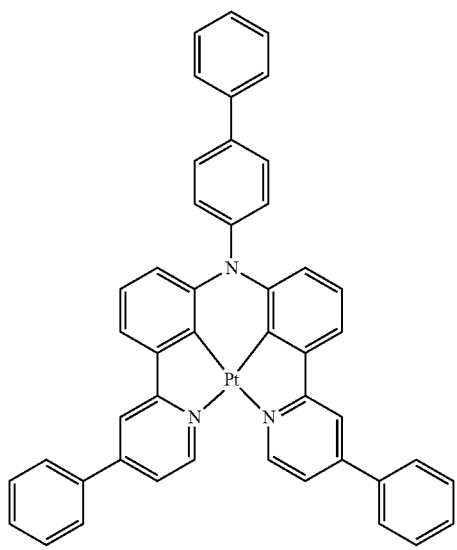
204
-continued
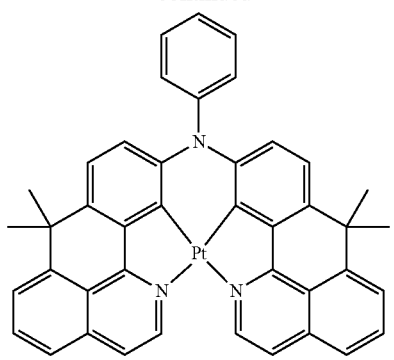
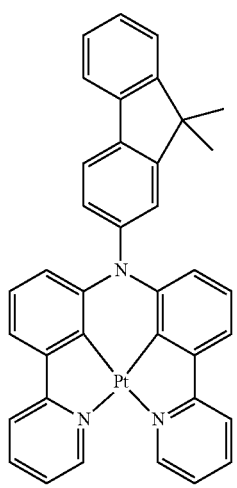
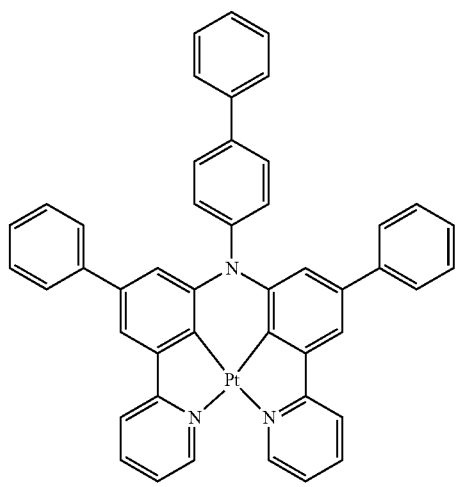
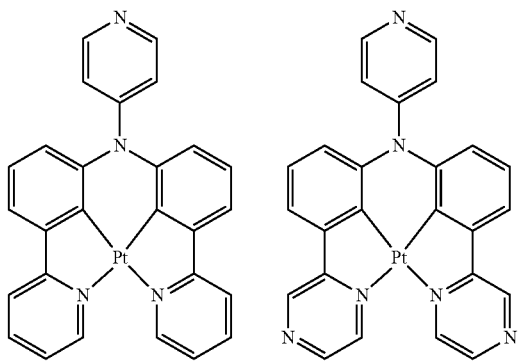

-continued
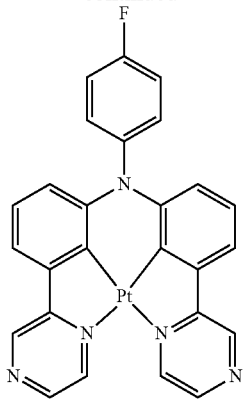
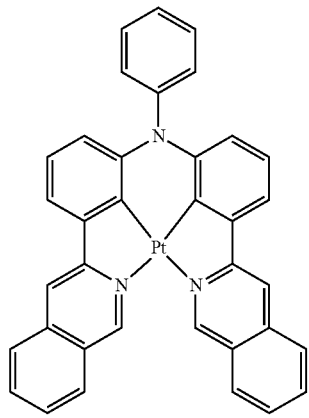
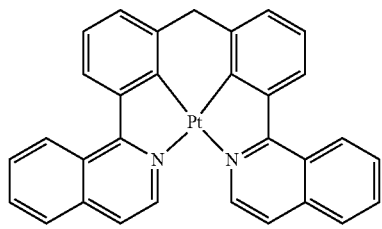
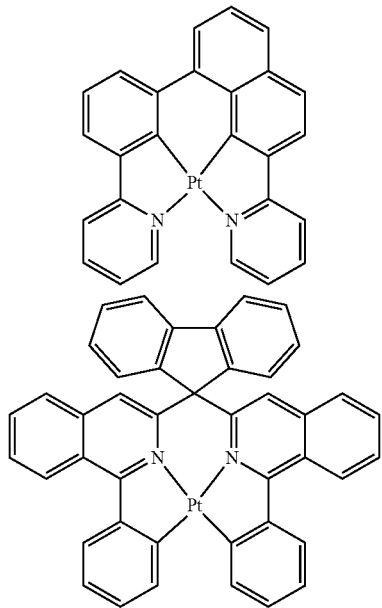
-continued
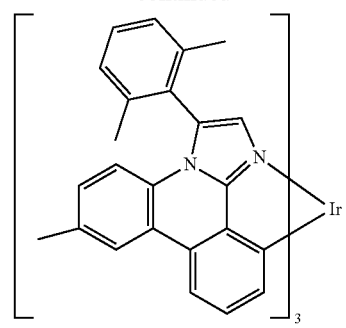
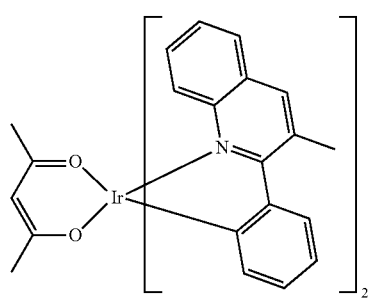
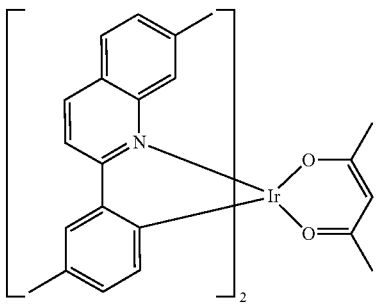
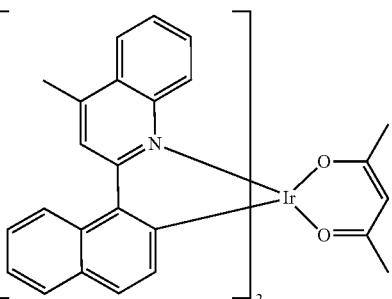

207
-continued
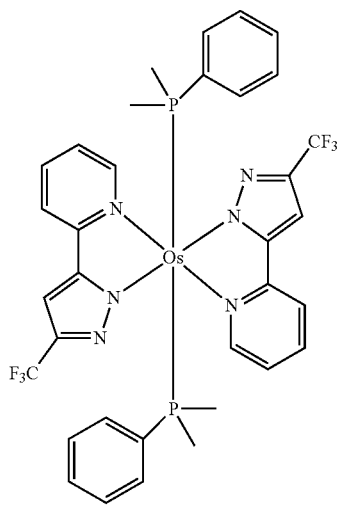
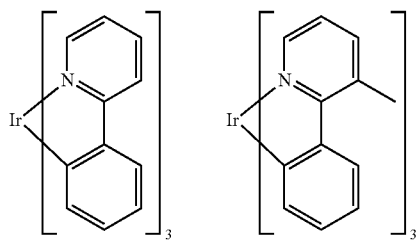
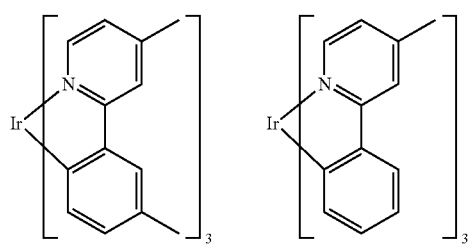
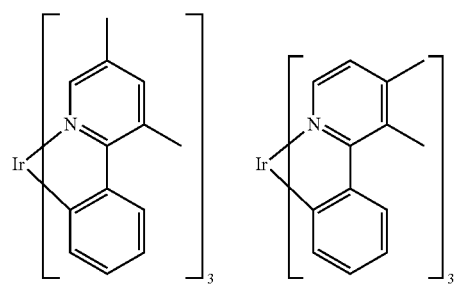
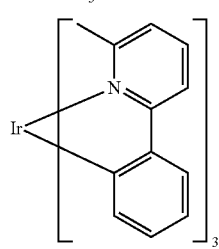
208
-continued
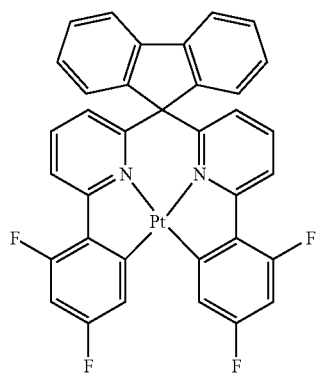
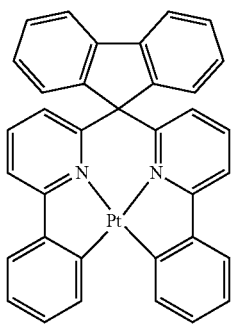
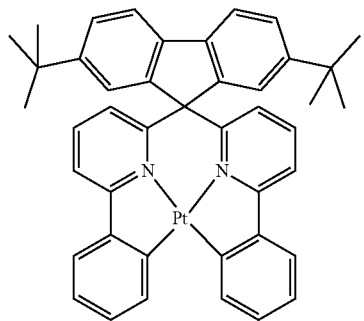
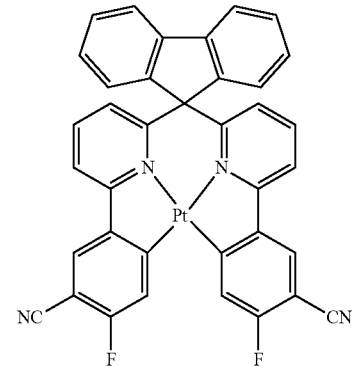

209
-continued
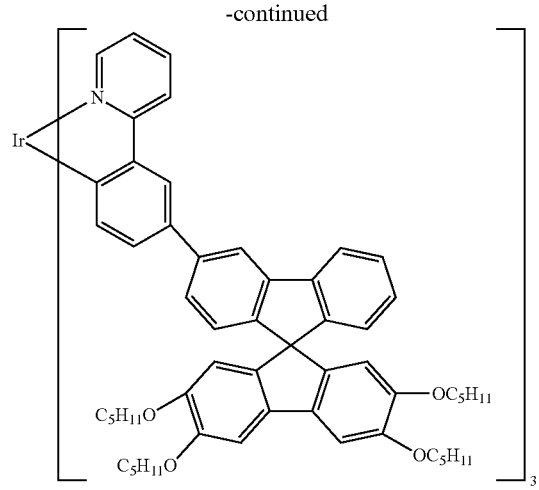
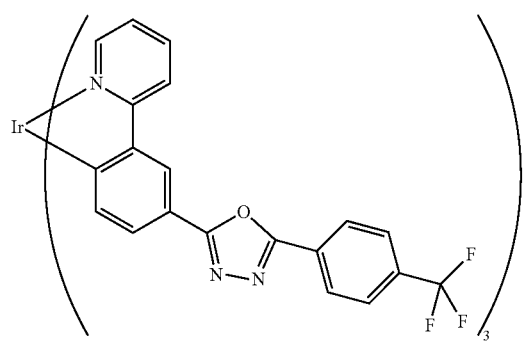
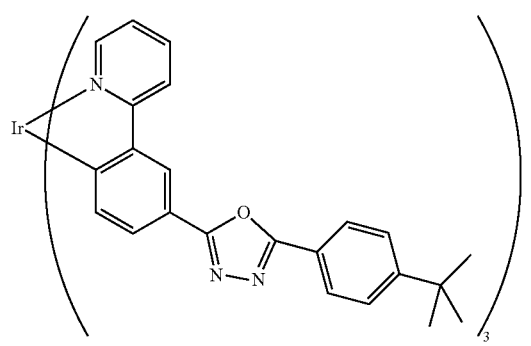
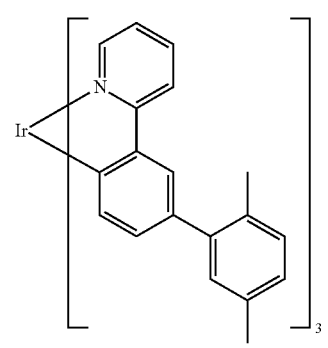
210
-continued
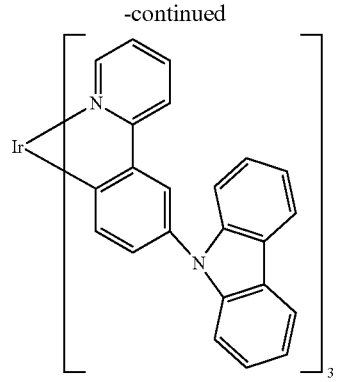
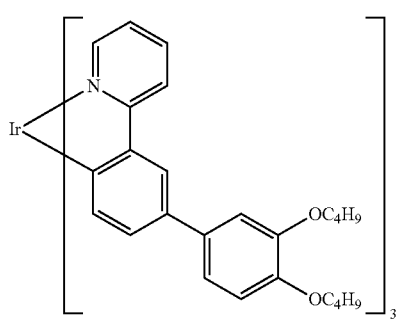
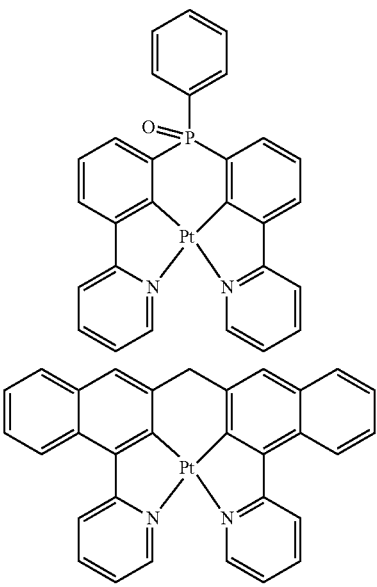
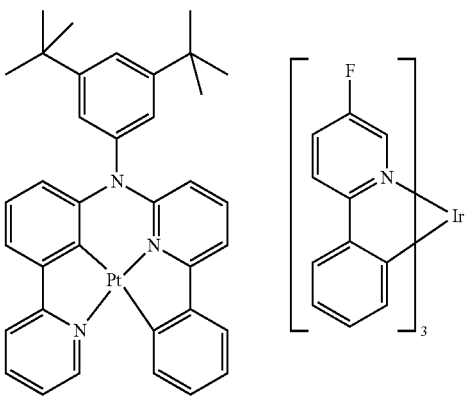

211
-continued
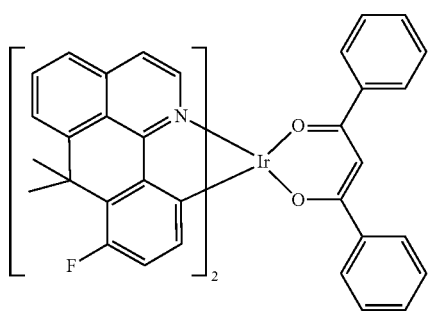
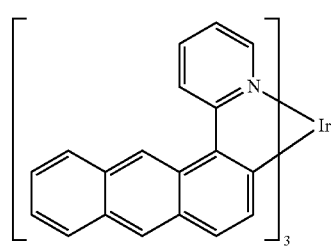
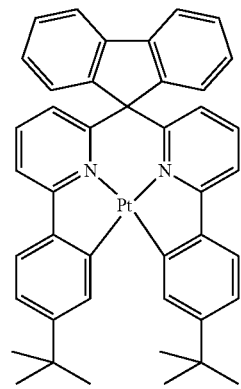
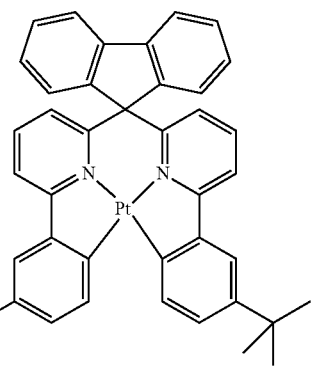
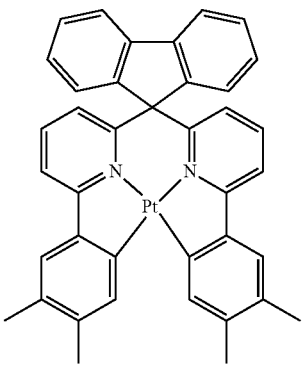
212
-continued
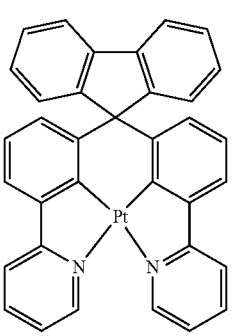 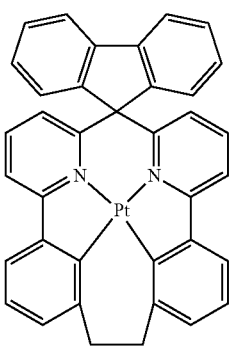
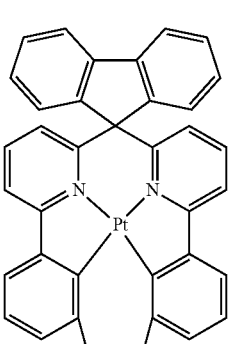 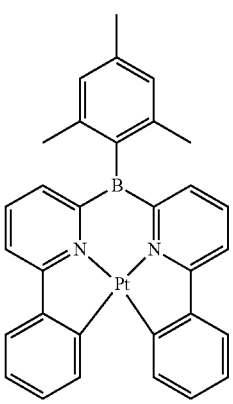
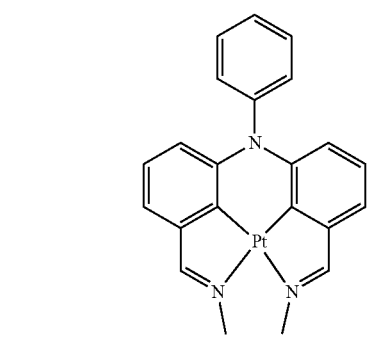
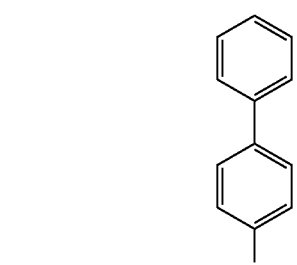
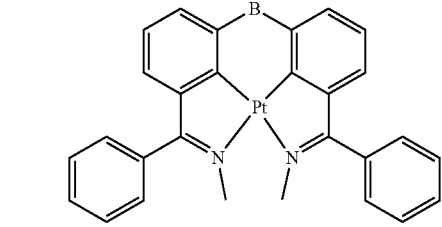

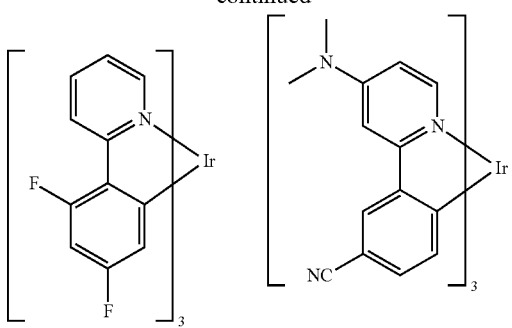
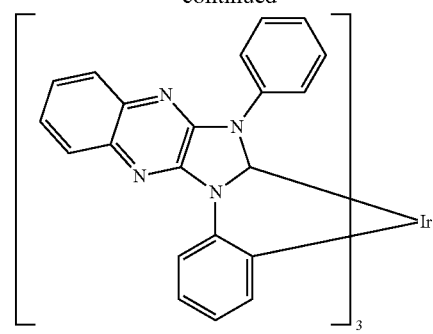
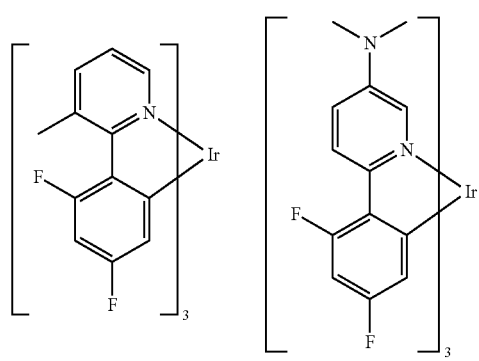
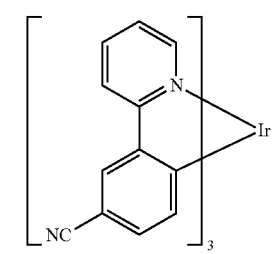
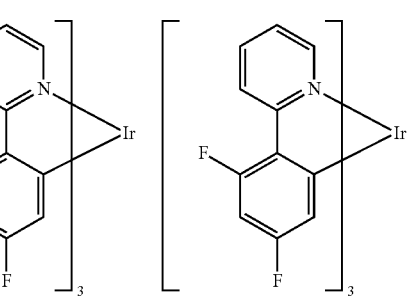
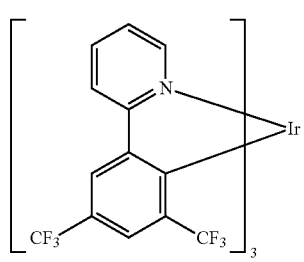
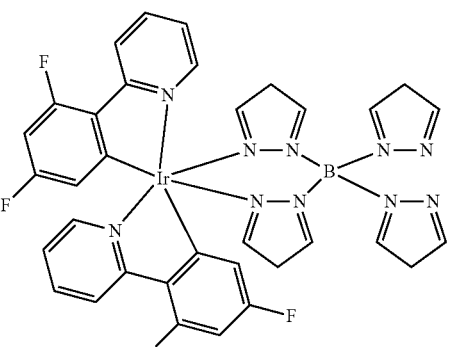
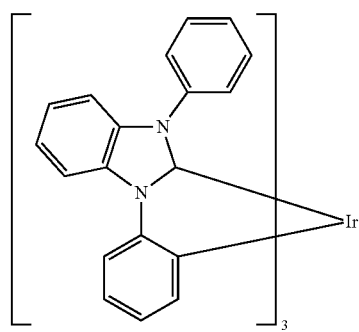
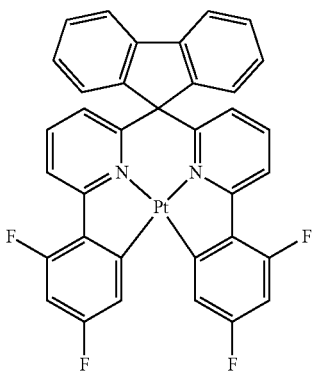

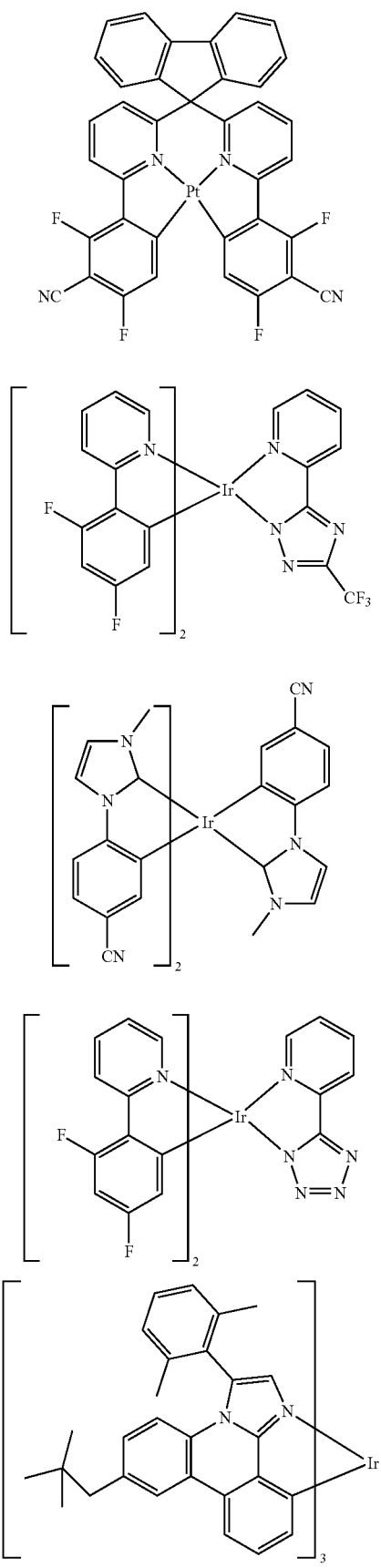

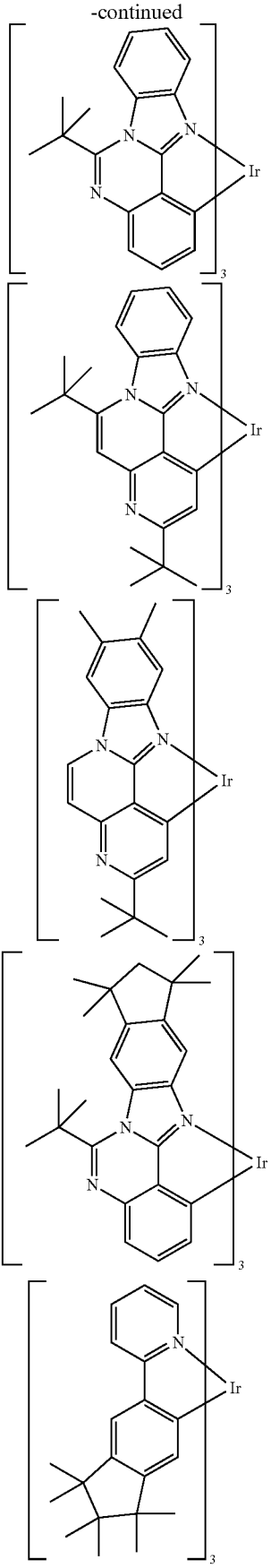
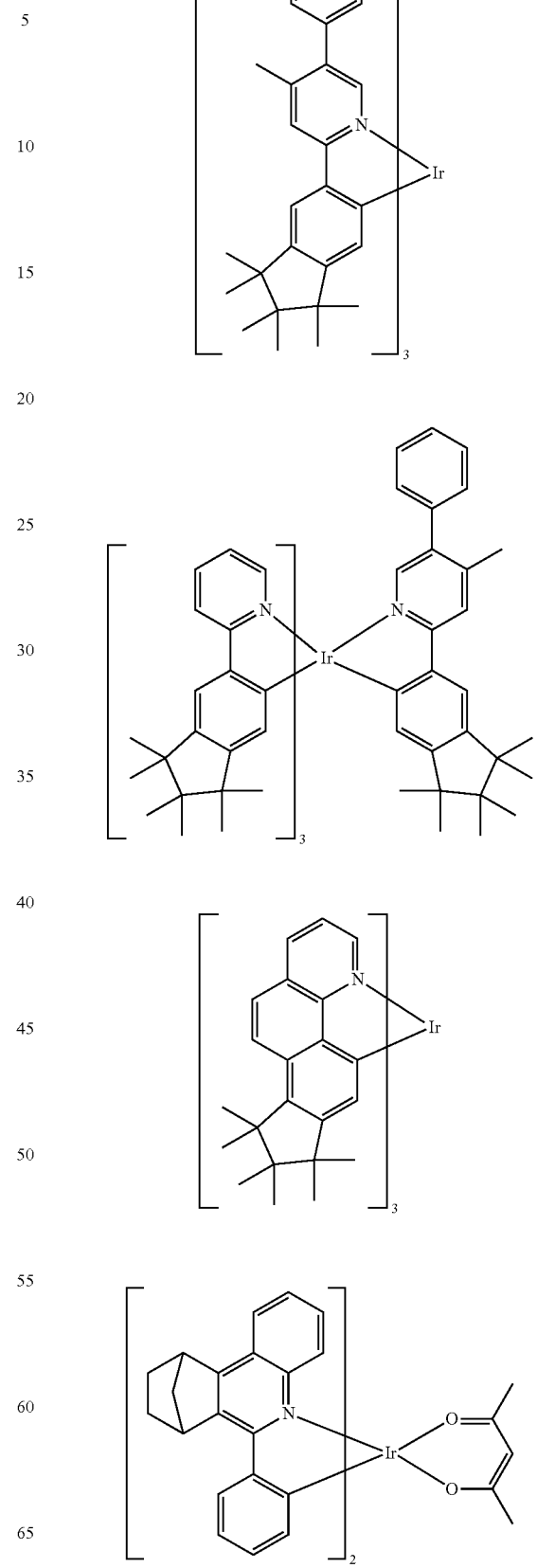

219
-continued
220
-continued
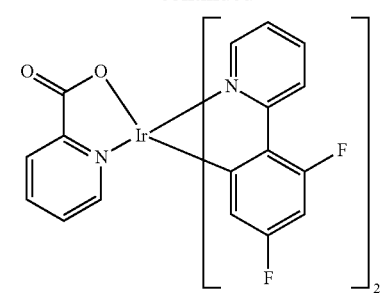
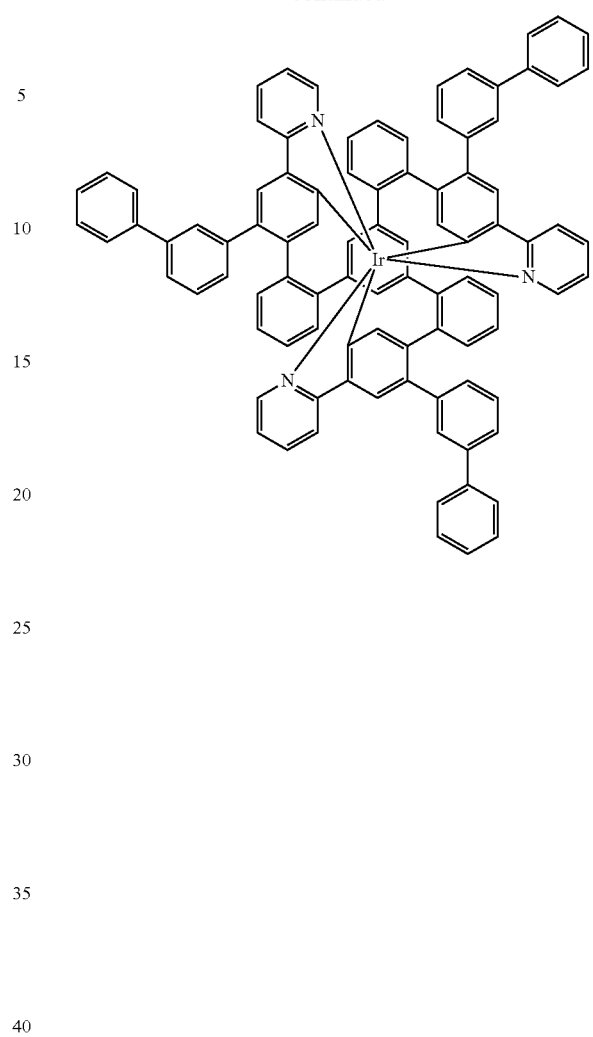
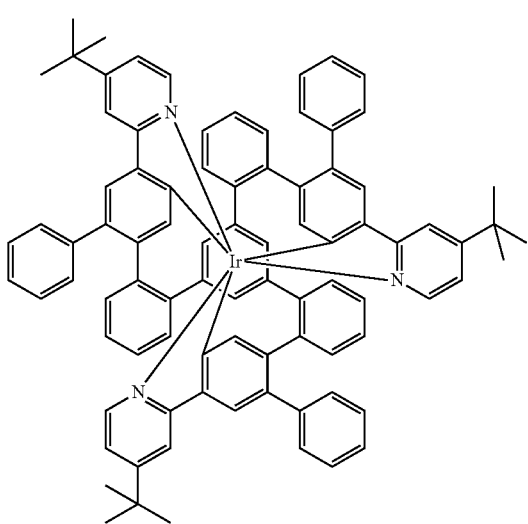
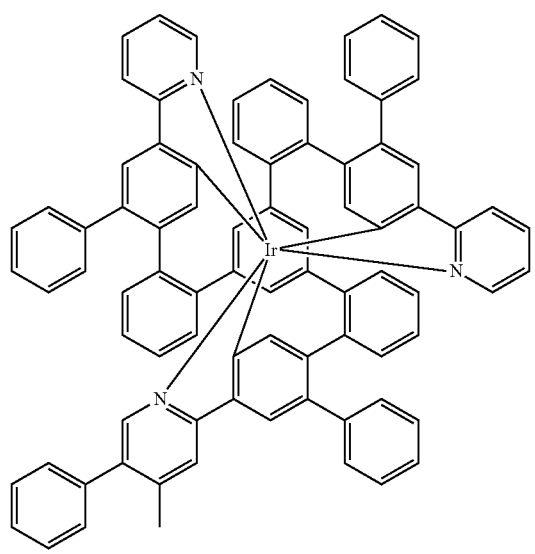

-continued

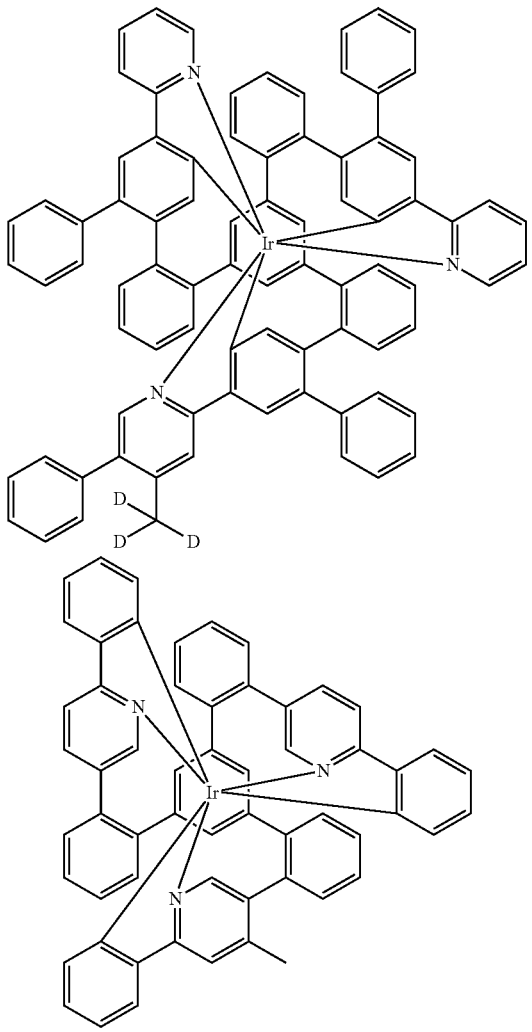

Fluorescent Emitters:

Preferred fluorescent emitting compounds are selected from the class of the arylamines. An arylamine or an aromatic amine in the context of this invention is understood to mean a compound containing three substituted or unsubstituted aromatic or heteroaromatic ring systems bonded directly to the nitrogen. Preferably, at least one of these aromatic or heteroaromatic ring systems is a fused ring system, more preferably having at least 14 aromatic ring atoms. Preferred examples of these are aromatic anthraceneamines, aromatic anthracenediamines, aromatic pyreneamines, aromatic pyrenediamines, aromatic chryseneamines or aromatic chrysenediamines. An aromatic anthraceneamine is understood to mean a compound in which a diarylamino group is bonded directly to an anthracene group, preferably in the 9 position. An aromatic anthracenediamine is understood to mean a compound in which two diarylamino groups are bonded directly to an anthracene group, preferably in the 9,10 positions. Aromatic pyreneamines, pyrenediamines, chryseneamines and chrysenediamines are defined analogously, where the diarylamino groups are bonded to the pyrene preferably in the 1 position or 1,6 positions. Further preferred emitting compounds are indenofluoreneamines or -diamines, benzoindenofluoreneamines or -diamines, and dibenzoindenofluoreneamines or -diamines, and indenofluorene derivatives having fused aryl groups. Likewise preferred are pyrenearylamines. Likewise preferred are benzoindenofluoreneamines, benzofluoreneamines, extended benzoindenofluorenes, phenoxazines, and fluorene derivatives joined to furan units or to thiophene units. Examples of fluorescent emitters are depicted in the following table:

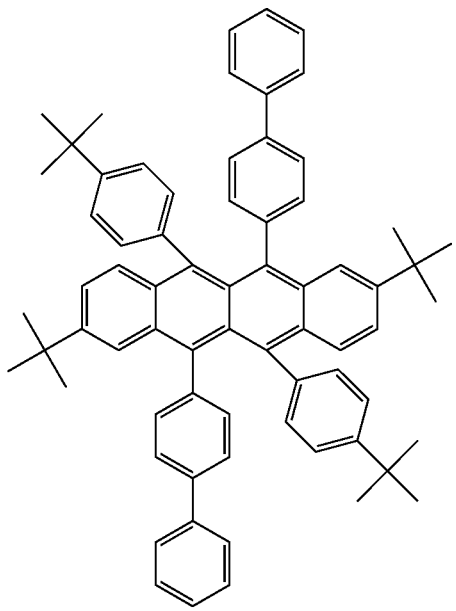

-continued
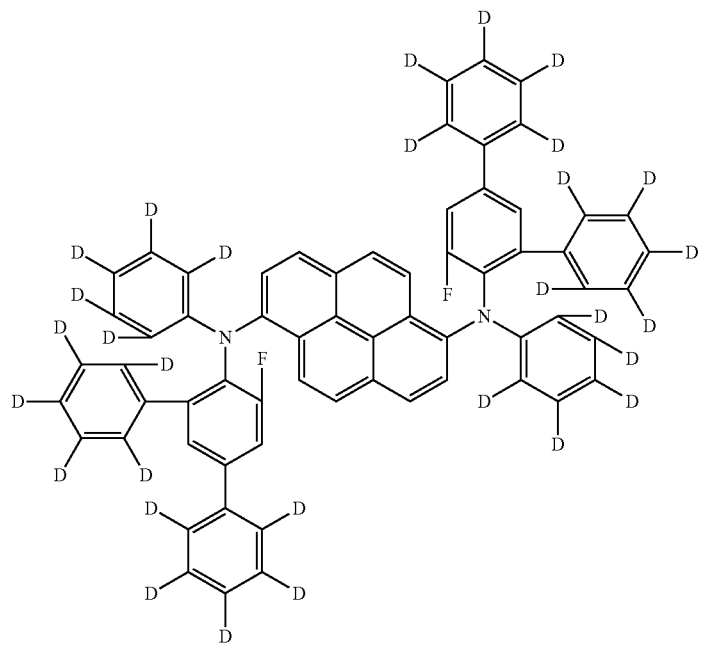
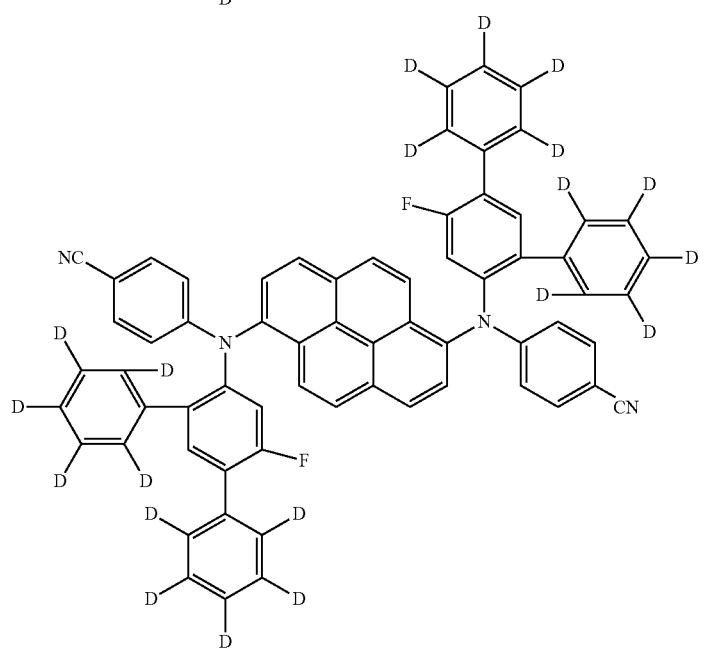
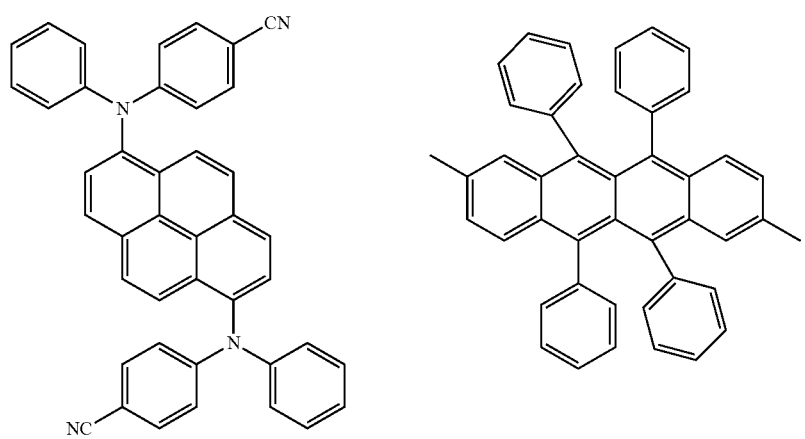

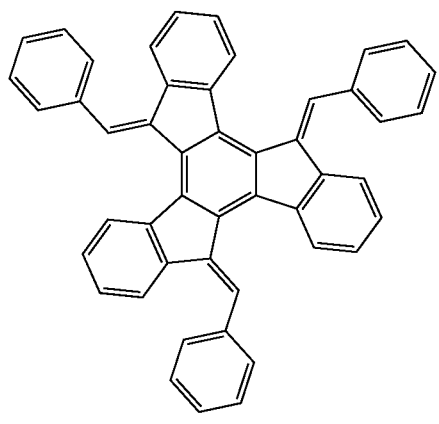
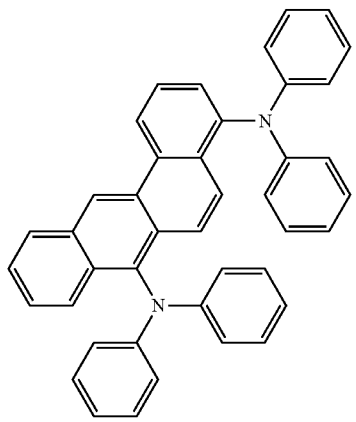
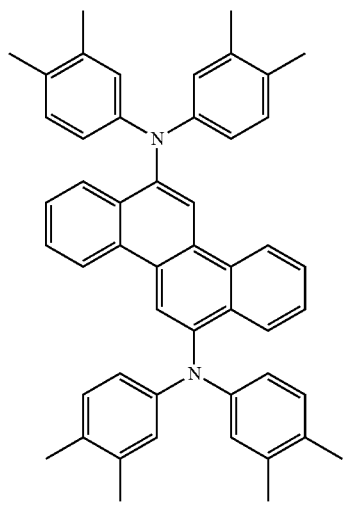
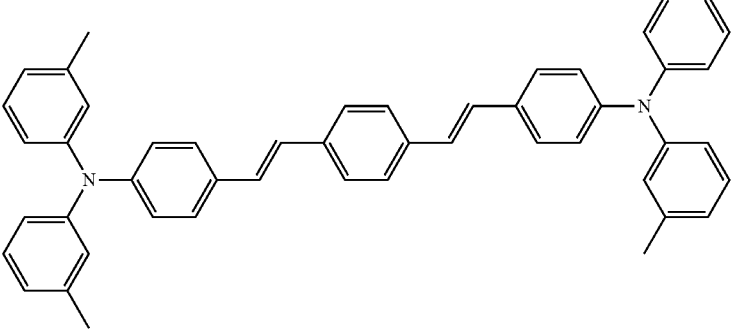
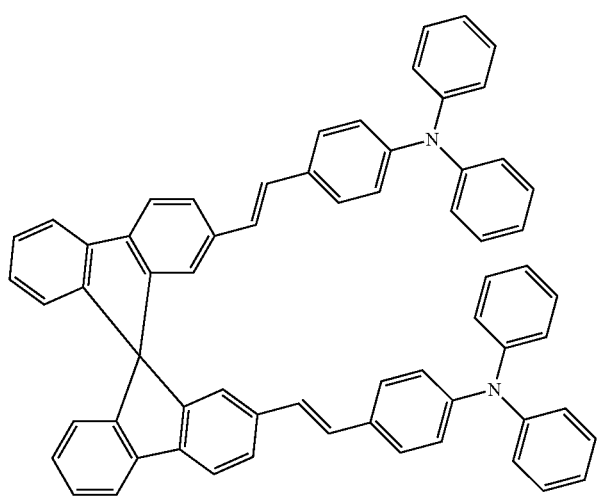

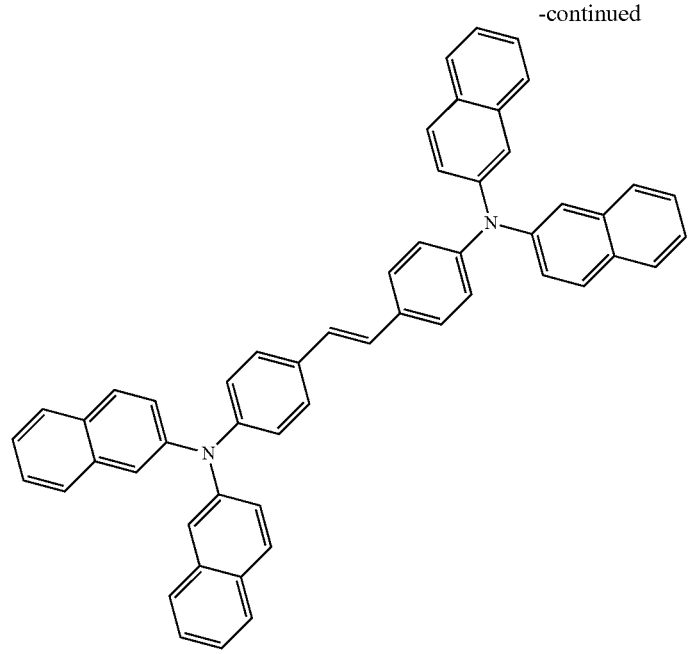
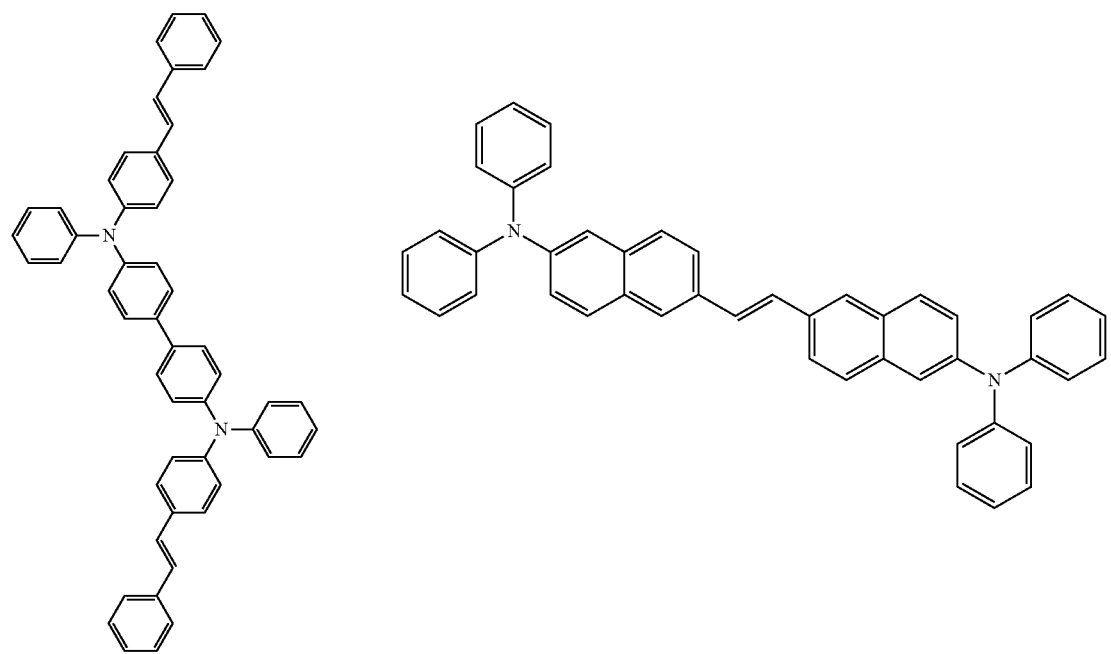

-continued
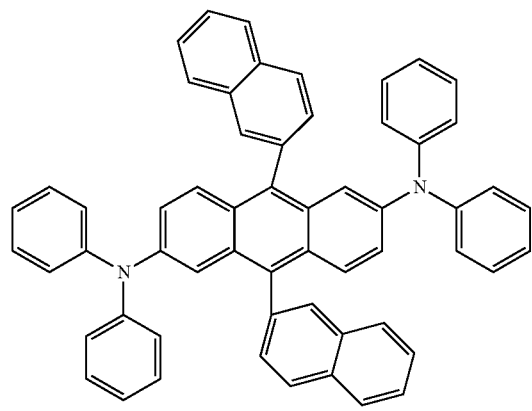
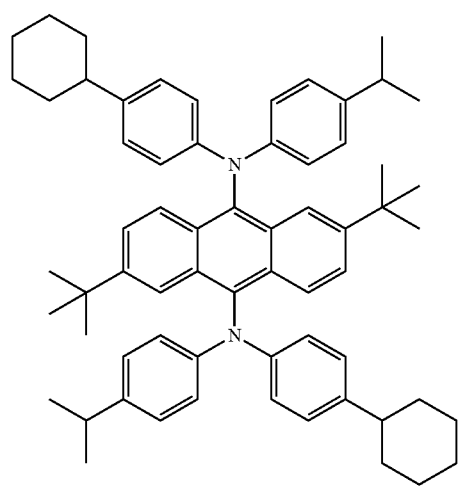
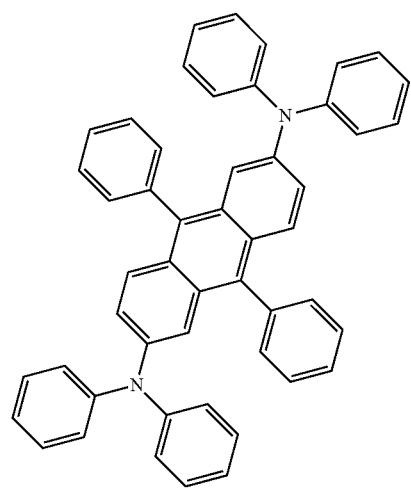
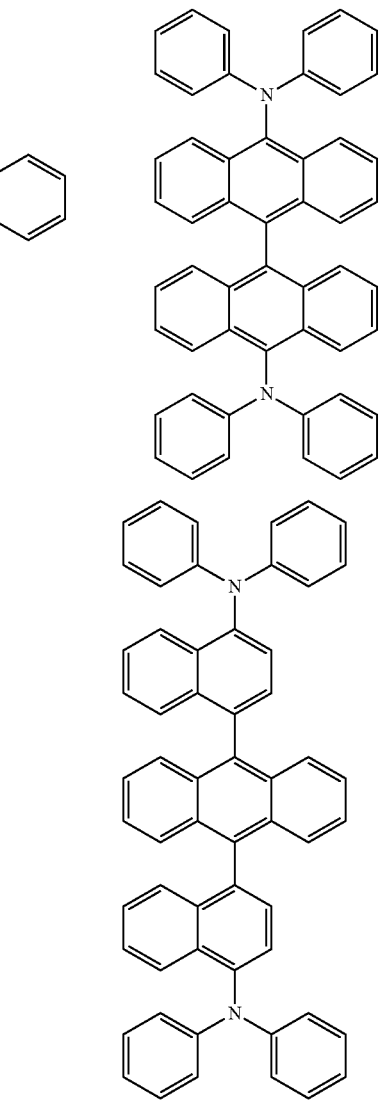
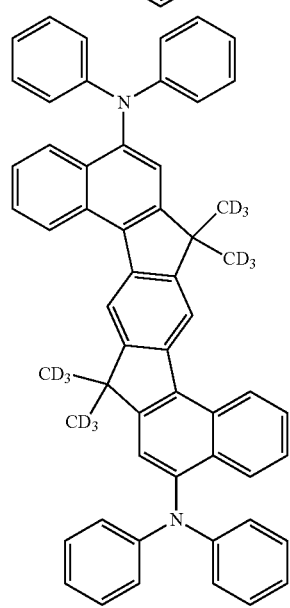
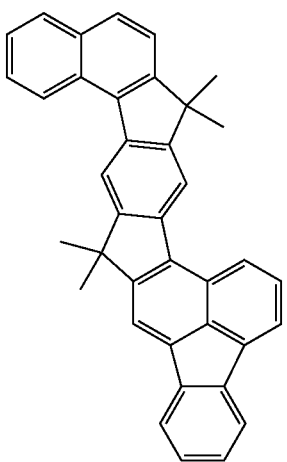

-continued
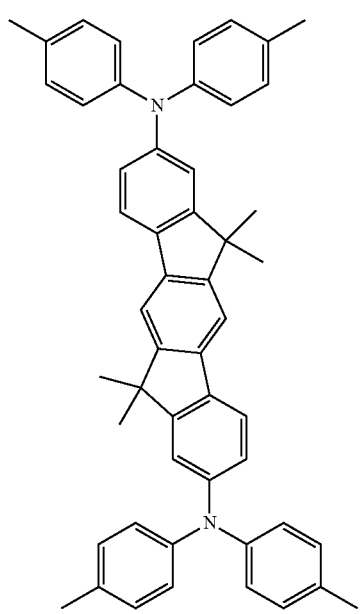
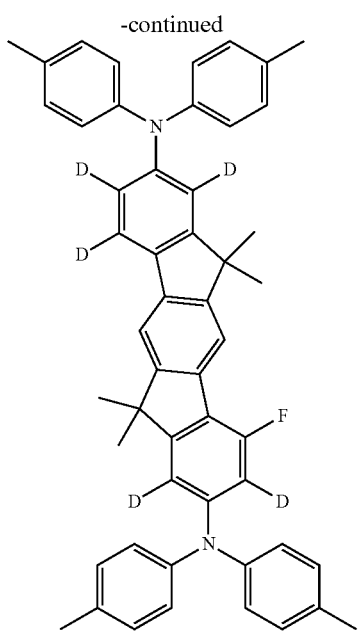
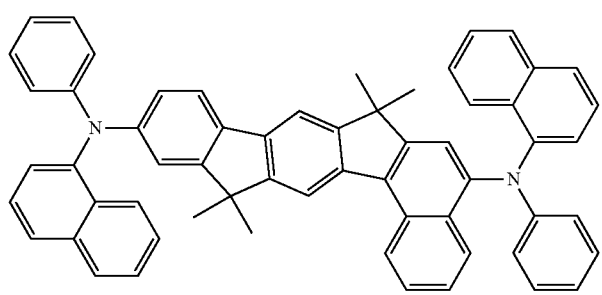
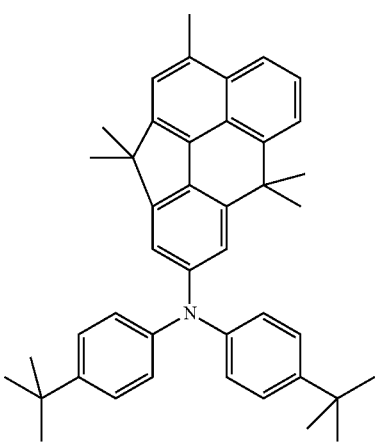
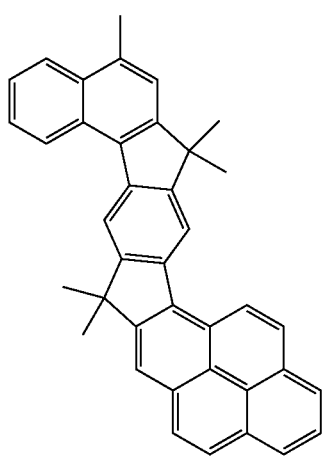
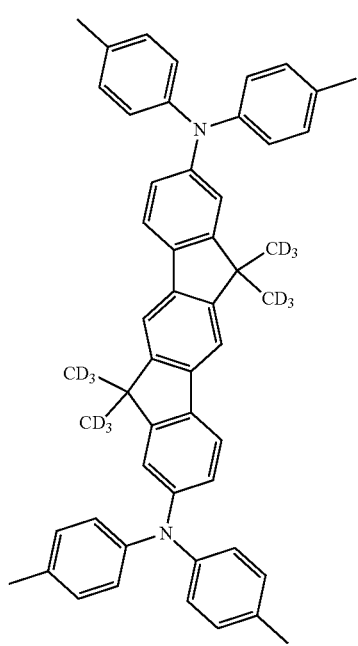

233
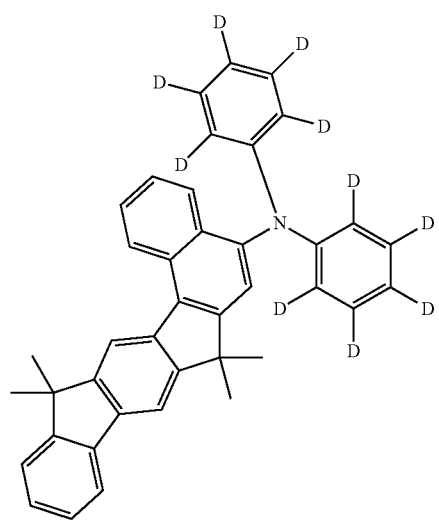
234
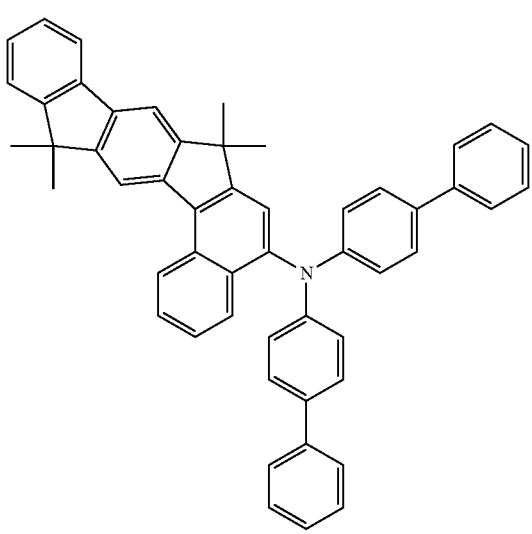
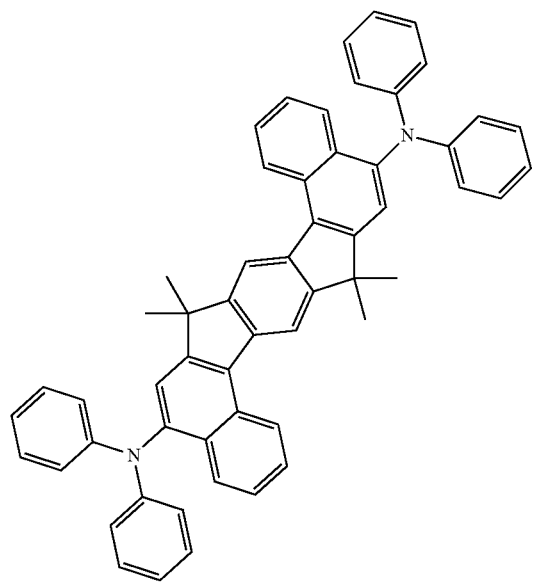
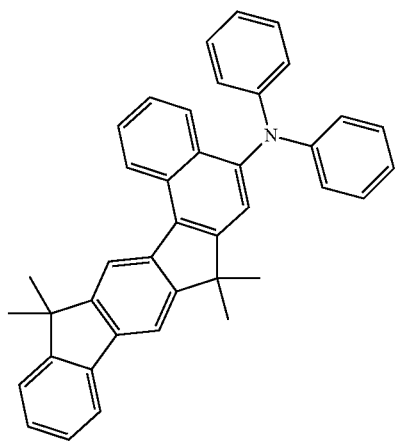
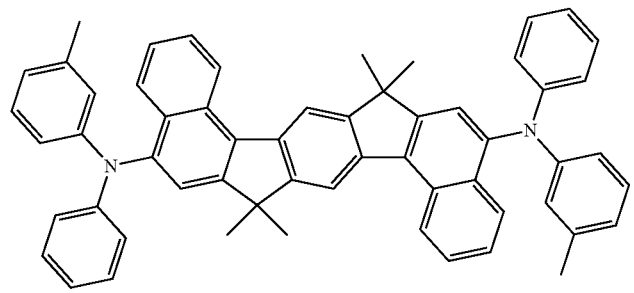

-continued
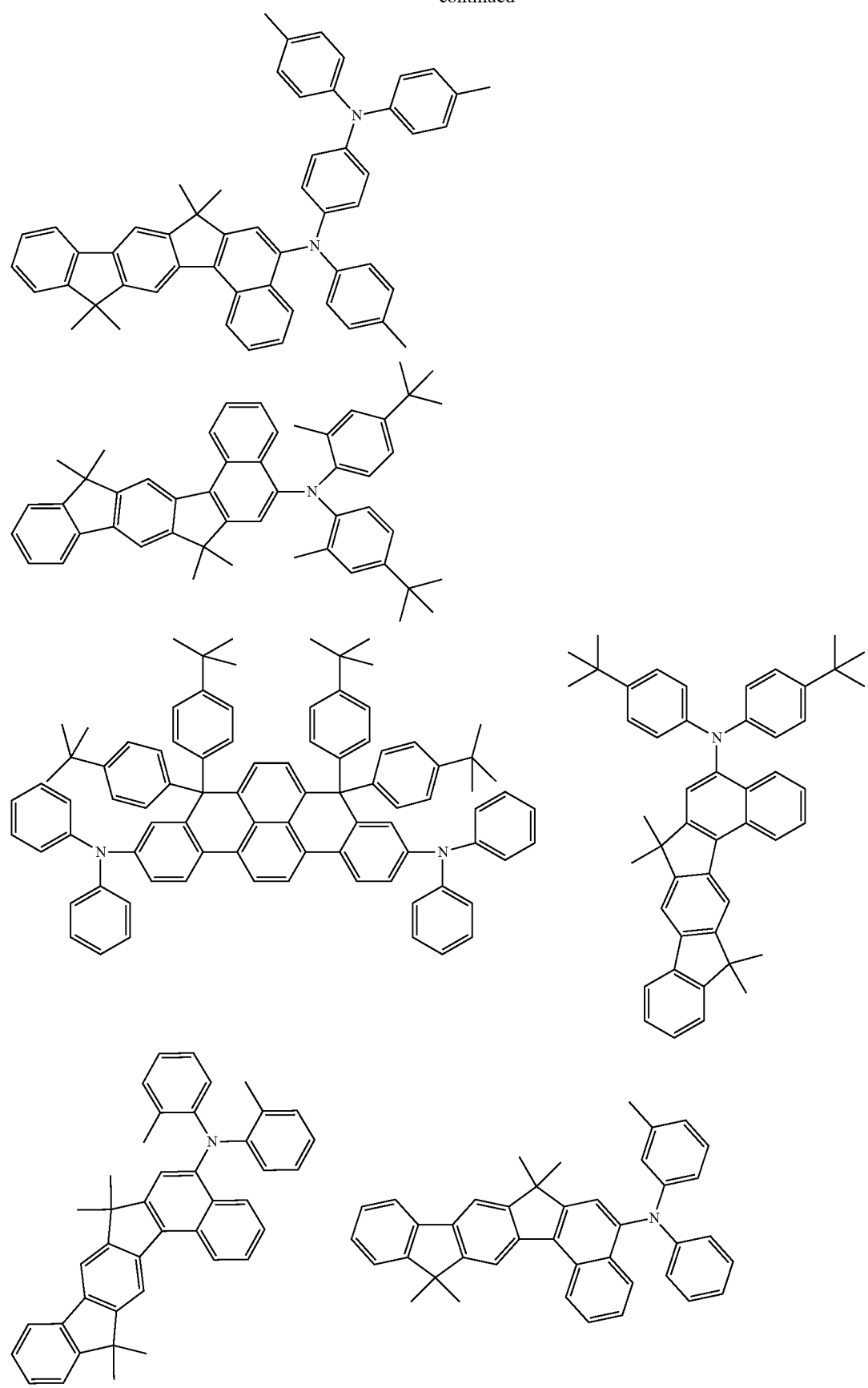

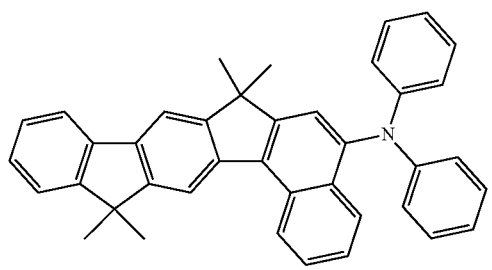
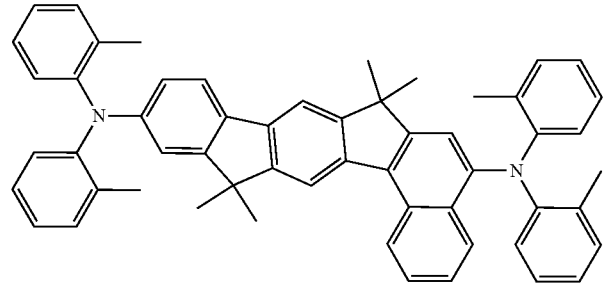
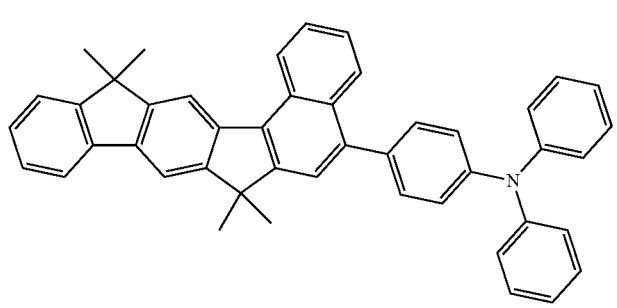
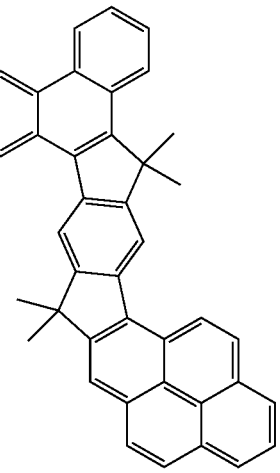
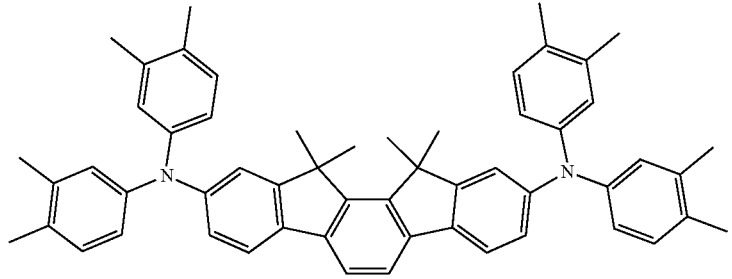
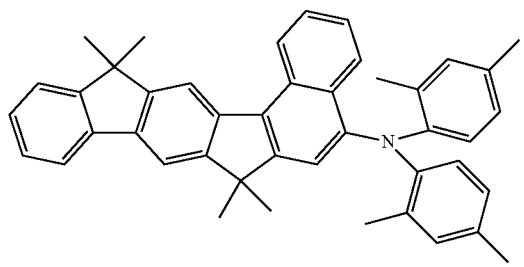
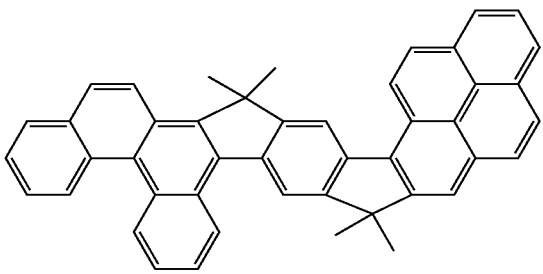
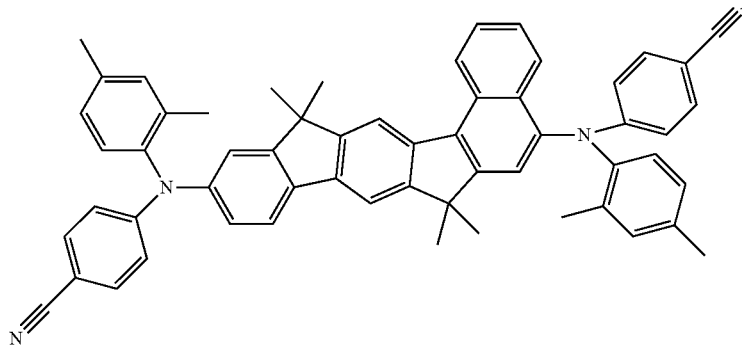

-continued
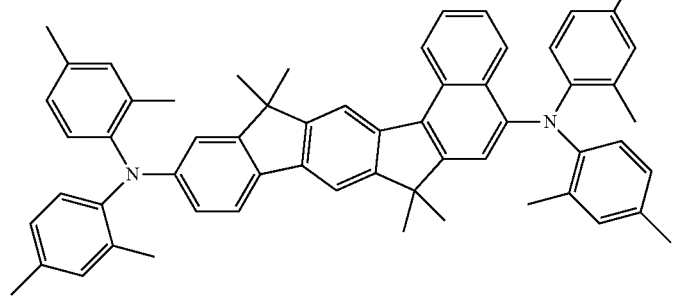
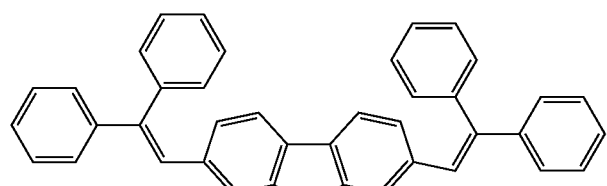
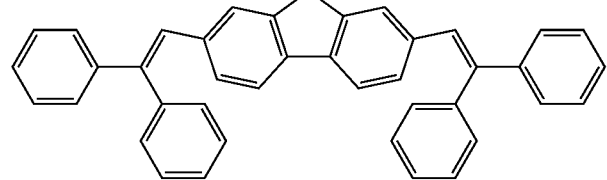
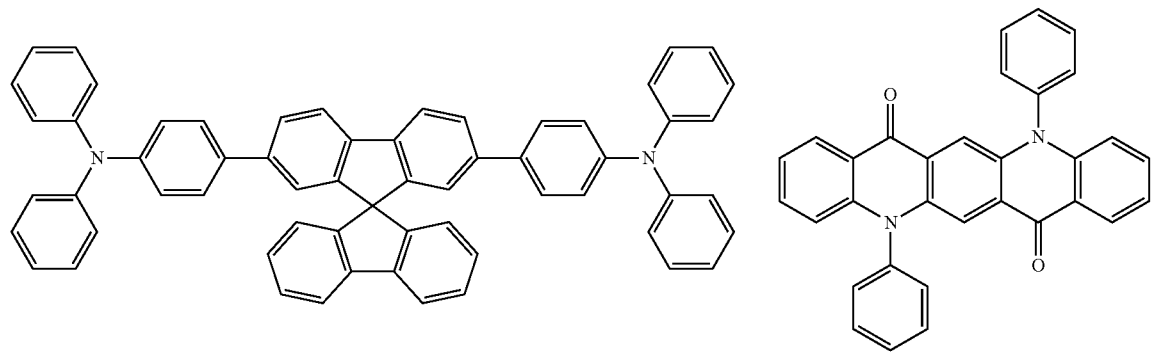
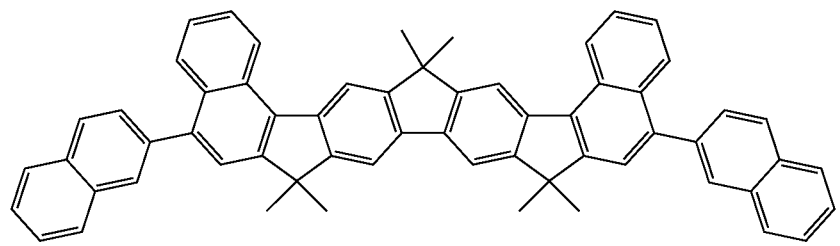
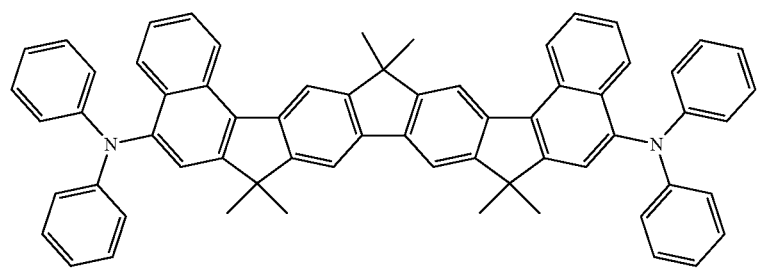

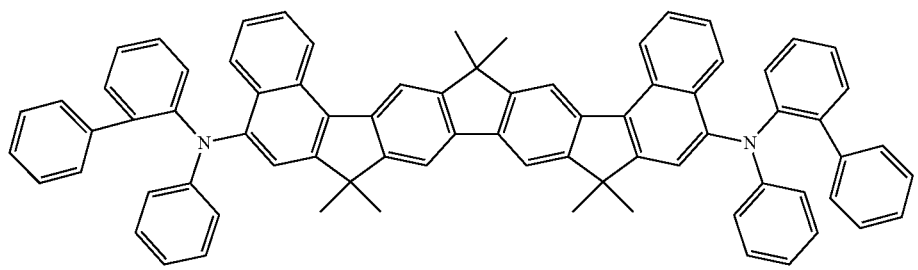
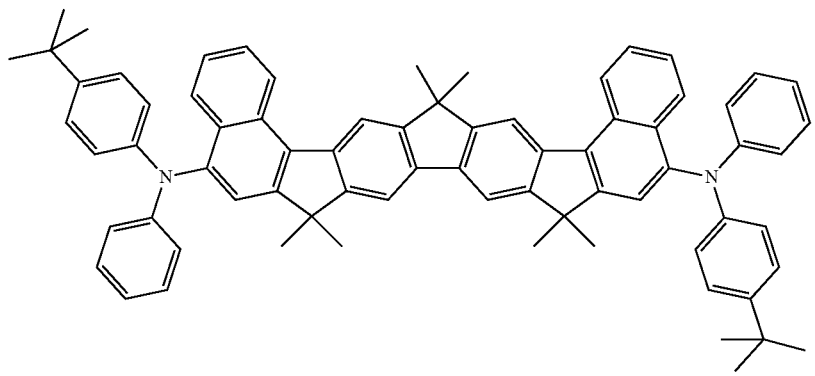
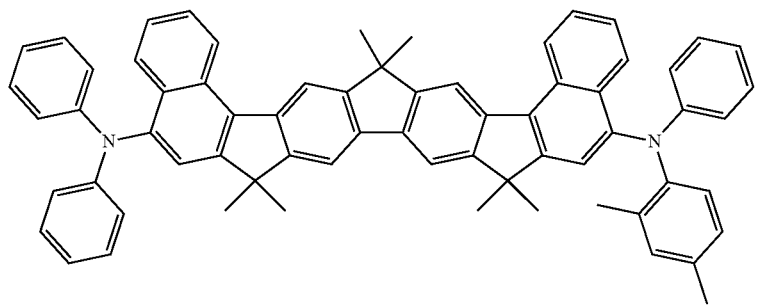
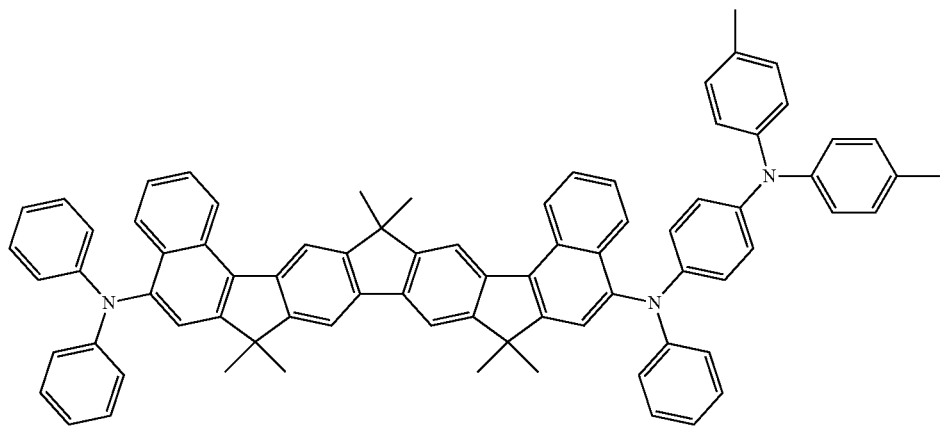
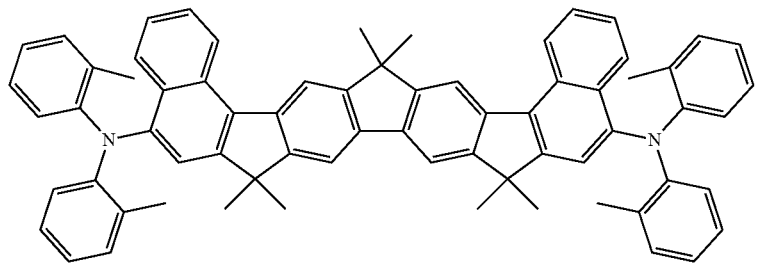

-continued
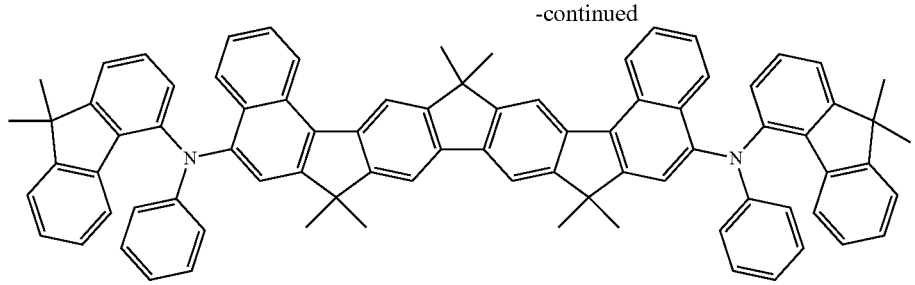
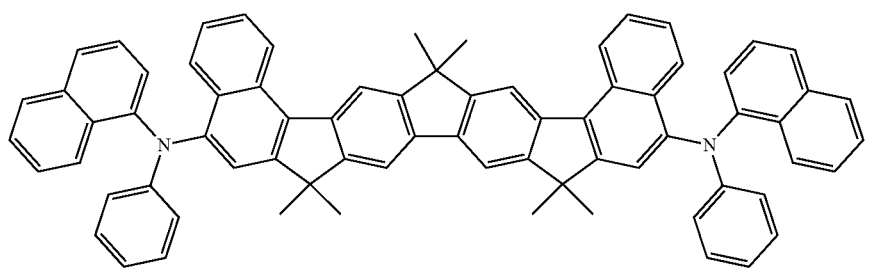
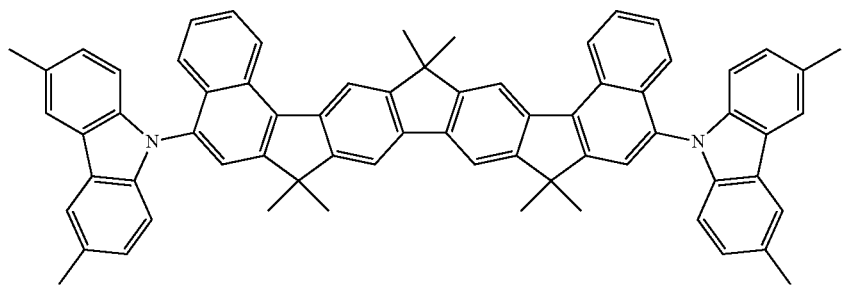
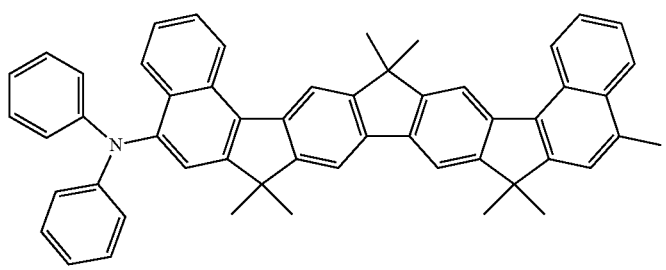
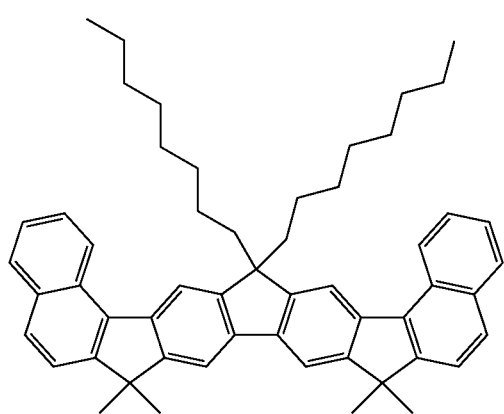

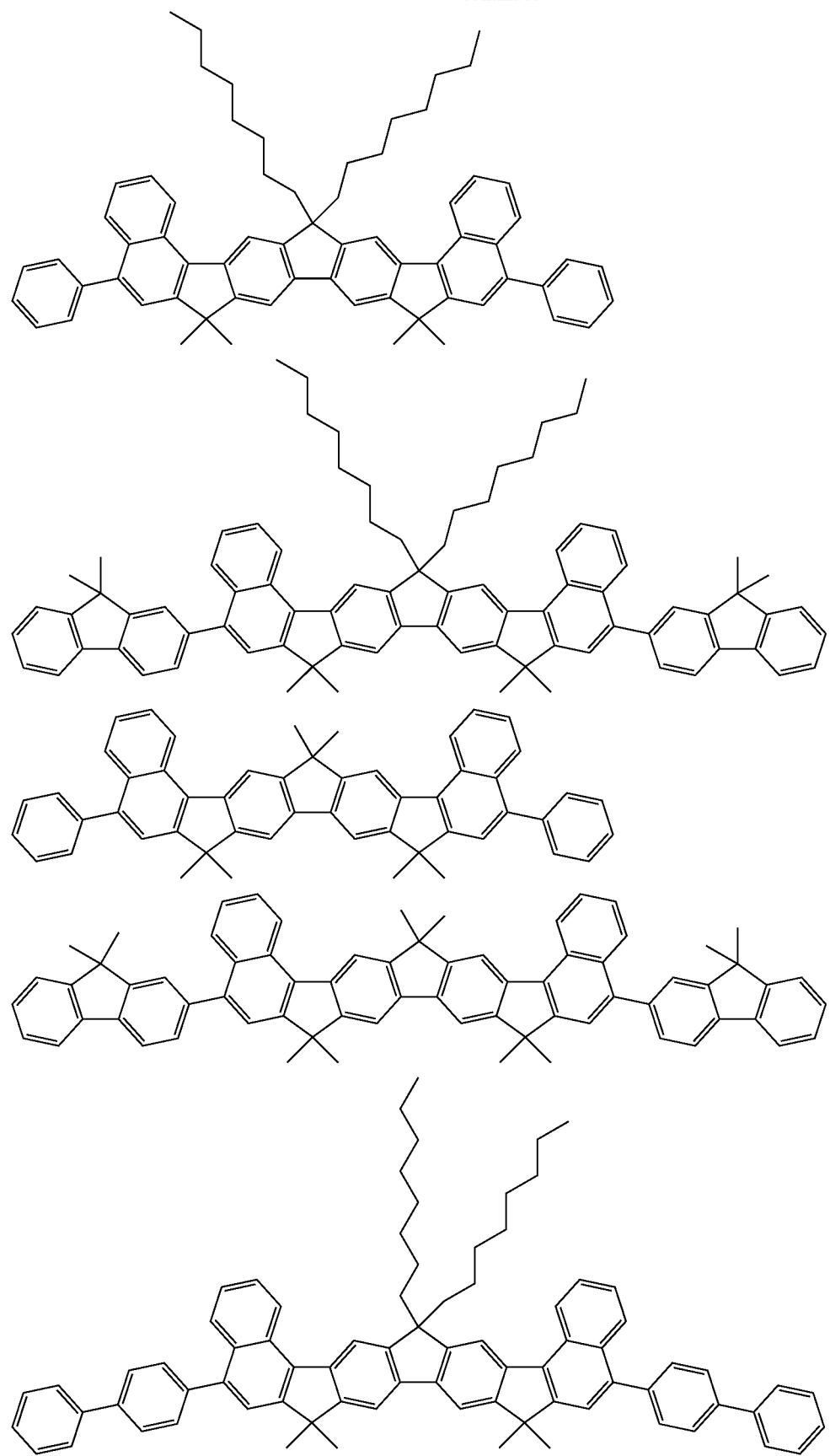

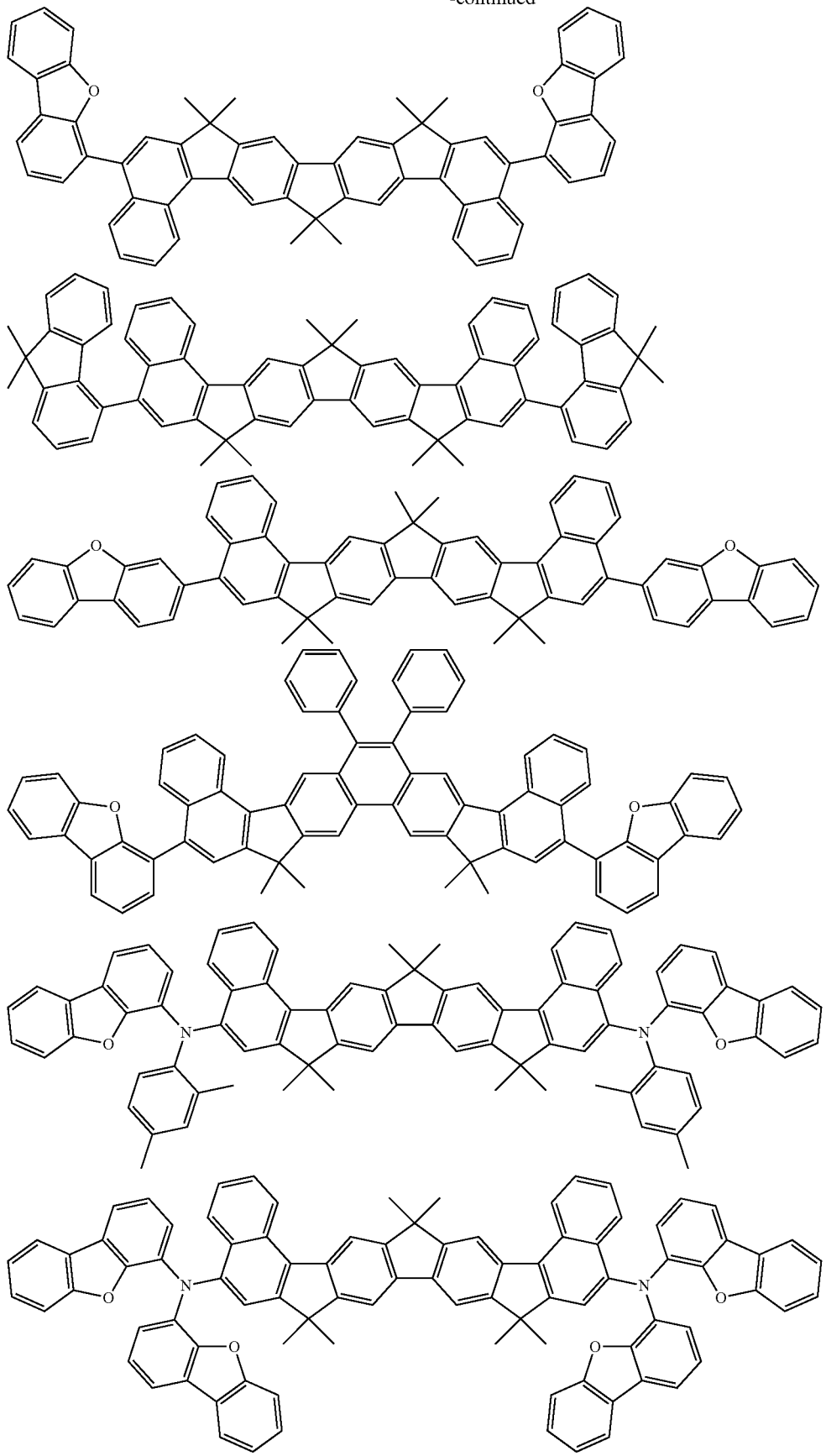

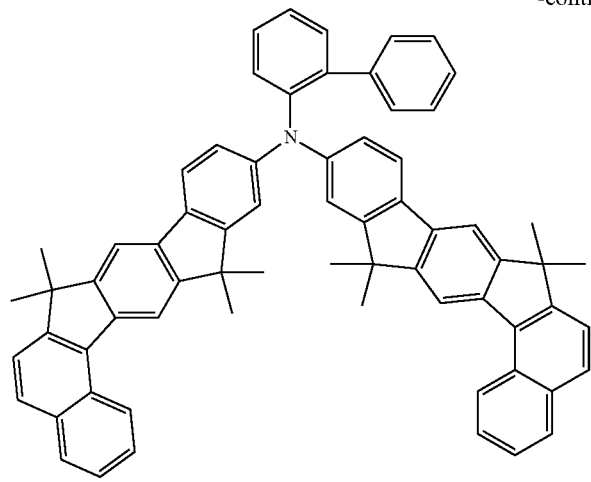

Matrix Materials for Fluorescent Emitters:

Preferred matrix materials for fluorescent emitters are selected from the classes of the oligoarylenes (e.g. 2,2',7,7'-tetraphenylspirobifluorene), especially the oligoarylenes containing fused aromatic groups, the oligoarylenevinylenes, the polypodal metal complexes, the hole-conducting compounds, the electron-conducting compounds, especially ketones, phosphine oxides and sulfoxides; the atropisomers, the boronic acid derivatives or the benzanthracenes. Particularly preferred matrix materials are selected from the classes of the oligoarylenes comprising naphthalene, anthracene, benzanthracene and/or pyrene or atropisomers of these compounds, the oligoarylenevinylenes, the ketones, the phosphine oxides and the sulfoxides. Very particularly preferred matrix materials are selected from the classes of the oligoarylenes comprising anthracene, benzanthracene, benzophenanthrene and/or pyrene or atropisomers of these compounds. An oligoarylene in the context of this invention shall be understood to mean a compound in which at least three aryl or arylene groups are bonded to one another. Preferred matrix materials for fluorescent emitters are depicted in the following table:

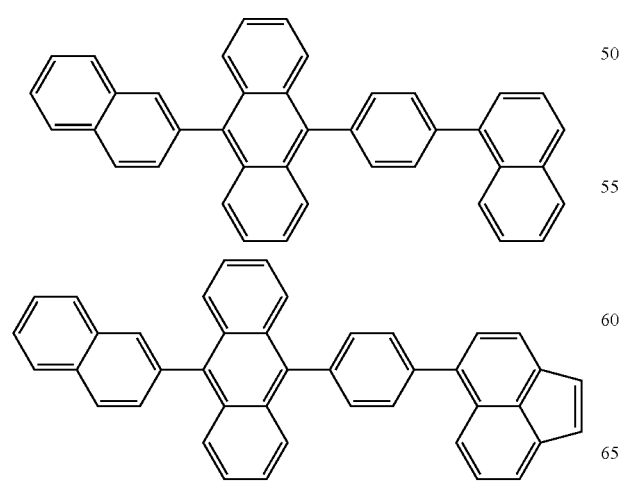

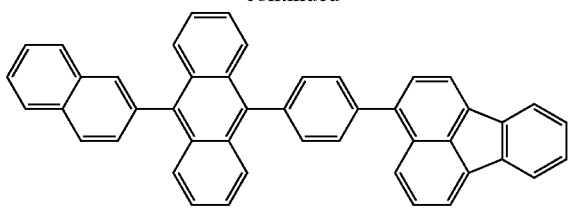

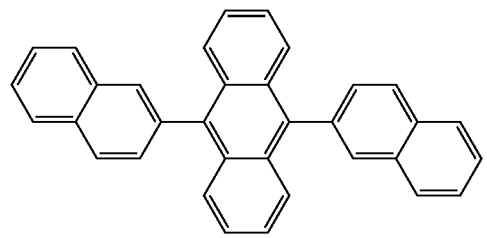

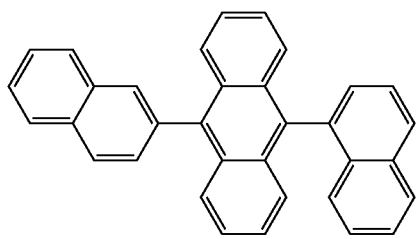

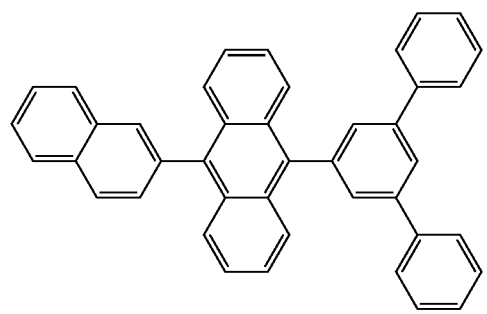

251
-continued
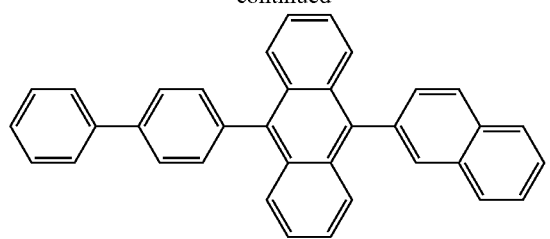
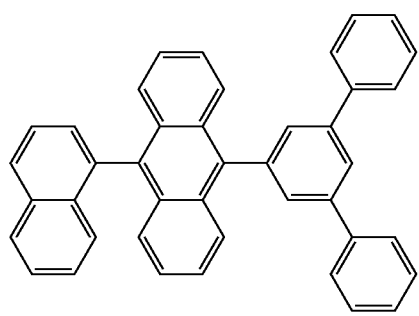
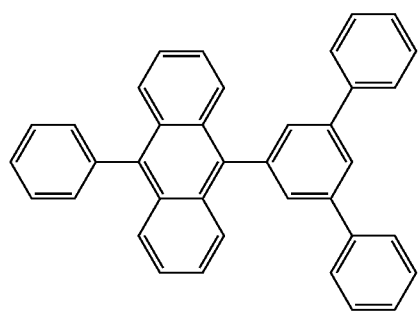
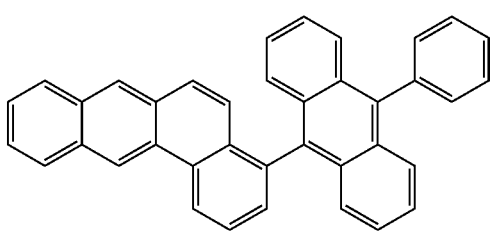
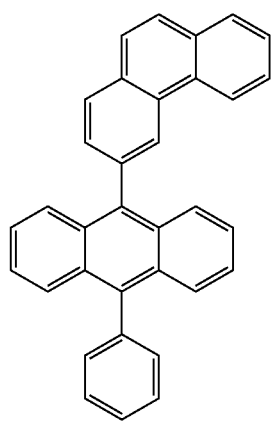
252
-continued
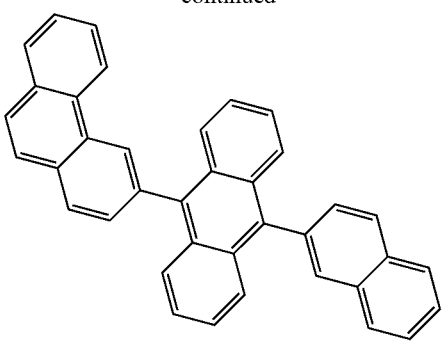
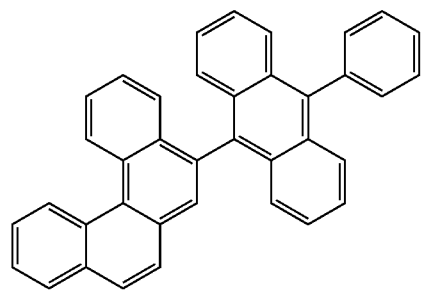
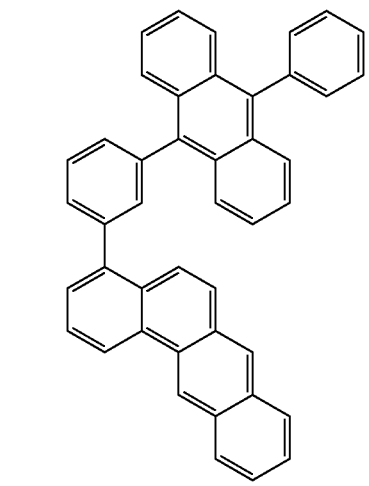
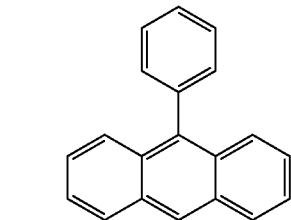
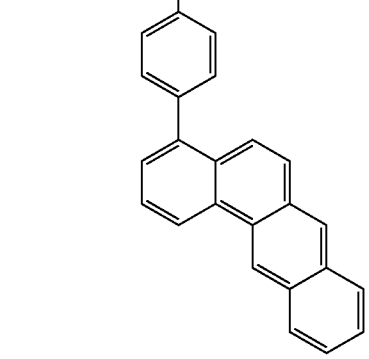

253
-continued
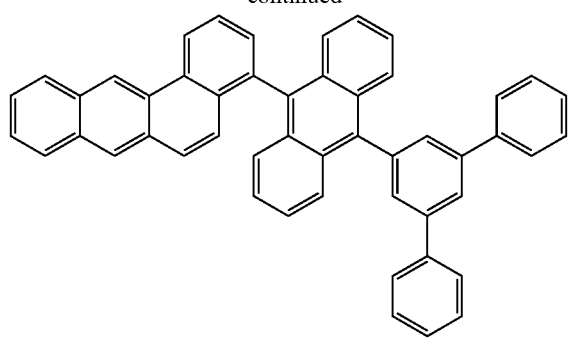
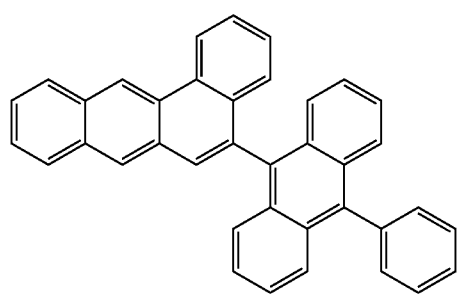
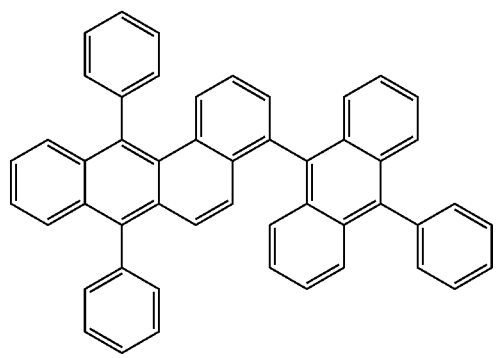
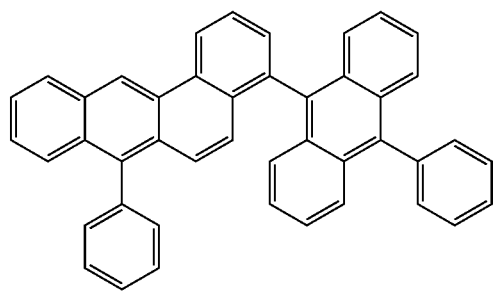
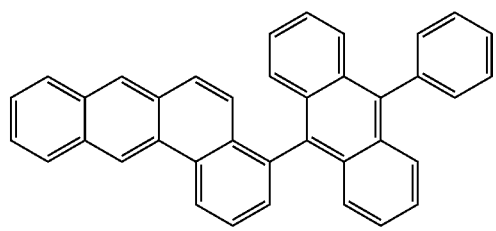
254
-continued
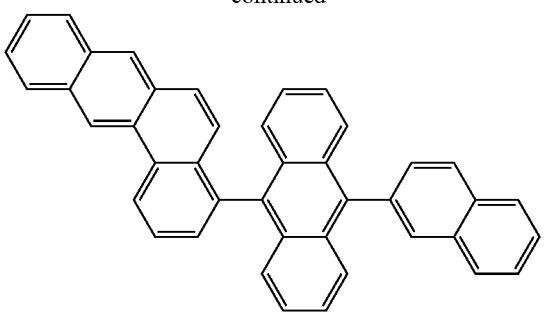
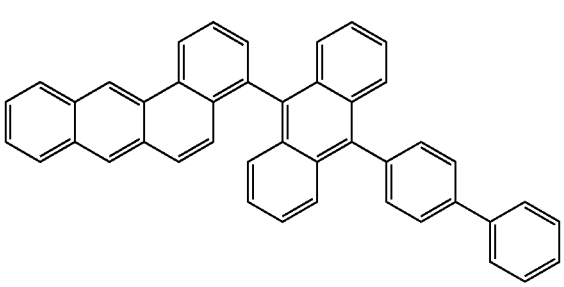
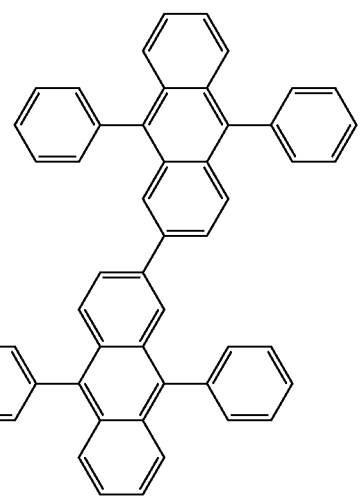
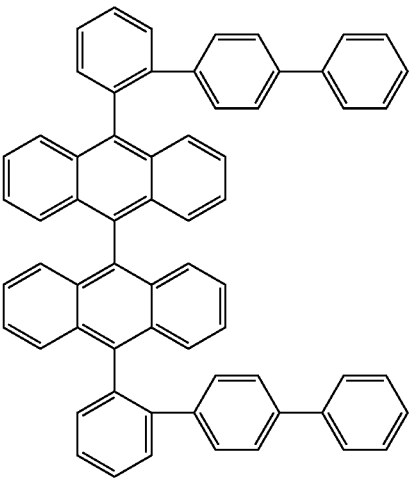

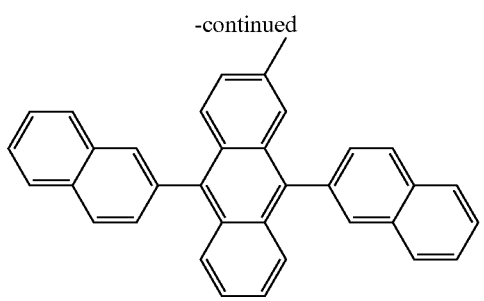
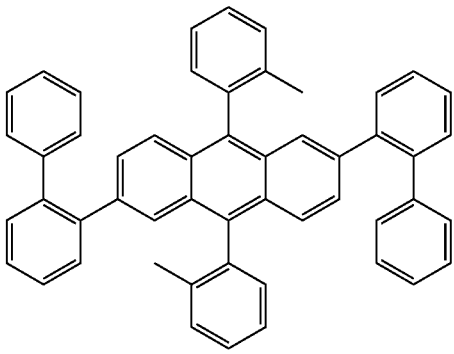
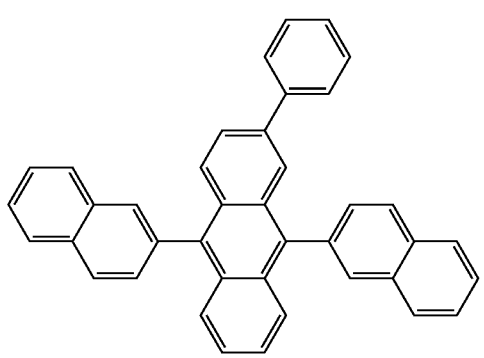
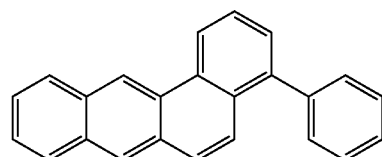
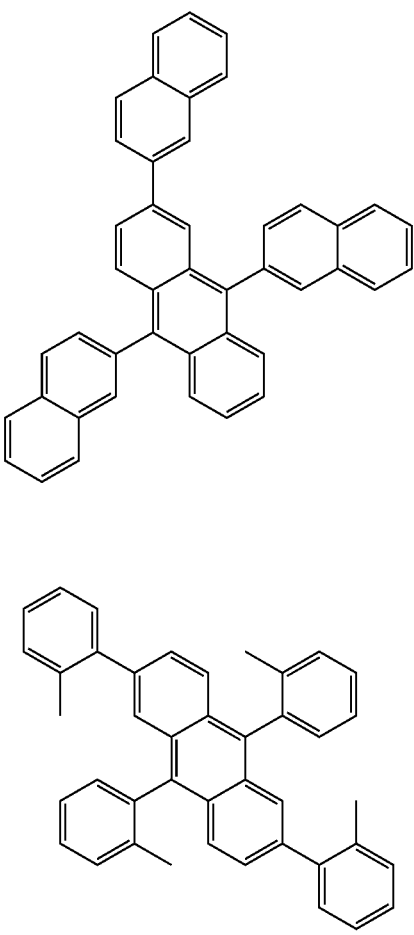
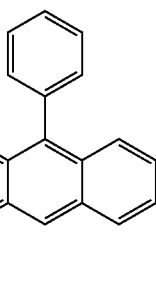
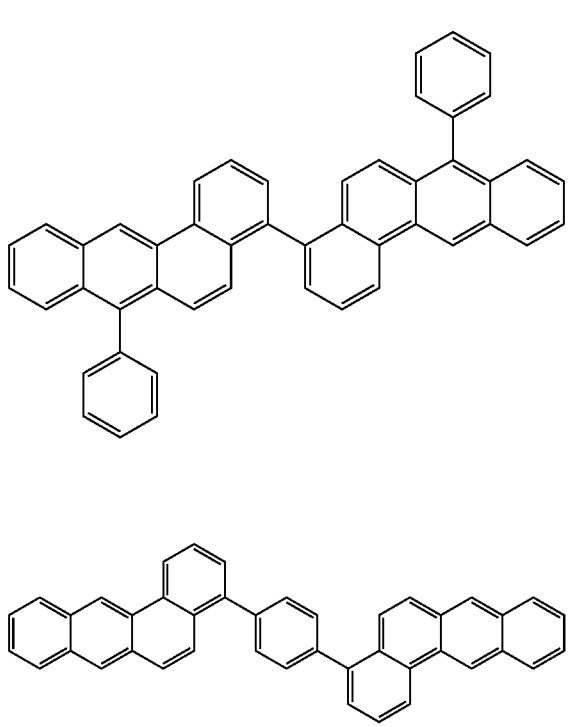

257
-continued
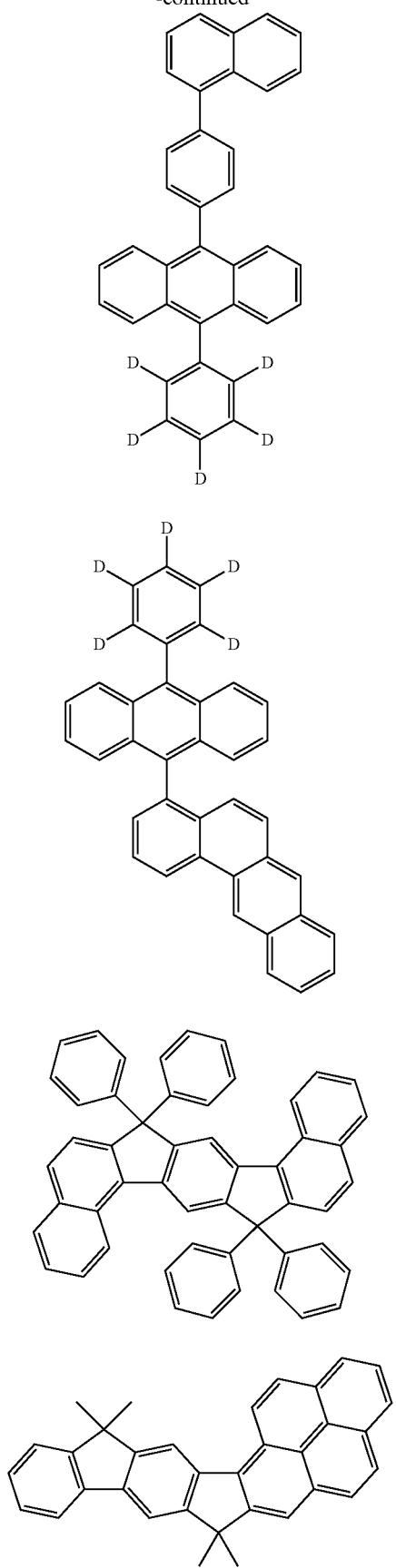
258
-continued
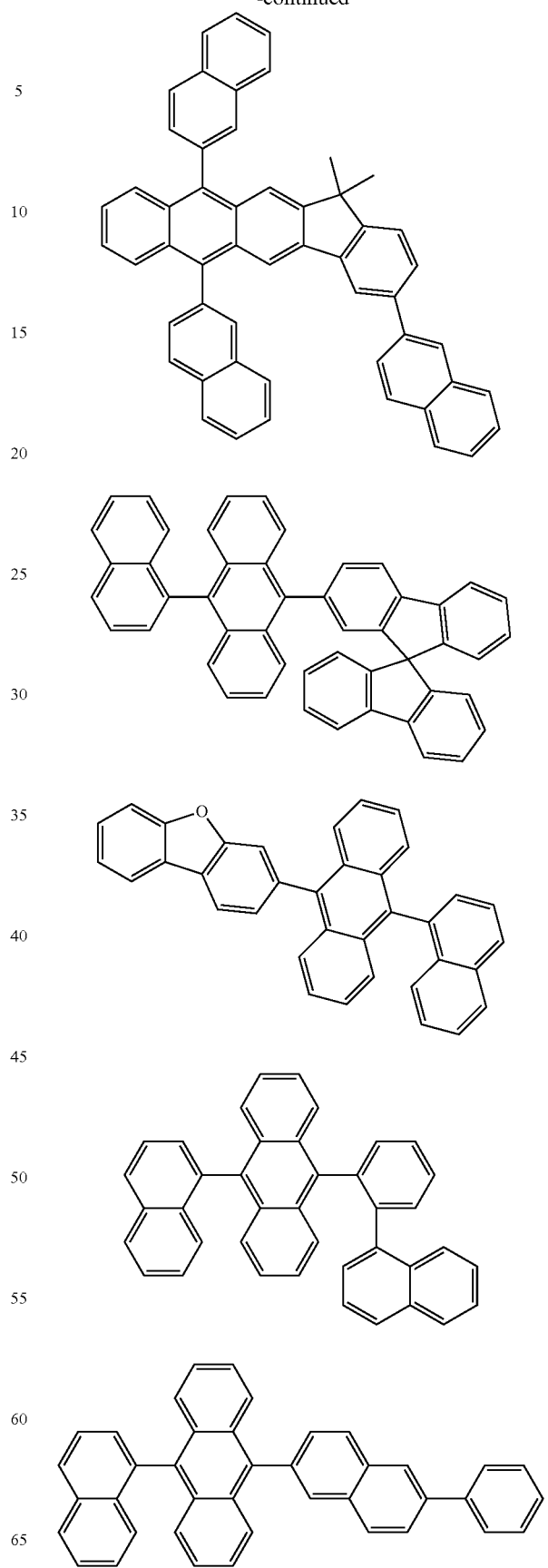

259
-continued
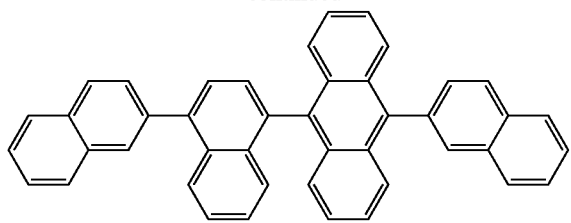
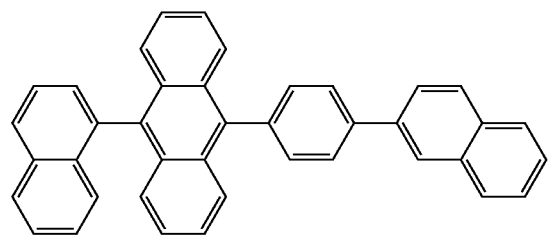
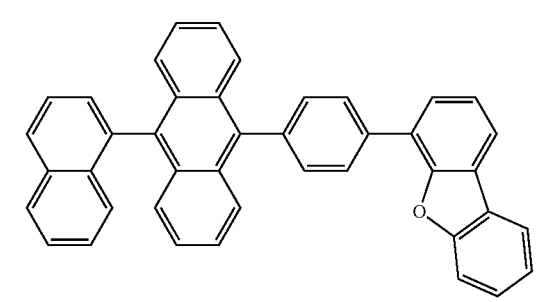
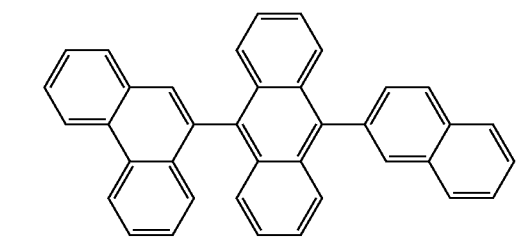
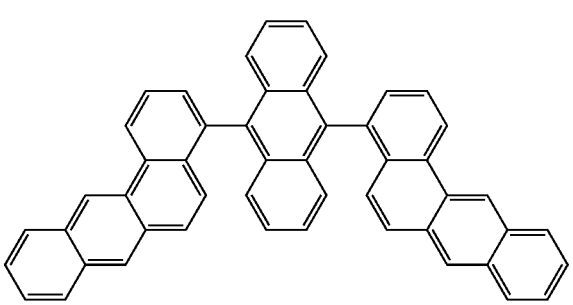
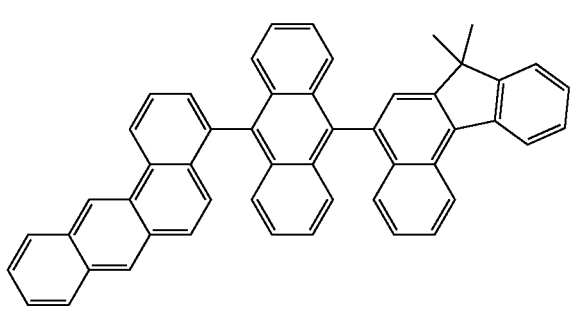
260
-continued
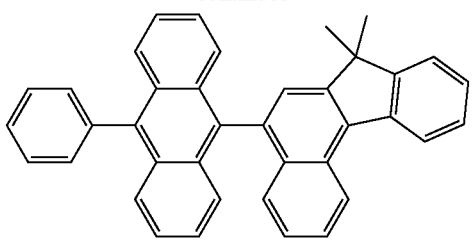
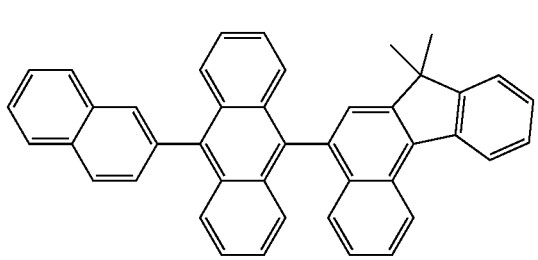
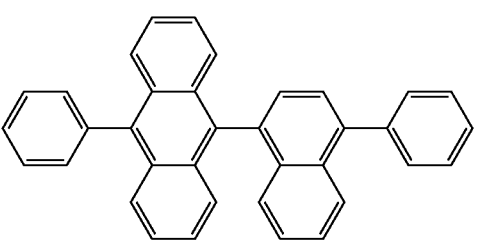
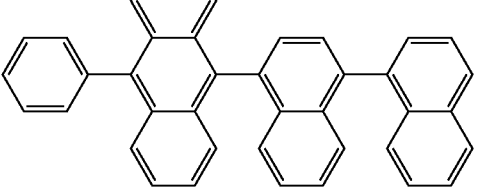
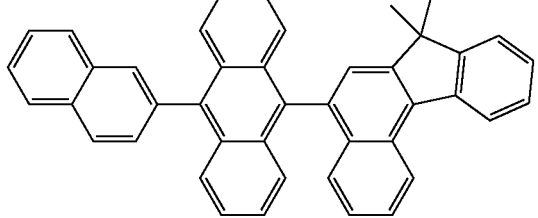
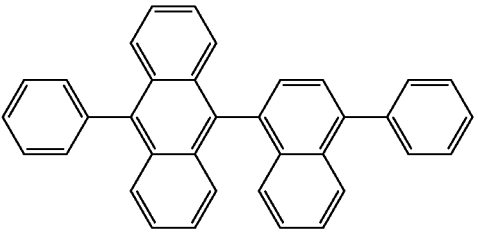
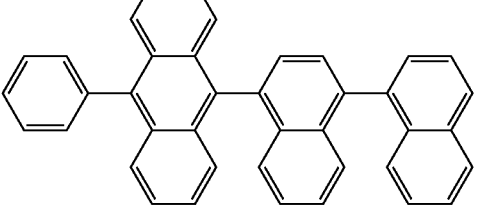

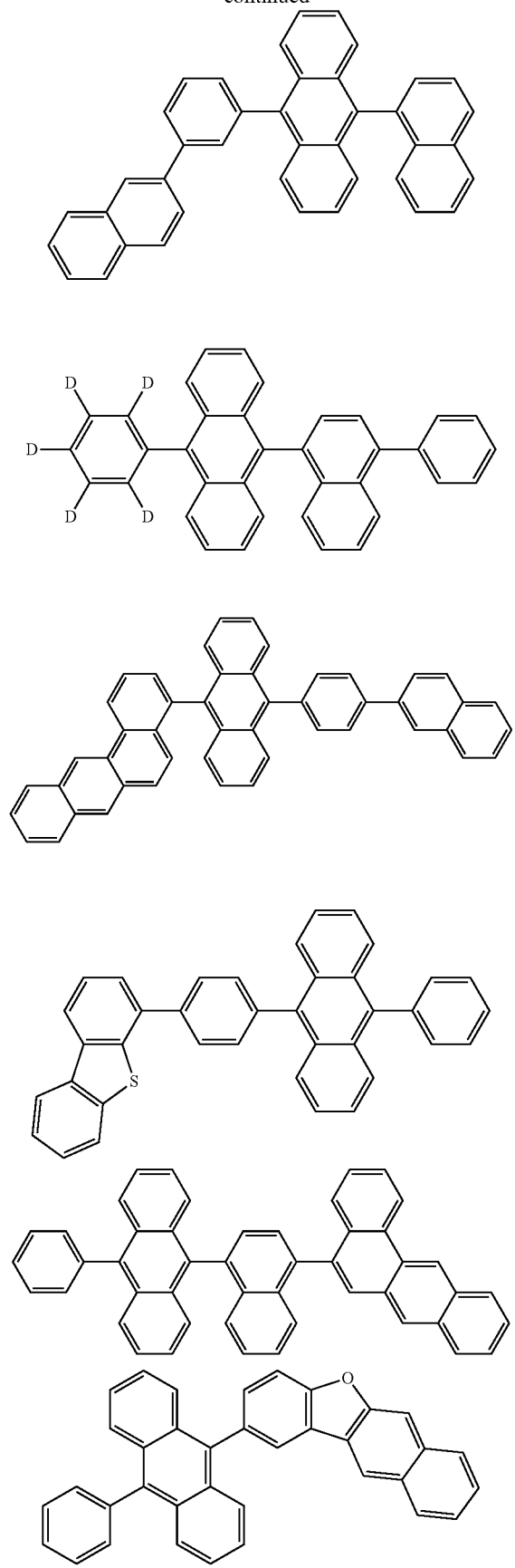
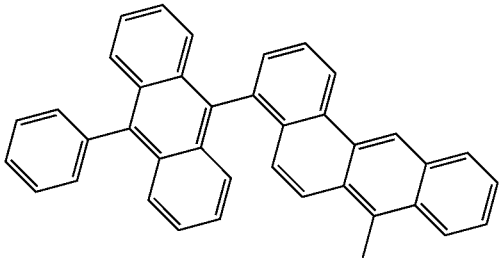
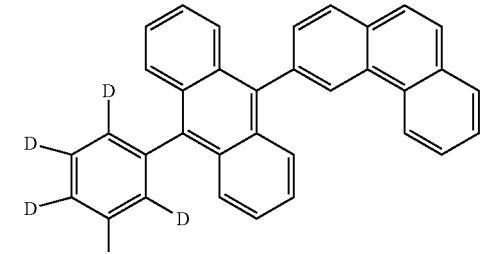
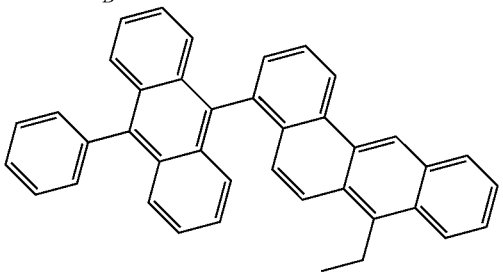
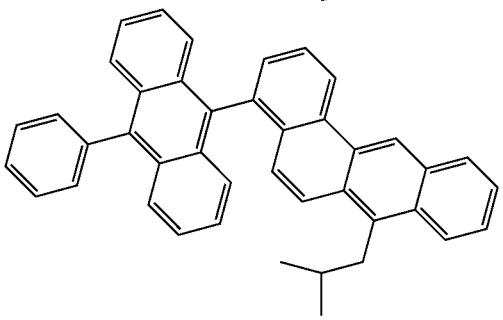
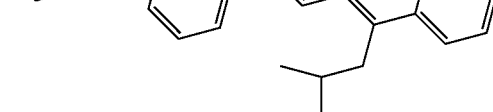

Matrix Materials for Phosphorescent Emitters:

Preferred matrix materials for phosphorescent emitters are, as well as the compounds of the formula (I), aromatic ketones, aromatic phosphine oxides or aromatic sulfoxides or sulfones, triarylamines, carbazole derivatives, e.g. CBP (N,N-biscarbazolylbiphenyl), indolocarbazole derivatives, indenocarbazole derivatives, azacarbazole derivatives, bipolar matrix materials, silanes, azaboroles or boronic esters, triazine derivatives, zinc complexes, diazasilole or tetraazasilole derivatives, diazaphosphole derivatives, bridged carbazole derivatives, triphenylene derivatives, or lactams.

Electron-Transporting Materials:

Suitable electron-transporting materials are, for example, the compounds disclosed in Y. Shirota et al., Chem. Rev. 2007, 107(4), 953-1010, or other materials used in these layers according to the prior art.

Materials used for the electron transport layer may be any materials that are used as electron transport materials in the electron transport layer according to the prior art. Especially suitable are aluminium complexes, for example $Alq_3$, zirconium complexes, for example $Zrq_4$, lithium complexes, for example Liq, benzimidazole derivatives, triazine derivatives, pyrimidine derivatives, pyridine derivatives, pyrazine derivatives, quinoxaline derivatives, quinoline derivatives, oxadiazole derivatives, aromatic ketones, lactams, boranes, diazaphosphole derivatives and phosphine oxide derivatives. Preferred electron-transporting compounds are shown in the following table:
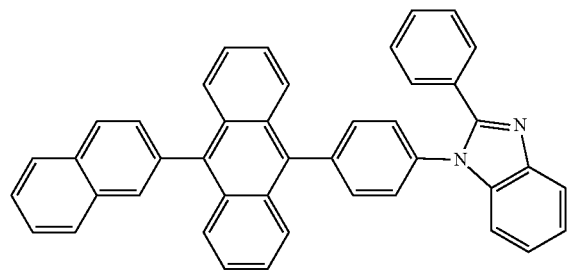
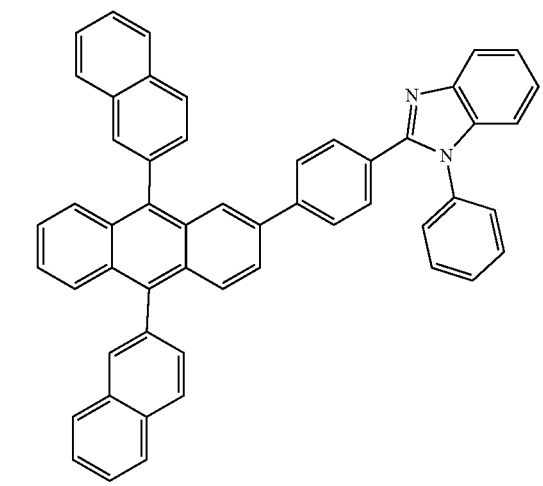
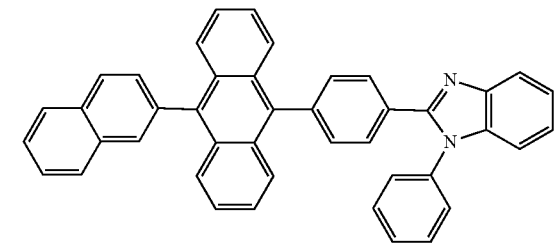
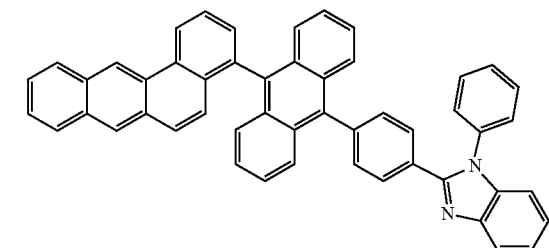
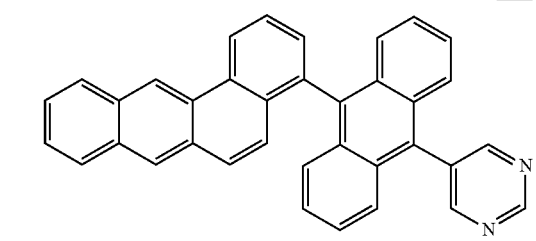
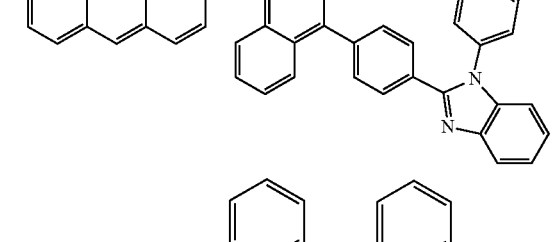
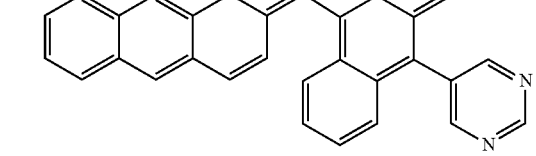
-continued
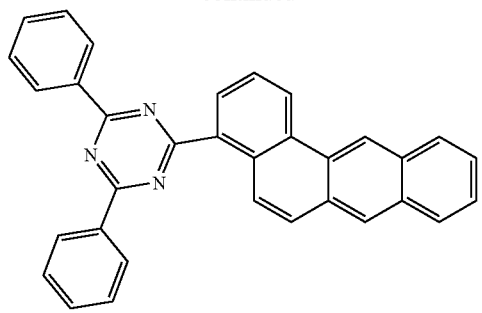
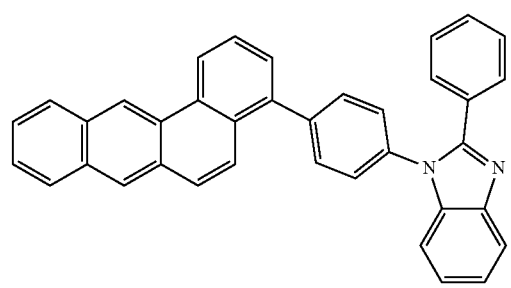
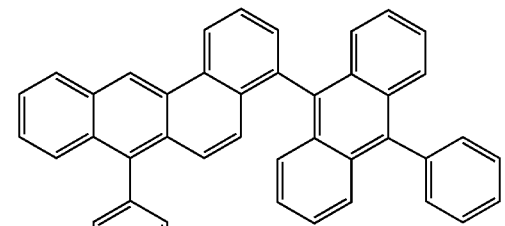
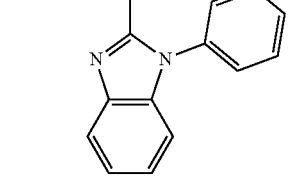
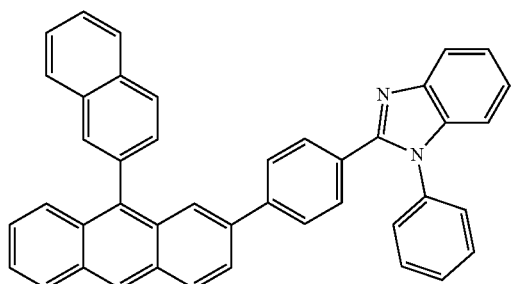
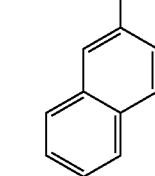

265
-continued
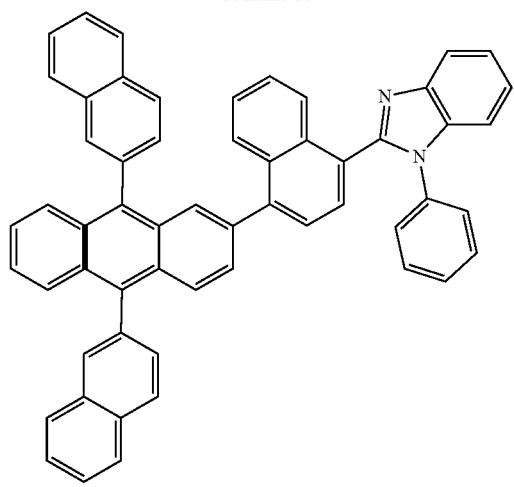
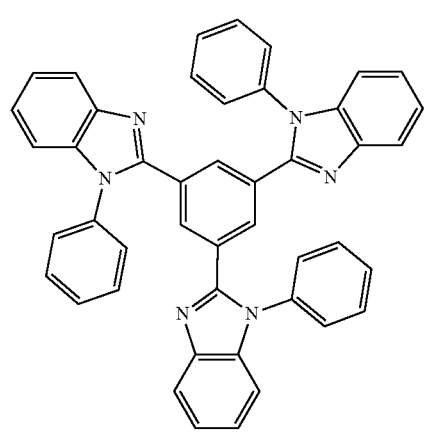
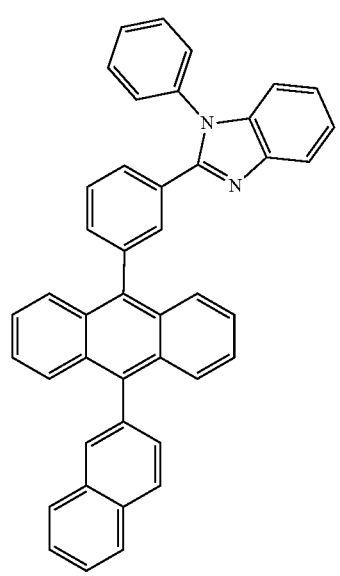
266
-continued
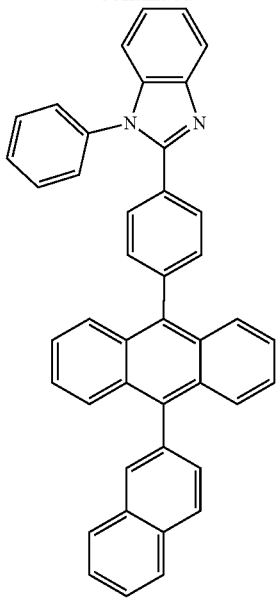
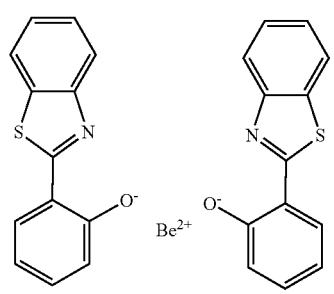
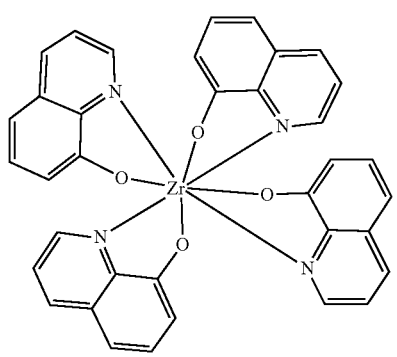

267
-continued
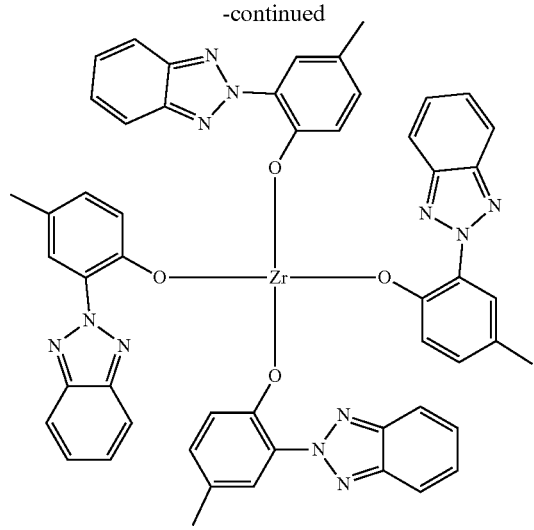
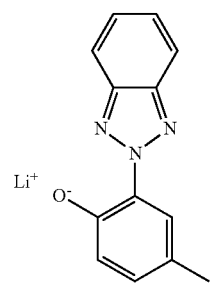
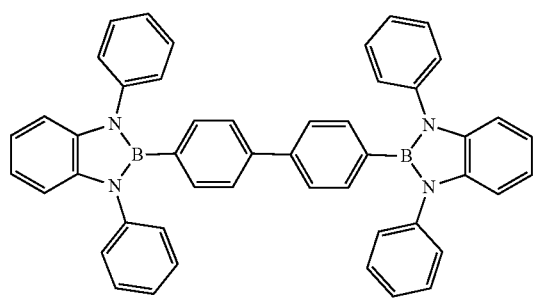
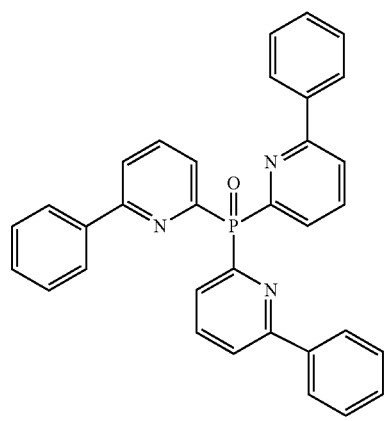
268
-continued
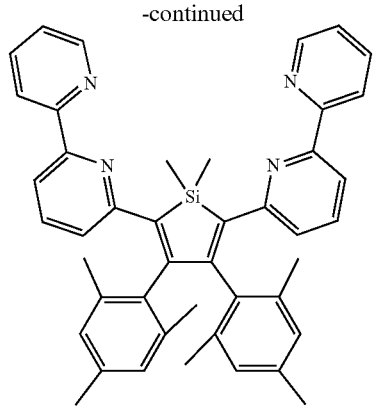

269
-continued

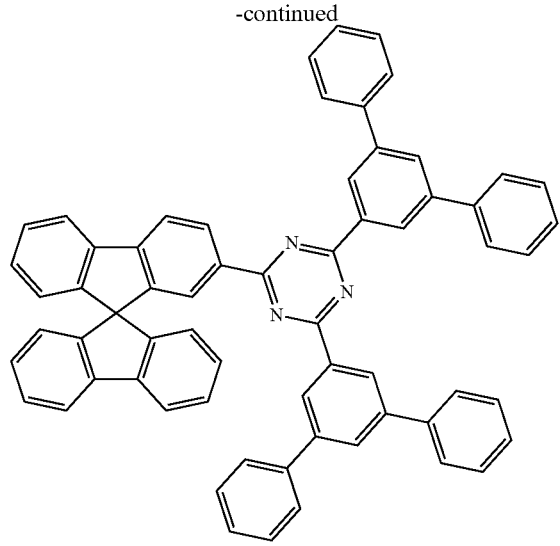

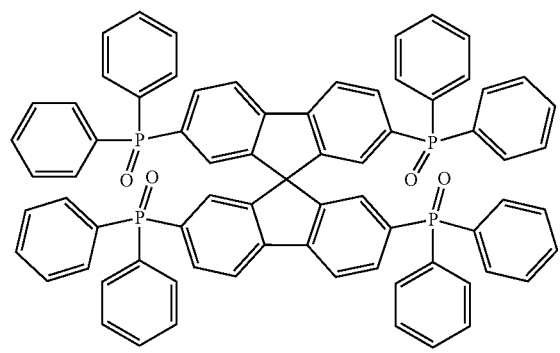

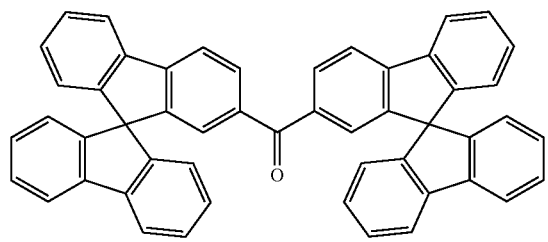

270
-continued

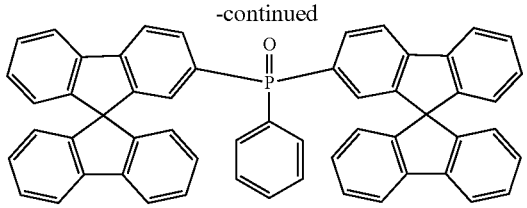

Hole-Transporting Materials:

Further compounds which, in addition to the compounds of the formula (I), are preferably used in hole-transporting layers of the OLEDs of the invention are indenofluoreneamine derivatives, amine derivatives, hexaazatriphenylene derivatives, amine derivatives with fused aromatic systems, monobenzoindenofluoreneamines, dibenzoindenofluoreneamines, spirobifluoreneamines, fluoreneamines, spirodibenzopyranamines, dihydroacridine derivatives, spirodibenzofurans and spirodibenzothiophenes, phenanthrenediarylamines, spirotribenzotropolones, spirobifluorenes having meta-phenyldiamine groups, spirobisacridines, xanthenediarylamines, and 9,10-dihydroanthracene spiro compounds having diarylamino groups. Preferred hole-transporting compounds are shown in the following table:

-continued
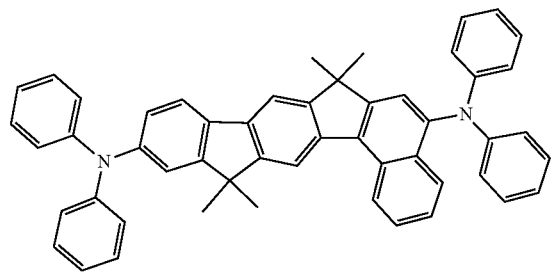
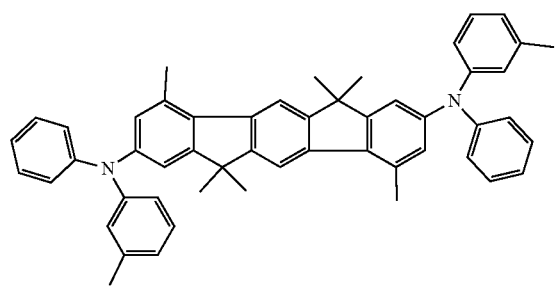
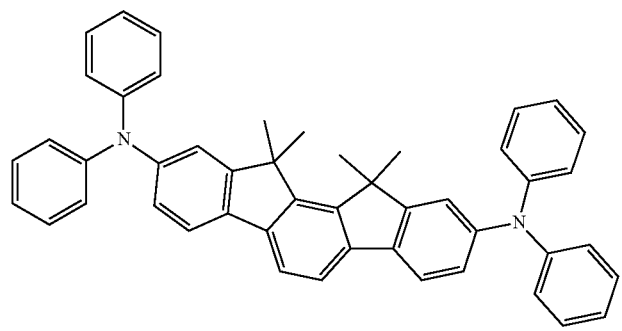
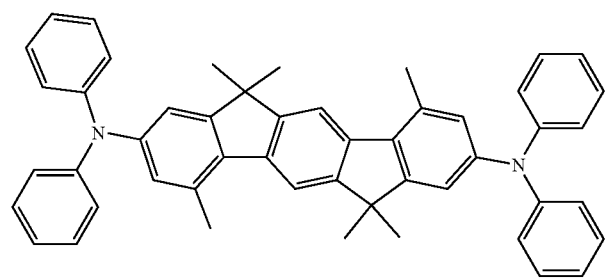
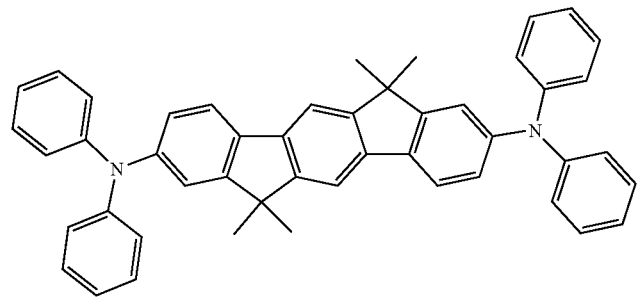

-continued
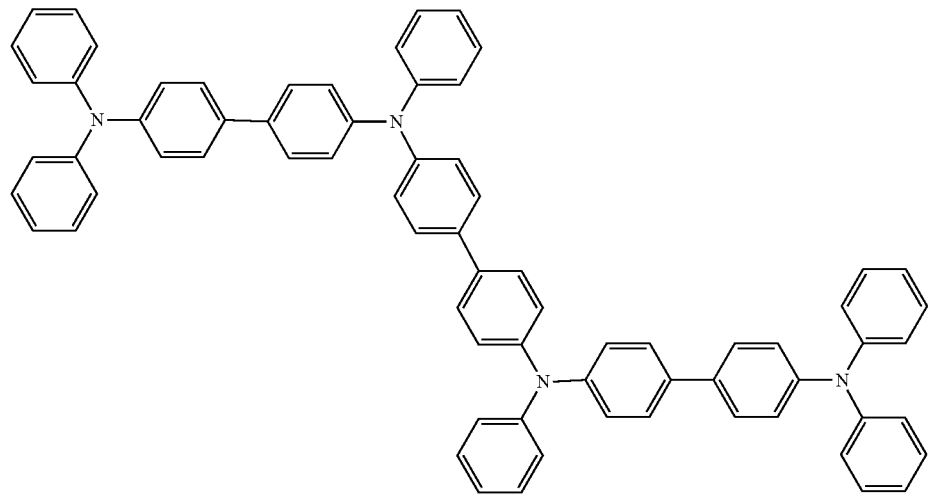
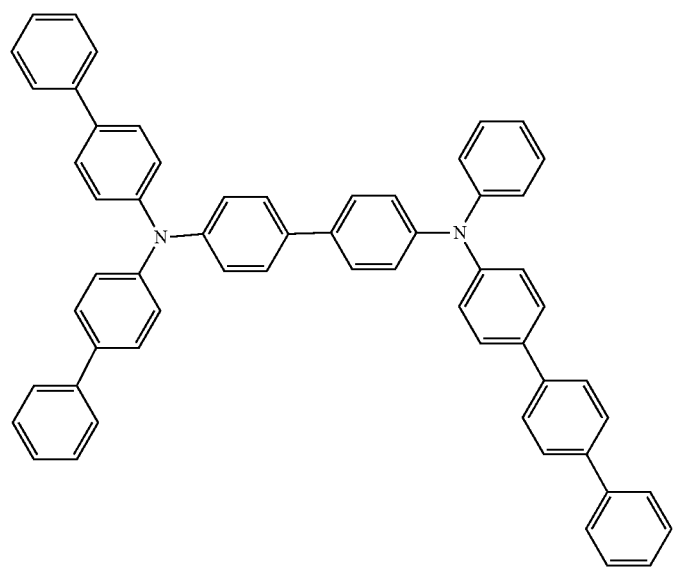
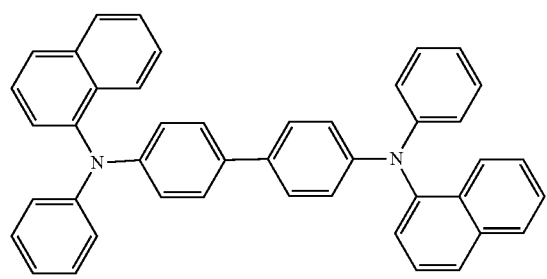

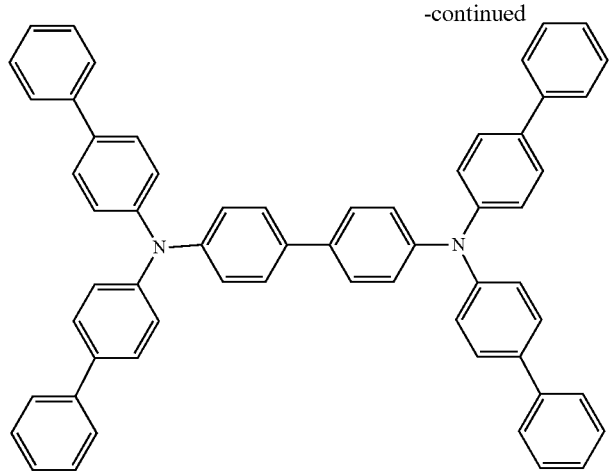
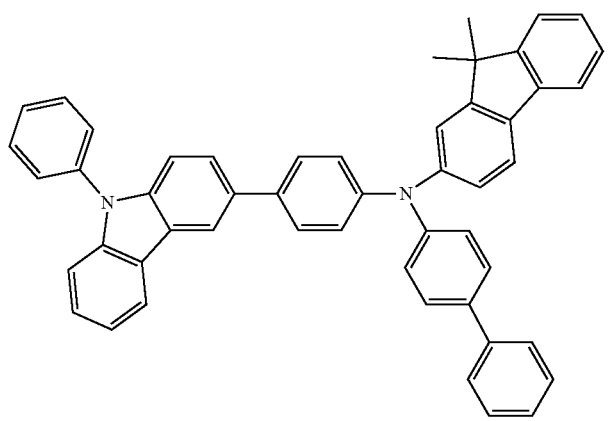
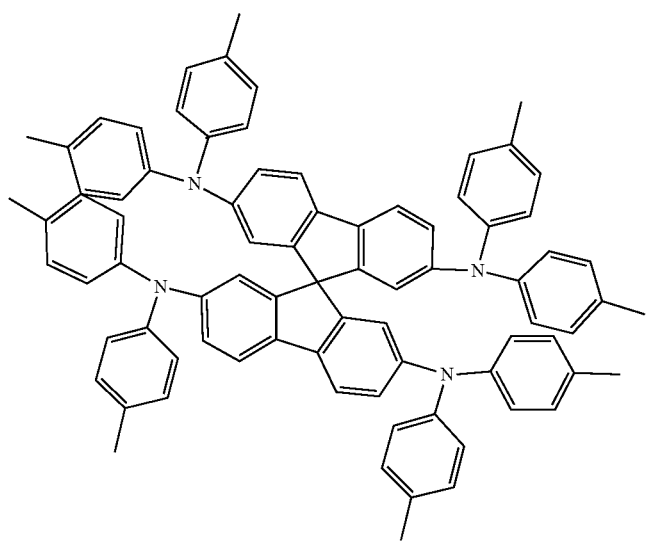

277
-continued
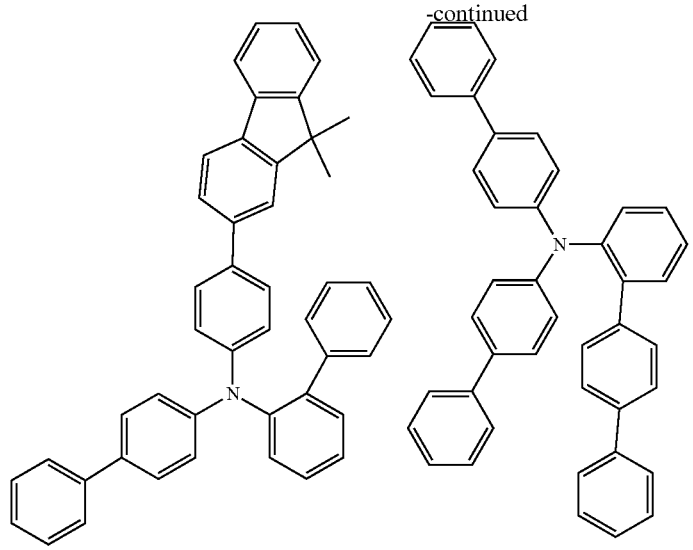
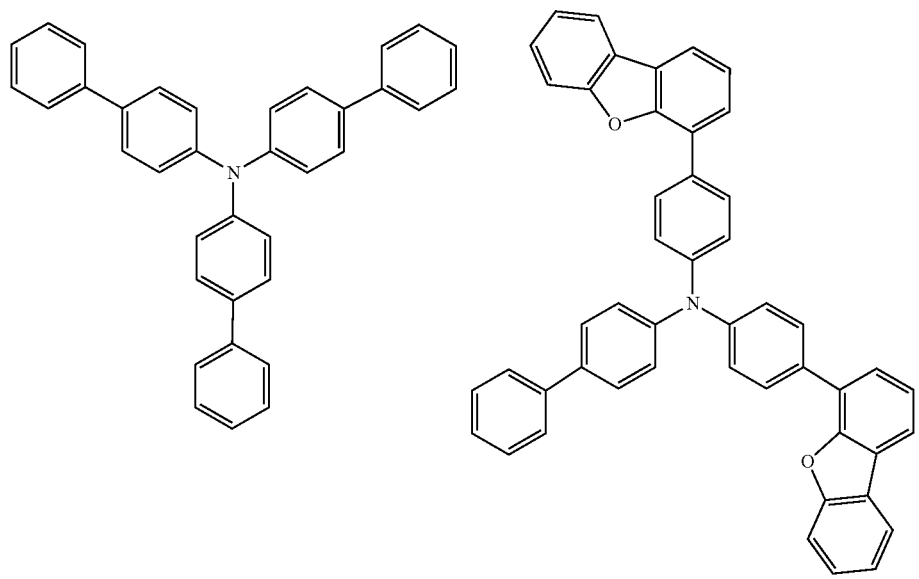
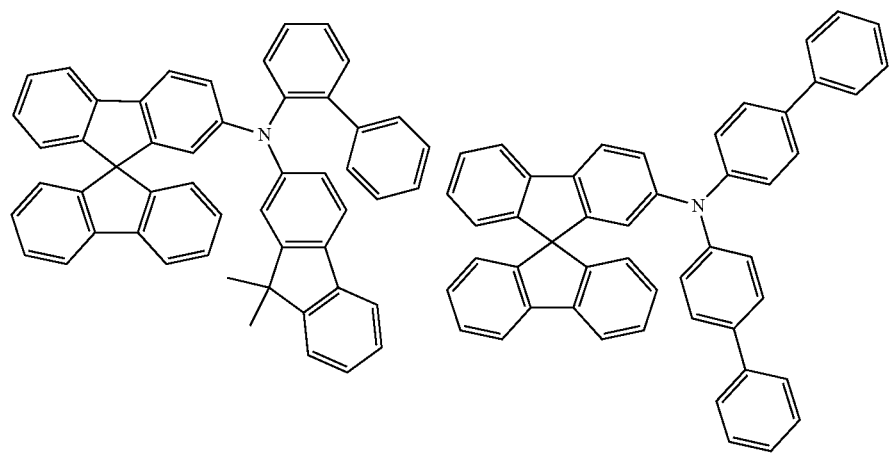
278

-continued
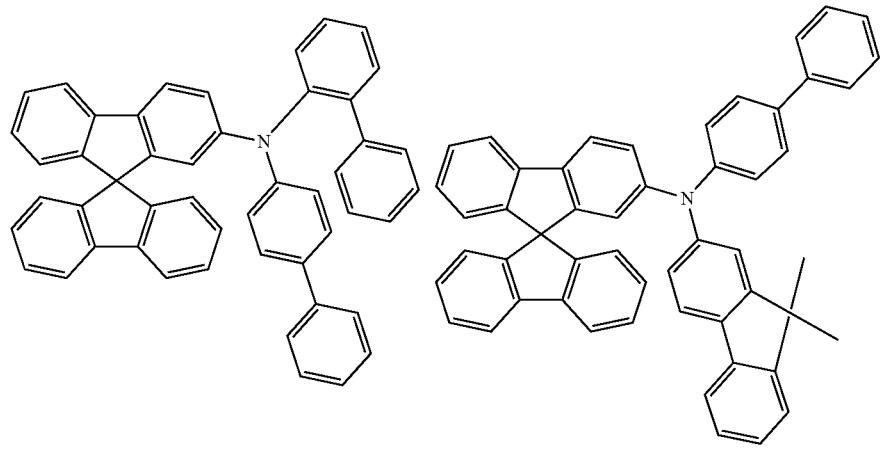
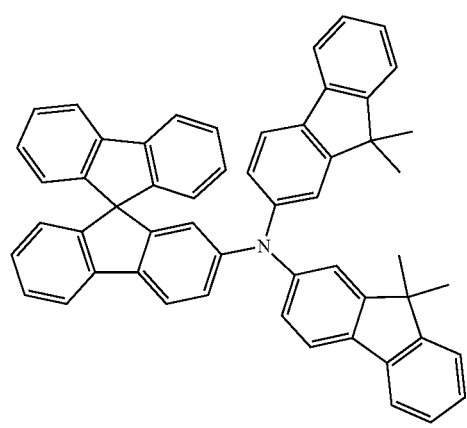
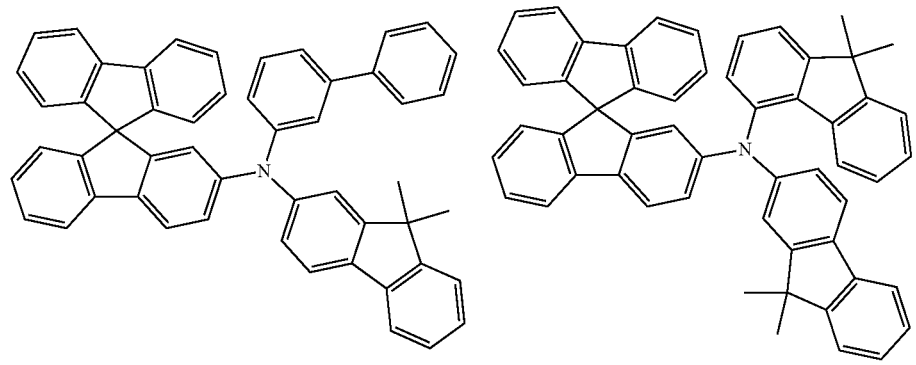
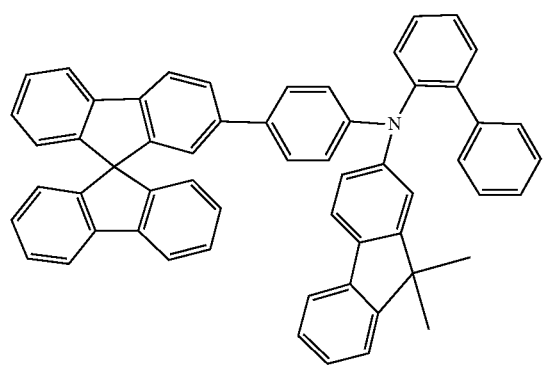

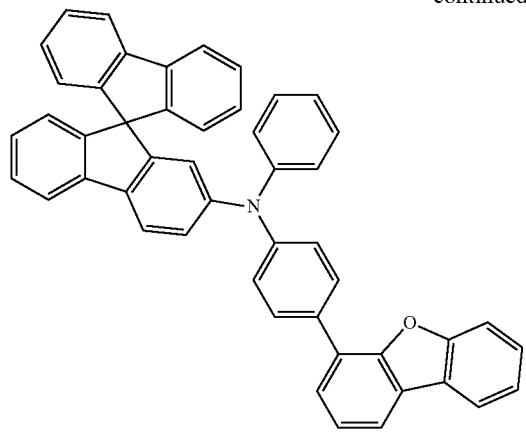
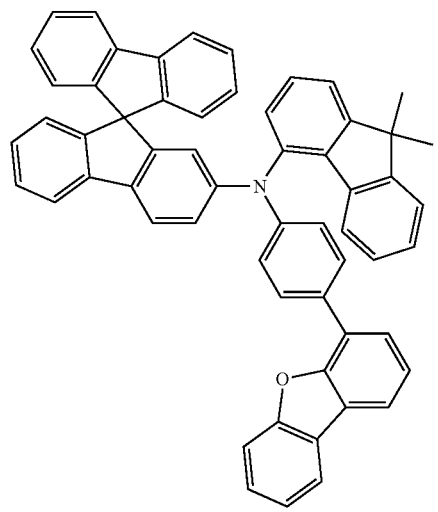
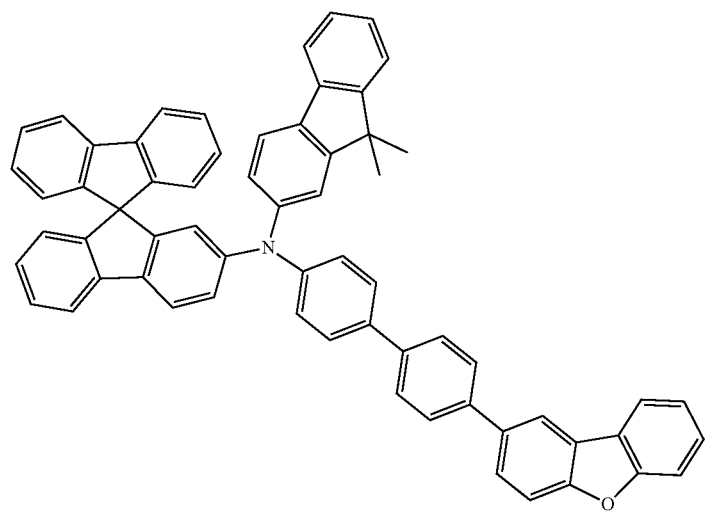

-continued
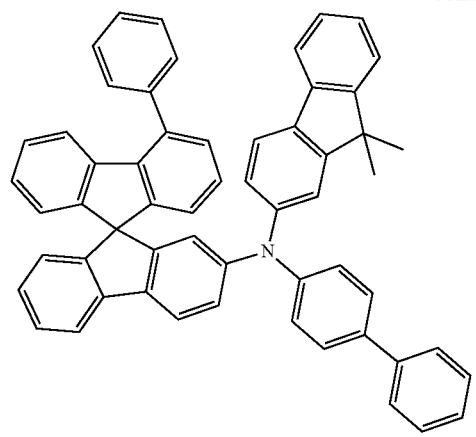
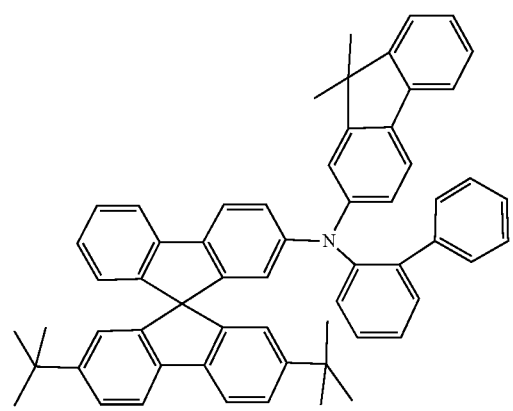
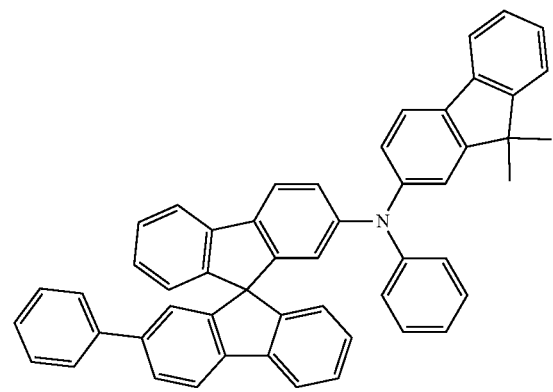

-continued
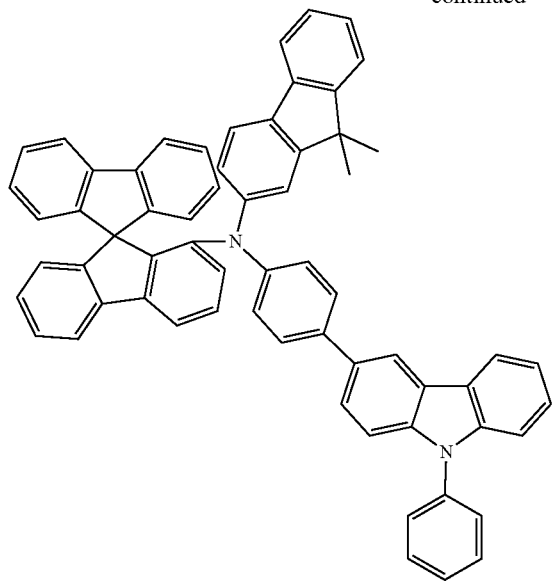
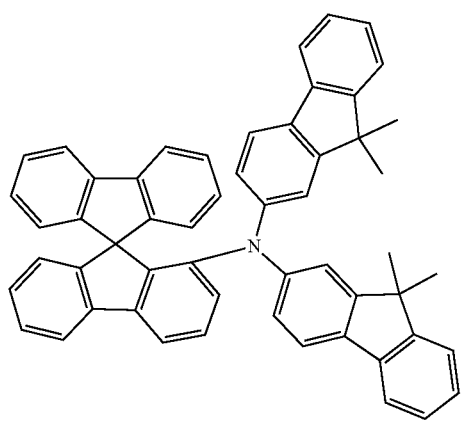
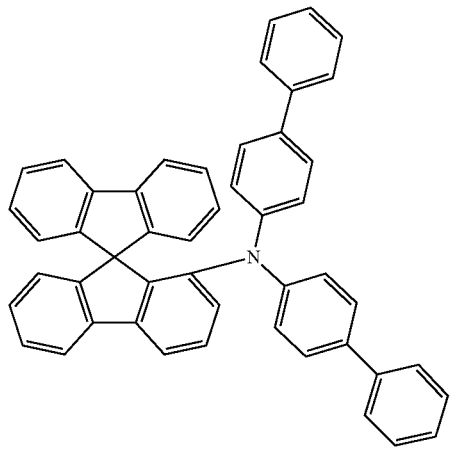

-continued
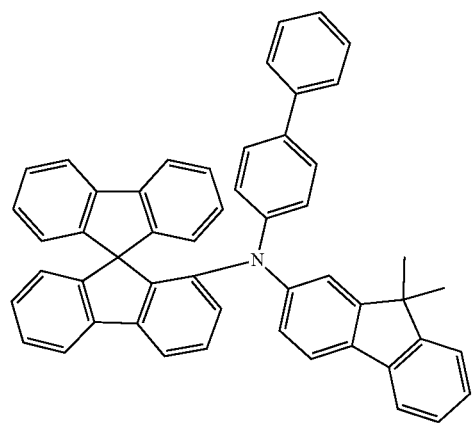
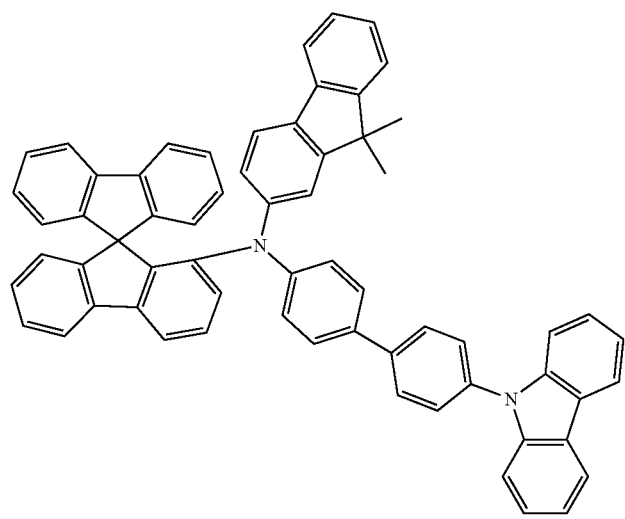
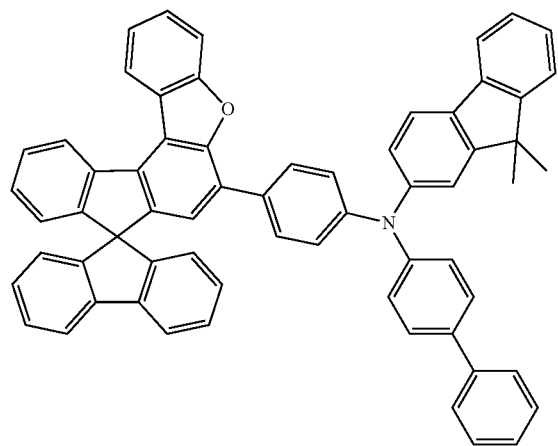

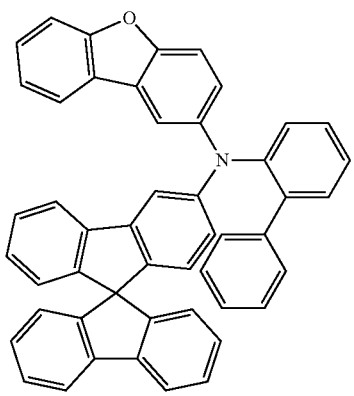
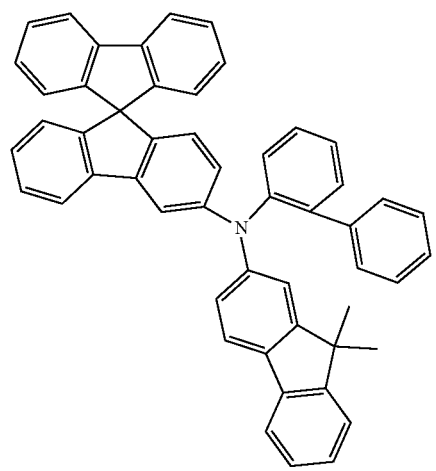
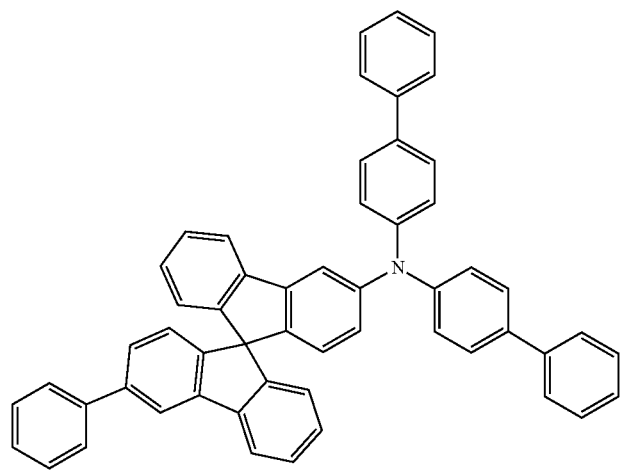

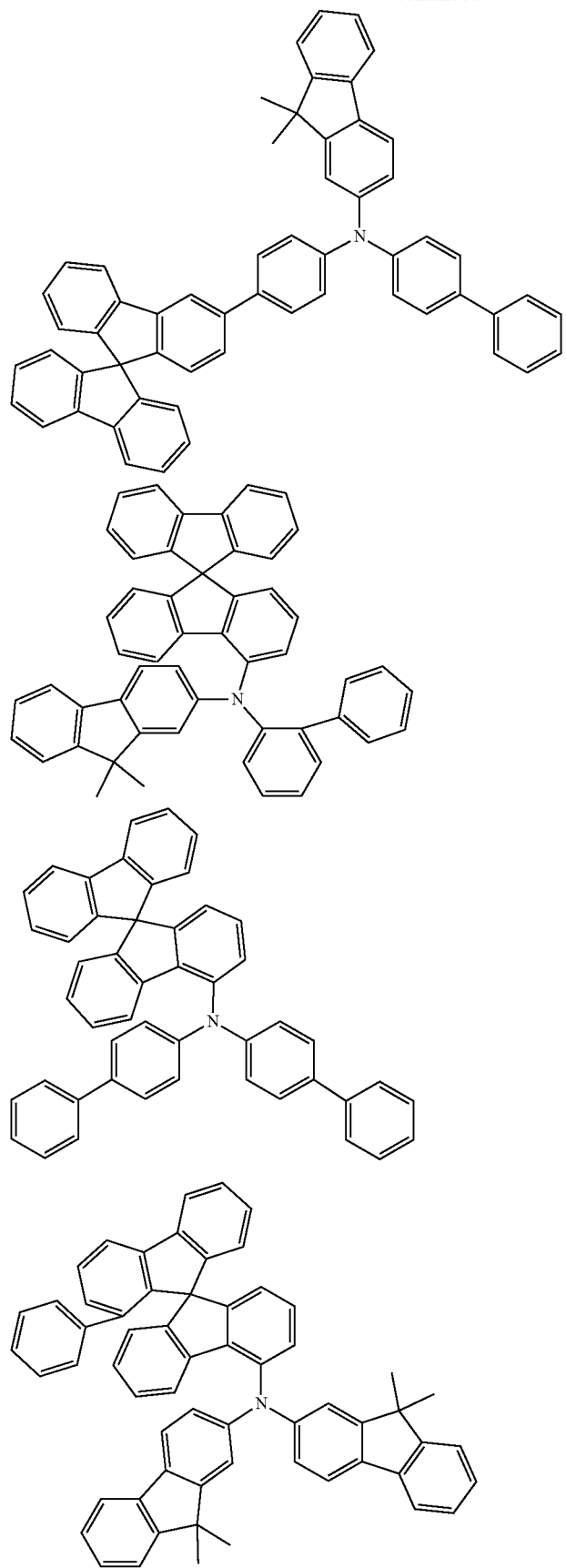

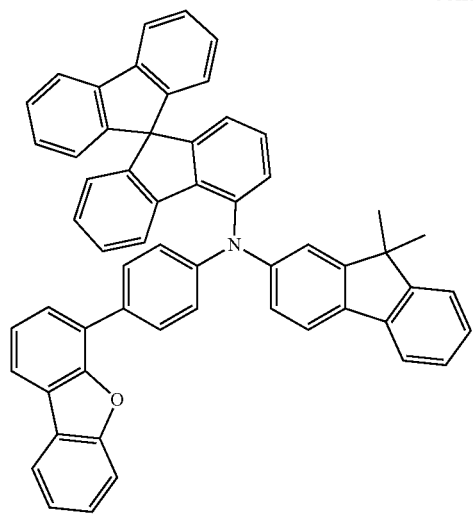
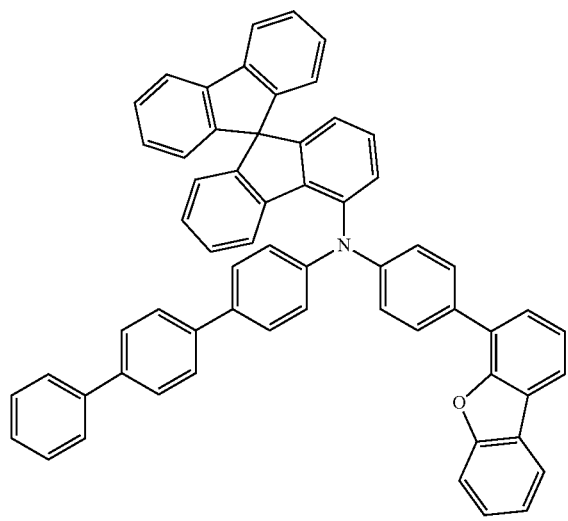
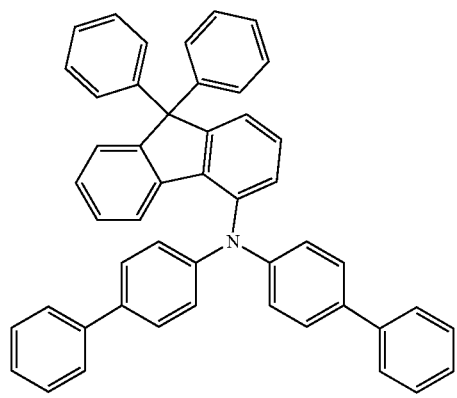

-continued
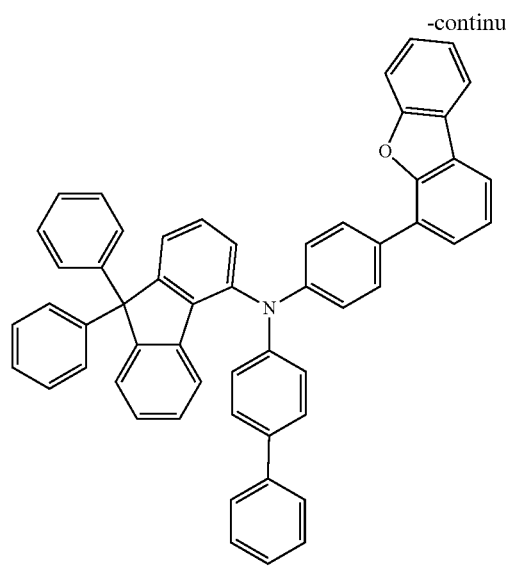
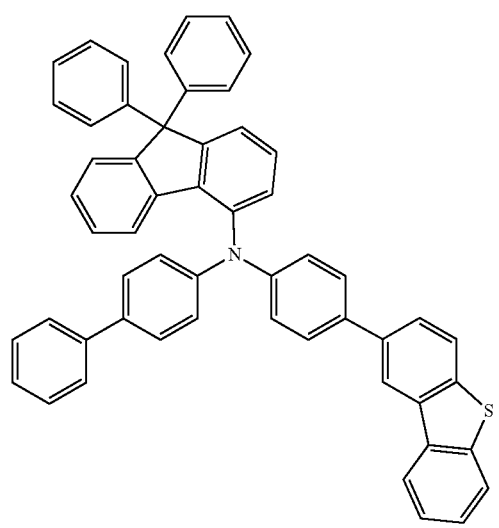
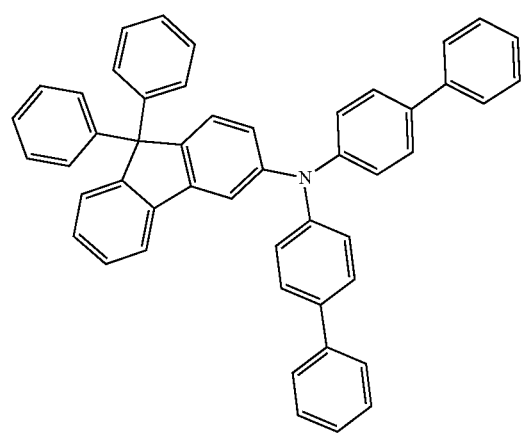

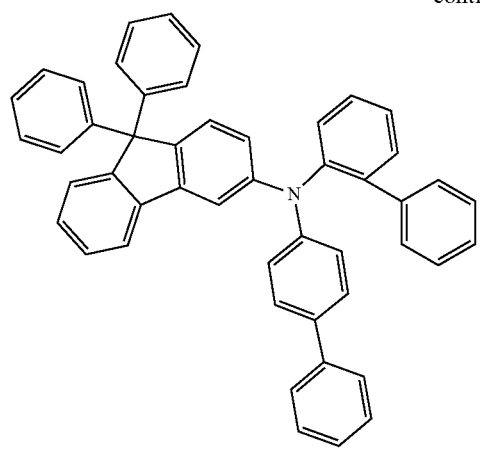
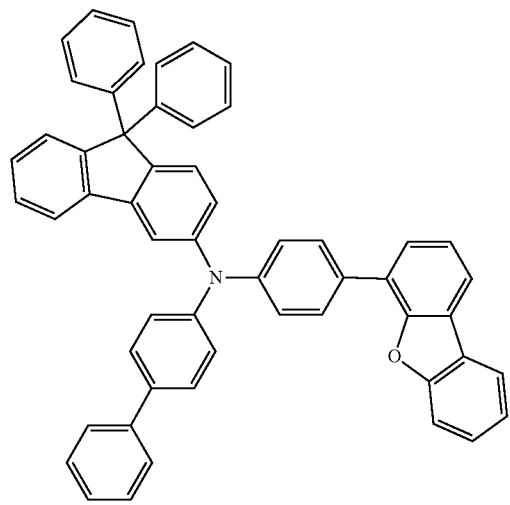
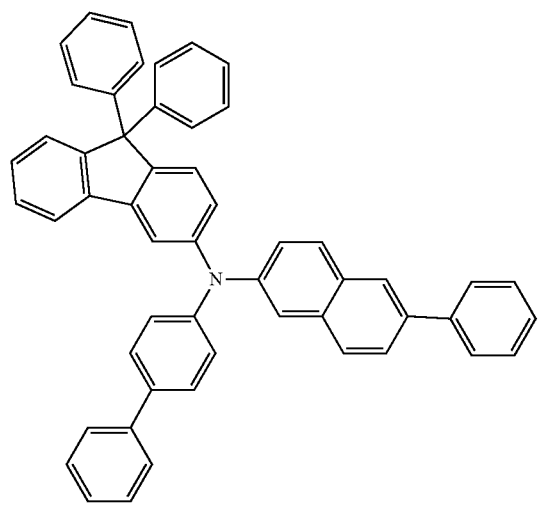

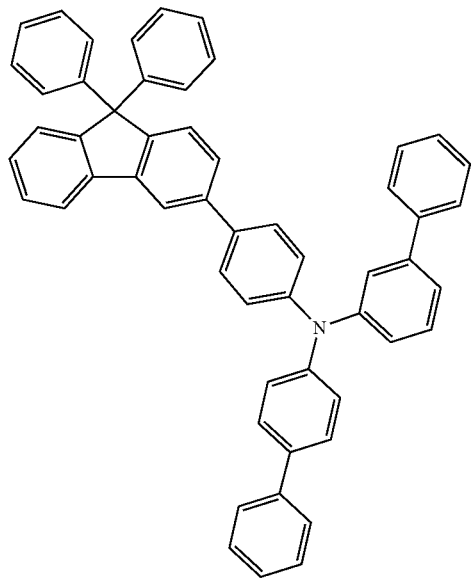
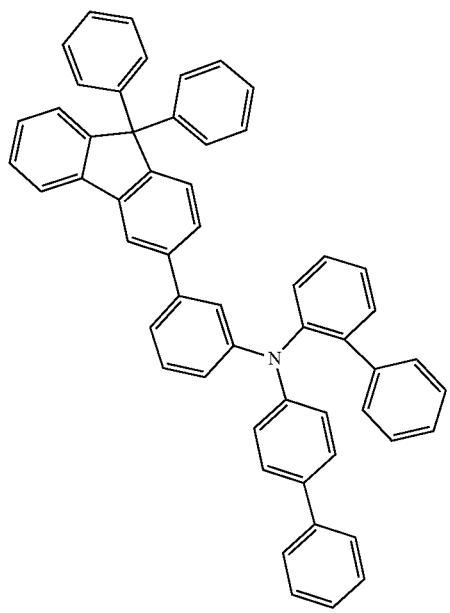
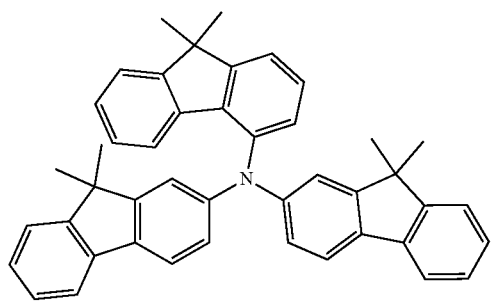

-continued
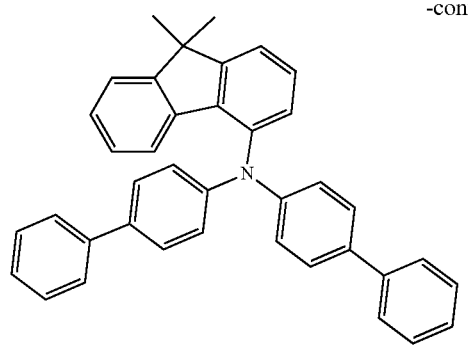
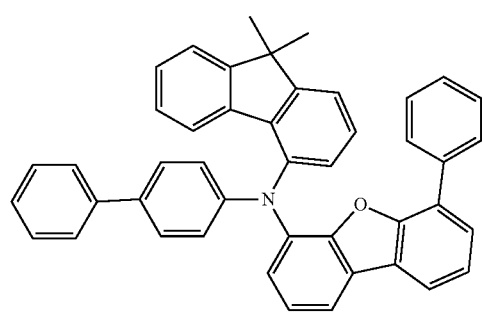
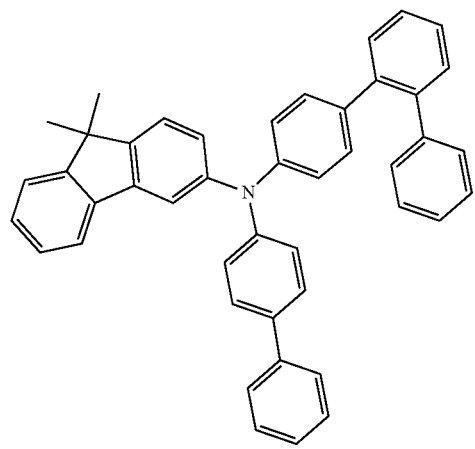
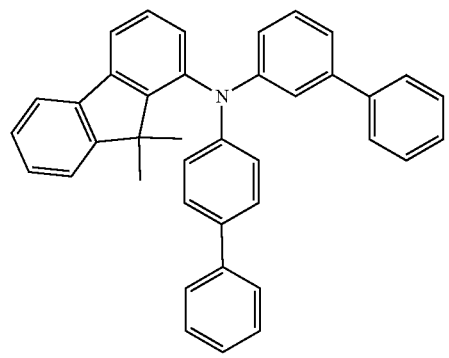

-continued
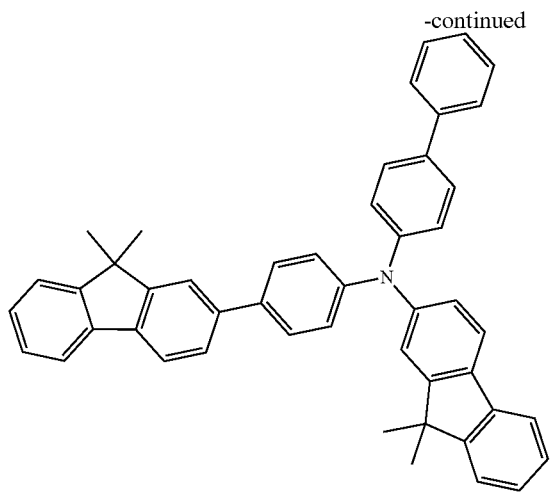
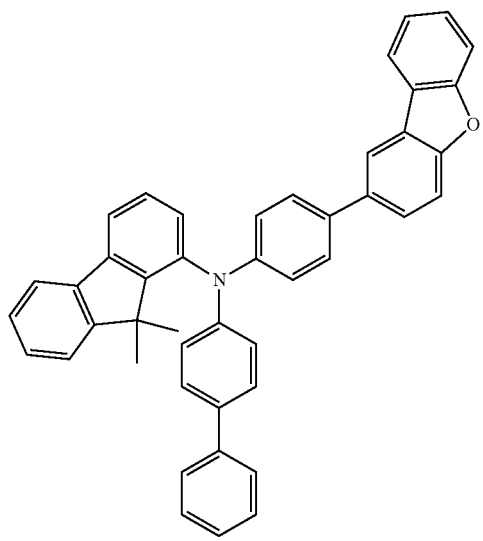
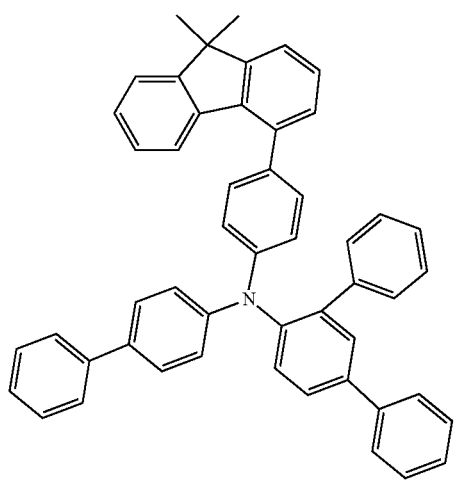

-continued
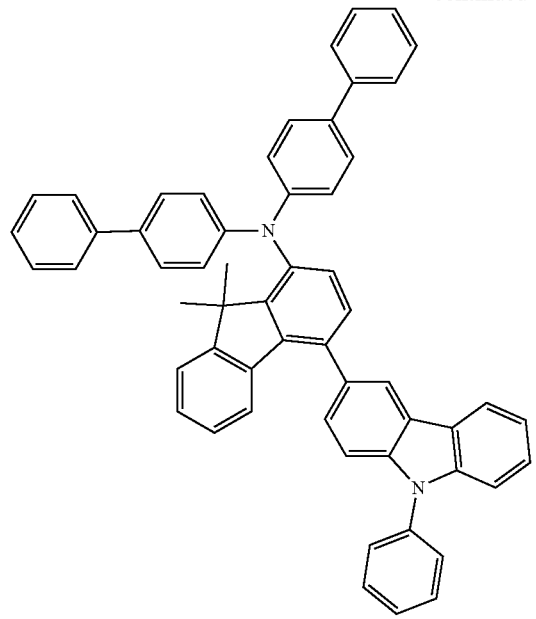
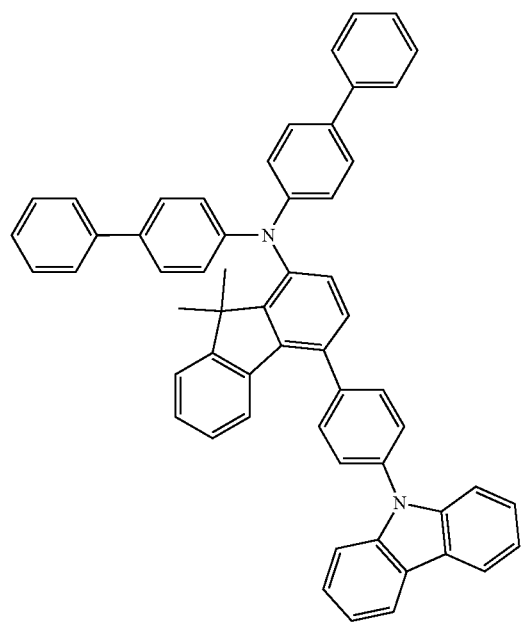

-continued
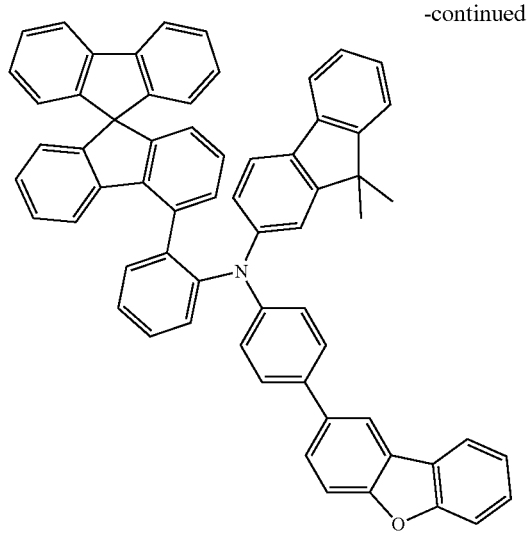
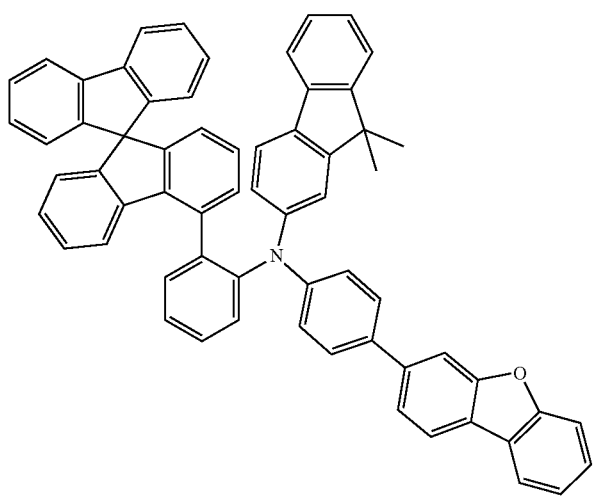
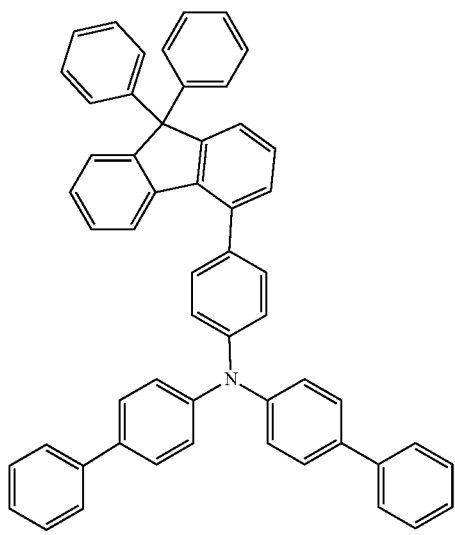

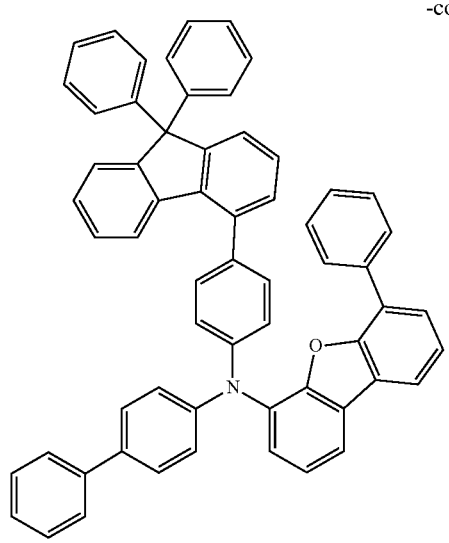
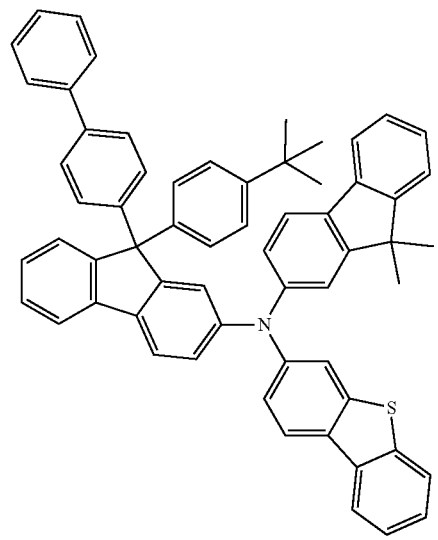
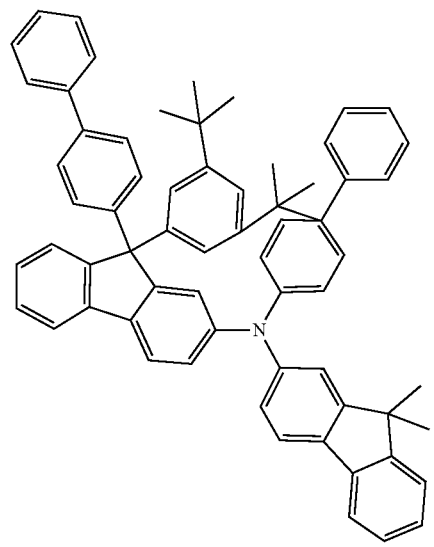

-continued
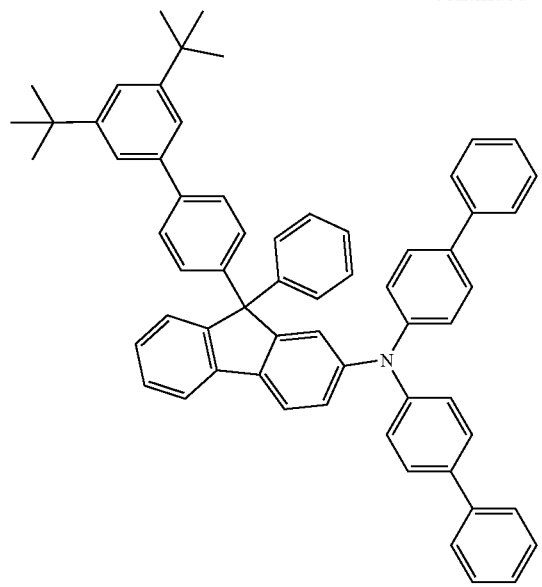
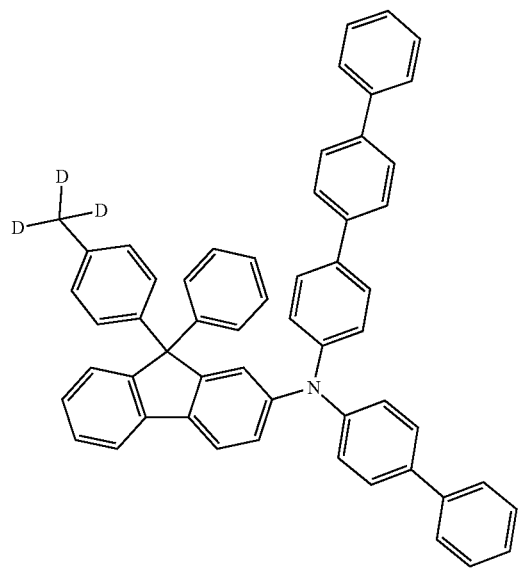
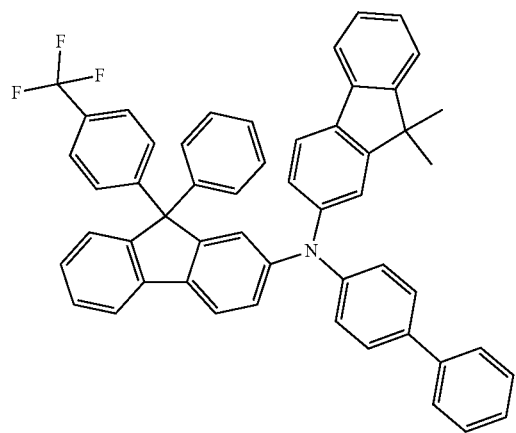

-continued
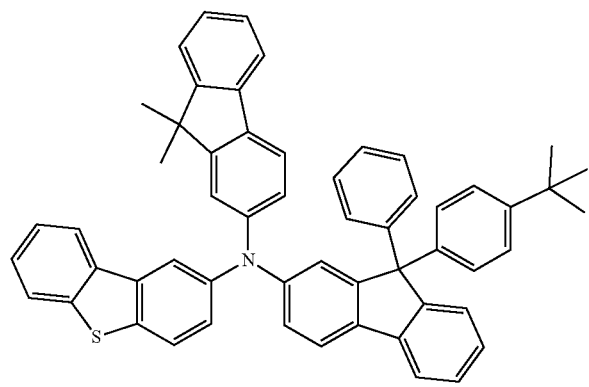
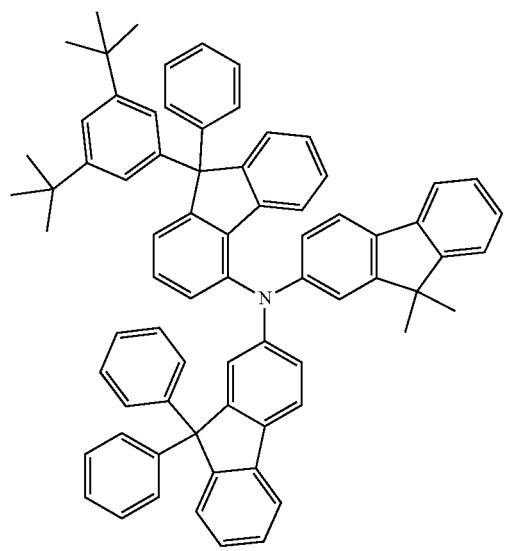
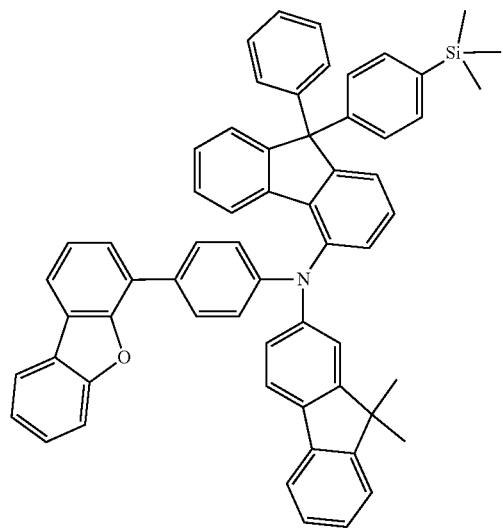

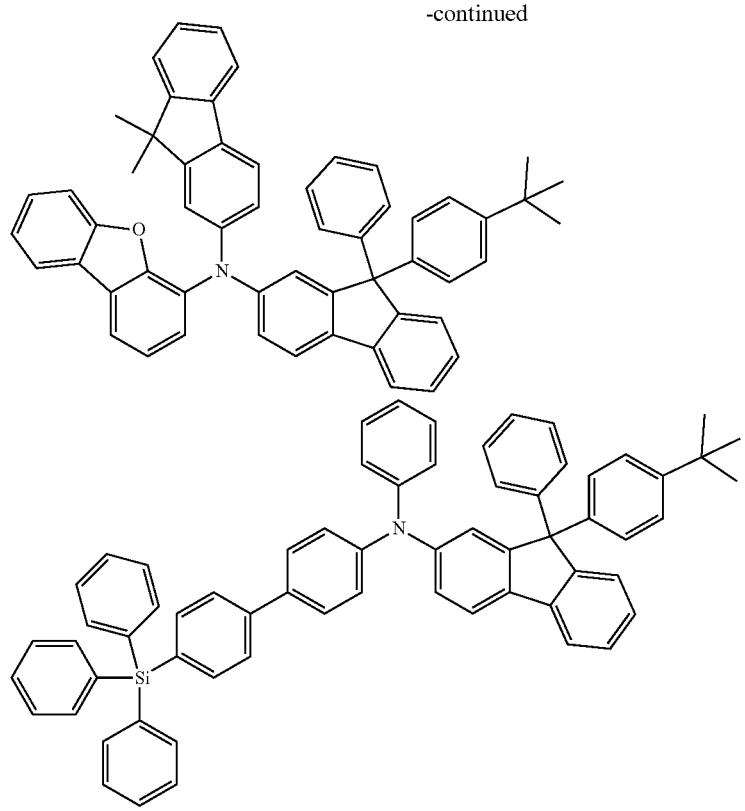

Cathode:

Preferred cathodes of the electronic device are metals having a low work function, metal alloys or multilayer structures composed of various metals, for example alkaline earth metals, alkali metals, main group metals or lanthanoids (e.g. Ca, Ba, Mg, Al, In, Mg, Yb, Sm, etc.). Additionally suitable are alloys composed of an alkali metal or alkaline earth metal and silver, for example an alloy composed of magnesium and silver. In the case of multilayer structures, in addition to the metals mentioned, it is also possible to use further metals having a relatively high work function, for example Ag or Al, in which case combinations of the metals such as Ca/Ag, Mg/Ag or Ba/Ag, for example, are generally used. It may also be preferable to introduce a thin interlayer of a material having a high dielectric constant between a metallic cathode and the organic semiconductor. Examples of useful materials for this purpose are alkali metal or alkaline earth metal fluorides, but also the corresponding oxides or carbonates (e.g. LiF, $Li_2O$, $BaF_2$, MgO, NaF, CsF, $Cs_2CO_3$, etc.). It is also possible to use lithium quinolinate (LiQ) for this purpose. The layer thickness of this layer is preferably between 0.5 and 5 nm.

Anode:

Preferred anodes are materials having a high work function. Preferably, the anode has a work function of greater than 4.5 eV versus vacuum. Firstly, metals having a high redox potential are suitable for this purpose, for example Ag, Pt or Au. Secondly, metal/metal oxide electrodes (e.g. Al/Ni/$NiO_x$, Al/$PtO_x$) may also be preferred. For some applications, at least one of the electrodes has to be transparent or partly transparent in order to enable either the irradiation of the organic material (organic solar cell) or the emission of light (OLED, O-LASER). Preferred anode materials here are conductive mixed metal oxides. Particular preference is given to indium tin oxide (ITO) or indium zinc oxide (IZO). Preference is further given to conductive doped organic materials, especially conductive doped polymers. In addition, the anode may also consist of two or more layers, for example of an inner layer of ITO and an outer layer of a metal oxide, preferably tungsten oxide, molybdenum oxide or vanadium oxide.

In a preferred embodiment, the electronic device is characterized in that one or more layers are coated by a sublimation process. In this case, the materials are applied by vapour deposition in vacuum sublimation systems at an initial pressure of less than $10^{-5}$ mbar, preferably less than $10^{-6}$ mbar. In this case, however, it is also possible that the initial pressure is even lower, for example less than $10^{-7}$ mbar.

Preference is likewise given to an electronic device, characterized in that one or more layers are coated by the OVPD (organic vapour phase deposition) method or with the aid of a carrier gas sublimation. In this case, the materials are applied at a pressure between $10^{-5}$ mbar and 1 bar. A special case of this method is the OVJP (organic vapour jet printing) method, in which the materials are applied directly by a nozzle and thus structured (for example M. S. Arnold et al., Appl. Phys. Lett. 2008, 92, 053301).

Preference is additionally given to an electronic device, characterized in that one or more layers are produced from solution, for example by spin-coating, or by any printing method, for example screen printing, flexographic printing, nozzle printing or offset printing, but more preferably LITI (light-induced thermal imaging, thermal transfer printing) or inkjet printing. For this purpose, soluble compounds of formula (I) are needed. High solubility can be achieved by suitable substitution of the compounds.

It is further preferable that an electronic device of the invention is produced by applying one or more layers from solution and one or more layers by a sublimation method.

After application of the layers, according to the use, the device is structured, contact-connected and finally sealed, in order to rule out damaging effects of water and air.

According to the invention, the electronic devices comprising one or more compounds of formula (I) can be used in displays, as light sources in lighting applications and as light sources in medical and/or cosmetic applications.

EXAMPLES

A) Synthesis Examples

Example 1-1

N,9-Bis({[1,1'-biphenyl]-4-yl})-N-(9,9-dimethyl-9H-fluoren-2-yl)-9-phenyl-9H-fluorene-4-amine

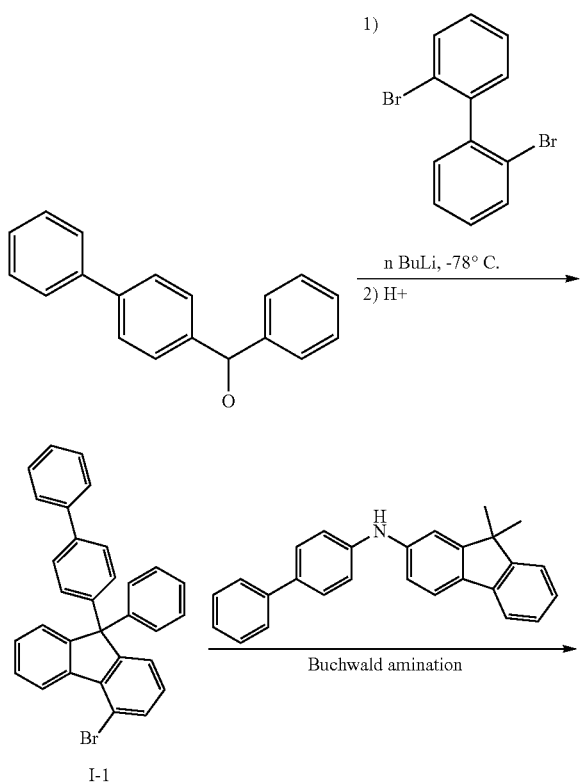

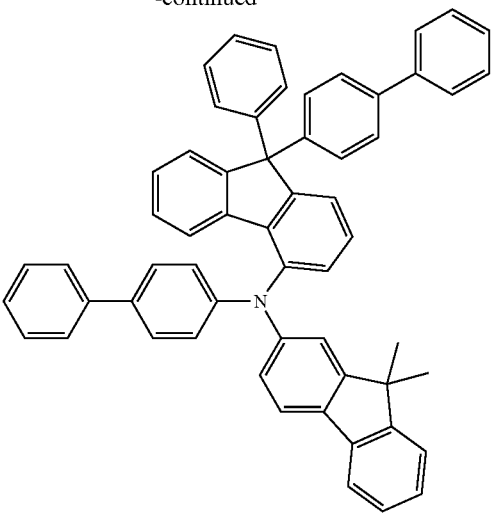

1-1

9-{[1,1'-Biphenyl]-4-yl}-4-bromo-9-phenylfluorene 14.5 g (46.3 mmol) of 2,2'-dibromobiphenyl is dissolved in a baked-out flask in 150 ml of dried THF. The reaction mixture is cooled to −78° C. At this temperature, 20.5 ml of a 2.3 M solution of n-BuLi in hexane (46.3 mmol) is slowly added dropwise. The mixture is stirred at −70° C. for a further 1 hour. Subsequently, 11.4 g of biphenyl-4-yl(phenyl)methanone (44.13 mmol) is dissolved in 80 ml of THF and added dropwise at −70° C. After the addition has ended, the reaction mixture is left to warm up gradually to room temperature, admixed with NH$_4$Cl and then concentrated on a rotary evaporator. 200 ml of acetic acid is added cautiously to the concentrated solution and then 50 ml of fuming HCl is added. The mixture is heated to 75° C. and kept there for 6 hours. During this time, a white solid precipitates out. The mixture is then left to cool to room temperature, and the precipitated solids are filtered off with suction and washed with methanol. The residue is dried at 40° C. under reduced pressure. Yield 19.5 g (41 mmol) (90% of theory).

The following compounds are prepared in an analogous manner: The yields here are between 40% and 90%

| | Reactant 1 | Reactant 2 | Product |
|---|---|---|---|
| I-2 | (structure, CAS No.: 2128-93-0) | (structure with Br and Cl) | (structure with Cl) |

-continued
| | Reactant 1 | Reactant 2 | Product |
|---|---|---|---|
| I-3 | 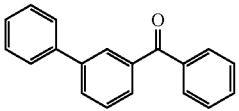 [SMILES: O=C(c1ccccc1)c1cccc(-c2ccccc2)c1]<br>CAS No.: 3378-09-4 | 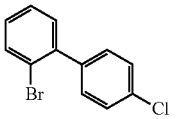 [SMILES: Clc1ccc(-c2ccccc2Br)cc1] | 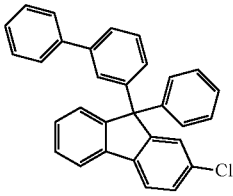 [SMILES: Clc1ccc2c(c1)C(c1ccccc1)(c1cccc(-c3ccccc3)c1)c1ccccc1-2] |
| I-4 | 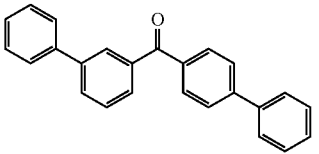 [SMILES: O=C(c1ccc(-c2ccccc2)cc1)c1cccc(-c2ccccc2)c1]<br>CAS No.: 14704-34-8 | 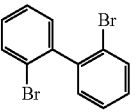 [SMILES: Brc1ccccc1-c1ccccc1Br] | 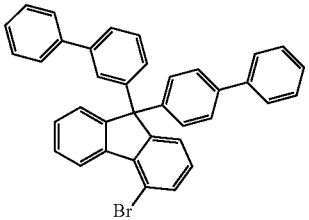 [SMILES: Brc1cccc2c1-c1ccccc1C2(c1ccc(-c2ccccc2)cc1)c1cccc(-c2ccccc2)c1] |
| I-5 | 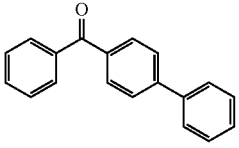 [SMILES: O=C(c1ccccc1)c1ccc(-c2ccccc2)cc1] | 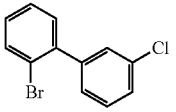 [SMILES: Clc1cccc(-c2ccccc2Br)c1] | 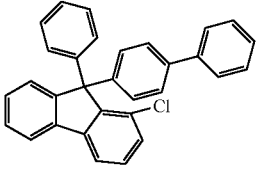 [SMILES: Clc1cccc2c1C(c1ccccc1)(c1ccc(-c3ccccc3)cc1)c1ccccc1-2]<br>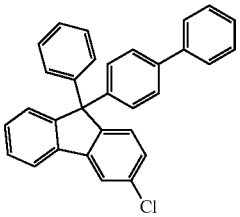 [SMILES: Clc1ccc2c(c1)-c1ccccc1C2(c1ccccc1)c1ccc(-c2ccccc2)cc1]<br>Isomeric compounds are separated by means of recrystallization |
| I-6 | 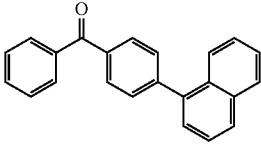 [SMILES: O=C(c1ccccc1)c1ccc(-c2cccc3ccccc23)cc1] |  | 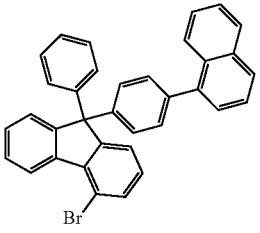 [SMILES: Brc1cccc2c1-c1ccccc1C2(c1ccccc1)c1ccc(-c2cccc3ccccc23)cc1] |
| I-7 | 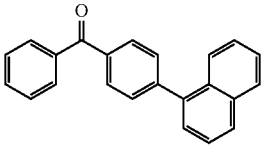 [SMILES: O=C(c1ccccc1)c1ccc(-c2cccc3ccccc23)cc1] | 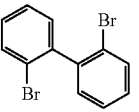 [SMILES: Brc1ccccc1-c1ccccc1Br] | 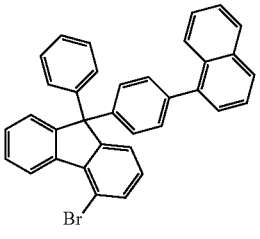 [SMILES: Brc1cccc2c1-c1ccccc1C2(c1ccccc1)c1ccc(-c2cccc3ccccc23)cc1] |

| | Reactant 1 | Reactant 2 | Product |
|---|---|---|---|
| I-8 | 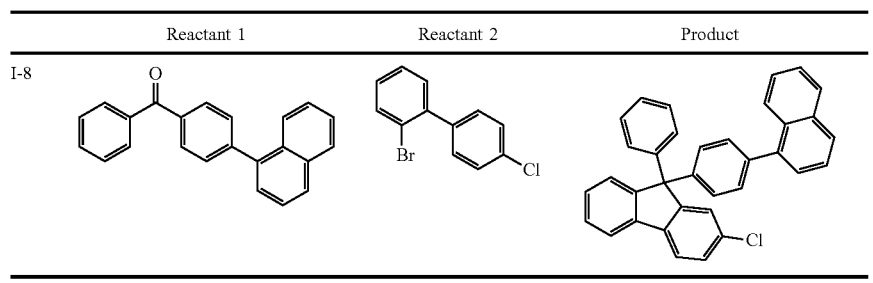 | | |

N,9-Bis({[1,1'-biphenyl]-4-yl})-N-(9,9-dimethyl-9H-fluoren-2-yl)-9-phenyl-9H-fluorene-4-amine 10.0 g of N-{1,1'-biphenyl]-4-yl}-9,9-dimethylfluoren-2-amine (27.7 mmol) and 13.1 g of 9-{[1,1'-biphenyl]-4-yl}-4-bromo-9-phenylfluorene (27.7 mol) are dissolved in 300 ml of toluene. The solution is degassed and saturated with $N_2$. Thereafter, 340 mg (0.83 mmol) of S-Phos and 250 mg (0.28 mmol) of $Pd_2(dba)_3$ are added thereto, and then 4.6 g of sodium tert-butoxide (41.5 mmol) is added. The reaction mixture is heated to boiling under a protective atmosphere for 3 h. The mixture is subsequently partitioned between toluene and water, and the organic phase is washed three times with water and dried over $Na_2SO_4$ and concentrated by rotary evaporation. After the crude product has been filtered through silica gel with toluene, the remaining residue is recrystallized from heptane/toluene. The yield is 16.7 g (80% of theory). The substance is finally sublimed under high vacuum; the purity is 99.9%.

The compounds below are prepared in an analogous manner. The yields here are between 65% and 90%.

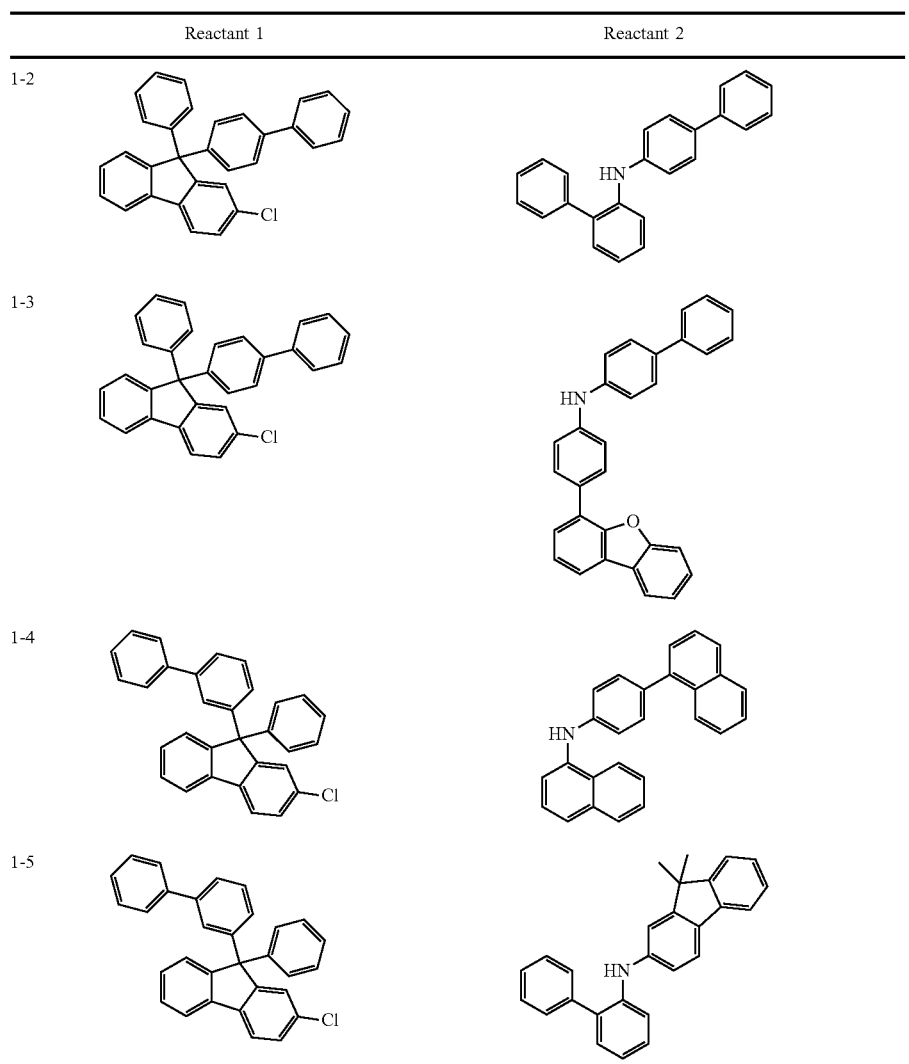

-continued
| | | |
|---|---|---|
| 1-6 | 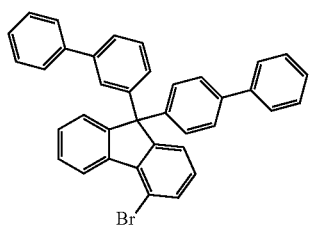 [SMILES: Brc1cccc2c1-c1ccccc1C2(c1ccc(-c2ccccc2)cc1)c1cccc(-c2ccccc2)c1] | 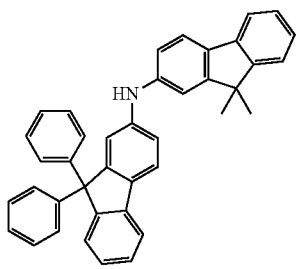 [SMILES: CC1(C)c2ccccc2-c2ccc(Nc3ccc4c(c3)C(c3ccccc3)(c3ccccc3)c3ccccc3-4)cc21] |
| 1-7 | 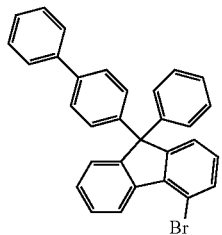 [SMILES: Brc1cccc2c1-c1ccccc1C2(c1ccccc1)c1ccc(-c2ccccc2)cc1] | 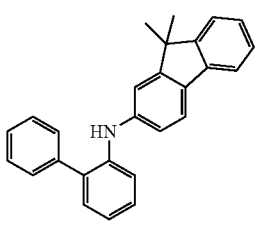 [SMILES: CC1(C)c2ccccc2-c2ccc(Nc3ccccc3-c3ccccc3)cc21] |
| 1-8 | 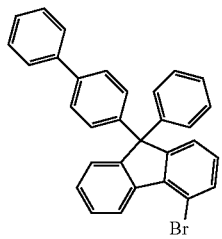 [SMILES: Brc1cccc2c1-c1ccccc1C2(c1ccccc1)c1ccc(-c2ccccc2)cc1] | 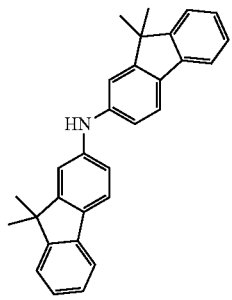 [SMILES: CC1(C)c2ccccc2-c2ccc(Nc3ccc4c(c3)C(C)(C)c3ccccc3-4)cc21] |
| 1-9 | 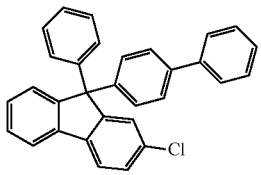 [SMILES: Clc1ccc2c(c1)C(c1ccccc1)(c1ccc(-c3ccccc3)cc1)c1ccccc1-2] | 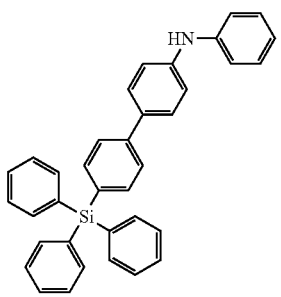 [SMILES: c1ccc(Nc2ccc(-c3ccc([Si](c4ccccc4)(c4ccccc4)c4ccccc4)cc3)cc2)cc1] |
| 1-10 | 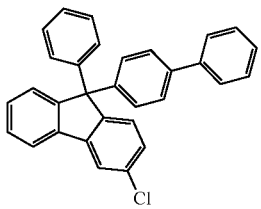 [SMILES: Clc1ccc2c(c1)-c1ccccc1C2(c1ccccc1)c1ccc(-c2ccccc2)cc1] | 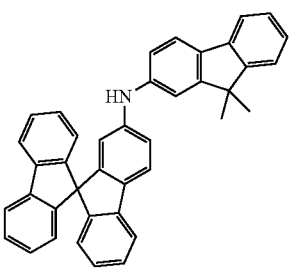 [SMILES: CC1(C)c2ccccc2-c2ccc(Nc3ccc4c(c3)C3(c5ccccc5-c5ccccc53)c3ccccc3-4)cc21] |

-continued
1-11 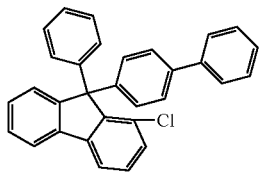 [SMILES: Clc1cccc2c1C(c1ccccc1)(c1ccc(-c3ccccc3)cc1)c1ccccc1-2] 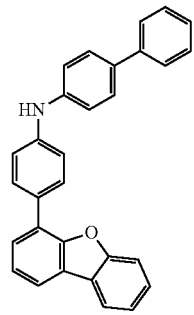 [SMILES: c1ccc(-c2ccc(Nc3ccc(-c4cccc5c4oc4ccccc45)cc3)cc2)cc1]
1-12 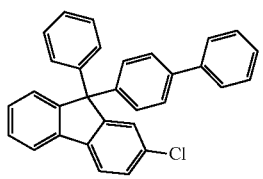 [SMILES: Clc1ccc2c(c1)C(c1ccccc1)(c1ccc(-c3ccccc3)cc1)c1ccccc1-2] 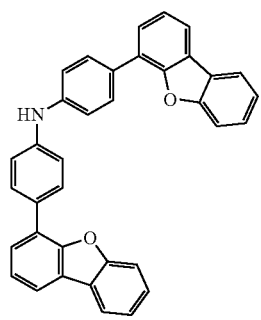 [SMILES: c1ccc2c(c1)oc1c(-c3ccc(Nc4ccc(-c5cccc6c5oc5ccccc56)cc4)cc3)cccc12]
1-13 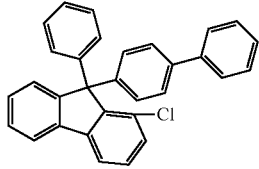 [SMILES: Clc1cccc2c1C(c1ccccc1)(c1ccc(-c3ccccc3)cc1)c1ccccc1-2] 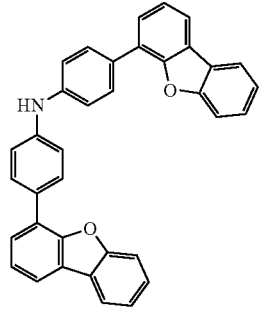 [SMILES: c1ccc2c(c1)oc1c(-c3ccc(Nc4ccc(-c5cccc6c5oc5ccccc56)cc4)cc3)cccc12]
1-14 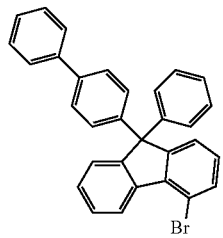 [SMILES: Brc1cccc2c1-c1ccccc1C2(c1ccccc1)c1ccc(-c2ccccc2)cc1] 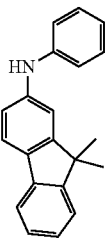 [SMILES: CC1(C)c2ccccc2-c2ccc(Nc3ccccc3)cc21]
1-15 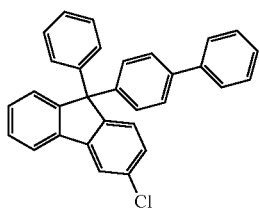 [SMILES: Clc1ccc2c(c1)-c1ccccc1C2(c1ccccc1)c1ccc(-c2ccccc2)cc1] 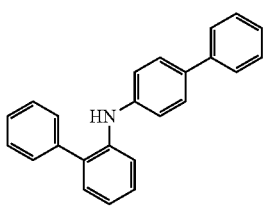 [SMILES: c1ccc(-c2ccc(Nc3ccccc3-c3ccccc3)cc2)cc1]

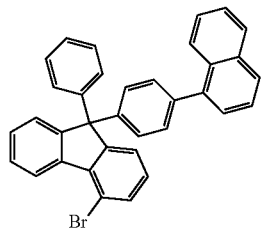 [SMILES: Brc1cccc2c1-c1ccccc1C2(c1ccccc1)c1ccc(-c2cccc3ccccc23)cc1]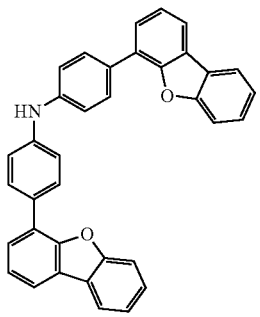 [SMILES: c1ccc2c(c1)oc1c(-c3ccc(Nc4ccc(-c5cccc6c5oc5ccccc56)cc4)cc3)cccc12]
1-17 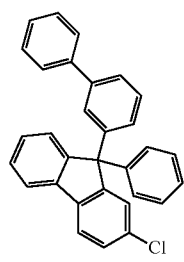 [SMILES: Clc1ccc2c(c1)C(c1ccccc1)(c1cccc(-c3ccccc3)c1)c1ccccc1-2]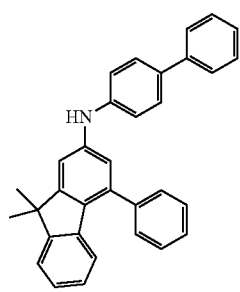 [SMILES: CC1(C)c2ccccc2-c2c(-c3ccccc3)cc(Nc3ccc(-c4ccccc4)cc3)cc21]
1-18 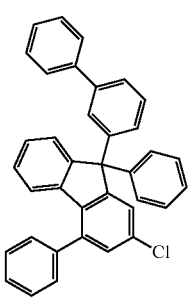 [SMILES: Clc1cc(-c2ccccc2)c2c(c1)C(c1ccccc1)(c1cccc(-c3ccccc3)c1)c1ccccc1-2]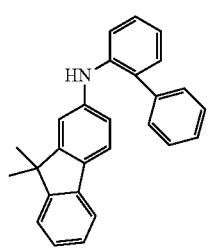 [SMILES: CC1(C)c2ccccc2-c2ccc(Nc3ccccc3-c3ccccc3)cc21]
| Product |
|---|
| 1-2 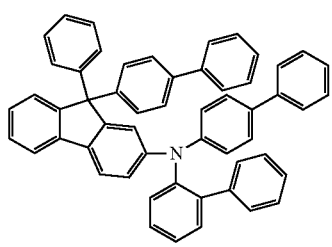 [SMILES: c1ccc(-c2ccc(N(c3ccc4c(c3)C(c3ccccc3)(c3ccc(-c5ccccc5)cc3)c3ccccc3-4)c3ccccc3-c3ccccc3)cc2)cc1] |
| 1-3 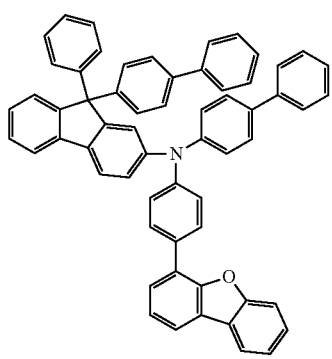 [SMILES: c1ccc(-c2ccc(N(c3ccc(-c4cccc5c4oc4ccccc45)cc3)c3ccc4c(c3)C(c3ccccc3)(c3ccc(-c5ccccc5)cc3)c3ccccc3-4)cc2)cc1] |

-continued
1-4
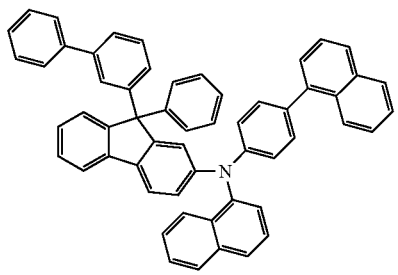 [SMILES: c1ccc(-c2cccc(C3(c4ccccc4)c4ccccc4-c4ccc(N(c5ccc(-c6cccc7ccccc67)cc5)c5cccc6ccccc56)cc43)c2)cc1]
1-5
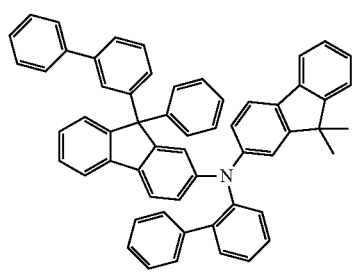 [SMILES: CC1(C)c2ccccc2-c2ccc(N(c3ccc4c(c3)C(c3ccccc3)(c3cccc(-c5ccccc5)c3)c3ccccc3-4)c3ccccc3-c3ccccc3)cc21]
1-6
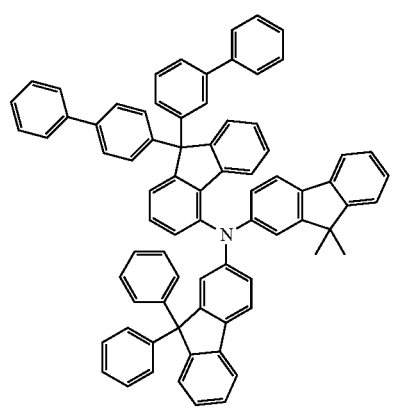 [SMILES: CC1(C)c2ccccc2-c2ccc(N(c3ccc4c(c3)C(c3ccccc3)(c3ccccc3)c3ccccc3-4)c3cccc4c3-c3ccccc3C4(c3ccc(-c4ccccc4)cc3)c3cccc(-c4ccccc4)c3)cc21]
1-7
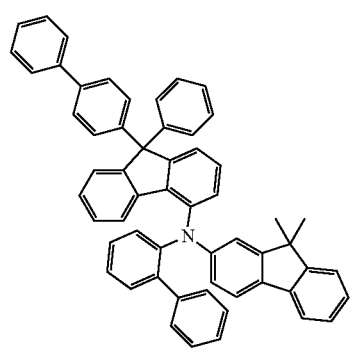 [SMILES: CC1(C)c2ccccc2-c2ccc(N(c3ccccc3-c3ccccc3)c3cccc4c3-c3ccccc3C4(c3ccccc3)c3ccc(-c4ccccc4)cc3)cc21]

1-8
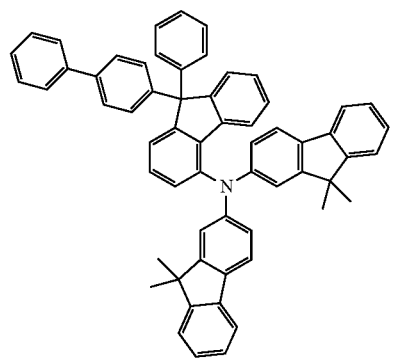 [SMILES: CC1(C)c2ccccc2-c2ccc(N(c3ccc4c(c3)C(C)(C)c3ccccc3-4)c3cccc4c3-c3ccccc3C4(c3ccccc3)c3ccc(-c4ccccc4)cc3)cc21]
1-9
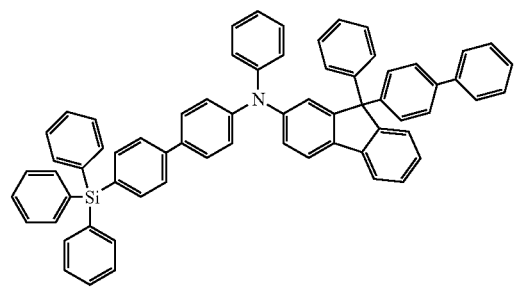 [SMILES: c1ccc(-c2ccc(C3(c4ccccc4)c4ccccc4-c4ccc(N(c5ccccc5)c5ccc(-c6ccc([Si](c7ccccc7)(c7ccccc7)c7ccccc7)cc6)cc5)cc43)cc2)cc1]
1-10
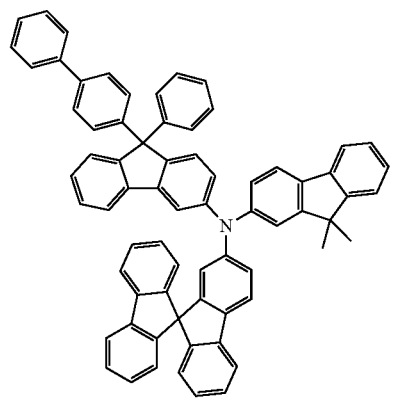 [SMILES: CC1(C)c2ccccc2-c2ccc(N(c3ccc4c(c3)-c3ccccc3C4(c3ccccc3)c3ccc(-c4ccccc4)cc3)c3ccc4c(c3)C3(c5ccccc5-c5ccccc53)c3ccccc3-4)cc21]
1-11
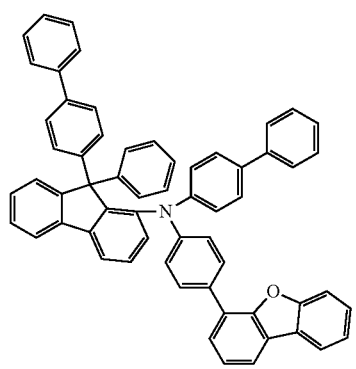 [SMILES: c1ccc(-c2ccc(N(c3ccc(-c4cccc5c4oc4ccccc45)cc3)c3cccc4c3C(c3ccccc3)(c3ccc(-c5ccccc5)cc3)c3ccccc3-4)cc2)cc1]

1-12 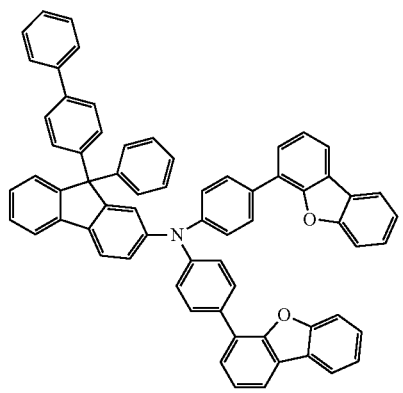 [SMILES: c1ccc(-c2ccc(C3(c4ccccc4)c4ccccc4-c4ccc(N(c5ccc(-c6cccc7c6oc6ccccc67)cc5)c5ccc(-c6cccc7c6oc6ccccc67)cc5)cc43)cc2)cc1]
1-13 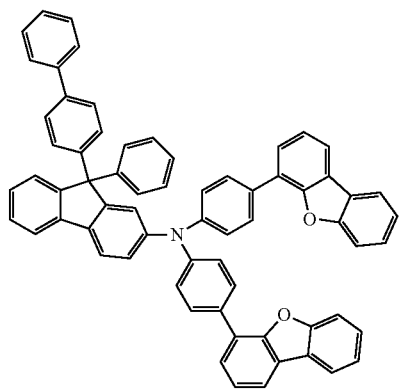 [SMILES: c1ccc(-c2ccc(C3(c4ccccc4)c4ccccc4-c4ccc(N(c5ccc(-c6cccc7c6oc6ccccc67)cc5)c5ccc(-c6cccc7c6oc6ccccc67)cc5)cc43)cc2)cc1]
1-14 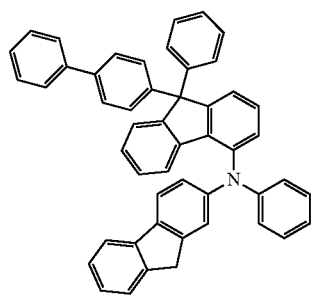 [SMILES: c1ccc(-c2ccc(C3(c4ccccc4)c4ccccc4-c4c(N(c5ccccc5)c5ccc6c(c5)Cc5ccccc5-6)cccc43)cc2)cc1]
1-15 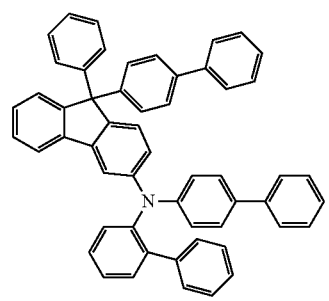 [SMILES: c1ccc(-c2ccc(N(c3ccc4c(c3)-c3ccccc3C4(c3ccccc3)c3ccc(-c4ccccc4)cc3)c3ccccc3-c3ccccc3)cc2)cc1]

1-16
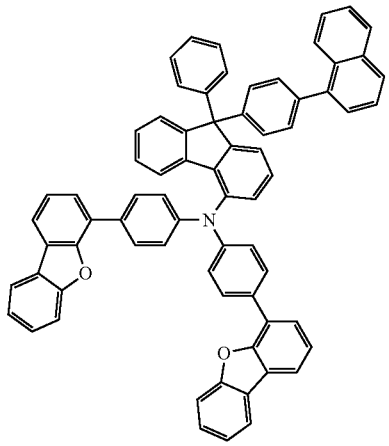 [SMILES: c1ccc(C2(c3ccc(-c4cccc5ccccc45)cc3)c3ccccc3-c3c(N(c4ccc(-c5cccc6c5oc5ccccc56)cc4)c4ccc(-c5cccc6c5oc5ccccc56)cc4)cccc32)cc1]
1-17
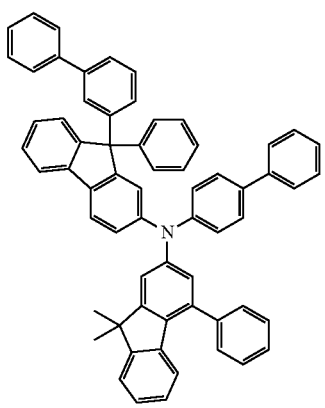 [SMILES: CC1(C)c2ccccc2-c2c(-c3ccccc3)cc(N(c3ccc(-c4ccccc4)cc3)c3ccc4c(c3)C(c3ccccc3)(c3cccc(-c5ccccc5)c3)c3ccccc3-4)cc21]
1-18
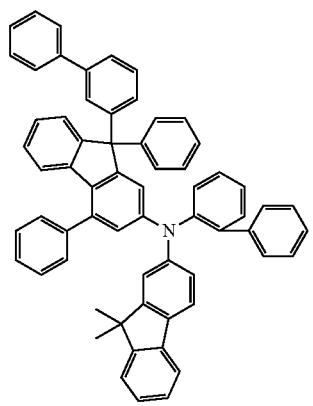 [SMILES: CC1(C)c2ccccc2-c2ccc(N(c3cc(-c4ccccc4)c4c(c3)C(c3ccccc3)(c3cccc(-c5ccccc5)c3)c3ccccc3-4)c3ccccc3-c3ccccc3)cc21]

Example 2-1

N-{[1,1'-Biphenyl]-4-yl}-N-[4-(9-{[1,1'-biphenyl]-4-yl}-9-phenyl-9H-fluoren-4-yl)phenyl]-9,9-dimethyl-9H-fluorene-2-amine

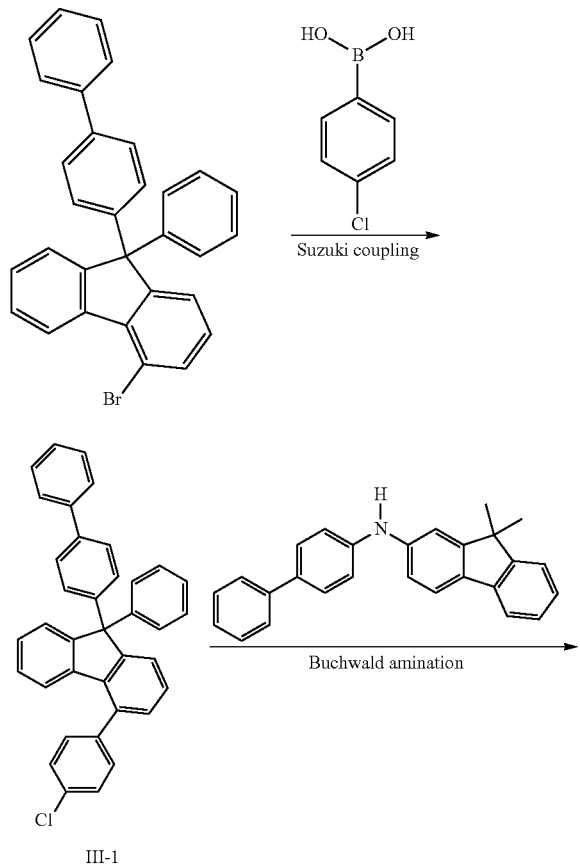

Intermediate III-1: 9-{[1,1'-Biphenyl]-4-yl}-4-(4-chlorophenyl)-9-phenylfluorene 5.90 g (37.7 mmol) of 4-chlorophenylboronic acid and 15 g (37.7 mmol) of Intermediate I-1 are suspended in 200 ml of THF and 38 ml of a 2M potassium carbonate solution (75.5 mmol). 0.87 g (0.76 mmol) of tetrakis(triphenylphosphine)palladium is added to this suspension, and the reaction mixture is heated under reflux for 12 h. After cooling, the organic phase is removed, filtered through silica gel, washed three times with 100 ml of water and then concentrated to dryness. After the crude product has been filtered through silica gel with toluene, 15.46 g (95%) of Intermediate III-1 is obtained.

The compounds below are prepared in an analogous manner. The yields here are between 40% and 90%.

| | Reactant 1 | Reactant 2 |
|---|---|---|
| III-2 | (biphenyl-phenyl-fluorene-Cl) | 2-chlorophenylboronic acid |
| III-3 | (biphenyl-phenyl-fluorene-Br) | 3-chlorophenylboronic acid |

-continued
| | | | |
|---|---|---|---|
| III-4 | 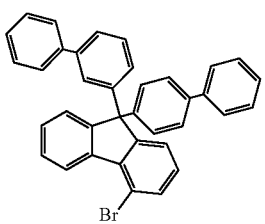 [SMILES: Brc1cccc2c1-c1ccccc1C2(c1ccc(-c2ccccc2)cc1)c1cccc(-c2ccccc2)c1] | | 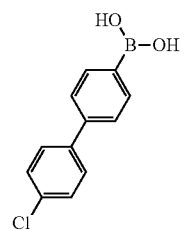 [SMILES: OB(O)c1ccc(-c2ccc(Cl)cc2)cc1] |
| III-5 | 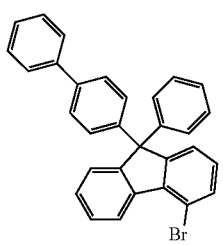 [SMILES: Brc1cccc2c1-c1ccccc1C2(c1ccccc1)c1ccc(-c2ccccc2)cc1] | | 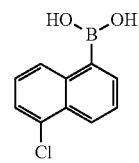 [SMILES: OB(O)c1cccc2c(Cl)cccc12] |
| III-6 | 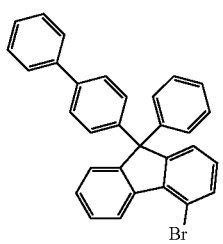 [SMILES: Brc1cccc2c1-c1ccccc1C2(c1ccccc1)c1ccc(-c2ccccc2)cc1] | | 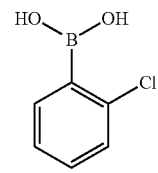 |
| 2-2 | 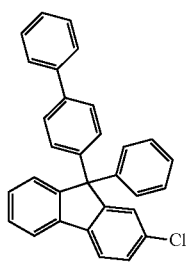 [SMILES: Clc1ccc2c(c1)C(c1ccccc1)(c1ccc(-c3ccccc3)cc1)c1ccccc1-2] | | 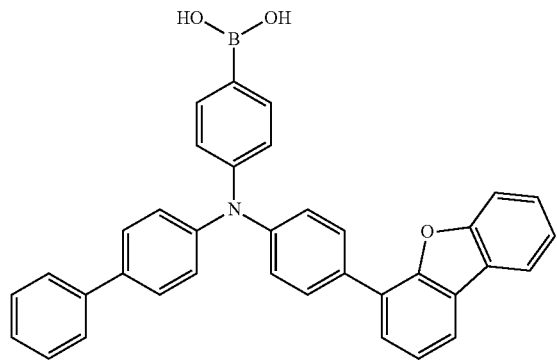 [SMILES: OB(O)c1ccc(N(c2ccc(-c3ccccc3)cc2)c2ccc(-c3cccc4c3oc3ccccc34)cc2)cc1] |
| III-7 | 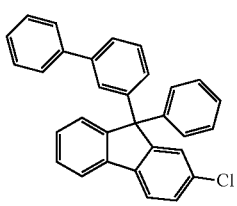 [SMILES: Clc1ccc2c(c1)C(c1ccccc1)(c1cccc(-c3ccccc3)c1)c1ccccc1-2] | | 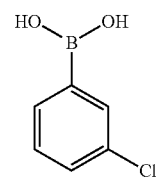 |
| III-8 | 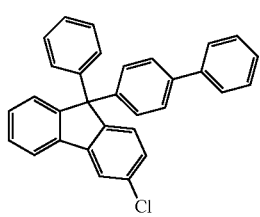 [SMILES: Clc1ccc2c(c1)-c1ccccc1C2(c1ccccc1)c1ccc(-c2ccccc2)cc1] | | 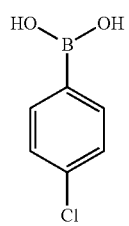 |

-continued
III-9
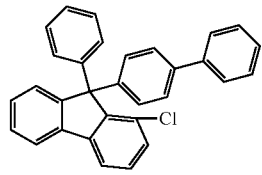 [SMILES: Clc1cccc2c1C(c1ccccc1)(c1ccc(-c3ccccc3)cc1)c1ccccc1-2]
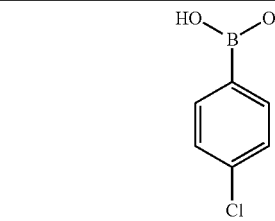
2-3
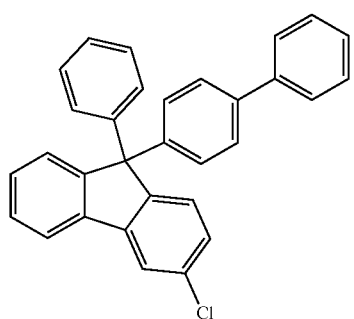 [SMILES: Clc1ccc2c(c1)-c1ccccc1C2(c1ccccc1)c1ccc(-c2ccccc2)cc1]
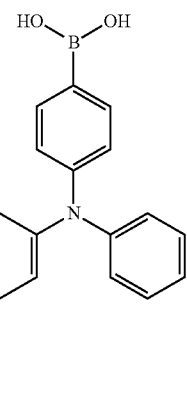
2-12
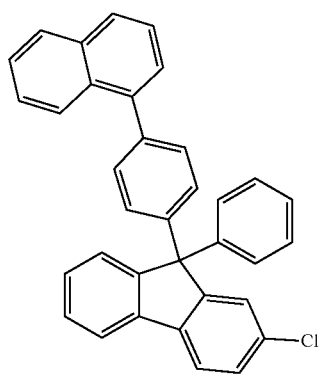 [SMILES: Clc1ccc2c(c1)C(c1ccccc1)(c1ccc(-c3cccc4ccccc34)cc1)c1ccccc1-2]
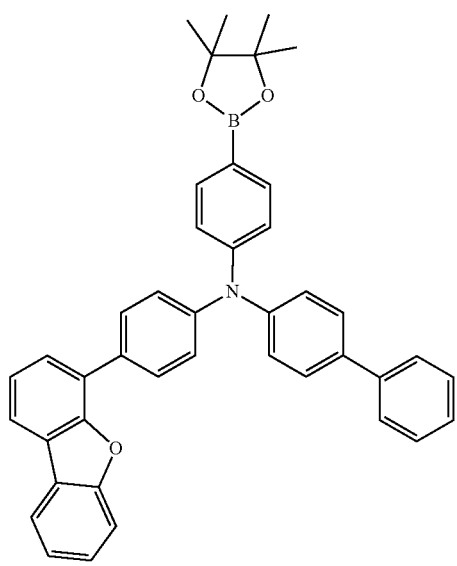 [SMILES: CC1(C)OB(c2ccc(N(c3ccc(-c4ccccc4)cc3)c3ccc(-c4cccc5c4oc4ccccc45)cc3)cc2)OC1(C)C]
2-13
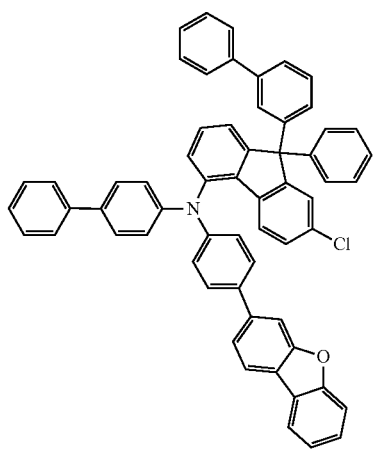 [SMILES: Clc1ccc2c(c1)C(c1ccccc1)(c1cccc(-c3ccccc3)c1)c1cccc(N(c3ccc(-c4ccccc4)cc3)c3ccc(-c4ccc5c(c4)oc4ccccc45)cc3)c1-2]
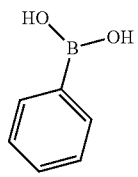

| | |
|---|---|
| III-10 | 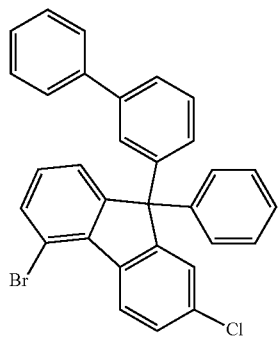 [SMILES: Clc1ccc2c(c1)C(c1ccccc1)(c1cccc(-c3ccccc3)c1)c1cccc(Br)c1-2] | 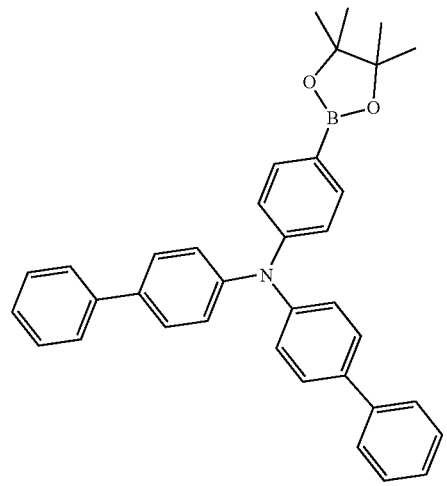 [SMILES: CC1(C)OB(c2ccc(N(c3ccc(-c4ccccc4)cc3)c3ccc(-c4ccccc4)cc3)cc2)OC1(C)C] |
| III-11 | 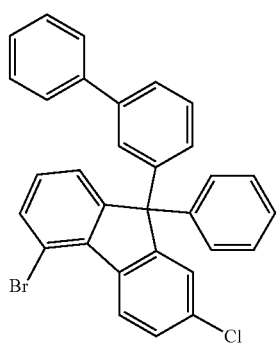 [SMILES: Clc1ccc2c(c1)C(c1ccccc1)(c1cccc(-c3ccccc3)c1)c1cccc(Br)c1-2] | 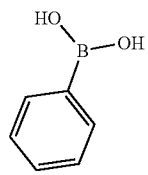 |
| | Product |
|---|---|
| III-2 | 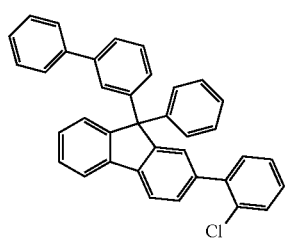 [SMILES: Clc1ccccc1-c1ccc2c(c1)C(c1ccccc1)(c1cccc(-c3ccccc3)c1)c1ccccc1-2] |
| III-3 | 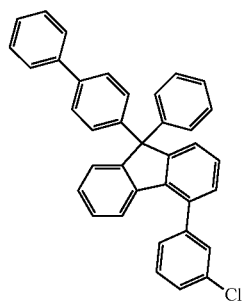 [SMILES: Clc1cccc(-c2cccc3c2-c2ccccc2C3(c2ccccc2)c2ccc(-c3ccccc3)cc2)c1] |

-continued
III-4
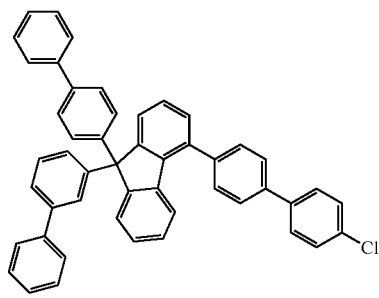 [SMILES: Clc1ccc(-c2ccc(-c3cccc4c3-c3ccccc3C4(c3ccc(-c4ccccc4)cc3)c3cccc(-c4ccccc4)c3)cc2)cc1]
III-5
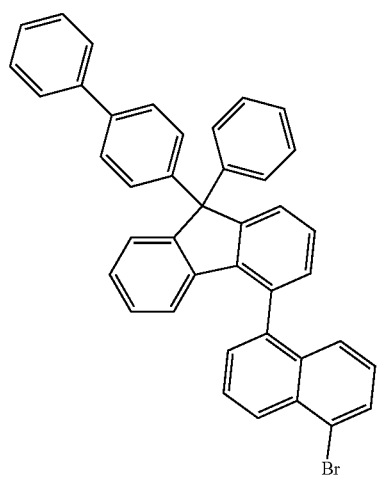 [SMILES: Brc1cccc2c(-c3cccc4c3-c3ccccc3C4(c3ccccc3)c3ccc(-c4ccccc4)cc3)cccc12]
III-6
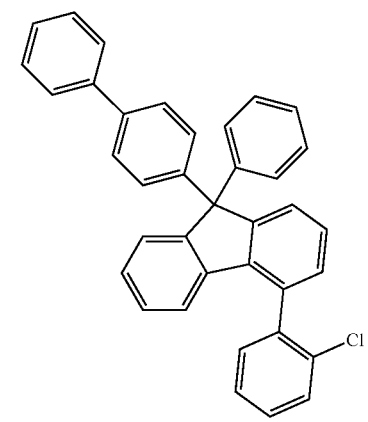 [SMILES: Clc1ccccc1-c1cccc2c1-c1ccccc1C2(c1ccccc1)c1ccc(-c2ccccc2)cc1]

2-2
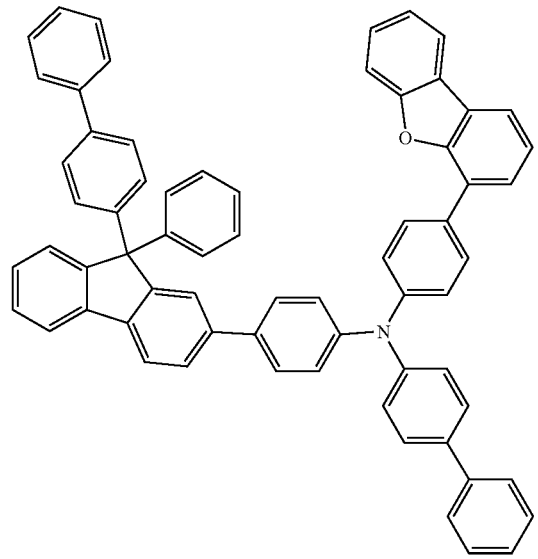 [SMILES: c1ccc(-c2ccc(N(c3ccc(-c4ccc5c(c4)C(c4ccccc4)(c4ccc(-c6ccccc6)cc4)c4ccccc4-5)cc3)c3ccc(-c4cccc5c4oc4ccccc45)cc3)cc2)cc1]
III-7
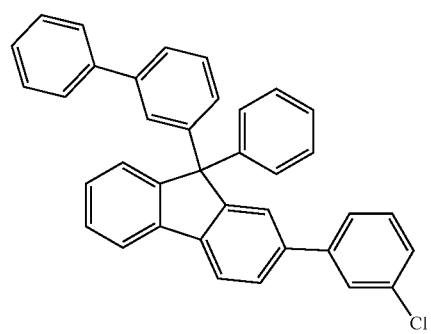 [SMILES: Clc1cccc(-c2ccc3c(c2)C(c2ccccc2)(c2cccc(-c4ccccc4)c2)c2ccccc2-3)c1]
III-8
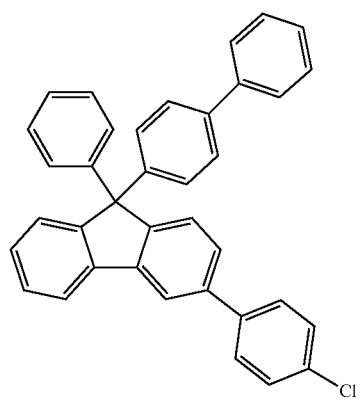 [SMILES: Clc1ccc(-c2ccc3c(c2)-c2ccccc2C3(c2ccccc2)c2ccc(-c3ccccc3)cc2)cc1]
III-9
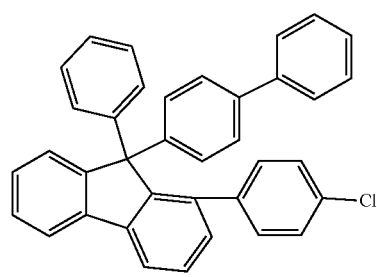 [SMILES: Clc1ccc(-c2cccc3c2C(c2ccccc2)(c2ccc(-c4ccccc4)cc2)c2ccccc2-3)cc1]

2-3
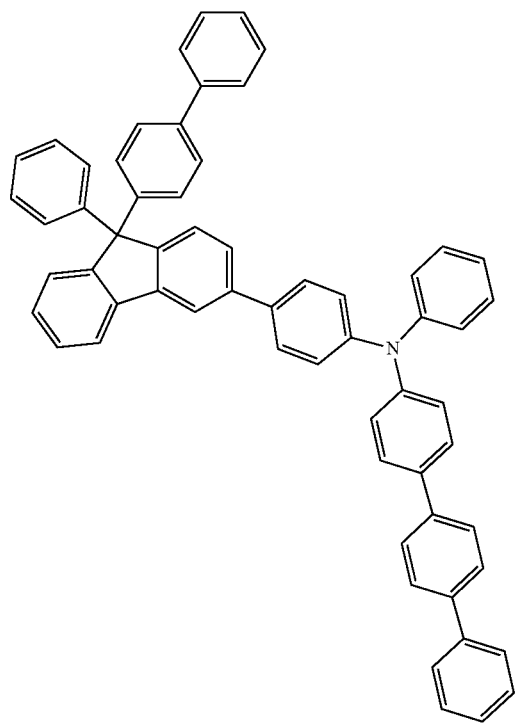 [SMILES: c1ccc(-c2ccc(-c3ccc(N(c4ccccc4)c4ccc(-c5ccc6c(c5)-c5ccccc5C6(c5ccccc5)c5ccc(-c6ccccc6)cc5)cc4)cc3)cc2)cc1]
2-12
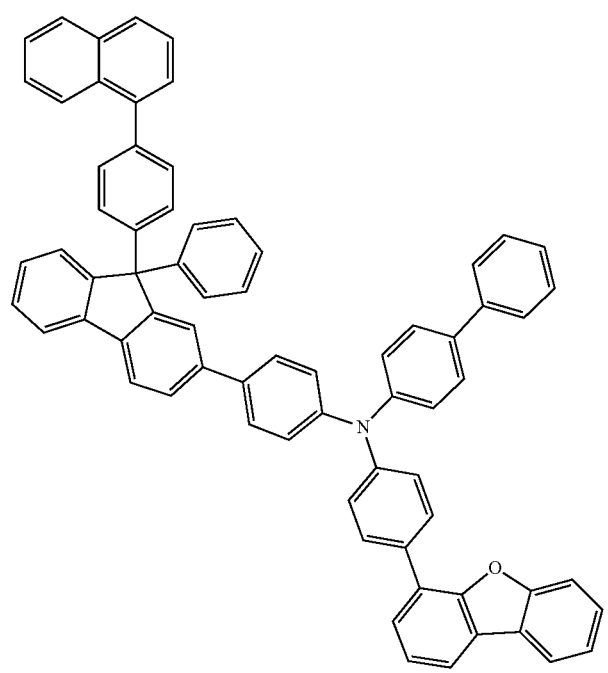 [SMILES: c1ccc(-c2ccc(N(c3ccc(-c4ccc5c(c4)C(c4ccccc4)(c4ccc(-c6cccc7ccccc67)cc4)c4ccccc4-5)cc3)c3ccc(-c4cccc5c4oc4ccccc45)cc3)cc2)cc1]

-continued
2-13
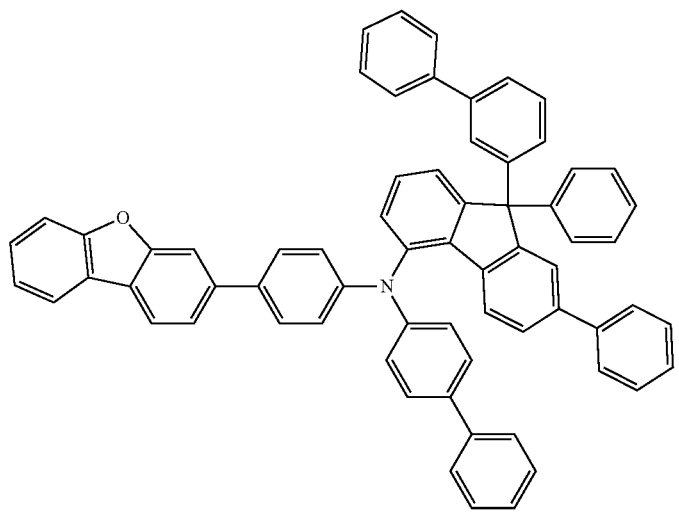 [SMILES: c1ccc(-c2ccc(N(c3ccc(-c4ccc5c(c4)oc4ccccc45)cc3)c3cccc4c3-c3ccc(-c5ccccc5)cc3C4(c3ccccc3)c3cccc(-c4ccccc4)c3)cc2)cc1]
III-10
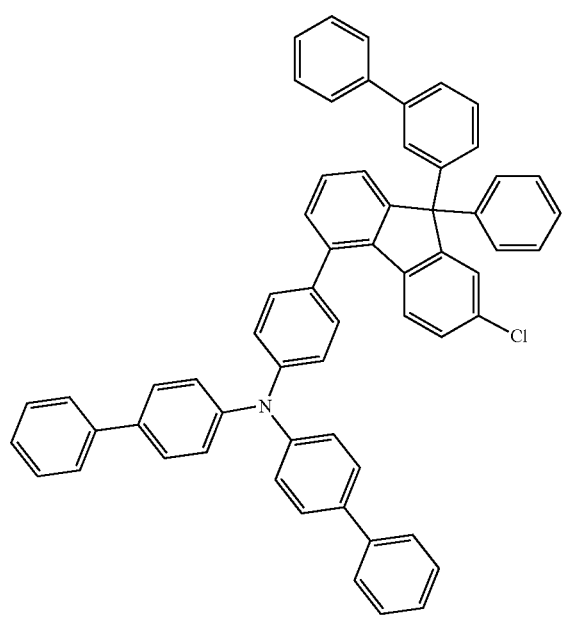 [SMILES: Clc1ccc2c(c1)C(c1ccccc1)(c1cccc(-c3ccccc3)c1)c1cccc(-c3ccc(N(c4ccc(-c5ccccc5)cc4)c4ccc(-c5ccccc5)cc4)cc3)c1-2]
III-11
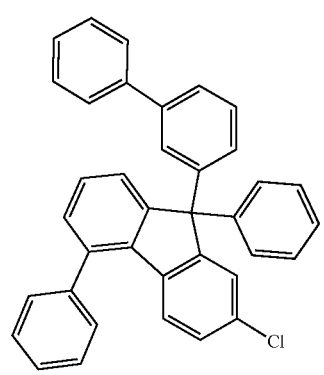 [SMILES: Clc1ccc2c(c1)C(c1ccccc1)(c1cccc(-c3ccccc3)c1)c1cccc(-c3ccccc3)c1-2]

N-{[1,1'-Biphenyl]-4-yl}-N-[4-(9-{[1,1'-biphenyl]-4-yl}-9-phenyl-9H-fluoren-4-yl)phenyl]-9,9-dimethyl-9H-fluorene-2-amine
Analogously to Example 1-1, N-{[1,1'-biphenyl]-4-yl}-N-[4-(9-{[1,1'-biphenyl]-4-yl}-9-phenyl-9H-fluoren-4-yl)phenyl]-9,9-dimethyl-9H-fluorene-2-amine (compound 2-1) and the compounds below are prepared. The yields here are between 40% and 85%.
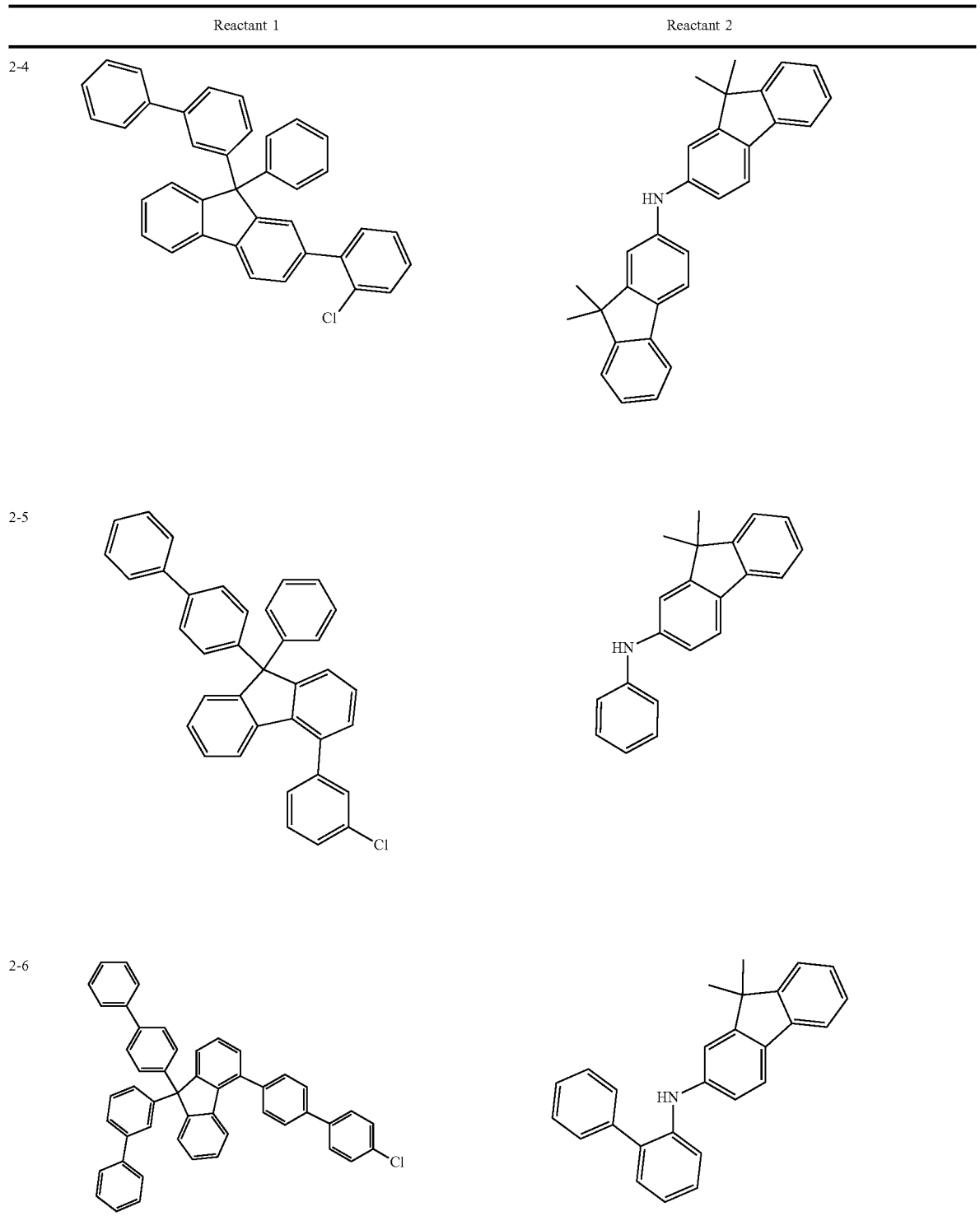

2-7
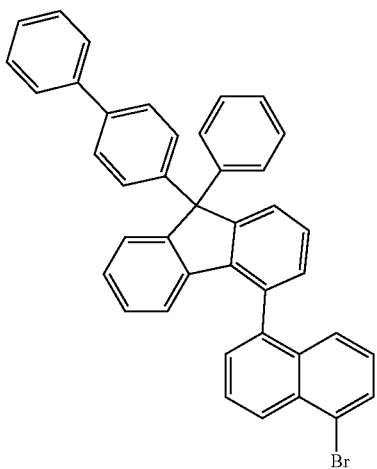 [SMILES: Brc1cccc2c(-c3cccc4c3-c3ccccc3C4(c3ccccc3)c3ccc(-c4ccccc4)cc3)cccc12]
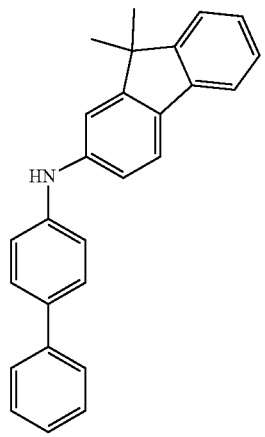 [SMILES: CC1(C)c2ccccc2-c2ccc(Nc3ccc(-c4ccccc4)cc3)cc21]
2-8
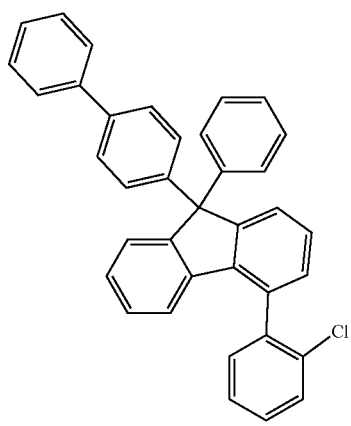 [SMILES: Clc1ccccc1-c1cccc2c1-c1ccccc1C2(c1ccccc1)c1ccc(-c2ccccc2)cc1]
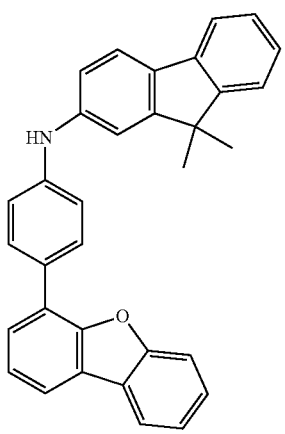 [SMILES: CC1(C)c2ccccc2-c2ccc(Nc3ccc(-c4cccc5c4oc4ccccc45)cc3)cc21]
2-9
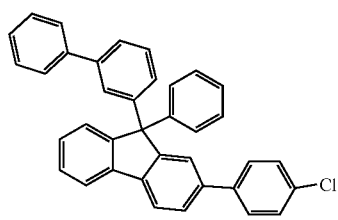 [SMILES: Clc1ccc(-c2ccc3c(c2)C(c2ccccc2)(c2cccc(-c4ccccc4)c2)c2ccccc2-3)cc1]
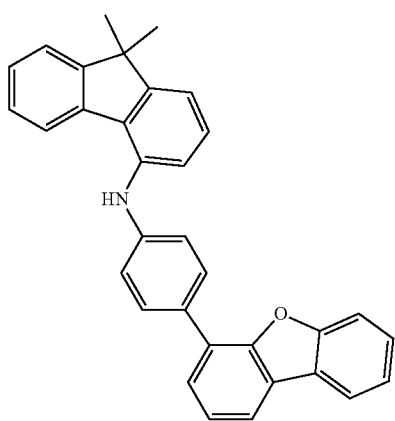 [SMILES: CC1(C)c2ccccc2-c2c(Nc3ccc(-c4cccc5c4oc4ccccc45)cc3)cccc21]

| | | |
|---|---|---|
| 2-10 | 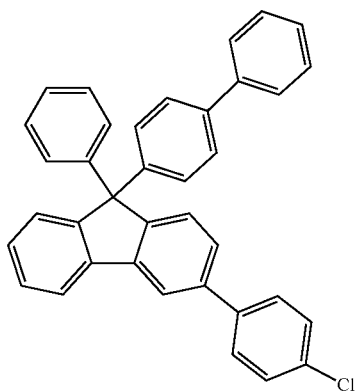 [SMILES: Clc1ccc(-c2ccc3c(c2)-c2ccccc2C3(c2ccccc2)c2ccc(-c3ccccc3)cc2)cc1] | 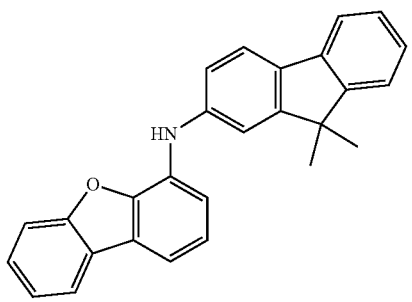 [SMILES: CC1(C)c2ccccc2-c2ccc(Nc3cccc4c3oc3ccccc34)cc21] |
| 2-11 | 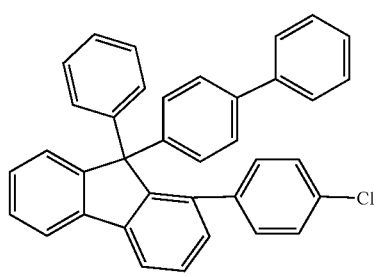 [SMILES: Clc1ccc(-c2cccc3c2C(c2ccccc2)(c2ccc(-c4ccccc4)cc2)c2ccccc2-3)cc1] | 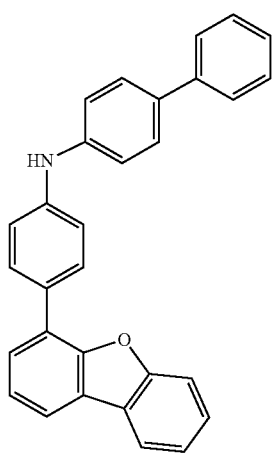 [SMILES: c1ccc(-c2ccc(Nc3ccc(-c4cccc5c4oc4ccccc45)cc3)cc2)cc1] |
| III-12 | 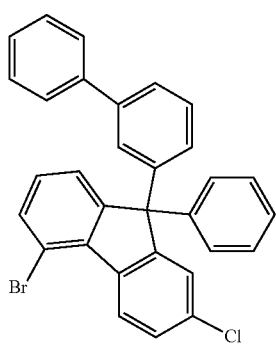 [SMILES: Clc1ccc2c(c1)C(c1ccccc1)(c1cccc(-c3ccccc3)c1)c1cccc(Br)c1-2] | 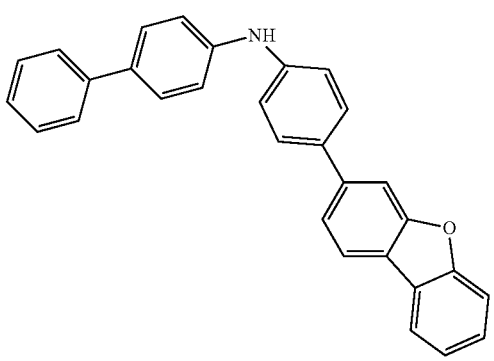 [SMILES: c1ccc(-c2ccc(Nc3ccc(-c4ccc5c(c4)oc4ccccc45)cc3)cc2)cc1] |
| 2-14 | 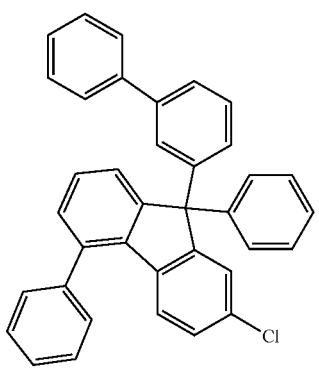 [SMILES: Clc1ccc2c(c1)C(c1ccccc1)(c1cccc(-c3ccccc3)c1)c1cccc(-c3ccccc3)c1-2] | 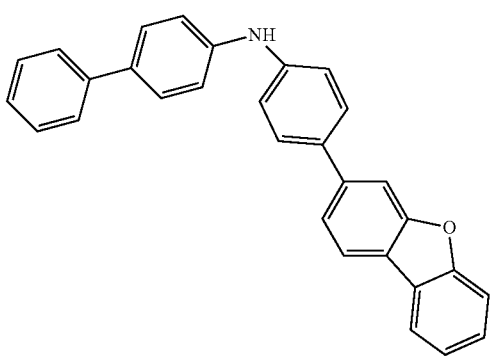 [SMILES: c1ccc(-c2ccc(Nc3ccc(-c4ccc5c(c4)oc4ccccc45)cc3)cc2)cc1] |

| | Product |
|---|---|
| 2-4 | 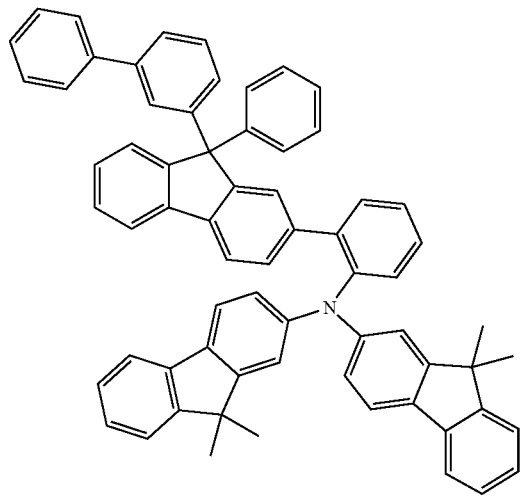 [SMILES: CC1(C)c2ccccc2-c2ccc(N(c3ccc4c(c3)C(C)(C)c3ccccc3-4)c3ccccc3-c3ccc4c(c3)C(c3ccccc3)(c3cccc(-c5ccccc5)c3)c3ccccc3-4)cc21] |
| 2-5 | 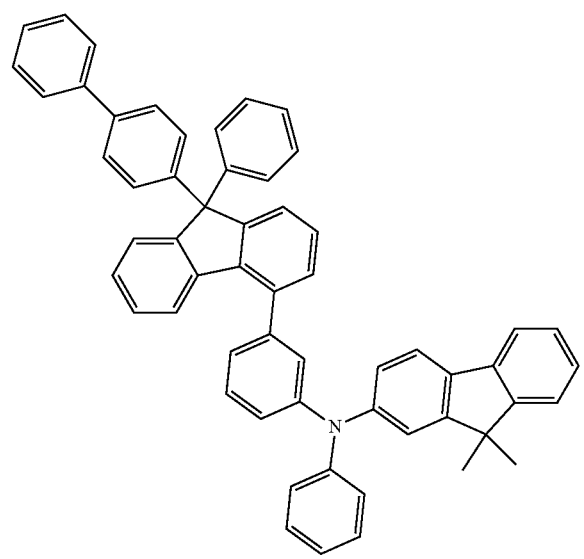 [SMILES: CC1(C)c2ccccc2-c2ccc(N(c3ccccc3)c3cccc(-c4cccc5c4-c4ccccc4C5(c4ccccc4)c4ccc(-c5ccccc5)cc4)c3)cc21] |
| 2-6 | 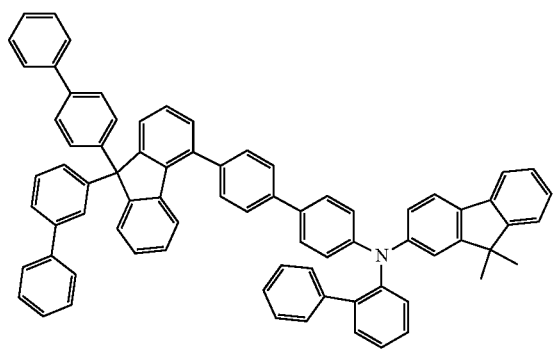 [SMILES: CC1(C)c2ccccc2-c2ccc(N(c3ccc(-c4ccc(-c5cccc6c5-c5ccccc5C6(c5ccc(-c6ccccc6)cc5)c5cccc(-c6ccccc6)c5)cc4)cc3)c3ccccc3-c3ccccc3)cc21] |

2-7
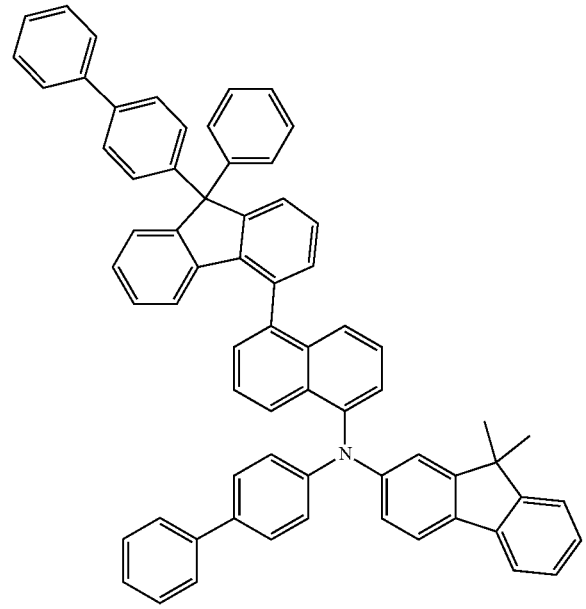 [SMILES: CC1(C)c2ccccc2-c2ccc(N(c3ccc(-c4ccccc4)cc3)c3cccc4c(-c5cccc6c5-c5ccccc5C6(c5ccccc5)c5ccc(-c6ccccc6)cc5)cccc34)cc21]
2-8
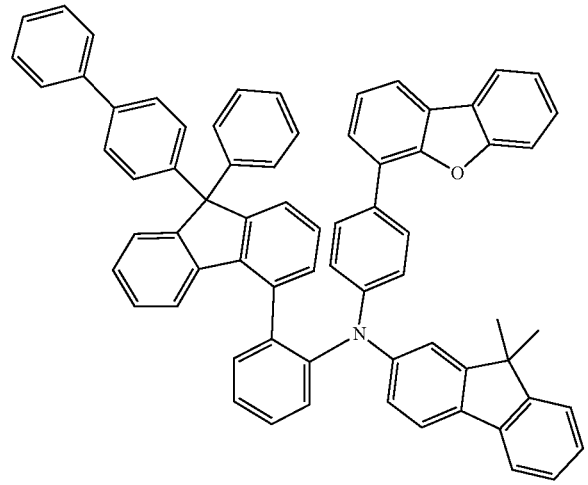 [SMILES: CC1(C)c2ccccc2-c2ccc(N(c3ccc(-c4cccc5c4oc4ccccc45)cc3)c3ccccc3-c3cccc4c3-c3ccccc3C4(c3ccccc3)c3ccc(-c4ccccc4)cc3)cc21]

2-9 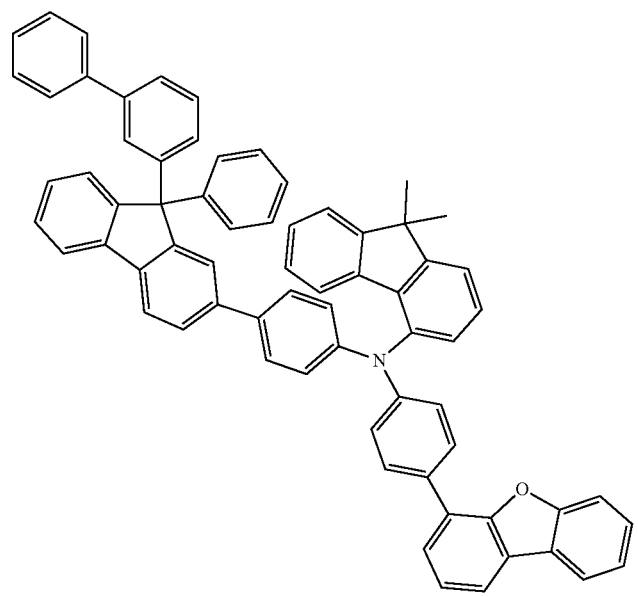 [SMILES: CC1(C)c2ccccc2-c2c(N(c3ccc(-c4ccc5c(c4)C(c4ccccc4)(c4cccc(-c6ccccc6)c4)c4ccccc4-5)cc3)c3ccc(-c4cccc5c4oc4ccccc45)cc3)cccc21]
2-10 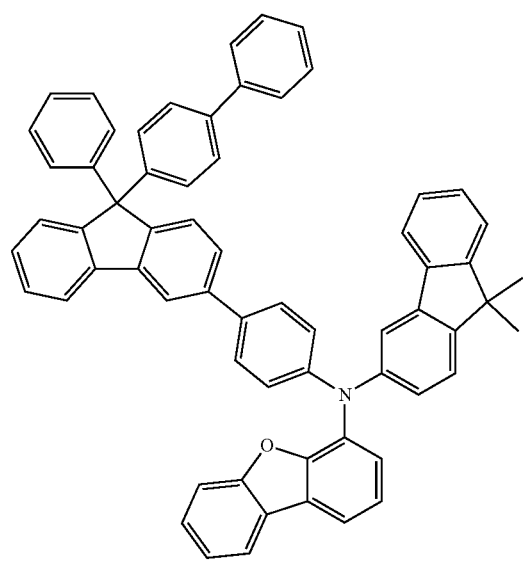 [SMILES: CC1(C)c2ccccc2-c2cc(N(c3ccc(-c4ccc5c(c4)-c4ccccc4C5(c4ccccc4)c4ccc(-c5ccccc5)cc4)cc3)c3cccc4c3oc3ccccc34)ccc21]
2-11 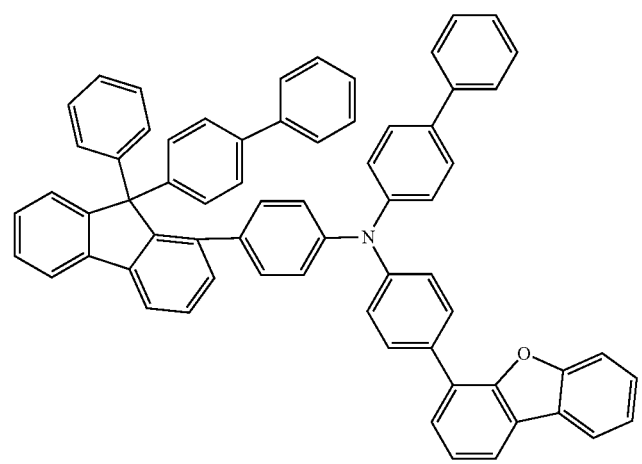 [SMILES: c1ccc(-c2ccc(N(c3ccc(-c4cccc5c4C(c4ccccc4)(c4ccc(-c6ccccc6)cc4)c4ccccc4-5)cc3)c3ccc(-c4cccc5c4oc4ccccc45)cc3)cc2)cc1]

III-12

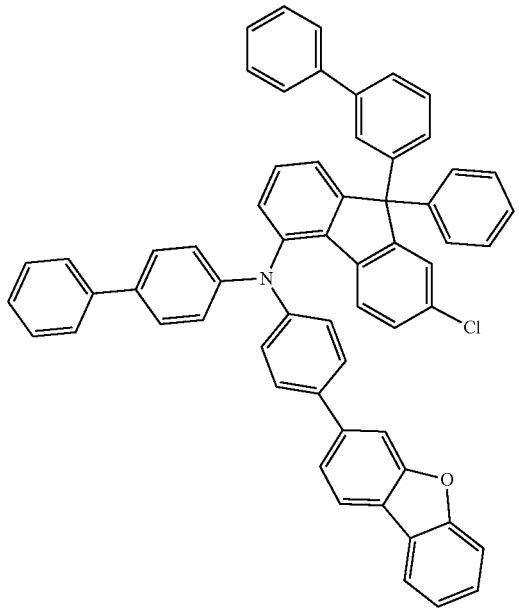 [SMILES: Clc1ccc2c(c1)C(c1ccccc1)(c1cccc(-c3ccccc3)c1)c1cccc(N(c3ccc(-c4ccccc4)cc3)c3ccc(-c4ccc5c(c4)oc4ccccc45)cc3)c1-2]

2-14

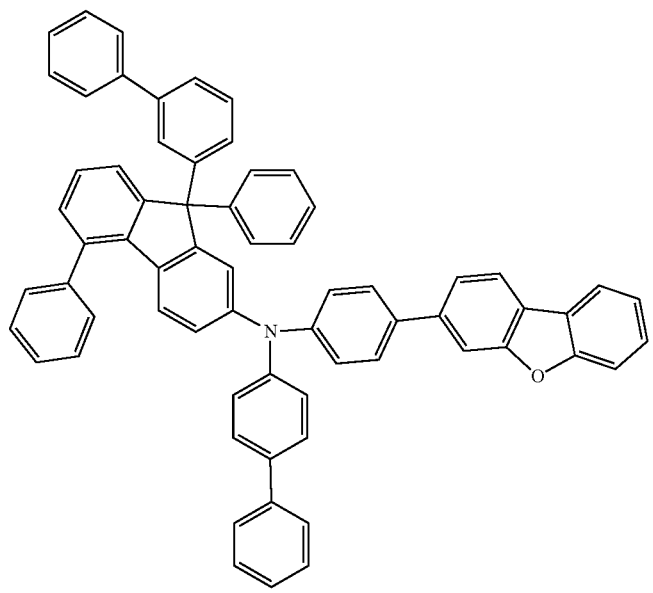 [SMILES: c1ccc(-c2ccc(N(c3ccc(-c4ccc5c(c4)oc4ccccc45)cc3)c3ccc4c(c3)C(c3ccccc3)(c3cccc(-c5ccccc5)c3)c3cccc(-c5ccccc5)c3-4)cc2)cc1]

B) Device Examples

1) General Production Process for the OLEDs and Characterization of the OLEDs

Glass plaques which have been coated with structured ITO (indium tin oxide) in a thickness of 50 nm are the substrates to which the OLEDs are applied.

The OLEDs basically have the following layer structure: substrate/hole injection layer (HIL)/hole transport layer (HTL)/electron blocker layer (EBL)/emission layer (EML)/ electron transport layer (ETL)/electron injection layer (EIL) and finally a cathode. The cathode is formed by an aluminium layer of thickness 100 nm. The exact structure of the OLEDs can be found in the tables which follow. The materials required for production of the OLEDs are shown in a table below.

All materials are applied by thermal vapour deposition in a vacuum chamber. In this case, the emission layer consists of at least one matrix material (host material) and an emitting dopant (emitter) which is added to the matrix material(s) in a particular proportion by volume by co-evaporation. Details given in such a form as H:SEB (95%: 5%) mean here that the material H is present in the layer in a proportion by volume of 95% and SEB in a proportion of 5%.

In an analogous manner, the electron transport layer and the hole injection layer also consist of a mixture of two materials. The structures of the materials that are used in the OLEDs are shown in Table 3.

The OLEDs are characterized in a standard manner. For this purpose, the electroluminescence spectra, the external quantum efficiency (EQE, measured in %) as a function of the luminance, calculated from current-voltage-luminance characteristics assuming Lambertian radiation characteristics, and the lifetime are determined. The parameter EQE @ 10 mA/cm² refers to the external quantum efficiency which is attained at 10 mA/cm². The parameter U @ 10 mA/cm² refers to the operating voltage at 10 mA/cm². The lifetime LT is defined as the time after which the luminance drops from the starting luminance to a certain proportion in the course of operation with constant current density. An LT80 figure means here that the lifetime reported corresponds to the time after which the luminance has dropped to 80% of its starting value. The figure @60 or 40 mA/cm² means here that the lifetime in question is measured at 60 or 40 mA/cm².

2) Use of the Compounds of the Invention in the HIL/HTL and EBL of Blue-Fluorescing and Green-Phosphorescing Devices OLEDs are produced with the following structure:

OLEDs I1 and I14 show the use of compounds HTM-4 and HTM-7 according to the application in the HIL (p-doped) and HTL of a blue-fluorescing OLED.

OLEDs I2 to I7 show the use of compounds HTM-1 to HTM-6 according to the application in the EBL of blue-fluorescing OLEDs.

OLEDs I8 to I13 show the use of compounds HTM-1 to HTM-6 according to the application in the EBL of green-phosphorescing OLEDs.

The OLEDs show the following values for operating voltage, EQE and lifetime:

TABLE 1

| | | | OLED structure | | | |
|---|---|---|---|---|---|---|
| Ex. | HIL | HTL | EBL | EML | ETL | EIL |
| | Thickness/nm | Thickness/nm | Thickness/nm | Thickness/nm | Thickness/nm | Thickness/nm |
| I1 | HTM-4:p-doped (5%) 20 nm | HTM-4 180 nm | EBM 10 nm | H:SEB(5%) 20 nm | ETM:LiQ(50%) 30 nm | LiQ 1 nm |
| I14 | HTM-7:p-doped (5%) 20 nm | HTM-7 180 nm | EBM 10 nm | H:SEB(5%) 20 nm | ETM:LiQ(50%) 30 nm | LiQ 1 nm |
| I2 | HTM:p-doped (5%) 20 nm | HTM 180 nm | HTM-1 10 nm | H:SEB(5%) 20 nm | ETM:LiQ(50%) 30 nm | LiQ 1 nm |
| I3 | HTM:p-doped (5%) 20 nm | HTM 180 nm | HTM-2 10 nm | H:SEB(5%) 20 nm | ETM:LiQ(50%) 30 nm | LiQ 1 nm |
| I4 | HTM:p-doped (5%) 20 nm | HTM 180 nm | HTM-3 10 nm | H:SEB(5%) 20 nm | ETM:LiQ(50%) 30 nm | LiQ 1 nm |
| I5 | HTM:p-doped (5%) 20 nm | HTM 180 nm | HTM-4 10 nm | H:SEB(5%) 20 nm | ETM:LiQ(50%) 30 nm | LiQ 1 nm |
| I6 | HTM:p-doped (5%) 20 nm | HTM 180 nm | HTM-5 10 nm | H:SEB(5%) 20 nm | ETM:LiQ(50%) 30 nm | LiQ 1 nm |
| I7 | HTM:p-doped (5%) 20 nm | HTM 180 nm | HTM-6 10 nm | H:SEB(5%) 20 nm | ETM:LiQ(50%) 30 nm | LiQ 1 nm |
| I8 | HTM:p-doped (5%) 20 nm | HTM 220 nm | HTM-1 10 nm | TMM-1: TMM-2(28%):TEG (12%) 30 nm | ETM:LiQ(50%) 30 nm | LiQ 1 nm |
| I9 | HTM:p-doped (5%) 20 nm | HTM 220 nm | HTM-2 10 nm | TMM-1: TMM-2(28%):TEG (12%) 30 nm | ETM:LiQ(50%) 30 nm | Lic 1 nm |
| I10 | HTM:p-doped (5%) 20 nm | HTM 220 nm | HTM-3 10 nm | TMM-1: TMM-2(28%):TEG (12%) 30 nm | ETM:LiQ(50%) 30 nm | LiQ 1 nm |
| I11 | HTM:p-doped (5%) 20 nm | HTM 220 nm | HTM-4 10 nm | TMM-1: TMM-2(28%):TEG (12%) 30 nm | ETM:LiQ(50%) 30 nm | LiQ 1 nm |
| I12 | HTM:p-doped (5%) 20 nm | HTM 220 nm | HTM-5 10 nm | TMM-1: TMM-2(28%): TEG (12%) 30 nm | ETM:LiQ(50%) 30 nm | LiQ 1 nm |
| I13 | HTM:p-doped (5%) 20 nm | HTM 220 nm | HTM-6 10 nm | TMM-1: TMM-2(28%): TEG (12%) 30 nm | ETM:LiQ(50%) 30 nm | LiQ 1 nm |

TABLE 2

| | OLED data | | |
|---|---|---|---|
| | U @ 10 mA/cm$^2$ (V) | EQE @ 10 mA/cm$^2$ (%) | LT80 @ 60/40* mA/cm$^2$ (h) |
| I1 | 4.1 | 8.8 | 220 |
| I14 | 4.3 | 8.4 | 310 |
| I2 | 3.9 | 8.5 | 280 |
| I3 | 4.0 | 8.9 | 250 |
| I4 | 3.8 | 8.8 | 260 |
| I5 | 3.8 | 8.9 | 250 |
| I6 | 4.0 | 8.6 | 200 |
| I7 | 3.9 | 8.7 | 300 |
| I8 | 3.9 | 17.2 | 310* |
| I9 | 4.0 | 17.8 | 270* |

TABLE 2-continued

| | OLED data | | |
|---|---|---|---|
| | U @ 10 mA/cm$^2$ (V) | EQE @ 10 mA/cm$^2$ (%) | LT80 @ 60/40* mA/cm$^2$ (h) |
| I10 | 3.9 | 16.8 | 270* |
| I11 | 3.8 | 16.6 | 340* |
| I12 | 3.9 | 16.8 | 220* |
| I13 | 4.1 | 17.2 | 300* |

The OLEDs show a good lifetime, high efficiency and low operating voltage. This result is obtained in all three OLED structures used and for all compounds according to the application used above.

TABLE 3

Materials used

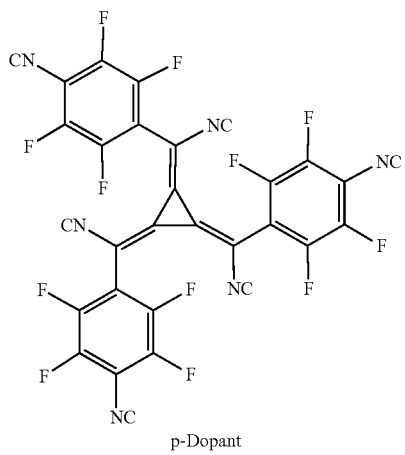

p-Dopant

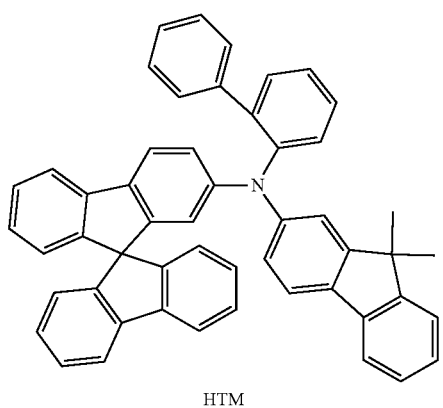

HTM

TABLE 3-continued
Materials used
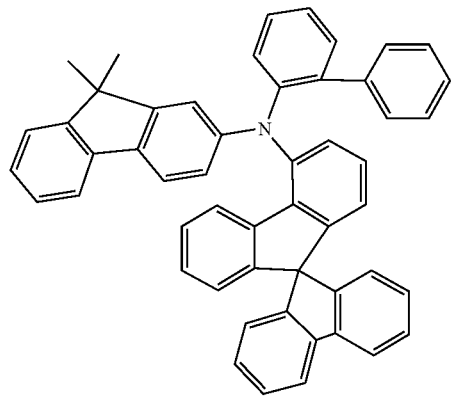 [SMILES: CC1(C)c2ccccc2-c2ccc(N(c3ccccc3-c3ccccc3)c3cccc4c3-c3ccccc3C43c4ccccc4-c4ccccc43)cc21]
EBM
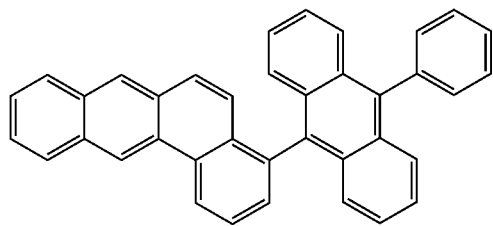 [SMILES: c1ccc(-c2c3ccccc3c(-c3cccc4c3ccc3cc5ccccc5cc34)c3ccccc23)cc1]
H
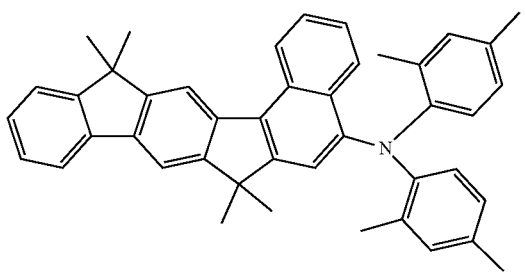 [SMILES: Cc1ccc(N(c2ccc(C)cc2C)c2cc3c(c4ccccc24)-c2cc4c(cc2C3(C)C)-c2ccccc2C4(C)C)c(C)c1]
SEB
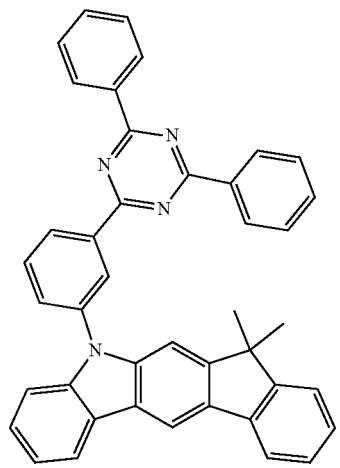 [SMILES: CC1(C)c2ccccc2-c2cc3c4ccccc4n(-c4cccc(-c5nc(-c6ccccc6)nc(-c6ccccc6)n5)c4)c3cc21]
TMM-1

TABLE 3-continued
Materials used
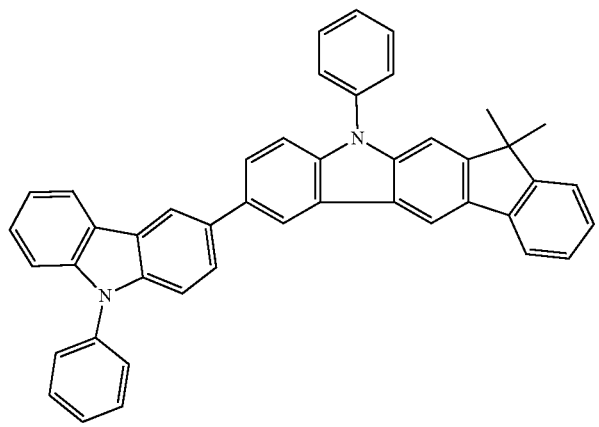 [SMILES: CC1(C)c2ccccc2-c2cc3c4cc(-c5ccc6c(c5)c5ccccc5n6-c5ccccc5)ccc4n(-c4ccccc4)c3cc21]
TMM-2
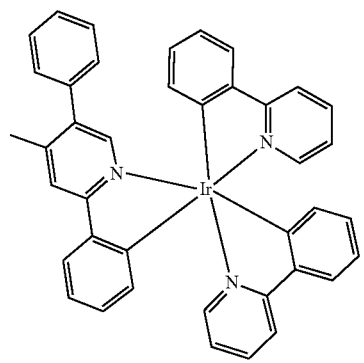
TEG
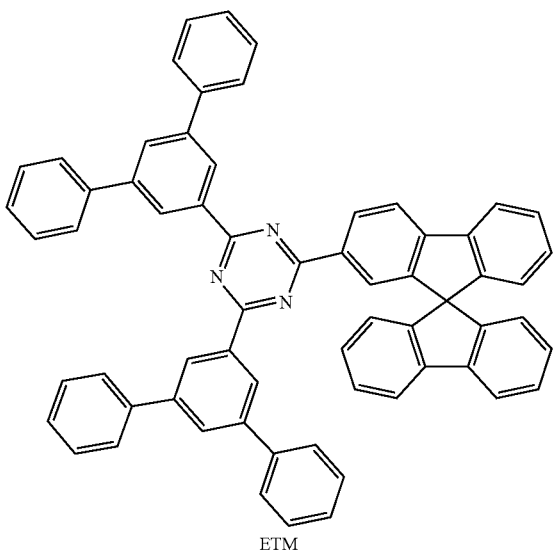
ETM
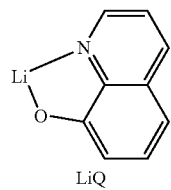
LiQ TABLE 3-continued
Materials used
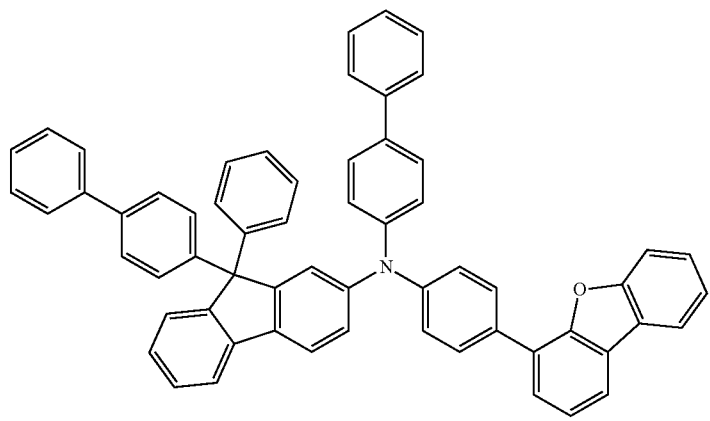 [SMILES: c1ccc(-c2ccc(N(c3ccc(-c4cccc5c4oc4ccccc45)cc3)c3ccc4c(c3)C(c3ccccc3)(c3ccc(-c5ccccc5)cc3)c3ccccc3-4)cc2)cc1]
HTM-1
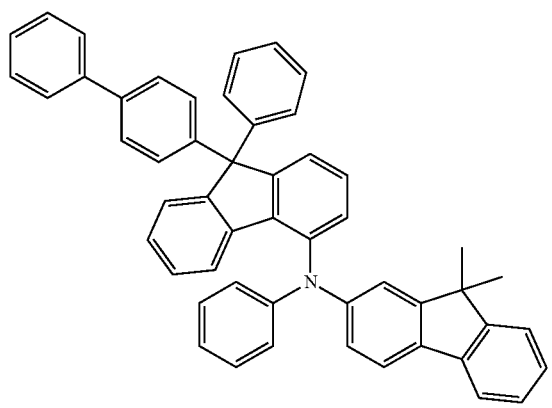 [SMILES: CC1(C)c2ccccc2-c2ccc(N(c3ccccc3)c3cccc4c3-c3ccccc3C4(c3ccccc3)c3ccc(-c4ccccc4)cc3)cc21]
HTM-2
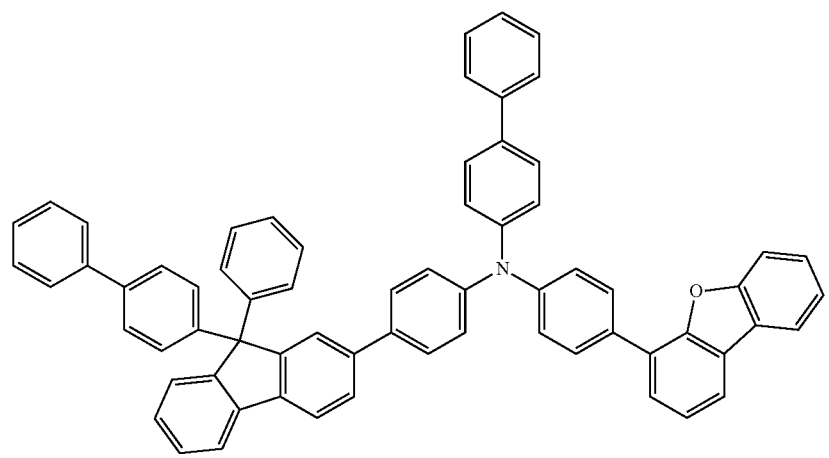 [SMILES: c1ccc(-c2ccc(N(c3ccc(-c4ccc5c(c4)C(c4ccccc4)(c4ccc(-c6ccccc6)cc4)c4ccccc4-5)cc3)c3ccc(-c4cccc5c4oc4ccccc45)cc3)cc2)cc1]
HTM-3

TABLE 3-continued
Materials used
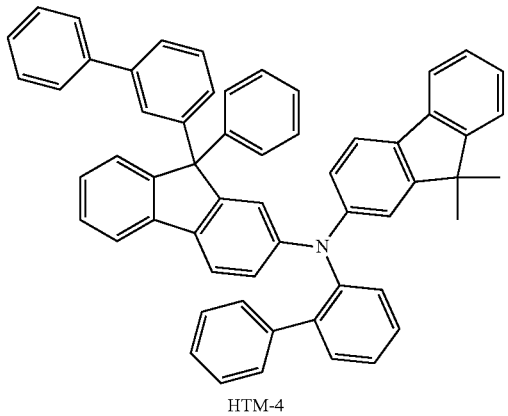
HTM-4
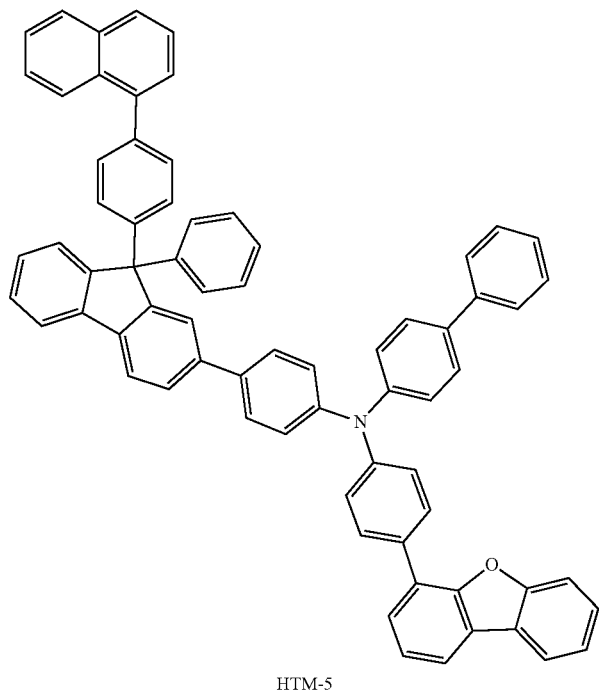
HTM-5

TABLE 3-continued
Materials used
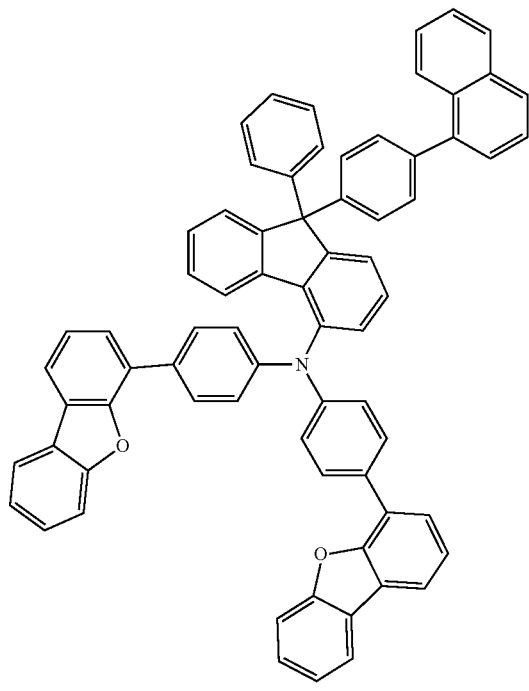 [SMILES: c1ccc(C2(c3ccc(-c4cccc5ccccc45)cc3)c3ccccc3-c3c(N(c4ccc(-c5cccc6c5oc5ccccc56)cc4)c4ccc(-c5cccc6c5oc5ccccc56)cc4)cccc32)cc1]
HTM-6
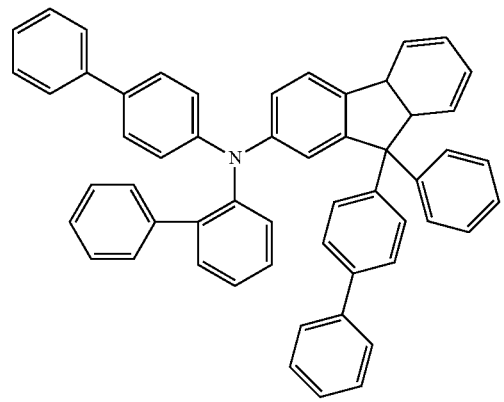 [SMILES: C1=CC2c3ccc(N(c4ccc(-c5ccccc5)cc4)c4ccccc4-c4ccccc4)cc3C(c3ccccc3)(c3ccc(-c4ccccc4)cc3)C2C=C1]
HTM-7
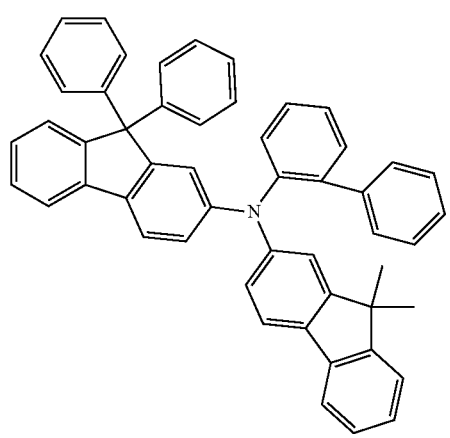 [SMILES: CC1(C)c2ccccc2-c2ccc(N(c3ccc4c(c3)C(c3ccccc3)(c3ccccc3)c3ccccc3-4)c3ccccc3-c3ccccc3)cc21]
Ref-1

TABLE 3-continued

Materials used

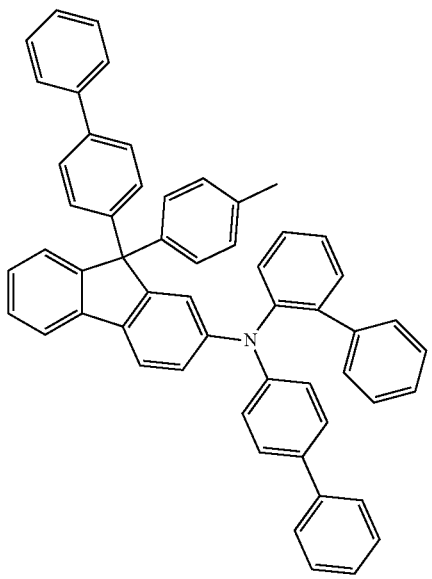 [SMILES: Cc1ccc(C2(c3ccc(-c4ccccc4)cc3)c3ccccc3-c3ccc(N(c4ccc(-c5ccccc5)cc4)c4ccccc4-c4ccccc4)cc32)cc1]

Ref-2

3) Comparative Experiment with Compounds HTM-4 and Ref-1

Compound HTM-4 according to the application is compared with reference compound Ref-1. The compounds differ merely in the substituents at the bridgehead carbon of the fluorene and are otherwise identical: in the case of HTM-4, there is asymmetric substitution there, with a phenyl group and a meta-biphenyl group as substituents. In Ref-1 there is symmetric substitution in the position mentioned, with two phenyl groups.

An OLED stack is used, as also used in Part 2), in which the compounds are present in the EBL in a blue-fluorescing stack. Ref-1 here shows a voltage at 10 mA/cm$^2$ of 3.7 V and EQE at 10 mA/cm$^2$ of 8.5%. HTM-4, in the equivalent structure 15, shows a better EQE of 8.9% at similar voltage (3.8 V).

This shows the advantage that results from the use of an asymmetric substitution at the bridgehead carbon atom, especially a substitution by biphenyl and phenyl on that atom, compared to a symmetric substitution by two phenyl groups.

4) Comparative Experiment with Compounds HTM-7 and Ref-2

Compound HTM-7 according to the application is compared with reference compound Ref-2. The compounds differ merely in the substituents at the bridgehead carbon atom of the fluorene: Ref-2 has alkyl substitution on the phenyl group at the bridgehead carbon atom mentioned, whereas HTM-7 does not have alkyl substitution.

An OLED structure is used, as also used in Part 2), in which the compounds are present in the HIL and HTL in a blue-fluorescing stack.

Reference compound Ref-2 here shows a voltage at 10 mA/cm$^2$ of 4.2 V. The lifetime LT80, measured at 60 mA/cm$^2$, is 150 h. HTM-7, by contrast, in the equivalent structure, shows a significantly better LT80 of 310 h at comparable voltage (4.3 V).

This shows the improvement that results from the omission of alkyl groups on the substituents at the bridgehead carbon atom. This improvement is not limited to the structures shown, but occurs in general.

TABLE 4

Device setup comparative example Ref-1 vs. HTM-4

| Ex. | HIL | HTL | EBL | EML | ETL | EIL |
|---|---|---|---|---|---|---|
| | Thickness/nm | Thickness/nm | Thickness/nm | Thickness/nm | Thickness/nm | Thickness/nm |
| C1 | HTM:p-doped (5%) 20 nm | HTM 180 nm | Ref-1 10 nm | H:SEB(5%) 20 nm | ETM:LiQ(50%) 30 nm | LiQ 1 nm |
| 15 | HTM:p-doped (5%) 20 nm | HTM 180 nm | HTM-4 10 nm | H:SEB(5%) 20 nm | ETM:LiQ(50%) 30 nm | LiQ 1 nm |

TABLE 5

| | Device setup comparative example Ref-2 vs. HTM-7 | | | | | |
|---|---|---|---|---|---|---|
| Ex. | HIL | HTL | EBL | EML | ETL | EIL |
| | Thickness/nm | Thickness/nm | Thickness/nm | Thickness/nm | Thickness/nm | Thickness/nm |
| C2 | Ref-2:p-doped (5%) 20 nm | Ref-2 180 nm | EBM 10 nm | H:SEB(5%) 20 nm | ETM:LiQ(50%) 30 nm | LiQ 1 nm |
| 114 | HTM-5:p-doped (5%) 20 nm | HTM-7 180 nm | EBM 10 nm | H:SEB(5%) 20 nm | ETM:LiQ(50%) 30 nm | LiQ 1 nm |

The invention claimed is:

1. A compound of formula (I)

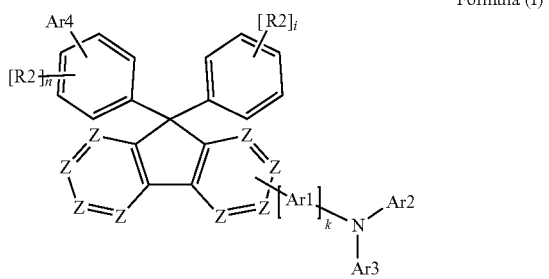

Formula (I)

where the variables that occur are as follows:

Z, when the -[Ar1]$_k$-N(Ar2)(Ar3) group is bonded thereto, is C, and Z, when the -[Ar1]$_k$-N(Ar2)(Ar3) group is not bonded thereto, is the same or different at each instance and is CR1 or N;

Ar1 is the same or different at each instance and is an aromatic ring system which has 6 to 40 aromatic ring atoms and is substituted by R3 radicals, or a heteroaromatic ring system which has 5 to 40 aromatic ring atoms and is substituted by R3 radicals;

Ar2 is an aromatic ring system which has 6 to 40 aromatic ring atoms and is substituted by R4 radicals, or a heteroaromatic ring system which has 5 to 40 aromatic ring atoms and is substituted by R4 radicals;

Ar3 is an aromatic ring system which has 6 to 40 aromatic ring atoms and is substituted by R4 radicals, or a heteroaromatic ring system which has 5 to 40 aromatic ring atoms and is substituted by R4 radicals;

provided that at least one group selected from the Ar2 and Ar3 groups is phenyl substituted by R4 radicals that are selected from H, D, F, CN and alkyl groups having 1 to 10 carbon atoms;

Ar4 is phenyl which may be substituted by R2 radicals or naphthyl which may be substituted by R2 radicals;

R1 is the same or different at each instance and is selected from H, D, F, Cl, Br, I, C(=O)R5, CN, Si(R5)$_3$, N(R5)$_2$, P(=O)(R5)$_2$, OR5, S(=O)R5, S(=O)$_2$R5, straight-chain alkyl or alkoxy groups having 1 to 20 carbon atoms, branched or cyclic alkyl or alkoxy groups having 3 to 20 carbon atoms, alkenyl or alkynyl groups having 2 to 20 carbon atoms, aromatic ring systems having 6 to 40 aromatic ring atoms, and heteroaromatic ring systems having 5 to 40 aromatic ring atoms; where two or more R1 radicals may be joined to one another and may form a ring; where the alkyl, alkoxy, alkenyl and alkynyl groups mentioned and the aromatic ring systems and heteroaromatic ring systems mentioned are each substituted by R5 radicals; and where one or more CH$_2$ groups in the alkyl, alkoxy, alkenyl and alkynyl groups mentioned may be replaced by —R5C=CR5-, —C≡C—, Si(R5)$_2$, C=O, C=NR5, —C(=O)O—, —C(=O)NR5-, NR5, P(=O)(R5), —O—, —S—, SO or SO$_2$;

R2 is the same or different at each instance and is selected from D, F, CN, Si(R5)$_3$, N(R5)$_2$, aromatic ring systems which have 6 to 40 aromatic ring atoms and are substituted by R5 radicals, and heteroaromatic ring systems which have 5 to 40 aromatic ring atoms and are substituted by R5 radicals;

R3 is the same or different at each instance and is selected from H, D, F, Cl, Br, I, C(=O)R5, CN, Si(R5)$_3$, N(R5)$_2$, P(=O)(R5)$_2$, OR5, S(=O)R5, S(=O)$_2$R5, straight-chain alkyl or alkoxy groups having 1 to 20 carbon atoms, branched or cyclic alkyl or alkoxy groups having 3 to 20 carbon atoms, alkenyl or alkynyl groups having 2 to 20 carbon atoms, aromatic ring systems having 6 to 40 aromatic ring atoms, and heteroaromatic ring systems having 5 to 40 aromatic ring atoms; where two or more R3 radicals may be joined to one another and may form a ring; where the alkyl, alkoxy, alkenyl and alkynyl groups mentioned and the aromatic ring systems and heteroaromatic ring systems mentioned are each substituted by R5 radicals; and where one or more CH$_2$ groups in the alkyl, alkoxy, alkenyl and alkynyl groups mentioned may be replaced by —R5C=CR5-, —C≡C—, Si(R5)$_2$, C=O, C=NR5, —C(=O)O—, —C(=O)NR5-, NR5, P(=O)(R5), —O—, —S—, SO or SO$_2$;

R4 is the same or different at each instance and is selected from H, D, F, Cl, Br, I, C(=O)R5, CN, Si(R5)$_3$, N(R5)$_2$, P(=O)(R5)$_2$, OR5, S(=O)R5, S(=O)$_2$R5, straight-chain alkyl or alkoxy groups having 1 to 20 carbon atoms, branched or cyclic alkyl or alkoxy groups having 3 to 20 carbon atoms, alkenyl or alkynyl groups having 2 to 20 carbon atoms, aromatic ring systems having 6 to 40 aromatic ring atoms, and heteroaromatic ring systems having 5 to 40 aromatic ring atoms; where two or more R4 radicals may be joined to one another and may form a ring; where the alkyl, alkoxy, alkenyl and alkynyl groups mentioned and the aromatic ring systems and heteroaromatic ring systems mentioned are each substituted by R5 radicals; and where one or more CH$_2$ groups in the alkyl, alkoxy, alkenyl and alkynyl groups mentioned may be replaced by —R5C=CR5-, —C≡C—, Si(R5)$_2$, C=O, C=NR5, —C(=O)O—, —C(=O)NR5-, NR5, P(=O)(R5), —O—, —S—, SO or SO$_2$;

R5 is the same or different at each instance and is selected from H, D, F, Cl, Br, I, C(=O)R6, CN, Si(R6)$_3$, N(R6)$_2$, P(=O)(R6)$_2$, OR6, S(=O)R6, S(=O)$_2$R6, straight-chain alkyl or alkoxy groups having 1 to 20 carbon atoms, branched or cyclic alkyl or alkoxy groups having 3 to 20 carbon atoms, alkenyl or alkynyl groups having 2 to 20 carbon atoms, aromatic ring systems having 6 to 40 aromatic ring atoms, and heteroaromatic ring systems having 5 to 40 aromatic ring atoms; where two or more R5 radicals may be joined to one another and may form a ring; where the alkyl, alkoxy, alkenyl and alkynyl groups mentioned and the aromatic ring systems and heteroaromatic ring systems mentioned are each substituted by R6 radicals; and where one or more CH$_2$ groups in the alkyl, alkoxy, alkenyl and alkynyl groups mentioned may be replaced by —R6C=CR6-, —C≡C—, Si(R6)$_2$, C=O, C=NR6, —C(=O)O—, —C(=O)NR6-, NR6, P(=O) (R6), —O—, —S—, SO or SO$_2$;

R6 is the same or different at each instance and is selected from H, D, F, Cl, Br, I, CN, alkyl or alkoxy groups having 1 to 20 carbon atoms, alkenyl or alkynyl groups having 2 to 20 carbon atoms, aromatic ring systems having 6 to 40 aromatic ring atoms and heteroaromatic ring systems having 5 to 40 aromatic ring atoms; where the alkyl, alkoxy, alkenyl and alkynyl groups, aromatic ring systems and heteroaromatic ring systems mentioned may be substituted by one or more radicals selected from F and CN;

k is 0, 1, 2, 3 or 4, where, in the case that k=0, the Ar1 group is absent and the groups that bind to Ar1 in formula (I) are bonded directly to one another;

i is 0, 1, 2, 3, 4 or 5;

n is 0, 1, 2, 3 or 4;

where the two groups

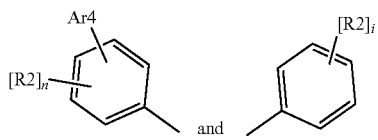

in formula (I), each as a whole including their substituents, are not the same.

2. The compound according to claim 1, wherein it is a monoamine.

3. The compound according to claim 1, wherein Z, when the -[Ar1]$_k$-N(Ar2)(Ar3) group is not bonded thereto, is CR1.

4. The compound according to claim 1, wherein k is 0.

5. The compound according to claim 1, wherein the -(Ar1)$_k$- group, if k=1, corresponds to one of the following formulae:

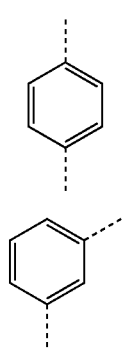

Ar1-1

Ar1-2

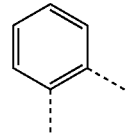

Ar1-3

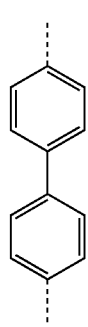

Ar1-4

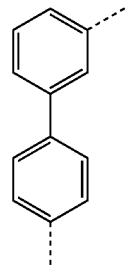

Ar1-5

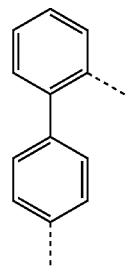

Ar1-6

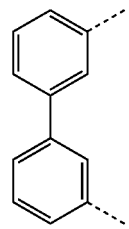

Ar1-7

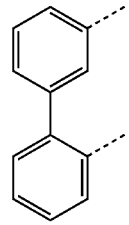

Ar1-8

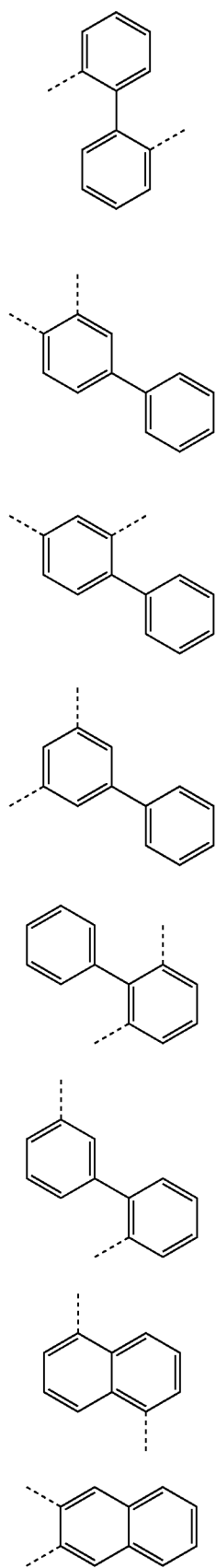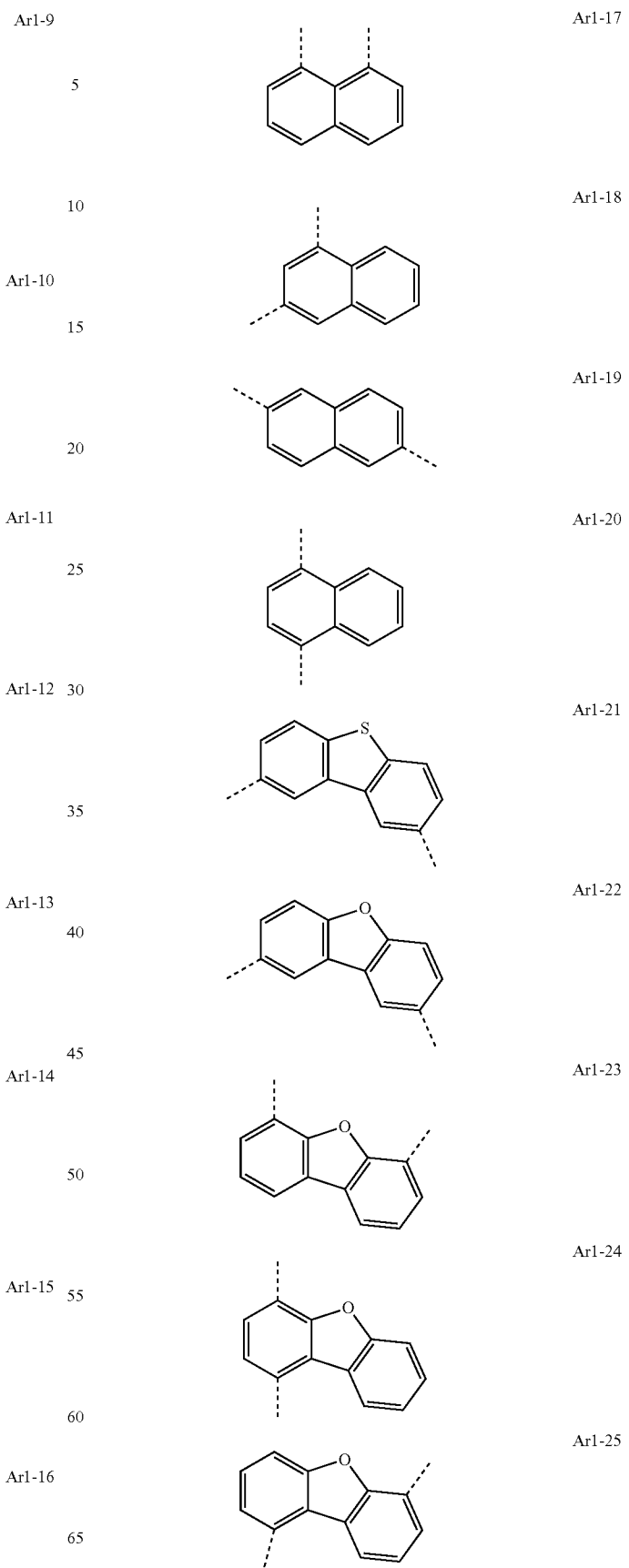

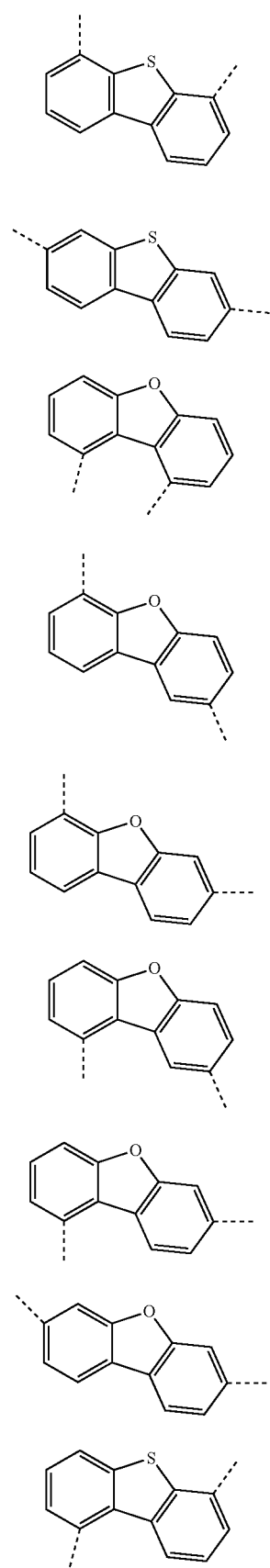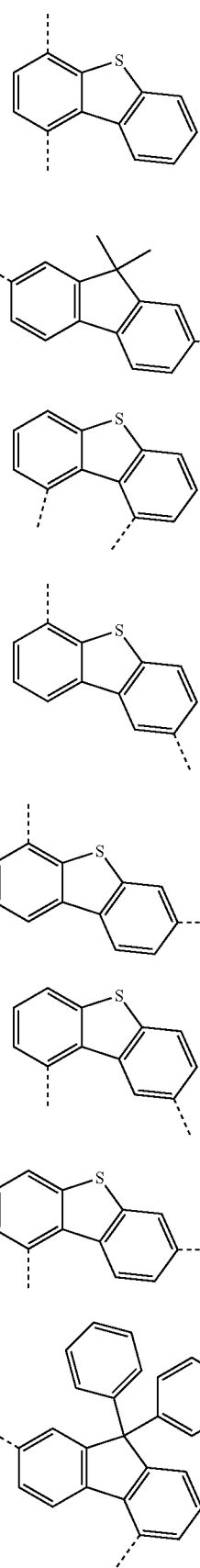

-continued
Ar1-43 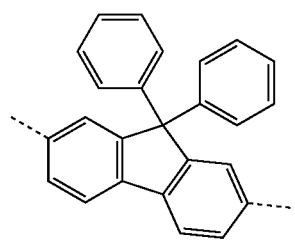
Ar1-44 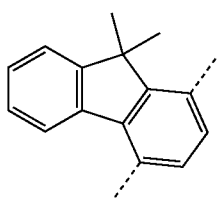
Ar1-45 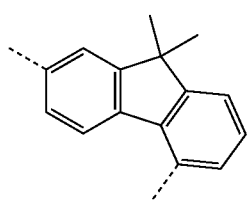
Ar1-46 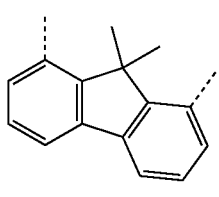
Ar1-47 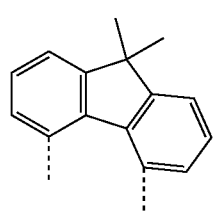
Ar1-48 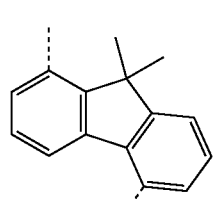
Ar1-49 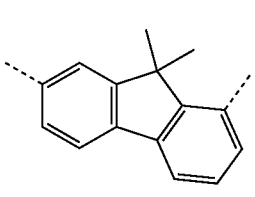
-continued
Ar1-50 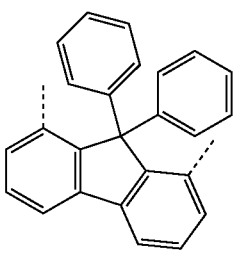
Ar1-51 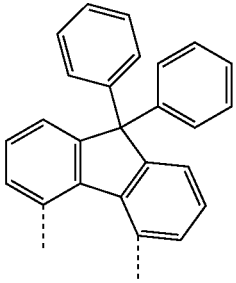
Ar1-52 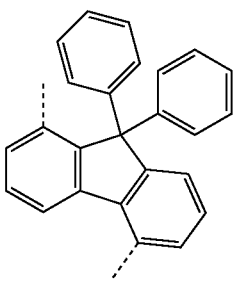
Ar1-53 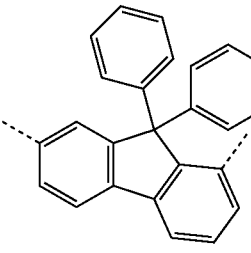
Ar1-54 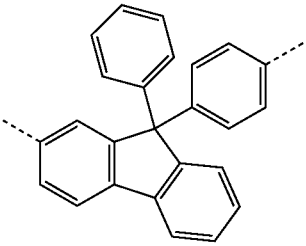
Ar1-55 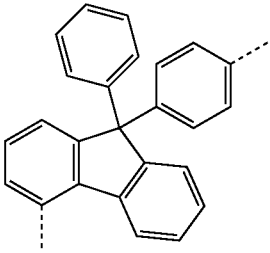

-continued
Ar1-56
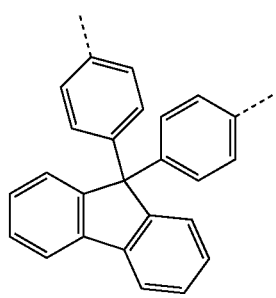
Ar1-57
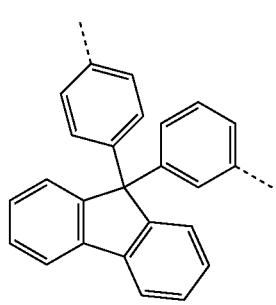
Ar1-58
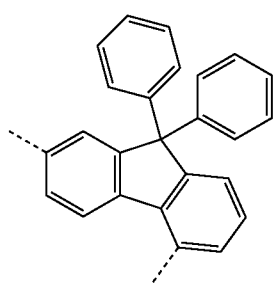
Ar1-59
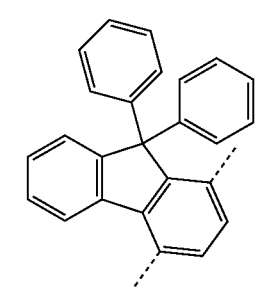
Ar1-60
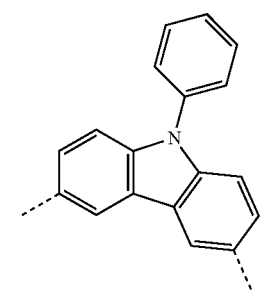
-continued
Ar1-61
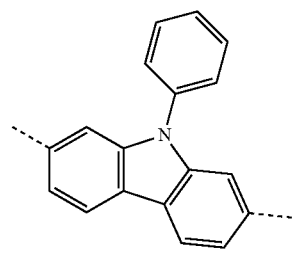
Ar1-62
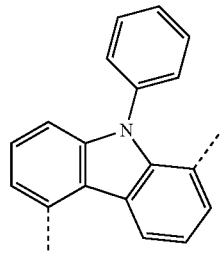
Ar1-63
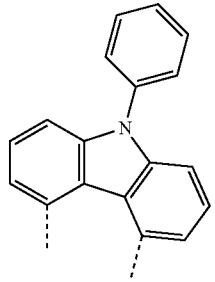
Ar1-64
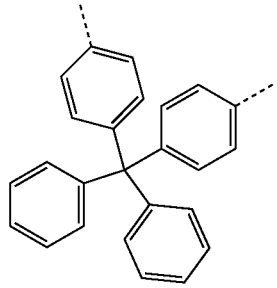
Ar1-65
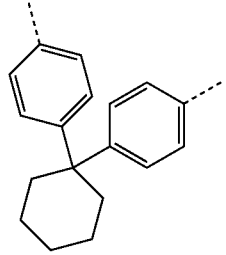
Ar1-66
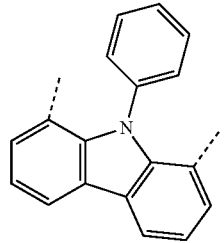

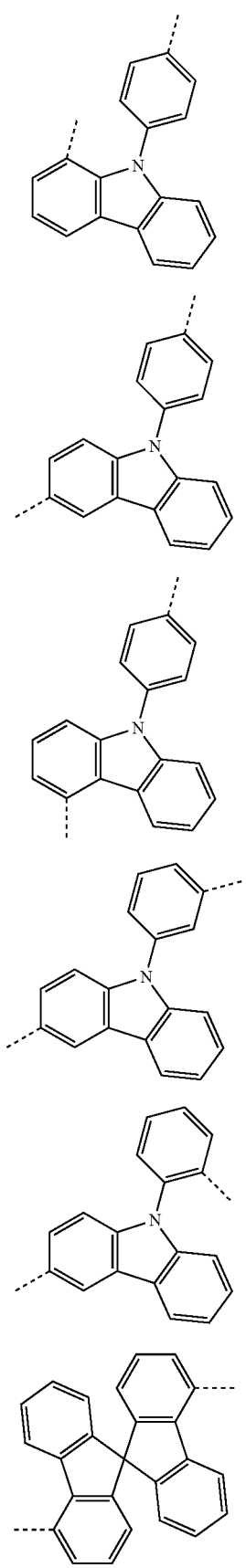
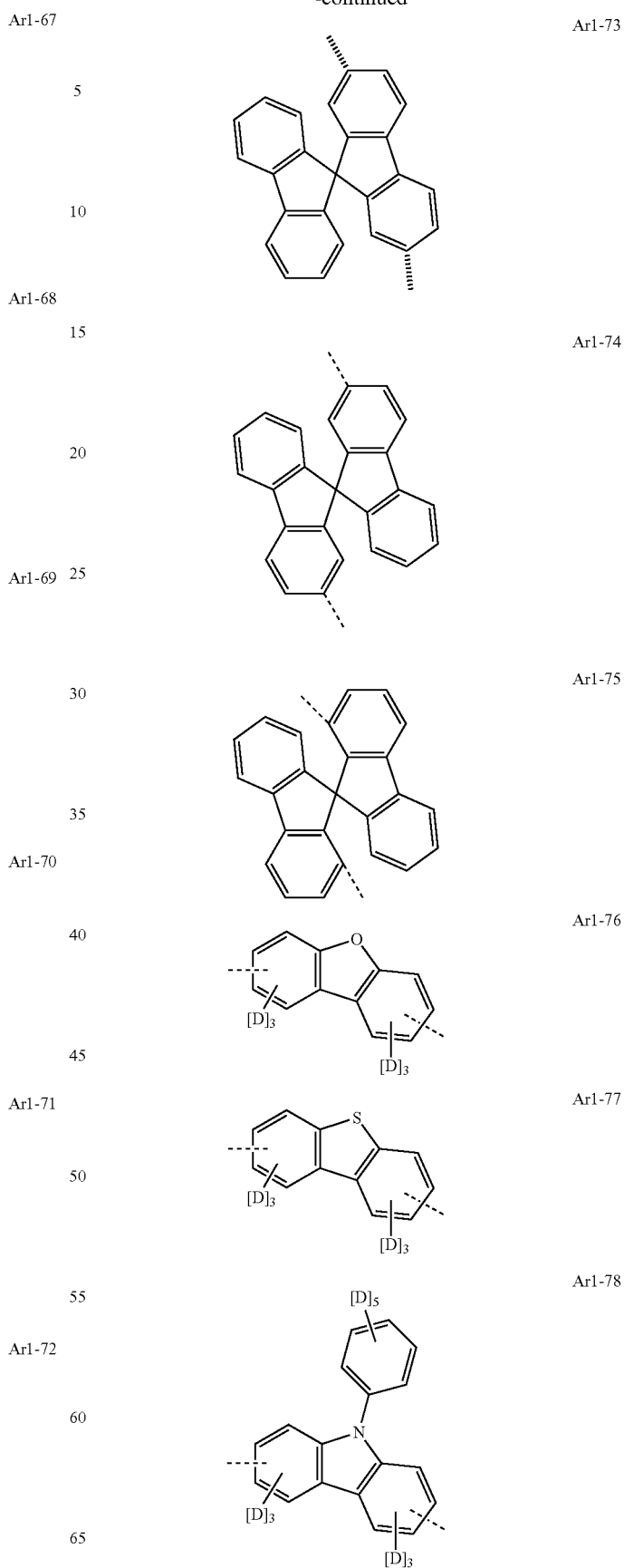

-continued

Ar1-79

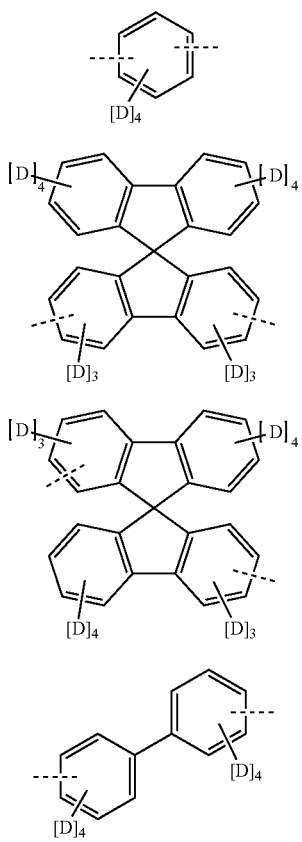

Ar1-80

Ar1-81

Ar1-82 where the dotted lines represent the bonds to the rest of the formula (I), and where the groups at the positions shown as unsubstituted are each substituted by R3 radicals, where the R3 radicals in these positions are preferably H.

6. The compound according to claim 1, wherein Ar2 and Ar3 are the same or different at each instance and are selected from phenyl, biphenyl, terphenyl, quaterphenyl, naphthyl, fluorenyl, especially 9,9'-dimethylfluorenyl and 9,9'-diphenylfluorenyl, benzofluorenyl, spirobifluorenyl, indenofluorenyl, indenocarbazolyl, dibenzofuranyl, dibenzothiophenyl, carbazolyl, benzofuranyl, benzothiophenyl, benzofused dibenzofuranyl, benzofused dibenzothiophenyl, naphthyl-substituted phenyl, fluorenyl-substituted phenyl, spirobifluorenyl-substituted phenyl, dibenzofuranyl-substituted phenyl, dibenzothiophenyl-substituted phenyl, carbazolyl-substituted phenyl, pyridyl-substituted phenyl, pyrimidyl-substituted phenyl, and triazinyl-substituted phenyl, where the groups mentioned are each substituted by one or more R4 radicals.

7. The compound according to claim 1, wherein at least one group selected from the Ar2 and Ar3 groups is unsubstituted phenyl.

8. The compound according to claim 1, wherein Ar2 and Ar3 are the same or different and are selected from the following formulae:

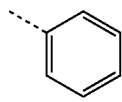

Ar-1

-continued

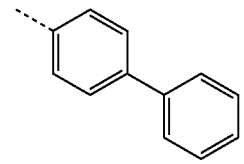

Ar-2

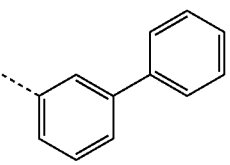

Ar-3

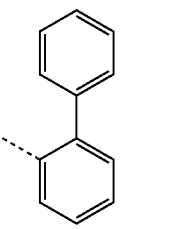

Ar-4

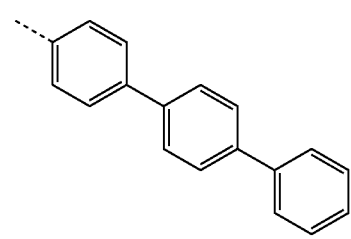

Ar-5

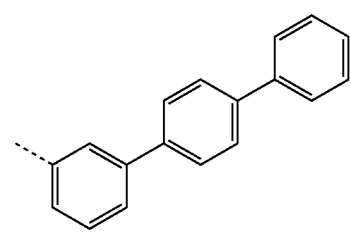

Ar-6

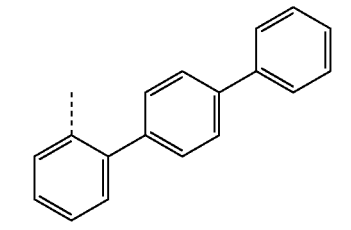

Ar-7

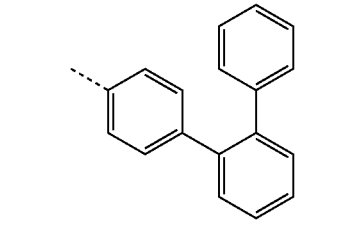

Ar-8

Ar-9
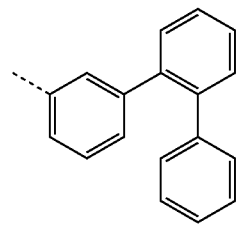
Ar-10
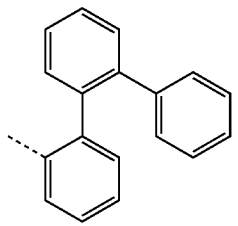
Ar-11
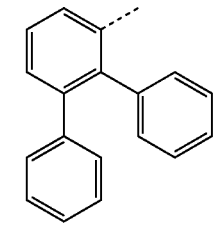
Ar-12
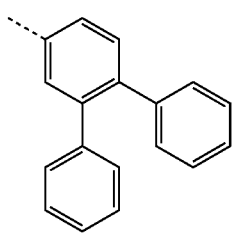
Ar-13
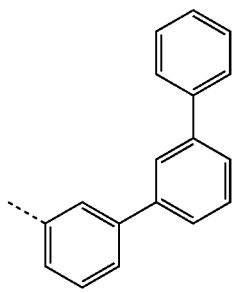
Ar-14
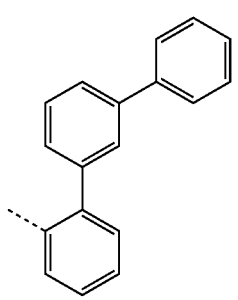
Ar-15
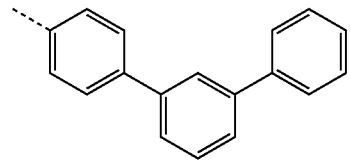
Ar-16
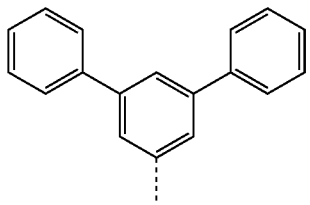
Ar-17
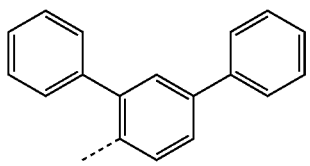
Ar-18
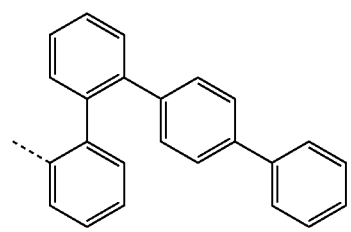
Ar-19
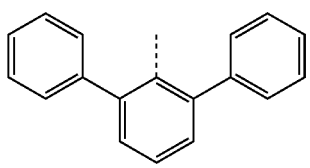
Ar-20
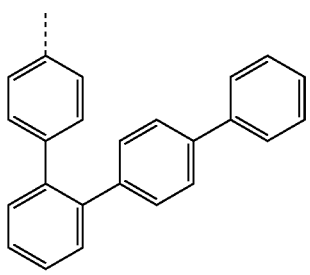
Ar-21

-continued
Ar-22
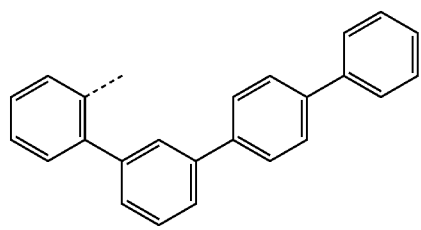
Ar-23
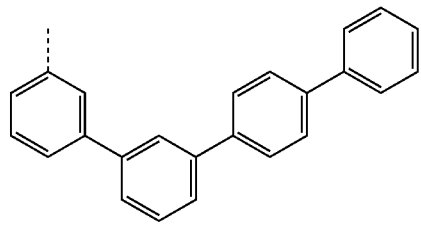
Ar-24
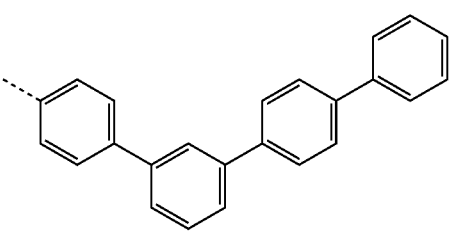
Ar-25
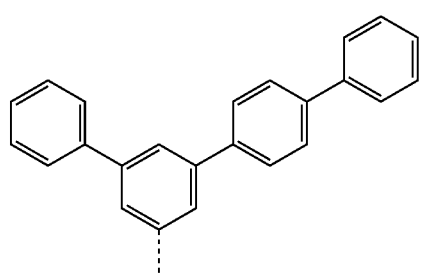
Ar-26
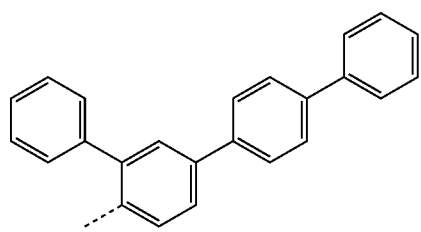
Ar-27
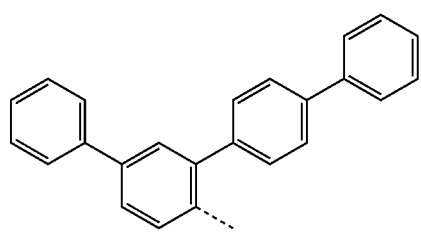
-continued
Ar-28
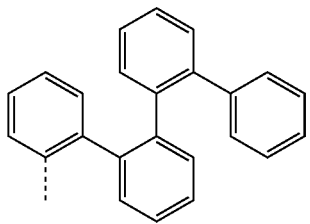
Ar-29
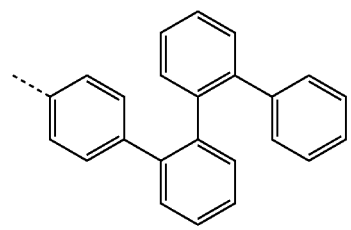
Ar-30
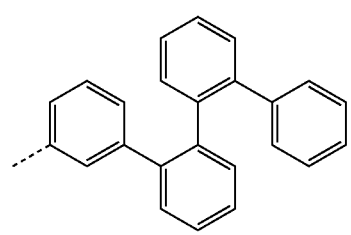
Ar-31
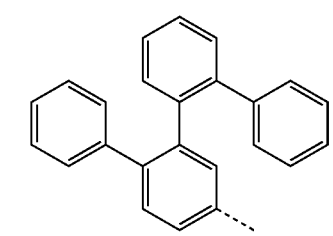
Ar-32
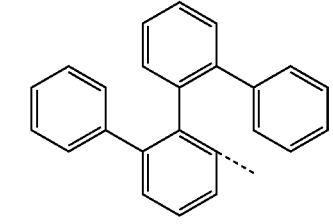
Ar-33
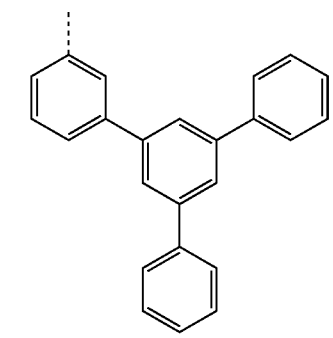

-continued
Ar-34
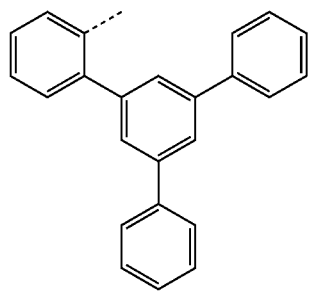
Ar-35
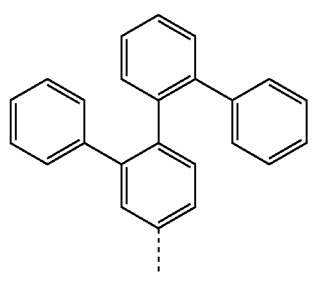
Ar-36
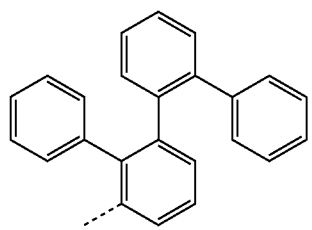
Ar-37
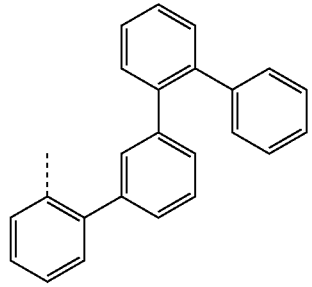
Ar-38
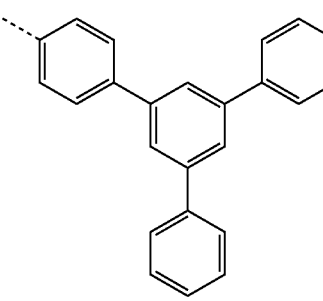
Ar-39
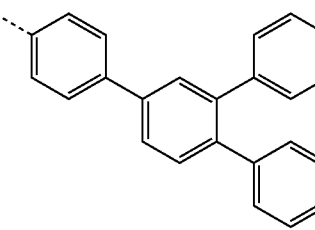
-continued
Ar-40
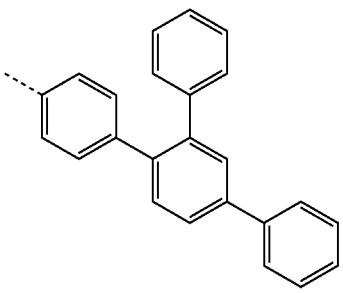
Ar-41
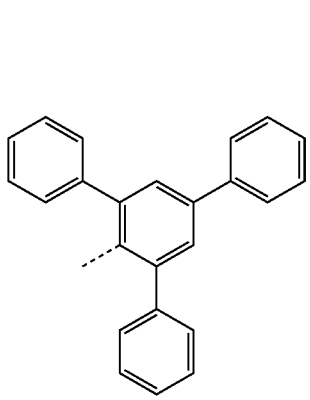
Ar-42
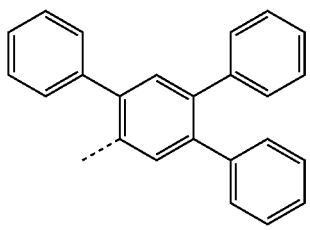
Ar-43
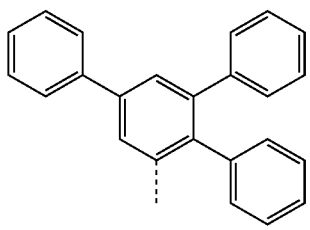
Ar-44
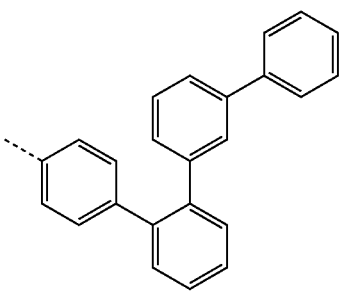

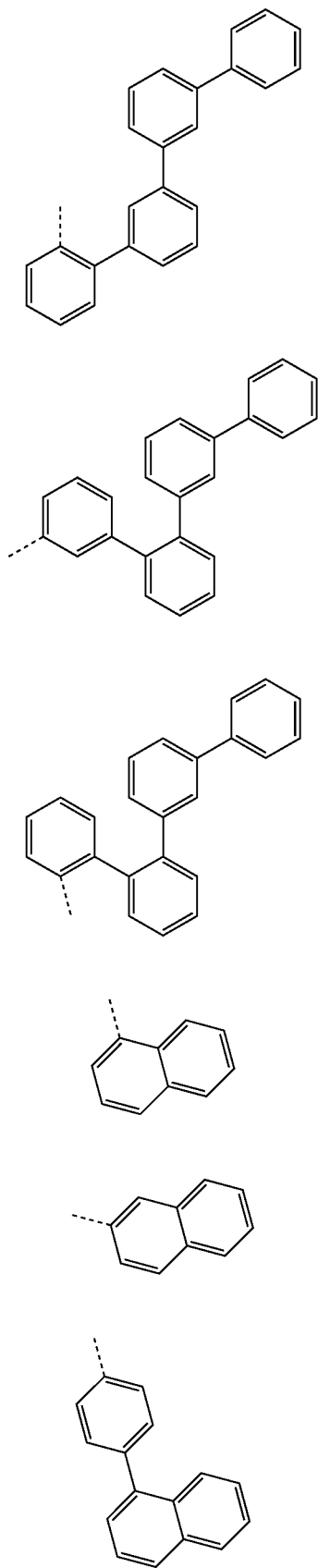
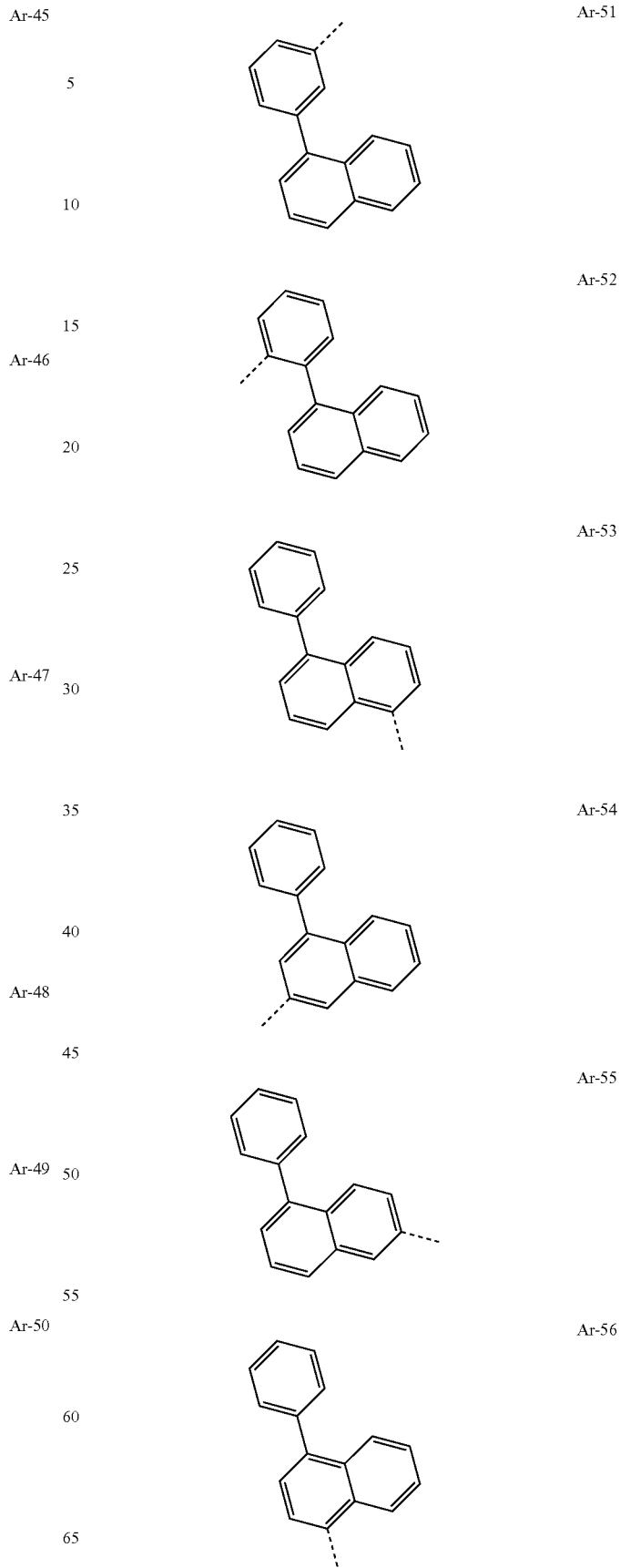

-continued
Ar-57
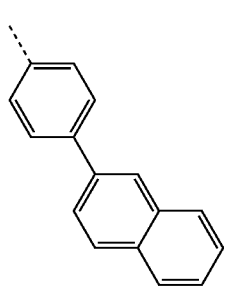
Ar-58
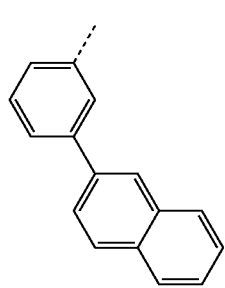
Ar-59
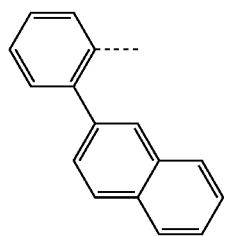
Ar-60
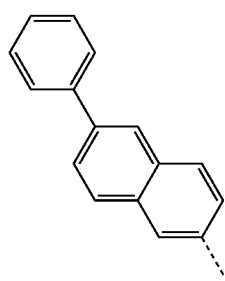
Ar-61
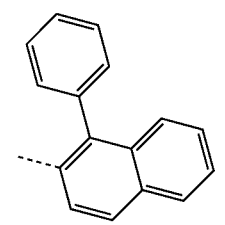
Ar-62
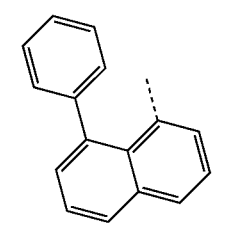
-continued
Ar-63
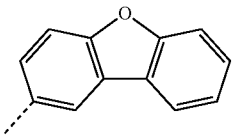
Ar-64
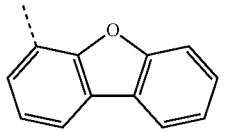
Ar-65
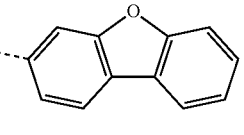
Ar-66
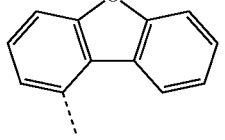
Ar-67
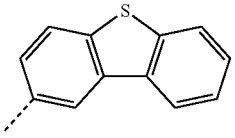
Ar-68
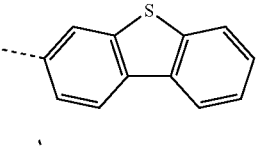
Ar-69
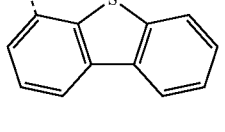
Ar-70
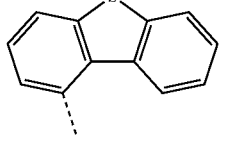
Ar-71
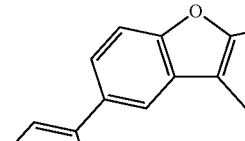
Ar-72
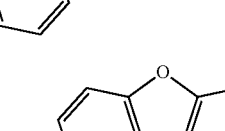

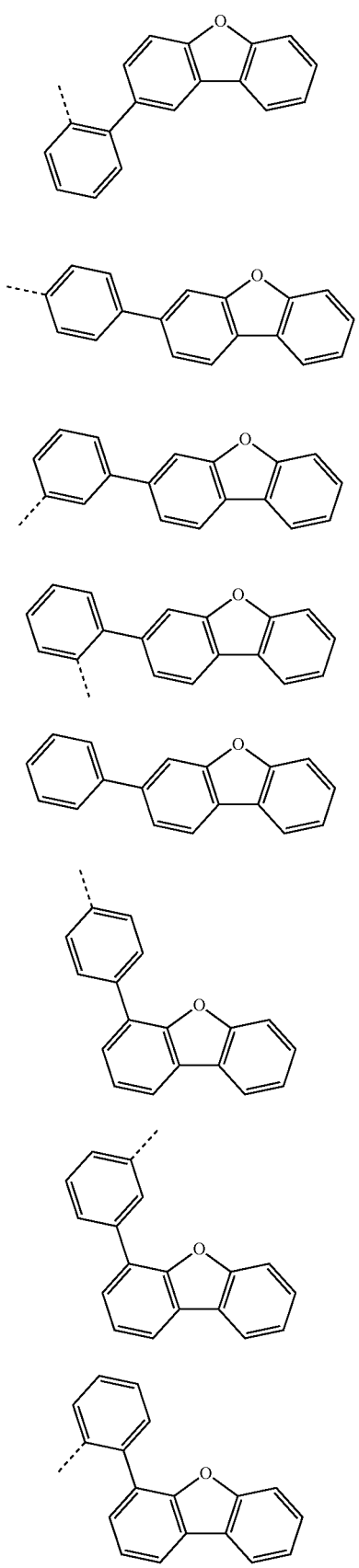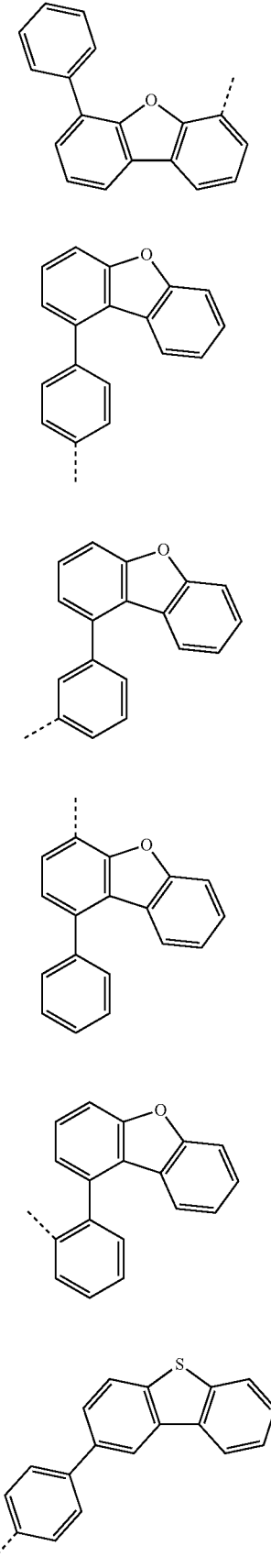

411
-continued
Ar-87
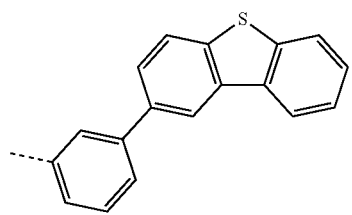
Ar-88
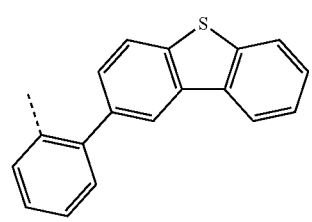
Ar-89
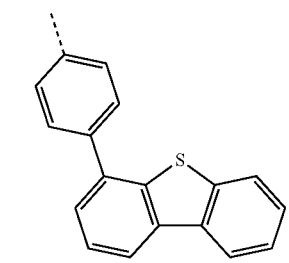
Ar-129
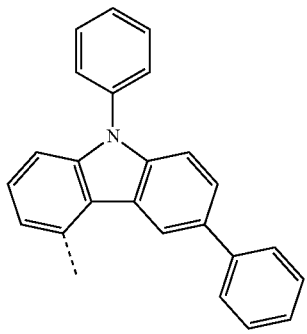
Ar-130
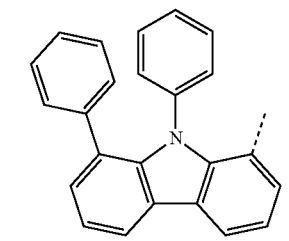
Ar-131
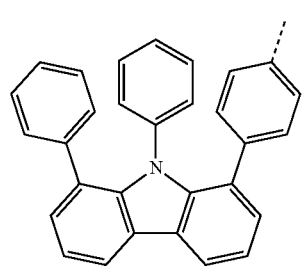
412
-continued
Ar-132
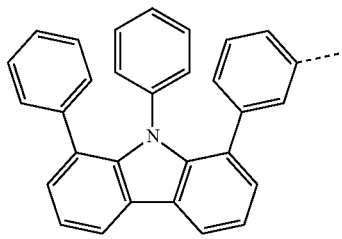
Ar-133
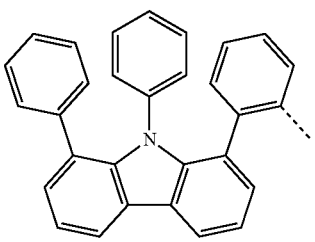
Ar-134
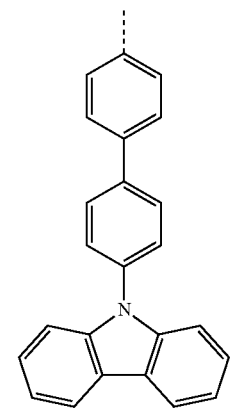
Ar-135
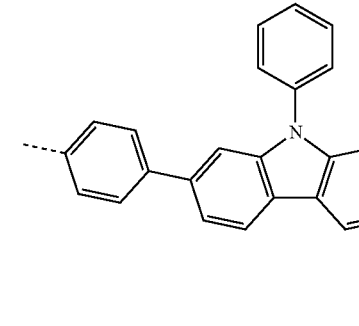
Ar-136
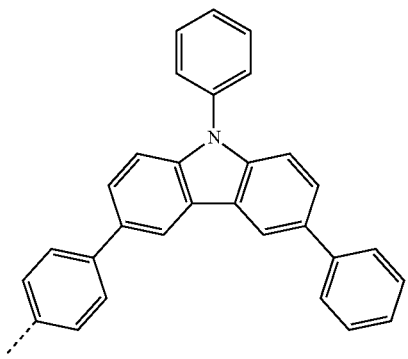

Ar-137
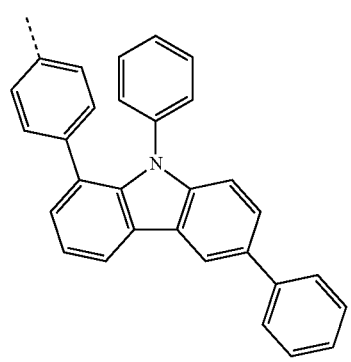
Ar-138
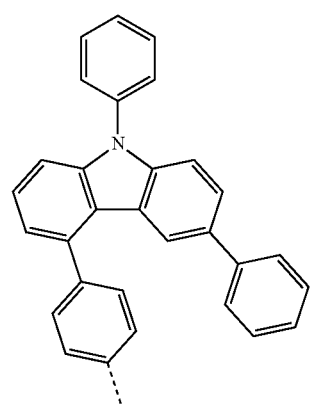
Ar-139
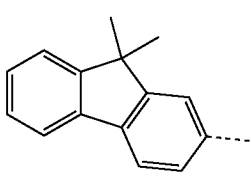
Ar-185
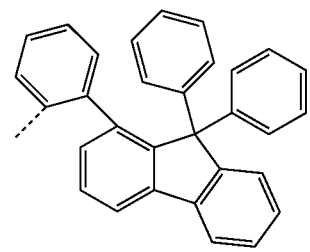
Ar-186
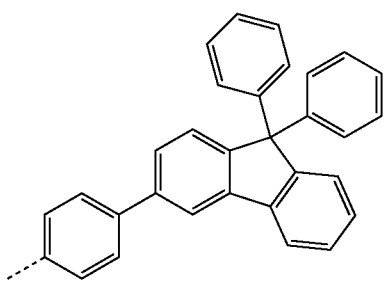
Ar-187
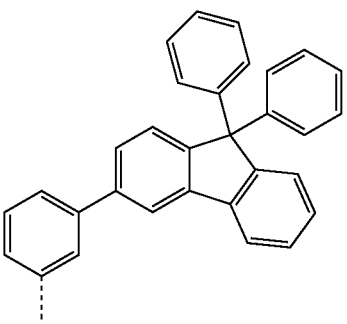
Ar-188
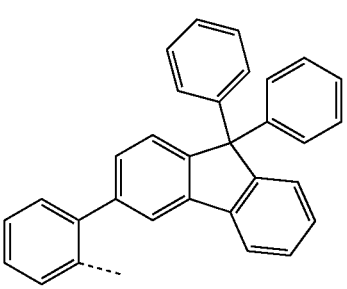
Ar-189
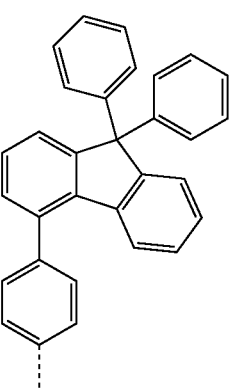
Ar-190
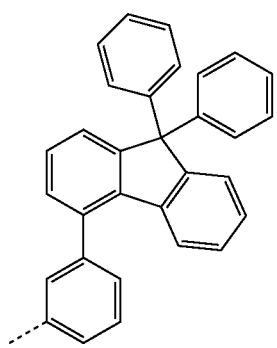

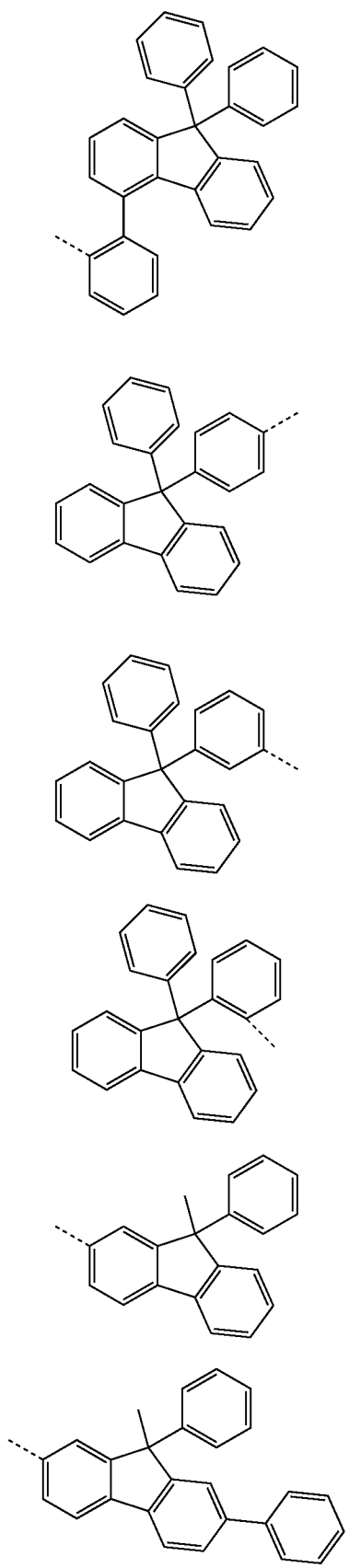

-continued
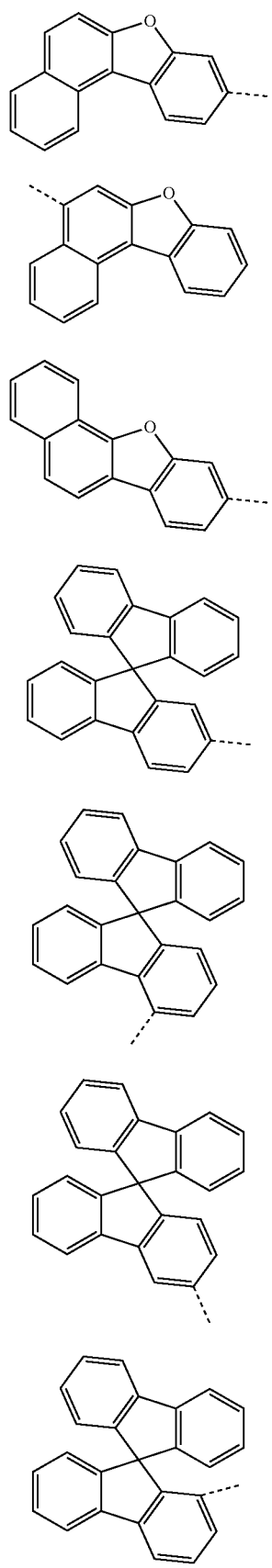
Ar-204
Ar-205
Ar-206
Ar-207
Ar-208
Ar-209
Ar-210
-continued
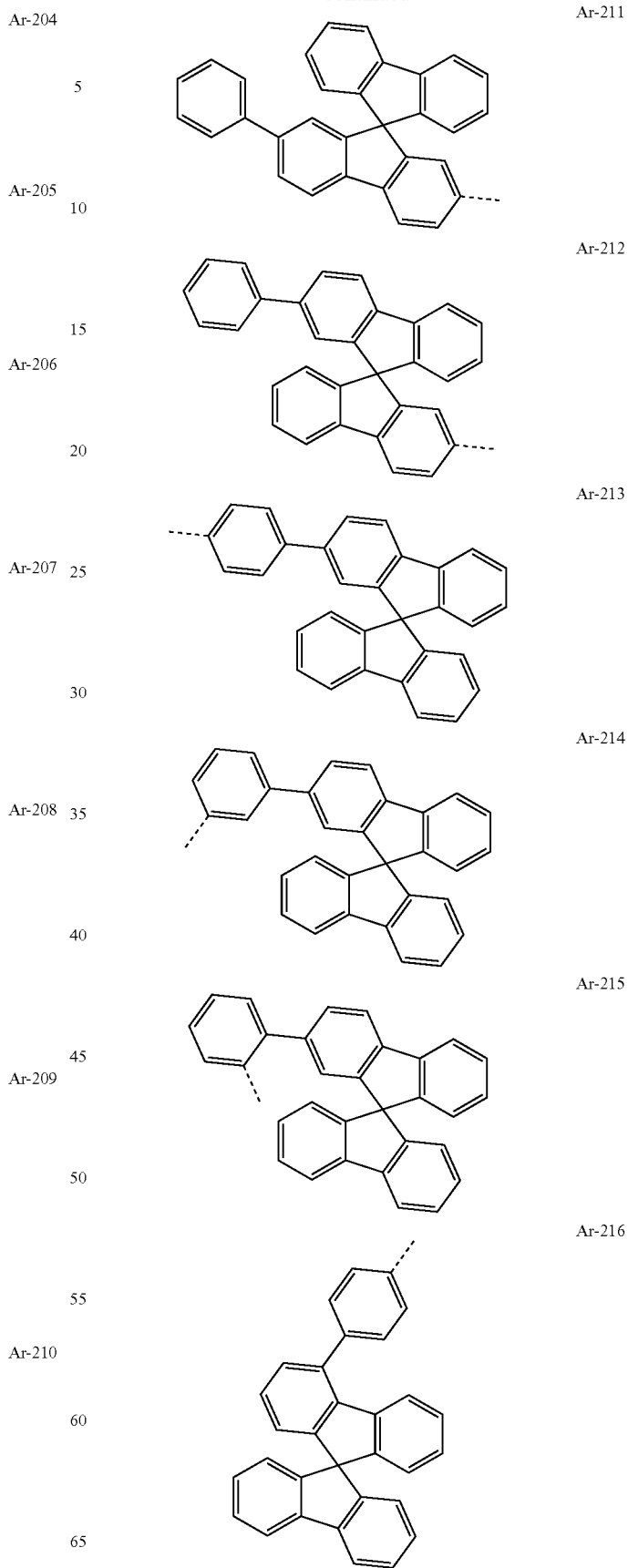
Ar-211
Ar-212
Ar-213
Ar-214
Ar-215
Ar-216

-continued
Ar-217
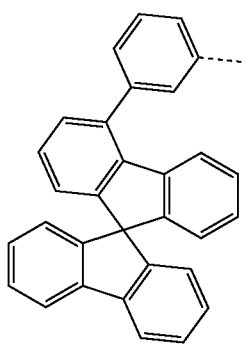
Ar-218
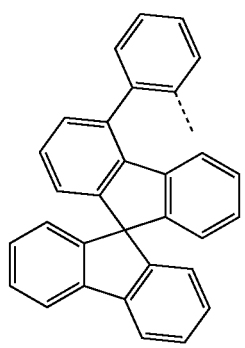
Ar-219
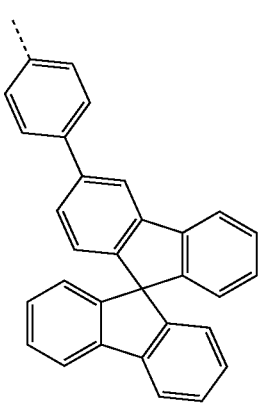
Ar-220
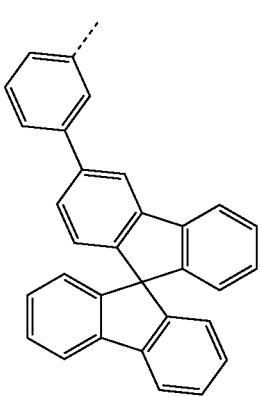
-continued
Ar-221
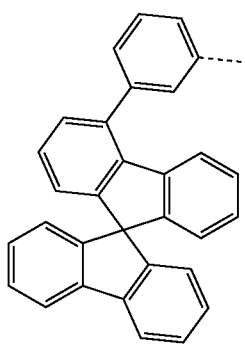
Ar-222
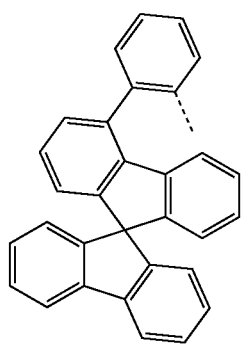
Ar-223
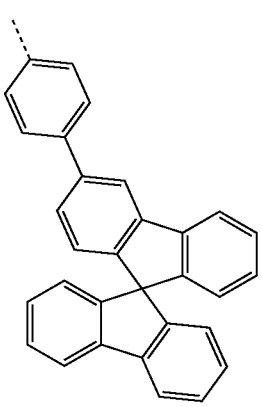
Ar-224
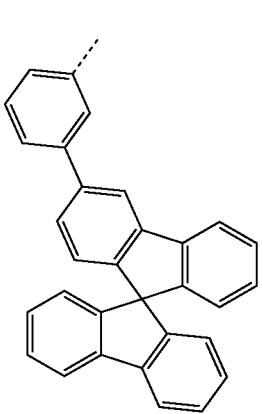
Ar-225
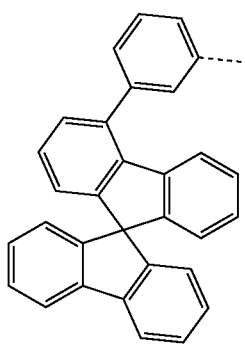
Ar-226
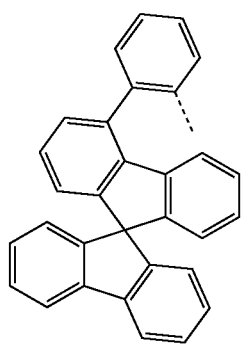

-continued

Ar-227

Ar-228

Ar-229

Ar-230

Ar-231

Ar-232

Ar-233

Ar-234

Ar-235

-continued

Ar-236

Ar-237

Ar-238

Ar-239

Ar-240

Ar-241

Ar-242

Ar-243

Ar-244

Ar-245

Ar-246 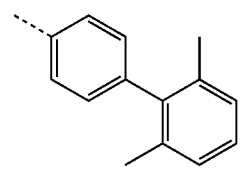
Ar-247 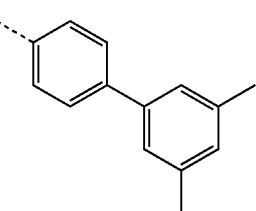
Ar-248 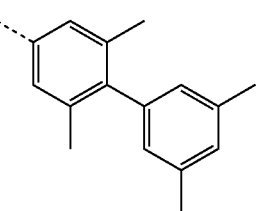
Ar-250 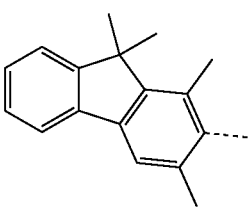
Ar-251 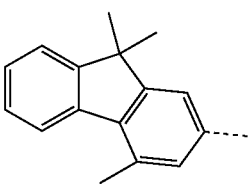
Ar-252 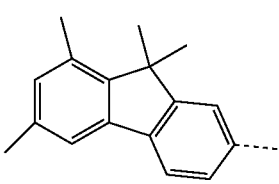
Ar-253 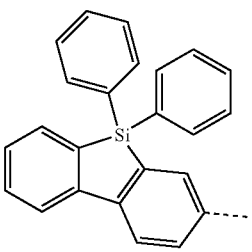
Ar-254 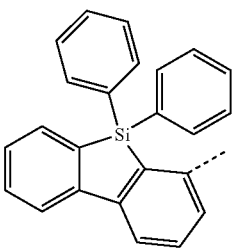
Ar-255 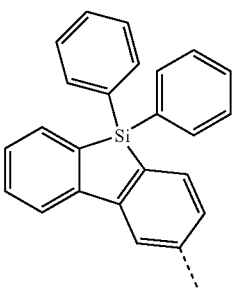
Ar-256 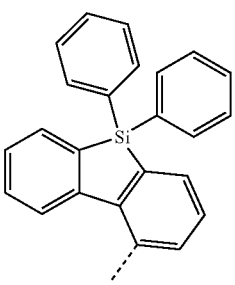
Ar-257 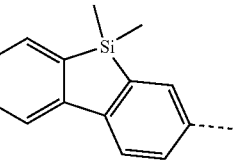
Ar-258 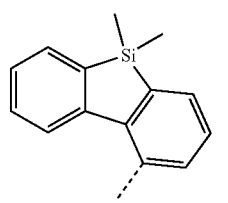
Ar-259 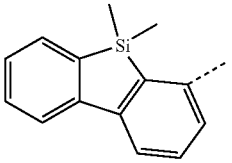
Ar-260 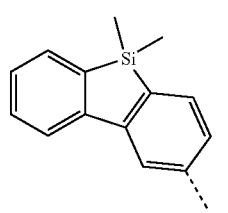

Ar-261
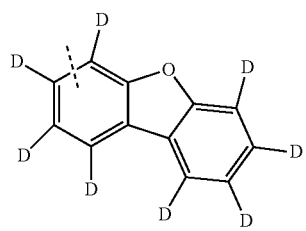
Ar-262
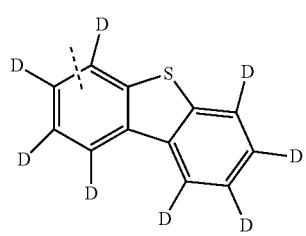
Ar-263
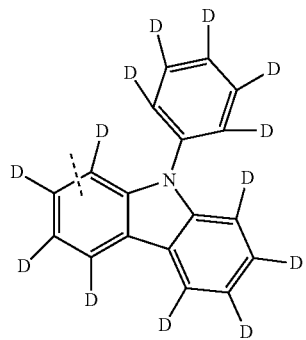
Ar-264
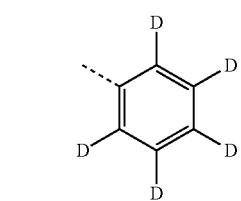
Ar-265
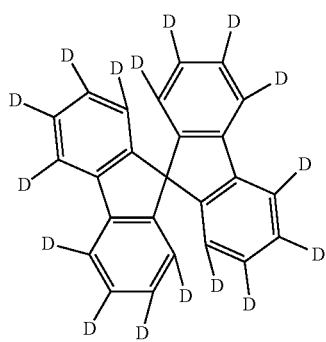
Ar-266
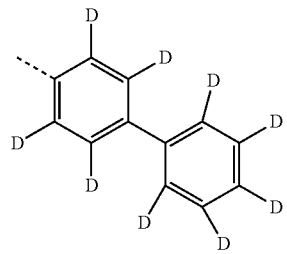
Ar-267
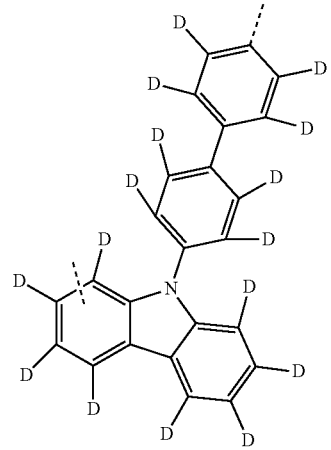
Ar-268
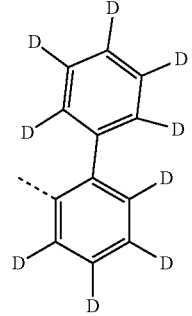
Ar-269
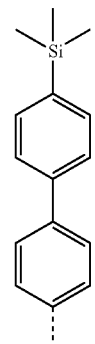
Ar-270
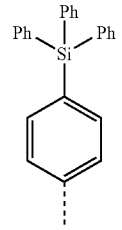

-continued

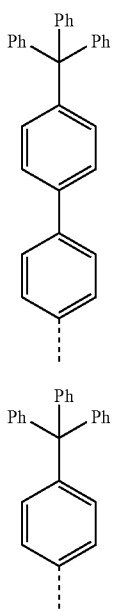

Ar-271

Ar-272 where the groups at the positions shown as unsubstituted are substituted by R4 radicals, where R4 in these positions is preferably H, and where the dotted bond is the bond to the amine nitrogen atom.

9. The compound according to claim 1, wherein Ar4 is phenyl which may be substituted by R2 radicals.

10. The compound according to claim 1, wherein
R1 is the same or different at each instance and is selected from H, aromatic ring systems having 6 to 40 aromatic ring atoms and heteroaromatic ring systems having 5 to 40 aromatic ring atoms, where the aromatic ring systems and the heteroaromatic ring systems are each substituted by R5 radicals; and
R2 is selected from aromatic ring systems which have 6 to 40 aromatic ring atoms and are substituted by R5 radicals; and
R3 is the same or different at each instance and is selected from H, N(R5)$_2$, straight-chain alkyl groups having 1 to 20 carbon atoms, branched or cyclic alkyl groups having 3 to 20 carbon atoms, aromatic ring systems having 6 to 40 aromatic ring atoms and heteroaromatic ring systems having 5 to 40 aromatic ring atoms, where the alkyl groups, the aromatic ring systems and the heteroaromatic ring systems are each substituted by R5 radicals; and
R4 is the same or different at each instance and is selected from H, N(R5)$_2$, straight-chain alkyl groups having 1 to 20 carbon atoms, branched or cyclic alkyl groups having 3 to 20 carbon atoms, aromatic ring systems having 6 to 40 aromatic ring atoms and heteroaromatic ring systems having 5 to 40 aromatic ring atoms, where the alkyl groups, the aromatic ring systems and the heteroaromatic ring systems are each substituted by R5 radicals; and
R5 is the same or different at each instance and is selected from H, straight-chain alkyl groups having 1 to 20 carbon atoms, branched or cyclic alkyl groups having 3 to 20 carbon atoms, aromatic ring systems having 6 to 40 aromatic ring atoms and heteroaromatic ring systems having 5 to 40 aromatic ring atoms, where the alkyl groups, the aromatic ring systems and the heteroaromatic ring systems are each substituted by R6 radicals.

11. The compound according to claim 1, wherein one or two R1 radicals are selected from aromatic ring systems which have 6 to 40 aromatic ring atoms and are substituted by R5 radicals, and heteroaromatic ring systems which have 5 to 40 aromatic ring atoms and are substituted by R5 radicals, and the other R1 radicals are H.

12. The compound according to claim 1, wherein i and n are 0.

13. The compound according to claim 1, wherein the -[Ar1]$_k$-N(Ar2)(Ar3) group is bonded to the fluorenyl group in formula (I) in the 2 position or in the 4 position.

14. The compound according to claim 1, wherein it corresponds to one of the following formulae:

Formula (I-A-1)

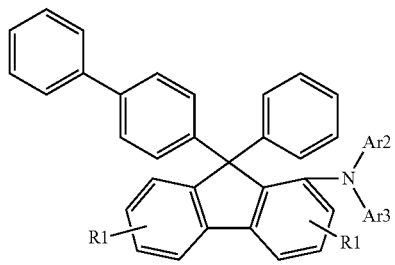

Formula (I-A-2)

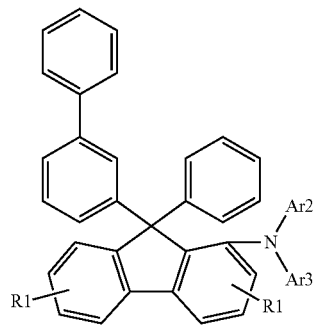

Formula (I-A-3)

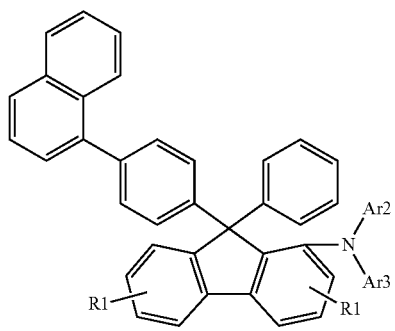

Formula (I-A-4)
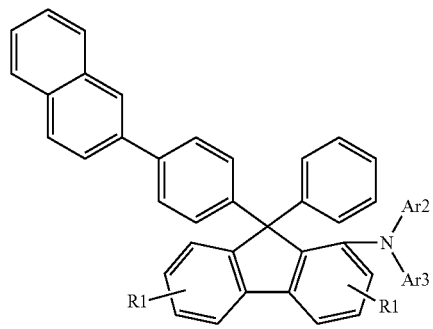
Formula (I-B-4)
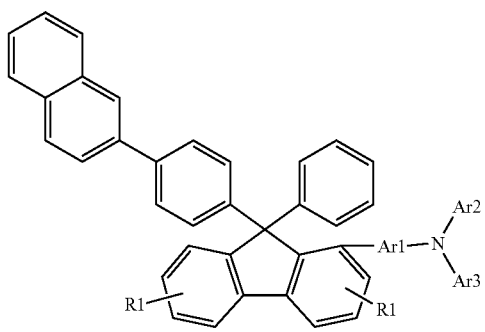
Formula (I-B-1)
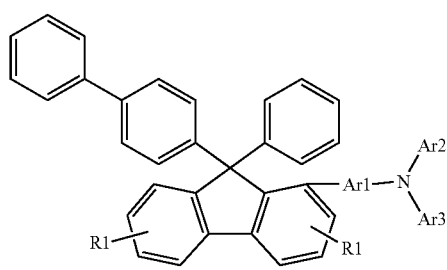
Formula (I-C-1)
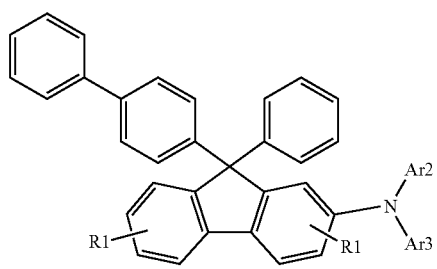
Formula (I-B-2)
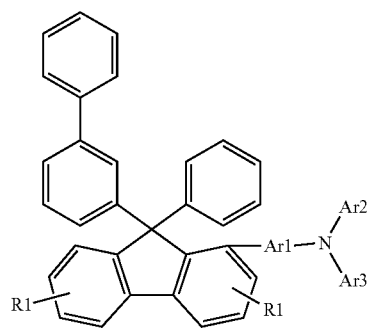
Formula (I-C-2)
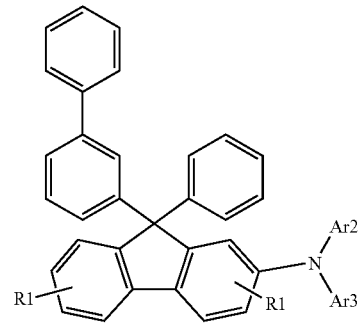
Formula (I-B-3)
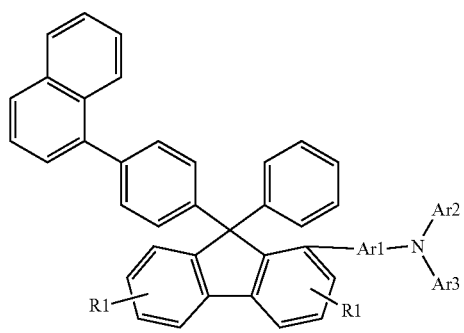
Formula (I-C-3)
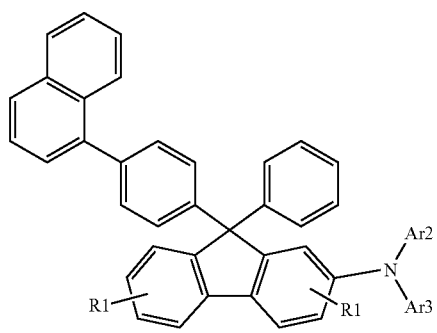

Formula (I-C-4)
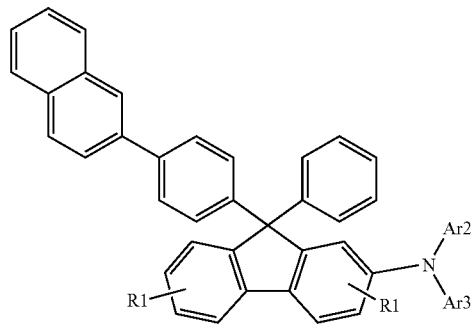
Formula (I-D-1)
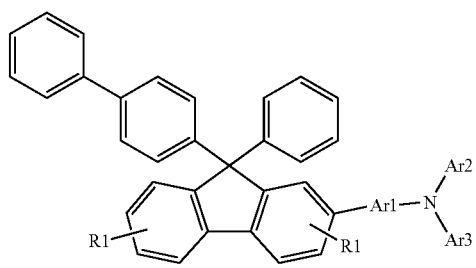
Formula (I-D-2)
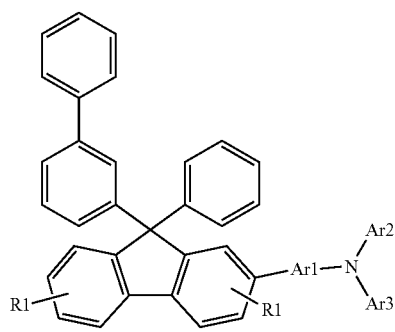
Formula (I-D-3)
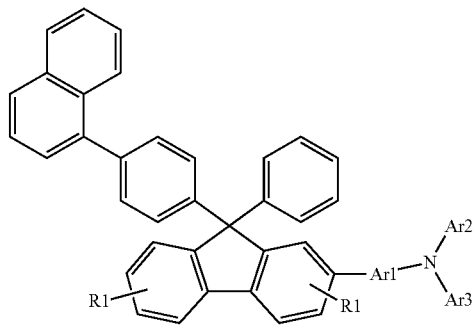
Formula (I-D-4)
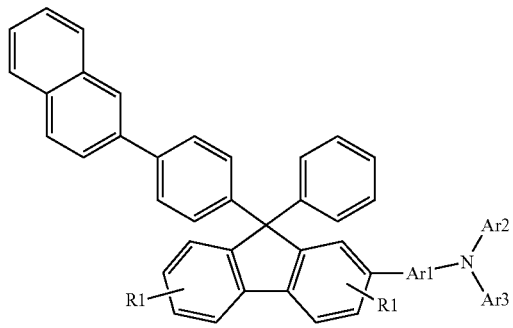
Formula (I-E-1)
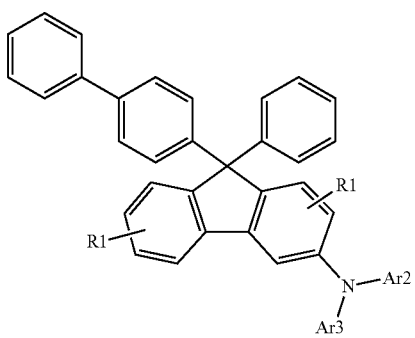
Formula (I-E-2)
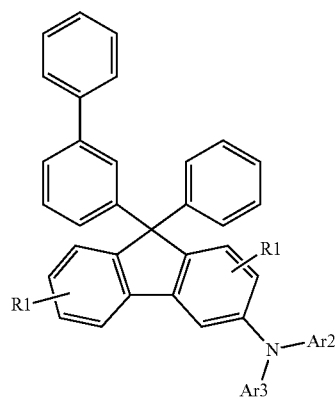
Formula (I-E-3)
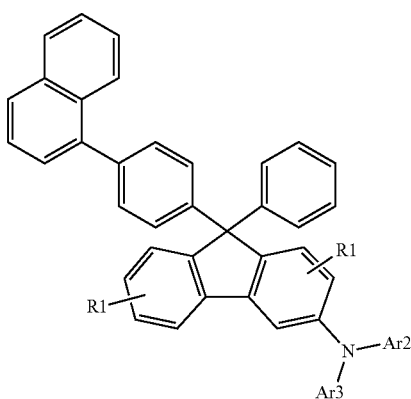

Formula (I-E-4)
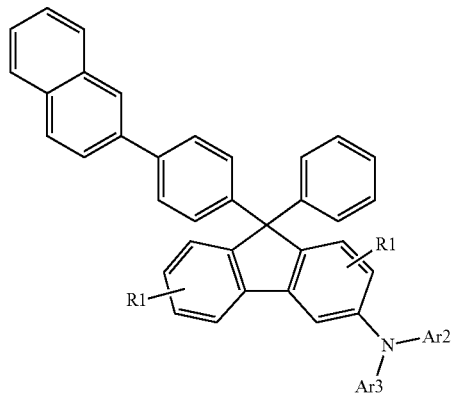
Formula (I-F-1)
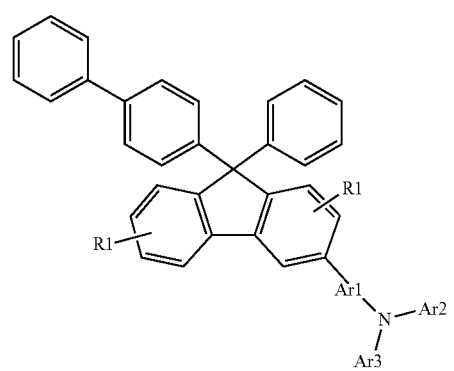
Formula (I-F-2)
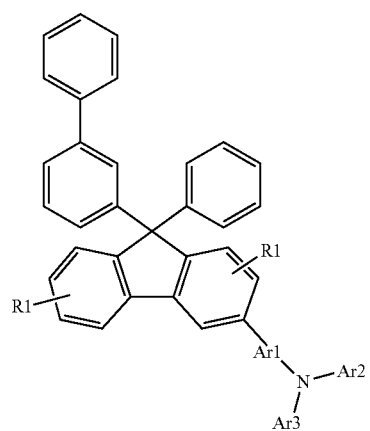
Formula (I-F-3)
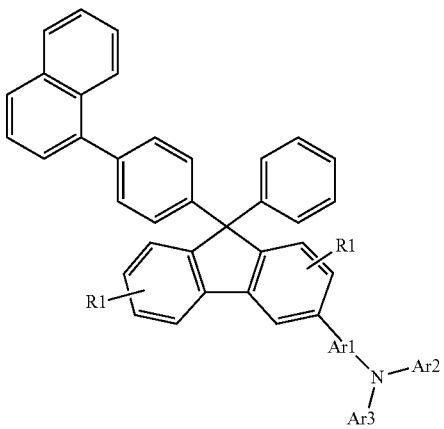
Formula (I-F-4)
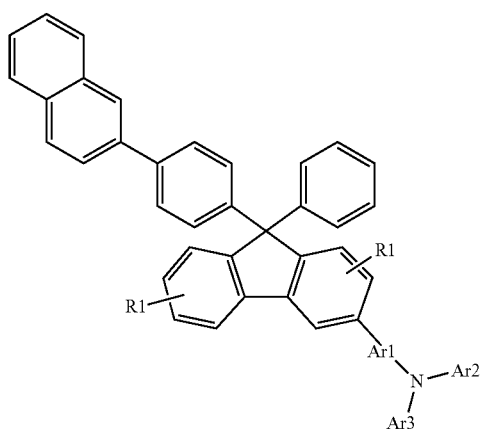
Formula (I-G-1)
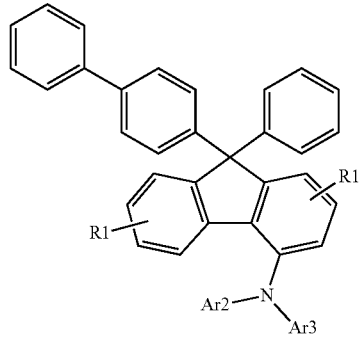

Formula (I-G-2)
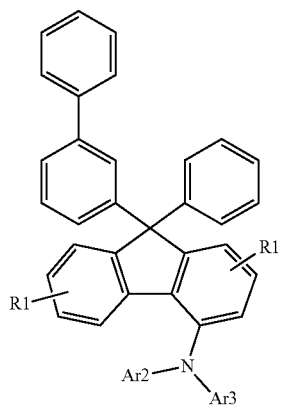
Formula (I-G-3)
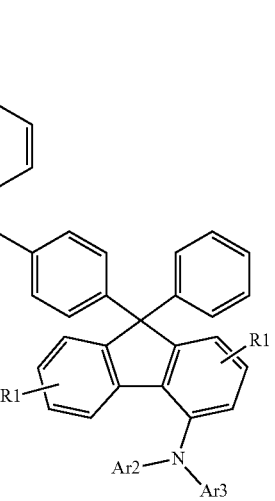
Formula (I-G-4)
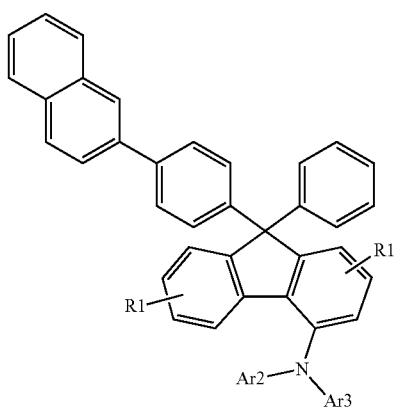
Formula (I-H-1)
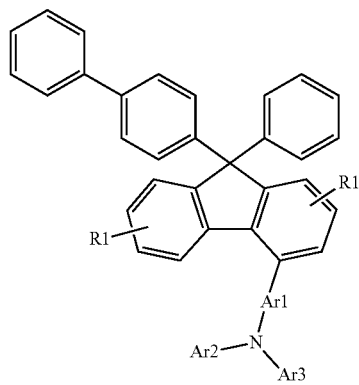
Formula (I-H-2)
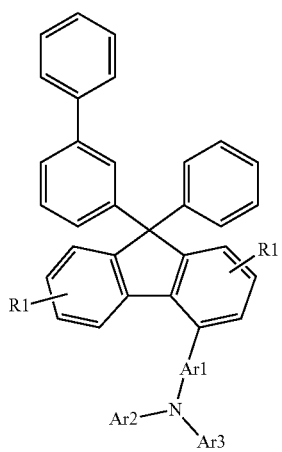
Formula (I-H-3)
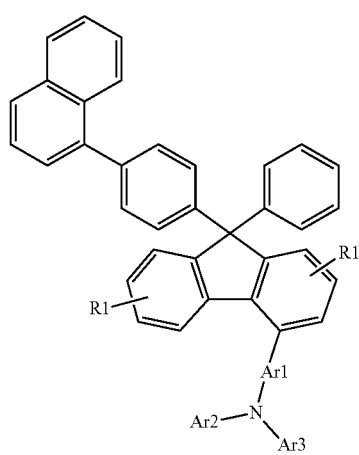

-continued

Formula (I-H-4)

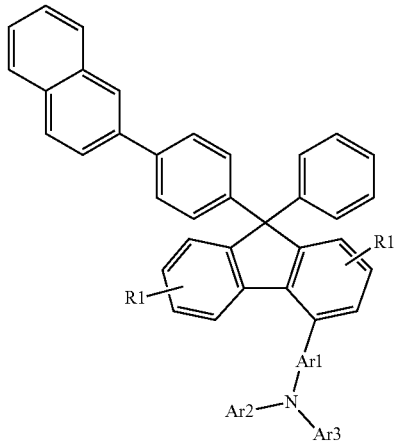

where the symbols and indices that occur are as defined in claim 1, and where the bonded R1 radical means that all positions shown as unsubstituted on the benzene ring in question are substituted by R1 radicals.

15. An oligomer, polymer or dendrimer containing one or more compounds according to claim 1, wherein the bond(s) to the polymer, oligomer or dendrimer may be localized at any desired positions substituted by R1, R2, R3 or R4 in formula (I).

16. A formulation comprising at least one compound according to claim 1 and at least one solvent.

17. An electronic device comprising at least one compound according to claim 1.

18. The electronic device according to claim 17, wherein it is an organic electroluminescent device and comprises anode, cathode and at least one emitting layer, and in that the compound is present in a hole-transporting layer or in an emitting layer of the device.

19. The device according to claim 18, wherein the compound is present in a hole-transporting layer which is a hole transport layer or an electron blocker layer.

20. A method comprising utilizing the compound according to claim 1 in an electronic device.

21. A process for preparing a compound of formula (I)

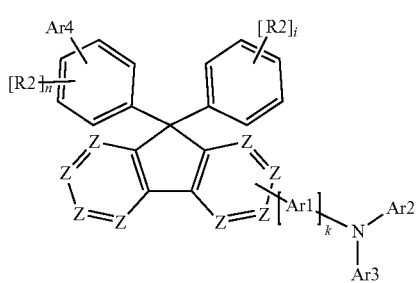

Formula (I)

where the variables that occur are as follows:
Z, when the -[Ar1]$_k$-N(Ar2)(Ar3) group is bonded thereto, is C, and Z, when the -[Ar1]$_k$-N(Ar2)(Ar3) group is not bonded thereto, is the same or different at each instance and is CR1 or N;
Ar1 is the same or different at each instance and is an aromatic ring system which has 6 to 40 aromatic ring atoms and is substituted by R3 radicals, or a heteroaromatic ring system which has 5 to 40 aromatic ring atoms and is substituted by R3 radicals;
Ar2 is an aromatic ring system which has 6 to 40 aromatic ring atoms and is substituted by R4 radicals, or a heteroaromatic ring system which has 5 to 40 aromatic ring atoms and is substituted by R4 radicals;
Ar3 is an aromatic ring system which has 6 to 40 aromatic ring atoms and is substituted by R4 radicals, or a heteroaromatic ring system which has 5 to 40 aromatic ring atoms and is substituted by R4 radicals;
provided that at least one group selected from the Ar2 and Ar3 groups is phenyl substituted by R4 radicals that are selected from H, D, F, CN and alkyl groups having 1 to 10 carbon atoms;
Ar4 is phenyl which may be substituted by R2 radicals or naphthyl which may be substituted by R2 radicals;
R1 is the same or different at each instance and is selected from H, D, F, Cl, Br, I, C(=O)R5, CN, Si(R5)$_3$, N(R5)$_2$, P(=O)(R5)$_2$, OR5, S(=O)R5, S(=O)$_2$R5, straight-chain alkyl or alkoxy groups having 1 to 20 carbon atoms, branched or cyclic alkyl or alkoxy groups having 3 to 20 carbon atoms, alkenyl or alkynyl groups having 2 to 20 carbon atoms, aromatic ring systems having 6 to 40 aromatic ring atoms, and heteroaromatic ring systems having 5 to 40 aromatic ring atoms; where two or more R1 radicals may be joined to one another and may form a ring; where the alkyl, alkoxy, alkenyl and alkynyl groups mentioned and the aromatic ring systems and heteroaromatic ring systems mentioned are each substituted by R5 radicals; and where one or more CH$_2$ groups in the alkyl, alkoxy, alkenyl and alkynyl groups mentioned may be replaced by —R5C=CR5-, —C≡C—, Si(R5)$_2$, C=O, C=NR5, —C(=O)O—, —C(=O)NR5-, NR5, P(=O)(R5), —O—, —S—, SO or SO$_2$;
R2 is the same or different at each instance and is selected from D, F, CN, Si(R5)$_3$, N(R5)$_2$, aromatic ring systems which have 6 to 40 aromatic ring atoms and are substituted by R5 radicals, and heteroaromatic ring systems which have 5 to 40 aromatic ring atoms and are substituted by R5 radicals;
R3 is the same or different at each instance and is selected from H, D, F, Cl, Br, I, C(=O)R5, CN, Si(R5)$_3$, N(R5)$_2$, P(=O)(R5)$_2$, OR5, S(=O)R5, S(=O)$_2$R5, straight-chain alkyl or alkoxy groups having 1 to 20 carbon atoms, branched or cyclic alkyl or alkoxy groups having 3 to 20 carbon atoms, alkenyl or alkynyl groups having 2 to 20 carbon atoms, aromatic ring systems having 6 to 40 aromatic ring atoms, and heteroaromatic ring systems having 5 to 40 aromatic ring atoms; where two or more R3 radicals may be joined to one another and may form a ring; where the alkyl, alkoxy, alkenyl and alkynyl groups mentioned and the aromatic ring systems and heteroaromatic ring systems mentioned are each substituted by R5 radicals; and where one or more CH$_2$ groups in the alkyl, alkoxy, alkenyl and alkynyl groups mentioned may be replaced by —R5C=CR5-, —C≡C—, Si(R5)$_2$, C=O, C=NR5, —C(=O)O—, —C(=O)NR5-, NR5, P(=O)(R5), —O—, —S—, SO or SO$_2$;
R4 is the same or different at each instance and is selected from H, D, F, Cl, Br, I, C(=O)R5, CN, Si(R5)$_3$, N(R5)$_2$, P(=O)(R5)$_2$, OR5, S(=O)R5, S(=O)$_2$R5, straight-chain alkyl or alkoxy groups having 1 to 20 carbon atoms, branched or cyclic alkyl or alkoxy groups having 3 to 20 carbon atoms, alkenyl or alkynyl groups having 2 to 20 carbon atoms, aromatic ring systems having 6 to 40 aromatic ring atoms, and heteroaromatic ring systems having 5 to 40 aromatic ring atoms; where two or more R4 radicals may be joined to one another and may form a ring; where the alkyl, alkoxy, alkenyl and alkynyl groups mentioned and the aromatic ring systems and heteroaromatic ring systems mentioned are each substituted by R5 radicals; and where one or more $CH_2$ groups in the alkyl, alkoxy, alkenyl and alkynyl groups mentioned may be replaced by —R5C=CR5-, —C≡C—, $Si(R5)_2$, C=O, C=NR5, —C(=O)O—, —C(=O)NR5-, NR5, P(=O)(R5), —O—, —S—, SO or $SO_2$;

R5 is the same or different at each instance and is selected from H, D, F, Cl, Br, I, C(=O)R6, CN, $Si(R6)_3$, $N(R6)_2$, $P(=O)(R6)_2$, OR6, S(=O)R6, $S(=O)_2R6$, straight-chain alkyl or alkoxy groups having 1 to 20 carbon atoms, branched or cyclic alkyl or alkoxy groups having 3 to 20 carbon atoms, alkenyl or alkynyl groups having 2 to 20 carbon atoms, aromatic ring systems having 6 to 40 aromatic ring atoms, and heteroaromatic ring systems having 5 to 40 aromatic ring atoms; where two or more R5 radicals may be joined to one another and may form a ring; where the alkyl, alkoxy, alkenyl and alkynyl groups mentioned and the aromatic ring systems and heteroaromatic ring systems mentioned are each substituted by R6 radicals; and where one or more $CH_2$ groups in the alkyl, alkoxy, alkenyl and alkynyl groups mentioned may be replaced by —R6C=CR6-, —C≡C—, $Si(R6)_2$, C=O, C=NR6, —C(=O)O—, —C(=O)NR6-, NR6, P(=O)(R6), —O—, —S—, SO or $SO_2$;

R6 is the same or different at each instance and is selected from H, D, F, Cl, Br, I, CN, alkyl or alkoxy groups having 1 to 20 carbon atoms, alkenyl or alkynyl groups having 2 to 20 carbon atoms, aromatic ring systems having 6 to 40 aromatic ring atoms and heteroaromatic ring systems having 5 to 40 aromatic ring atoms; where the alkyl, alkoxy, alkenyl and alkynyl groups, aromatic ring systems and heteroaromatic ring systems mentioned may be substituted by one or more radicals selected from F and CN;

k is 0, 1, 2, 3 or 4, where, in the case that k=0, the Ar1 group is absent and the groups that bind to Ar1 in formula (I) are bonded directly to one another;

i is 0, 1, 2, 3, 4 or 5;

n is 0, 1, 2, 3 or 4;

where the two groups

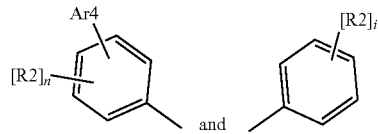

in formula (I), each as a whole including their substituents, are not the same;

wherein a biphenyl derivative bearing two reactive groups, at least one of which is in the ortho position, is metallated and then is added onto a carbonyl derivative containing a phenyl- or naphthyl-substituted phenyl group and a phenyl group bonded to the carbonyl group.

* * * * *